United States Patent
Uehling et al.

(10) Patent No.: US 7,807,673 B2
(45) Date of Patent: Oct. 5, 2010

(54) 2-PYRIMIDINYL PYRAZOLOPYRIDINE ERBB KINASE INHIBITORS

(75) Inventors: David Edward Uehling, Durham, NC (US); Robert Dale Hubbard, Durham, NC (US); Alex Gregory Waterson, Durham, NC (US); Kimberly Petrov, Durham, NC (US); Neil Bifulco, Jr., Durham, NC (US); Joseph Wendell Wilson, Durham, NC (US); Jennifer Gabriel Badiang, Durham, NC (US); Mul Cheung, Collegeville, PA (US); Mariko Yamabe, Tokyo (JP)

(73) Assignee: GlaxoSmithKline LLC, Philadelphia, PA (US)

( * ) Notice: Subject to any disclaimer, the term of this patent is extended or adjusted under 35 U.S.C. 154(b) by 298 days.

(21) Appl. No.: 12/095,762

(22) PCT Filed: Dec. 4, 2006

(86) PCT No.: PCT/US2006/046316

§ 371 (c)(1), (2), (4) Date: Jun. 2, 2008

(87) PCT Pub. No.: WO2007/067506

PCT Pub. Date: Jun. 14, 2007

(65) Prior Publication Data

US 2009/0149456 A1    Jun. 11, 2009

Related U.S. Application Data

(60) Provisional application No. 60/742,351, filed on Dec. 5, 2005.

(51) Int. Cl.
*C07D 471/04*    (2006.01)
*A61K 31/437*    (2006.01)

(52) U.S. Cl. .............................. 514/235.8; 514/252.14; 514/275; 544/122; 544/295; 544/331

(58) Field of Classification Search ................. 544/122, 544/295, 331; 514/235.8, 252.14, 275
See application file for complete search history.

(56) References Cited

U.S. PATENT DOCUMENTS

| | | | |
|---|---|---|---|
| 6,727,256 | B1 | 4/2004 | Carter et al. |
| 6,855,719 | B1 | 2/2005 | Beattie et al. |
| 6,919,352 | B2 | 7/2005 | Chamberlain et al. |
| 6,962,914 | B2 | 11/2005 | Gudmundsson et al. |
| 7,141,569 | B2 | 11/2006 | Cheung et al. |
| 7,153,863 | B2 | 12/2006 | Gudmundsson et al. |
| 2004/0053942 | A1 | 3/2004 | Alberti et al. |

FOREIGN PATENT DOCUMENTS

| | | |
|---|---|---|
| WO | 9935146 | 7/1999 |
| WO | 0216359 | 2/2002 |
| WO | 2004021988 A2 | 3/2004 |
| WO | 2005068452 A2 | 7/2005 |
| WO | 2006068826 | 6/2006 |

OTHER PUBLICATIONS

Traxler, Protein Tyrosine Kinase Inhibitors in Cancer Treatment, Expert Opinion on Therapeutic Patents, 7(6):571-588, 1997.*
Simone, Oncology: Introduction, Cecil Textbook of Medicine, 20th Edition, vol. 1, pp. 1004-1010, 1996.*
R. Hubbard, et al.,; Pyrazolo[3,4-d]pyrimidines as potent inhibitors of the insulin-like growth factor receptor (IGF-1R); Bioorganic & Med Chem Lttrs; Jul. 25, 2007; 17; 5406-5409.

* cited by examiner

*Primary Examiner*—Deepak Rao
(74) *Attorney, Agent, or Firm*—J. Scott Young

(57) ABSTRACT

The present invention provides 2-pyrimidinyl pyrazolopyridine compounds, compositions containing the same, as well as processes for the preparation and their use as pharmaceutical agents.

25 Claims, No Drawings

2-PYRIMIDINYL PYRAZOLOPYRIDINE ERBB KINASE INHIBITORS

This application is a 371 of PCT Application No. PCT/US2006/046316, filed 4 Dec. 2006, which claims priority to U.S. Provisional Patent Application Ser. No. 60/742,351, filed 5 Dec. 2005.

FIELD OF THE INVENTION

The present invention relates to pyrimidine derivatives, compositions and medicaments containing the same, as well as processes for the preparation and use of such compounds, compositions and medicaments. Such pyrimidine derivatives are useful in the treatment of diseases associated with inappropriate ErbB family kinase activity.

BACKGROUND OF THE INVENTION

An important large family of enzymes is the protein kinase enzyme family. Currently, there are about 500 different known protein kinases. Protein kinases serve to catalyze the phosphorylation of an amino acid side chain in various proteins by the transfer of the γ-phosphate of the ATP-Mg2+ complex to said amino acid side chain. These enzymes control the majority of the signaling processes inside cells, thereby governing cell function, growth, differentiation and destruction (apoptosis) through reversible phosphorylation of the hydroxyl groups of serine, threonine and tyrosine residues in proteins. Studies have shown that protein kinases are key regulators of many cell functions, including signal transduction, transcriptional regulation, cell motility, and cell division. Several oncogenes have also been shown to encode protein kinases, suggesting that kinases play a role in oncogenesis. These processes are highly regulated, often by complex intermeshed pathways where each kinase will itself be regulated by one or more kinases. Consequently, aberrant or inappropriate protein kinase activity can contribute to the rise of disease states associated with such aberrant kinase activity. Due to their physiological relevance, variety and ubiquitousness, protein kinases have become one of the most important and widely studied family of enzymes in biochemical and medical research.

One type of protein kinases is protein tyrosine kinases (PTK). Aberrant PTK activity has been implicated in a variety of disorders including psoriasis, rheumatoid arthritis, bronchitis, as well as cancer. Development of effective treatments for such disorders is a constant and ongoing enterprise in the medical field. The ErbB family of PTKs, which includes c-ErbB-2, EGFR, and ErbB-4, is one group of PTKs that has attracted interest as a therapeutic target. Currently, of special interest, is the role of ErbB family PTKs in hyperproliferative disorders, particularly human malignancies. Elevated EGFR activity has, for example, been implicated in non-small cell lung, bladder, and head and neck cancers. Furthermore, increased c-ErbB-2 activity has been implicated in breast, ovarian, gastric and pancreatic cancers. Consequently, inhibition of ErbB family PTKs should provide a treatment for disorders characterized by aberrant ErbB family PTK activity. The biological role of ErbB family PTKs and their implication in various disease states is discussed, for instance in U.S. Pat. No. 5,773,476; International Patent Application WO 99/35146; M. C. Hung et al, Seminars in Oncology, 26: 4, Suppl. 12 (August) 1999, 51-59; Ullrich et al, Cell, 61: 203-212, Apr. 20, 1990; Modjtahedi et al, Int'l. J. of Oncology, 13: 335-342, 1998; J. R. Woodburn, Pharmacol. Ther., 82: 2-3, 241-250, 1999; Normanno, N., Bianco, C., Strizzi, L., Mancino, M., Maiello, M. R., DeLuca, A., Caponigro, F., Salomon, D. S. *Current Drug Targets,* 2005, 6, 243-257; Hynes, N. E., Lane, H. A. *Nature Reviews Cancer,* 2005, 5, 341-345; and Ben-Baruch, N., Yarden, Y. *Progress in Oncology,* 2004, 46-72.

The present inventors have discovered novel pyrimidine compounds, which are inhibitors of ErbB family kinase activity. Such derivatives are believed to be useful in the treatment of disorders associated with inappropriate ErbB family kinase activity.

SUMMARY OF THE INVENTION

In a first aspect of the present invention, there is provided a compound of formula (I):

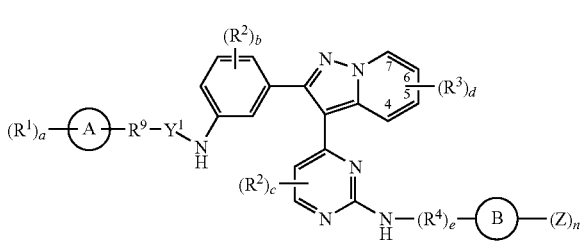

I wherein:
a is 0, 1, 2 or 3;
each $R^1$ is the same or different and is independently selected from halo, alkyl, alkenyl, alkynyl, cycloalkyl, cycloalkenyl, Ay, Het, —$OR^6$, —$R^4OR^6$, —$OC(O)R^6$, —$C(O)R^6$, —$R^4C(O)R^6$, —$C(O)NR^6R^7$, —$R^4C(O)NR^6R^7$, —$CO_2R^6$, —$C(S)R^6$, —$C(S)NR^6R^7$, —$S(O)_fR^6$, —$R^4S(O)_fR^6$, —$S(O)_2NR^6R^7$, —$NR^6R^7$, —$R^4NR^6R^7$, —$N(R^6)$—$R^4R^7$, —$N(R^6)$—$R^4$—$OR^7$, —$N(R^6)$—$R^4$—$S(O)_fR^7$, —$N(R^6)$—$R^4$—CN, —$C(NH)NR^6R^7$, —$N(R^6)C(O)R^6$, —$N(R^6)S(O)_2R^6$, —$N(R^6)$—$C(O)$—$NR^6R^7$, —$N(R^6)$—$S(O)_2$—$NR^6R^7$, —CN, and —$NO_2$;
f is 0, 1 or 2;
Ay is aryl optionally substituted 1, 2 or 3 times with a substituent selected from halo, $C_{1-3}$alkyl, $C_{1-3}$alkoxy, $NH_2$, $N(H)C_{1-3}$alkyl, $N(C_{1-3}$alkyl$)_2$, CN and $NO_2$;
Het is a 5-6 membered heterocycle or heteroaryl having 1 or 2 heteroatoms selected from N, O and S and optionally substituted 1, 2 or 3 times with a substituent selected from halo, $C_{1-3}$alkyl, $C_{1-3}$alkoxy, hydroxyl, oxo, $C(O)(C_{1-3}$alkyl), $SO_3(H)$, $SO_2(C_{1-3}$alkyl), $C_{1-3}$alkyl-$SO_3(H)$, $C_{1-3}$alkyl-$SO_2(C_{1-3}$alkyl), $NH_2$, $N(H)C_{1-3}$alkyl, $N(C_{1-3}$alkyl$)_2$, CN and $NO_2$;
Ring A is selected from aryl, heterocycle and heteroaryl;
$R^9$ is $C_{1-4}$alkylene, $C_{2-4}$alkenylene or $C_{3-4}$cycloalkylene;
$Y^1$ is —C(O)—, —N(H)C(O)—, —C(S)— or —N(H)C(S)—;
b and c are each the same or different and are each independently 0, 1 or 2;
each $R^2$ is the same or different and is independently selected from halo, alkyl, —$OR^6$, —$S(O)_fR^6$, —$NR^6R^7$, —CN and —$NO_2$;
d is 0, 1 or 2;
each $R^3$ is the same or different and is independently selected from halo, alkyl, alkenyl, alkynyl, cycloalkyl, cycloalkenyl, Ay, Het, —$OR^6$, —$R^4OR^6$, —OAy, —$R^4OAy$, —$OC(O)R^6$, —$COR^6$, —$R^4C(O)R^6$, —C(O)Ay, —$C(O)NR^6R^7$, —$R^4C(O)NR^6R^7$, —C(O)N(H)Ay, —C(O)N(H)Het, —CO₂R⁶, —CO₂Ay, —C(S)R⁶, —C(S)NR⁶R⁷, —S(O)_f R⁶, —R⁴S(O)_fR⁶, —S(O)_fAy, —S(O)₂NR⁶R⁷, —NR⁶R⁷, —R⁴NR⁶R⁷, —N(R⁸)Ay, —R⁴N(H)Ay, —N(H)Het, —N(H)R⁴Het, —N(R⁶)—R⁴R⁷, —N(R⁶)—R⁴OR⁷—N (R⁶)R⁴—S(O)_fR⁷, —N(R⁶)—R⁴—CN, —C(NH)NR⁶R⁷, —N(H)C(O)R⁶, —N(H)C(O)Ay, —N(H)SO₂R⁶, —N(R⁶)—C(O)—NR⁶R⁷, —N(R⁶)—S(O)₂—NR⁶R⁷, —CN and —NO₂;

each R⁴ is the same or different and is independently C₁₋₄alkylene or C₃₋₄alkenylene;
e is 0 or 1;
Ring B is selected from aryl and heteroaryl;
g is 0, 1, 2, 3 or 4;
each Z is the same or different and is independently a moiety of formula ii:

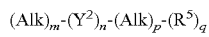

wherein:
  m, n and p are the same or different and are each independently 0 or 1;
  each Alk is the same or different and is independently selected from C₁₋₄alkylene and C₃₋₄alkenylene;
  Y² is —O—, —C(O)—, —S(O)_f—, —N(H)— or —N(Alk)-;
  q is 1 or 2;
  each R⁵ is the same or different and is independently selected from H, halo, alkyl, alkenyl, cycloalkyl, cycloalkenyl, Ay, Het, oxo, —OR⁶, —OAy, —C(O)R⁶, —OC(O)R⁶, —C(O)Ay, —OC(O)Ay, —C(O)NR⁶R⁷, —CO₂R⁶, —CO₂Ay, —S(O)_fR⁶, —S(O)_fAy, —S(O)₂NR⁶R⁷, —C(S)R⁶, —C(S)NR⁶R⁷, —C(S)N(H)Ay, —NR⁶R⁷, —N(R⁸)Ay, —N(R⁸)Het, —N(R⁶)—R⁴R⁷, —N(R⁶)—R⁴—OR⁷, —N(R⁶)—R⁴—S(O)_fR⁷, —N(R⁶)—R⁴—CN, —NHC(O)R⁶, —N(H)S(O)₂R⁶, —C(NH)NR⁶R⁷, —N(R⁶)—C(O)—NR⁶R⁷, —N(R⁶)—S(O)₂—NR⁶R⁷, —N(R⁶)—C(O)—R⁴NR⁶R⁷, —N(R⁶)—S(O)₂—R⁴NR⁶R⁷, —CN and —NO₂;
  each R⁶ and R⁷ are the same or different and are each independently selected from H, alkyl, alkenyl, alkynyl, C₃₋₆cycloalkyl and C₃₋₆cycloalkenyl; and
  each R⁸ is the same or different and is H or alkyl,
or a pharmaceutically acceptable salt or solvate thereof.

In a second aspect of the present invention, there is provided a pharmaceutical composition comprising a compound of formula (I) or a pharmaceutically acceptable salt or solvate thereof. In one embodiment, the pharmaceutical composition further comprises one or more of pharmaceutically acceptable carriers, diluents and excipients.

In a third aspect of the present invention, there is provided a method of treating a condition in a mammal, said condition being mediated by inappropriate activity of at least one ErbB family kinase, comprising administering to said mammal a therapeutically effective amount of a compound of formula (I) or a pharmaceutically acceptable salt or solvate thereof.

In a fourth aspect of the present invention, there is provided a method of treating a condition in a mammal, said condition being mediated by inappropriate activity of at least two ErbB family kinases, comprising administering to said mammal a therapeutically effective amount of a compound of formula (I) or a pharmaceutically acceptable salt or solvate thereof.

In a fifth aspect, the present invention provides a method of treating a susceptible neoplasm in a mammal comprising administering to said mammal a therapeutically effective amount of a compound of formula (I) or a pharmaceutically acceptable salt or solvate thereof.

In a sixth aspect of the present invention, there is provided a process for preparing a compound of formula (I). The process comprises the steps of:

a) reacting a compound of formula (VII):

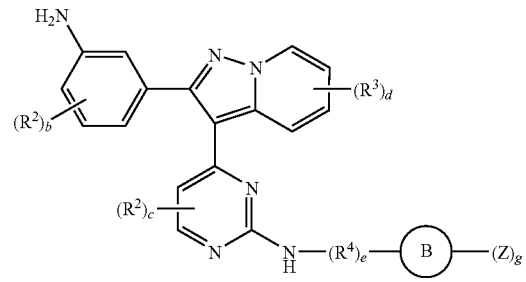

with a compound of formula (VIII) or a compound of formula (IX):

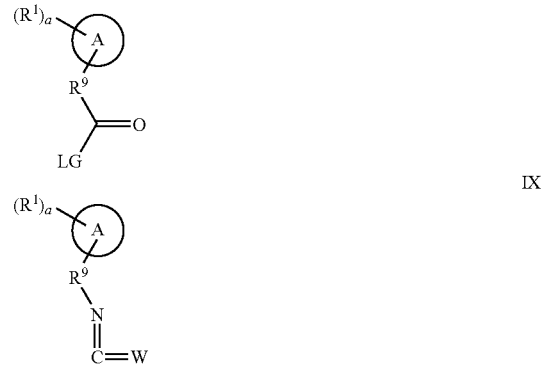

wherein LG is a leaving group and W is O or S;

to prepare a compound of formula (I);

b) optionally converting the compound of formula (I) to a pharmaceutically acceptable salt or solvate thereof; and c) optionally converting the compound of formula (I) or a pharmaceutically acceptable salt or solvate thereof to a different compound of formula (I) or a pharmaceutically acceptable salt or solvate thereof.

In a seventh aspect of the present invention, there is provided a compound of formula (I), or a pharmaceutically acceptable salt or solvate thereof for use in therapy.

In an eighth aspect of the present invention, there is provided the use of a compound of formula (I), or a pharmaceutically acceptable salt or solvate thereof in the preparation of a medicament for use in the treatment of a condition mediated by inappropriate activity of at least one ErbB family kinase.

In a ninth aspect of the present invention, there is provided the use of a compound of formula (I), or a pharmaceutically acceptable salt or solvate thereof in the preparation of a medicament for use in the treatment of a condition mediated by inappropriate activity of at least two ErbB family kinases.

In another aspect of the present invention, there is provided the use of a compound of formula (I) or a pharmaceutically acceptable salt or solvate thereof in the preparation of a medicament for use in the treatment of a susceptible neoplasm.

DETAILED DESCRIPTION OF THE INVENTION

As used herein the term "ErbB family kinase" refers to those ErbB kinases including EGFR (also known as ErbB-1), ErbB-2, and ErbB-4.

As used herein, "a compound of the invention" or "a compound of formula (I)" means a compound of formula (I) or a pharmaceutically acceptable salt or solvate thereof. Similarly, with respect to isolatable intermediates such as for example, compounds of formula (IV), (V), (VI), (VII), (XVI), (XVII), (XVIII) and (XIX) the phrase "a compound of formula (number)" means a compound having that formula and pharmaceutically acceptable salts and solvates thereof.

As used herein, the terms "alkyl" (and "alkylene") refer to straight or branched hydrocarbon chains containing from 1 to 8 carbon atoms, unless a different number of atoms is specified. Examples of "alkyl" as used herein include, but are not limited to, methyl, ethyl, n-propyl, n-butyl, n-pentyl, isobutyl, isopropyl, and tert-butyl. Examples of "alkylene" as used herein include, but are not limited to, methylene, ethylene, propylene, butylene, and isobutylene. "Alkyl" also includes substituted alkyl. The alkyl (and alkylene) groups may be optionally substituted one or more times with a halogen or hydroxyl. Thus, the term "alkyl" includes for example, trifluoromethyl and trifluoroethyl, among other halogenated alkyls, and hydroxymethyl and other hydroxylated alkyls.

As used herein, the term "alkenyl" (and "alkylene") refers to straight or branched hydrocarbon chains containing from 2 to 8 carbon atoms, unless a different number of atoms is specified, and at least one and up to three carbon-carbon double bonds. Examples of "alkenyl" as used herein include, but are hot limited to ethenyl and propenyl. Examples of "alkenylene" as used herein include, but are not limited to, ethenylene, propenylene and butenylene. "Alkenyl" (and "alkenylene") also includes substituted alkenyl. The alkenyl groups may optionally be substituted one or more times with a halogen or hydroxyl.

As used herein, the term "alkynyl" refers to straight or branched hydrocarbon chains containing from 2 to 8 carbon atoms, unless a different number of atoms is specified, and at least one and up to three carbon-carbon triple bonds. Examples of "alkynyl" as used herein include, but are not limited to ethynyl and propynyl. "Alkynyl" also includes substituted alkynyl. The alkynyl groups may optionally be substituted one or more times with a halogen and hydroxyl.

As used herein, the term "cycloalkyl" refers to a saturated monocyclic carbocyclic ring having from 3 to 8 carbon atoms, unless a different number of atoms is specified. "Cycloalkyl" includes by way of example cyclopropyl, cyclobutyl, cyclopentyl, cyclohexyl, cycloheptyl and cyclooctyl. "Cycloalkyl" also includes substituted cycloalkyl. The cycloalkyl may optionally be substituted on any available carbon with one or more substituents selected from the group consisting of halo, $C_{1-3}$alkyl (including haloalkyl, e.g., perfluoroalkyl), —H and oxo. Preferred cycloalkyl groups include $C_{3-6}$cycloalkyl and substituted $C_{3-6}$cycloalkyl.

As used herein, the term "cycloalkenyl" refers to a non-aromatic monocyclic carbocyclic ring having from 3 to 8 carbon atoms, unless a different number of atoms is specified, and up to 3 carbon-carbon double bonds. "Cycloalkenyl" includes by way of example cyclobutenyl, cyclopentenyl and cyclohexenyl. "Cycloalkenyl" also includes substituted cycloalkenyl. The cycloalkenyl may optionally be substituted on any available carbon with one or more substituents selected from the group consisting of halo, $C_{1-3}$alkyl (including haloalkyl, e.g., perfluoroalkyl), —OH and oxo.

The term "halo" or "halogen" refers to fluoro, chloro, bromo and iodo.

The term "oxo" as used herein refers to the group =O attached directly to a carbon atom of a hydrocarbon ring (i.e., cycloalkenyl, aryl, heterocycle or heteroaryl ring) as well as —N-oxides, sulfones and sulfoxides wherein the N or S are atoms of a heterocyclic or heteroaryl ring.

As used herein, the term "alkoxy" refers to the group —O-alkyl, where alkyl is as defined above. Examples of "alkoxy" as used herein include, but are not limited to, methoxy, ethoxy, n-propoxy, isopropoxy, n-butoxy, and t-butoxy. "Alkoxy" also includes substituted alkoxy. The alkoxy groups may be optionally substituted one or more times with a halogen.

The term "aryl" refers to aromatic monocyclic carbocyclic groups and fused bicyclic carbocyclic groups having from 6 to 10 carbon atoms, unless a different number of atoms is specified, and having at least one aromatic ring. Examples of particular aryl groups include but are not limited to phenyl, indenyl and naphthyl. One particular aryl group according to the invention is phenyl.

The terms "heterocycle" and "heterocyclic" refer to monocyclic saturated or unsaturated non-aromatic groups and fused bicyclic saturated or unsaturated non-aromatic groups, having from 5 to 10 members (unless otherwise specified) including 1, 2, 3 or 4 heteroatoms selected from N, O and S, unless a different number of heteroatoms is specified. Examples of particular heterocyclic groups include but are not limited to tetrahydrofuran, dihydropyran, tetrahydropyran, pyran, thietane, 1,4-dioxane, 1,3-dioxane, 1,3-dioxalane, piperidine, piperazine, pyrrolidine, morpholine, thiomorpholine, thiazolidine, oxazolidine, tetrahydrothiopyran, tetrahydrothiophene and the like.

The term "heteroaryl" refers to aromatic monocyclic groups and fused bicyclic groups wherein at least one ring is aromatic, having from 5 to 10 members (unless otherwise specified) including 1, 2, 3, or 4 heteroatoms selected from N, O and S, unless a different number of heteroatoms is specified. "Heteroaryl" also includes heteroaryl groups substituted by oxo, e.g., N-oxides, sulfur oxides and dioxides. Examples of particular heteroaryl groups include but are not limited to furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, tetrahydropyrimidine, triazine, quinoline, tetrahydroquinoline isoquinoline, tetrahydroisoquinoline, benzofuran, benzothiophene, indole, indazole, benzodioxane, benzodioxin, benzodithiane, benzopiperidine and benzopiperzine.

The term "members" (and variants thereof e.g., "membered") in the context of heterocyclic and heteroaryl groups refers to the total atoms, carbon and heteroatoms N, O and/or S, which form the ring. Thus, an example of a 6-membered heterocyclic ring is piperidine and an example of a 6-membered heteroaryl ring is pyridine.

The present invention provides compounds of formula (I):

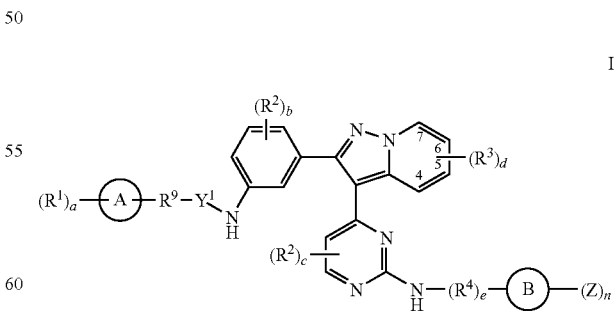

I wherein:
a is 0, 1, 2 or 3;
each $R^1$ is the same or different and is independently selected from halo, alkyl, alkenyl, alkynyl, cycloalkyl, cycloalkenyl, Ay, Het, —OR⁶, —R⁴OR⁶, —OC(O)R⁶—C(O)R⁶, —R⁴C(O)R⁶, —C(O)NR⁶R⁷, —R⁴C(O)NR⁶R⁷, —CO₂R⁶, —C(S)R⁶, —C(S)NR⁶R⁷, —S(O)ᵣR⁶, —R⁴S(O)ᵣR⁶, —S(O)₂NR⁶R⁷, —NR⁶R⁷, —R⁴NR⁶R⁷, —N(R⁶)—R⁴R⁷, —N(R⁶)—R⁴—OR⁷, —N(R⁶)—R⁴—S(O)ᵣR⁷, —N(R⁶)—R⁴—CN, —C(NH)NR⁶R⁷, —N(R⁶)C(O)R⁶, —N(R⁶)S(O)₂R⁶, —N(R⁶)—C(O)—NR⁶R⁷, —N(R⁶)—S(O)₂—NR⁶R⁷, —CN, and —NO₂;

f is 0, 1 or 2;

Ay is aryl optionally substituted 1, 2 or 3 times with a substituent selected from halo, $C_{1-3}$alkyl, $C_{1-3}$alkoxy, $NH_2$, $N(H)C_{1-3}$alkyl, $N(C_{1-3}$alkyl$)_2$, CN and $NO_2$;

Het is a 5-6 membered heterocycle or heteroaryl having 1 or 2 heteroatoms selected from N, O and S and optionally substituted 1, 2 or 3 times with a substituent selected from halo, $C_{1-3}$alkyl, $C_{1-3}$alkoxy, hydroxyl, oxo, $C(O)(C_{1-3}$alkyl), $SO_3(H)$, $SO_2(C_{1-3}$alkyl), $C_{1-3}$alkyl-$SO_3(H)$, $C_{1-3}$alkyl-$SO_2(C_{1-3}$alkyl), $NH_2$, $N(H)C_{1-3}$alkyl, $N(C_{1-3}$alkyl$)_2$, CN and $NO_2$;

Ring A is selected from aryl, heterocycle and heteroaryl;

$R^9$ is $C_{1-4}$alkylene, $C_{2-4}$alkenylene or $C_{3-4}$cycloalkylene;

$Y^1$ is —C(O)—, —N(H)C(O)—, —C(S)— or —N(H)C(S)—;

b and c are each the same or different and are each independently 0, 1 or 2;

each $R^2$ is the same or different and is independently selected from halo, alkyl, —OR⁶, —S(O)ᵣR⁶, —NR⁶R⁷, —CN and —NO₂;

d is 0, 1 or 2;

each $R^3$ is the same or different and is independently selected from halo, alkyl, alkenyl, alkynyl, cycloalkyl, cycloalkenyl, Ay, Het, —OR⁶, —R⁴OR⁶, —OAy, —R⁴OAy, —OC(O)R⁶, —COR⁶, —R⁴C(O)R⁶, —C(O)Ay, —C(O)NR⁶R⁷, —R⁴C(O)NR⁶R⁷, —C(O)N(H)Ay, —C(O)N(H)Het, —CO₂R⁶, —CO₂Ay, —C(S)R⁶, —C(S)NR⁶R⁷, —S(O)ᵣR⁶, —R⁴S(O)ᵣR⁶, —S(O)ᵣAy, —S(O)₂NR⁶R⁷, —NR⁶R⁷, —R⁴NR⁶R⁷, —N(R⁸)Ay, —R⁴N(H)Ay, —N(H)Het, —N(H)R⁴Het, —N(R⁶)—R⁴R⁷, —N(R⁶)—R⁴—OR⁷, —N(R⁶)—R⁴—S(O)ᵣR⁷, —N(R⁶)—R⁴—CN, —C(NH)NR⁶R⁷, —N(H)C(O)R⁶, —N(H)C(O)Ay, —N(H)SO₂R⁶, —N(R⁶)—C(O)—NR⁶R⁷, —N(R⁶)—S(O)₂—NR⁶R⁷, —CN and —NO₂;

each $R^4$ is the same or different and is independently $C_{1-4}$alkylene or $C_{3-4}$alkenylene;

e is 0 or 1;

Ring B is selected from aryl and heteroaryl;

g is 0, 1, 2, 3 or 4;

each Z is the same or different and is independently a moiety of formula ii:

$$(Alk)_m\text{-}(Y^2)_n\text{-}(Alk)_p\text{-}(R^5)_q$$

wherein:
m, n and p are the same or different and are each independently 0 or 1;

each Alk is the same or different and is independently selected from $C_{1-4}$alkylene and $C_{3-4}$alkenylene;

$Y^2$ is —O—, —C(O)—, —S(O)ᵣ—, —N(H)— or —N(Alk)-;

q is 1 or 2;

each $R^5$ is the same or different and is independently selected from H, halo, alkyl, alkenyl, cycloalkyl, cycloalkenyl, Ay, Het, oxo, —OR⁶, —OAy, —C(O)R⁶, —OC(O)R⁶, —C(O)Ay, —OC(O)Ay, —C(O)NR⁶R⁷, —CO₂R⁶, —CO₂Ay, —S(O)ᵣR⁶, —S(O)ᵣAy, —S(O)₂NR⁶R⁷, —C(S)R⁶, —C(S)NR⁶R⁷, —C(S)N(H)Ay, —NR⁶R⁷, —N(R⁸)Ay, —N(R⁸)Het, —N(R⁶)—R⁴R⁷, —N(R⁶)—R⁴—OR⁷, —N(R⁶)—R⁴—S(O)ᵣR⁷, —N(R⁶)—R⁴—CN, —NHC(O)R⁶, —N(H)S(O)₂R⁶, —C(NH)NR⁶R⁷, —N(R⁶)—C(O)—NR⁶R⁷, —N(R⁶)—S(O)₂—NR⁶R⁷, —N(R⁶)—C(O)—R⁴NR⁶R⁷, —N(R⁶)—S(O)₂—R⁴NR⁶R⁷, —CN and —NO₂;

each $R^6$ and $R^7$ are the same or different and are each independently selected from H, alkyl, alkenyl, alkynyl, $C_{3-6}$cycloalkyl and $C_{3-6}$cycloalkenyl; and each $R^8$ is the same or different and is H or alkyl, or a pharmaceutically acceptable salt or solvate thereof.

In one embodiment, the compounds of formula (I) are defined wherein a is 1 or 2. In one particular embodiment, a is 0. In one particular embodiment, a is 2.

Each $R^1$ may be bound to Ring A through any suitable carbon or heteroatom (to provide, for example, N-methyl or N-oxides). In one embodiment, the compounds of formula (I) are defined wherein each $R^1$ is the same or different and is independently selected from halo, alkyl, alkenyl, alkynyl, cycloalkyl, cycloalkenyl, Ay, Het, —OR⁶, —R⁴OR⁶—OC(O)R⁶, —C(O)R⁶, —R⁴C(O)R⁶, —C(O)NR⁶R⁷, —CO₂R⁶, C(S)R⁶, C(S)NR⁶R⁷, —S(O)ᵣR⁶, —R⁴S(O)ᵣR⁶, —S(O)₂NR⁶R⁷, —NR⁶R⁷, —R⁴NR⁶R⁷, —N(R⁶)C(O)R⁶, —N(R⁶)S(O)₂R⁶, —N(R⁶)—C(O)—NR⁶R⁷, —N(R⁶)—S(O)₂—NR⁶R⁷, —CN and —NO₂, or any subset thereof. In one particular embodiment, the compounds of formula (I) are defined wherein each $R^1$ is the same or different and is independently selected from halo, alkyl, alkenyl, alkynyl, cycloalkyl, cycloalkenyl, —OR⁶, —R⁴OR⁶, —OC(O)R⁶, —C(O)R⁶, —R⁴C(O)R⁶, —C(O)NR⁶R⁷, —S(O)ᵣR⁶, —R⁴S(O)ᵣR⁶, —NR⁶R⁷, —R⁴NR⁶R⁷, —N(R⁶)C(O)R⁶, —N(R⁶)S(O)₂R⁶, —CN and —NO₂ or any subset thereof. In one particular embodiment, the compounds of formula (I) are defined wherein each $R^1$ is the same or different and is independently selected from halo, alkyl, alkenyl, alkynyl, —OR⁶, —C(O)NR⁶R⁷, —S(O)ᵣR⁶, —S(O)₂NR⁶R⁷, —NR⁶R⁷, —N(H)C(O)R⁶, —N(H)S(O)₂R⁶, —CN and —NO₂, or any subset thereof. In one preferred embodiment, each $R^1$ is the same or different and is independently selected from F, Cl, alkyl and —OR⁶ or any subset thereof.

Specific examples of groups defining $R^1$ include but are not limited to F, Cl, Br, $CH_3$, $CF_3$, $CH_2CH_3$, $CH(CH_3)_2$, $OCH_3$, $OCF_3$, $OCH_2CH_3$, $NH_2$, $N(H)$alkyl (e.g., $N(H)CH_3$), $N(H)C(O)$alkyl (e.g., $N(H)C(O)CH_3$), CN and $NO_2$. In one particular embodiment, each $R^1$ is the same or different and is independently selected from F, Cl, $CH_3$, $CF_3$, $OCH_3$, and $OCF_3$.

(A)

in formula (I) is referred to herein as "Ring A." Ring A is selected from aryl, heterocycle and heteroaryl.

Ring A may be bonded to $R^4$ through any suitable carbon or heteroatom. In one embodiment, Ring A is aryl. In another embodiment, Ring A is heterocycle or heteroaryl. In one embodiment, the compounds of formula (I) are defined wherein Ring A is aryl or heteroaryl. In one particular embodiment, Ring A is phenyl. In another particular embodiment, Ring A is a 5-6 membered heteroaryl having 1 or 2 heteroatoms selected from N, O and S.

Specific examples of groups defining Ring A include but are not limited to furan, tetrahydrofuran, thiophene, pyrrole, pyrroline, pyrrolidine, oxazole, isoxazole, thiazole, isothiazole, imidazole, imidazolidine, pyrazole, pyrazoline, pyrazolidine, triazole, phenyl, pyran, tetrahydropyran, pyridine, piperidine, isoxane, morpholine, thiomorpholine, pyridazine, pyrimidine, pyrazine, piperizine, naphthyl, dihydro-naphthyline, indene, dihydro-indene, benzofuran, benzothiophene, indole, isoindole, indoline, indazole, benzimidazole, quinoline, tetrahydroquinoline, isoquinoline, tetrahydroisoquinoline, quinazoline, quinoxaline, benzopiperidine, benzopiperazine, benzotriazole, benzopyran, chroman, isochroman, benzodioxane, and benzodioxolane, or any subset thereof. In one embodiment, Ring A is selected from phenyl, furan, pyrrole, pyrazole, thiophene, isoxazole, pyridine, benzofuran and benzodioxane, or any subset thereof. In one particular embodiment Ring A is phenyl.

In one embodiment, $R^9$ is $C_{1-4}$alkylene. In one embodiment, $R^9$ is $C_{1-3}$alkylene. In one particular embodiment, $R^9$ is selected from methylene, ethylene and isopropylene. In one particular embodiment, $R^9$ is methylene.

In one embodiment, $Y^1$ is —C(O)— or N(H)C(O). In one particular embodiment, $Y^1$ is —C(O)—.

In one embodiment, the compounds of formula (I) are defined wherein b is 0 or 1. In one preferred embodiment, b is 0.

In one embodiment, the compounds of formula (I) are defined wherein c is 0 or 1. In one preferred embodiment, c is 0.

In certain embodiments wherein b and/or c is 1 or 2, each $R^2$ is the same or different and is independently selected from halo, alkyl, —$OR^6$, —$NR^6R^7$ and —CN. In one particular embodiment, each $R^2$ is the same or different and is independently selected from halo, alkyl, —$OR^6$ and —CN. In one preferred embodiment, when b is 1 or 2, each $R^2$ is the same or different and is independently selected from halo and alkyl; more preferably halo, particularly F or Cl.

In one embodiment, the compounds of formula (I) are defined wherein d is 0 or 1. In one particular embodiment, d is 1. In one preferred embodiment, d is 0.

In particular embodiments of the present invention wherein d is 1 or 2, each $R^3$ is the same or different and is independently selected from halo, alkyl, alkenyl, alkynyl, cycloalkyl, Ay, Het, —$OR^6$, —$R^4OR^6$, —$OC(O)R^6$, —$COR^6$, —$R^4C(O)R^6$, —$C(O)NR^6R^7$, —$S(O)_fR^6$, —$R^4S(O)_fR^6$, —$S(O)_2NR^6R^7$, —$NR^6R^7$, —$R^4NR^6R^7$, —$N(R^8)Ay$, —$R^4N(H)Ay$, —$N(H)Het$, —$N(R^6)$—$R^4$—$OR^7$, —$N(R^6)$—$R^4$—$S(O)_fR^7$, —$N(R^6)$—$R^4$—CN, —$N(H)C(O)R^6$, —$N(H)SO_2R^6$, —$N(R^6)$—$C(O)$—$NR^6R^7$, —$N(R^6)$—$S(O)_2$—$NR^6R^7$, —CN and —$NO_2$. In one particular embodiment the compounds of formula (I) are defined wherein each $R^3$ is the same or different and is independently selected from halo, alkyl, cycloalkyl, Ay, Het, —$OR^6$, —$COR^6$, —$C(O)NR^6R^7$, —$S(O)_fR^6$, —$S(O)_2NR^6R^7$, —$NR^6R^7$, —$R^4NR^6R^7$, —$N(R^8)Ay$, —$N(H)Het$, —$N(H)C(O)R^6$, —$N(H)SO_2R^6$, —CN and —$NO_2$. In one embodiment wherein d is 1 or 2, the compounds of formula (I) are defined wherein each $R^3$ is the same or different and is independently selected from halo, alkyl, cycloalkyl, —$OR^6$, —$COR^6$, —$C(O)NR^6R^7$, —$S(O)_fR^6$, —$S(O)_2NR^6R^7$, —$NR^6R^7$ and —CN.

In one embodiment, $R^4$ in the definition of other variables is $C_{1-4}$alkylene. In one particular embodiment, $R^4$ is $C_{1-3}$alkylene. In one particular embodiment, $R^4$ is methylene.

In one embodiment, the compounds of formula (I) are defined wherein e is 0. In one embodiment wherein e is 1, the group $(R^4)_e$ is $C_{1-4}$alkylene. In one particular embodiment, the group $(R^4)_e$ is $C_{1-3}$alkylene. In one embodiment, the group $(R^4)_e$ is methylene. In another embodiment, the group $(R^4)_e$ is —$CH(CH_3)$—. In another embodiment, the group $(R^4)_e$ is propylene or isopropylene.

in formula (I) is referred to herein as "Ring B." Ring B may be bonded to $R^4$ or —N(H)— (when e is 0) through any suitable carbon or heteroatom. In one preferred embodiment, Ring B is aryl. In another embodiment, Ring B is heteroaryl. In one particular embodiment, Ring B is phenyl. In another particular embodiment, Ring B is a 5-10 membered heteroaryl group having 1, 2 or 3 heteroatoms selected from N, O and S.

Specific groups defining Ring B include but are not limited to furan, tetrahydrofuran, thiophene, pyrrole, pyrroline, pyrrolidine, oxazole, isoxazole, thiazole, isothiazole, imidazole, imidazolidine, pyrazole, pyrazoline, pyrazolidine, triazole, phenyl, pyran, tetrahydropyrane, pyridine, piperidine, isoxane, morpholine, thiomorpholine, pyridazine, pyrimidine, pyrazine, piperazine, naphthyl, dihydro-naphthyline, indene, dihydro-indene, benzofuran, benzothiophene, indole, isoindole, indoline, indazole, benzimidazole, quinoline, isoquinoline, tetrahydroisoquinoline, quinazoline, quinoxaline, benzopiperidine, benzopiperazine, benzotriazole, benzopyran, chroman, isochroman, benzodioxane, and benzodioxolane, or any subset thereof. In one embodiment, Ring B is selected from phenyl, furan, pyrrole, pyrazole, thiophene, isoxazole, pyridine, benzofuran, benzodioxane and tetrahydroisoquinoline, or any subset thereof.

The definition of the variable g, indicating the number of possible substituents Z on Ring B should be understood to be consistent with and dependent upon the size of ring B. The substituents Z may be bound to Ring B through any available carbon or heteroatom.

Similarly, the moiety Z should be understood to be defined in view of the definition of Ring B so as to avoid embodiments which the organic chemist of ordinary skill would consider to be obviously inoperative. For example, in those embodiments wherein Ring B is a heterocycle or heteroaryl, g is not 0, and Z is bound to a heteroatom of Ring B; then Z is defined as a moiety bound to Ring B through either a carbon or a heteroatom suitable for binding to the heteroatom of Ring B. Thus, when Ring B is a N-containing heteroaryl and Z is bound to a N of Ring B, then Z is defined as a moiety capable of binding to the N of Ring B; accordingly in such embodiment, Z may not for example, be halo. Examples of Z moieties capable of binding to a N of Ring B include but are not limited to H, alkyl (e.g., N-methyl) and oxo (e.g., N-oxide). Other suitable definitions of Z for binding to a heteroatom of Ring B will be apparent to those skilled in the art.

In one embodiment, the compounds of formula (I) are defined wherein g is 0, 1, 2 or 3. In one particular embodiment, g is 0, 1 or 2. In one preferred embodiment g is 1. In another preferred embodiment, g is 2.

In the embodiments wherein g is 1, 2, 3 or 4, each Z is the same or different and is independently a moiety of formula ii:

$$(Alk)_m\text{-}(Y^2)_n\text{-}(Alk)_p\text{-}(R^5)_q \qquad (ii)$$

wherein:

m, n and p are the same or different and are each independently 0 or 1 (meaning that the variables Alk, $Y^2$ and Alk, respectively in formula (II) above are either present or absent);

each Alk is the same or different and is independently selected from $C_{1-4}$alkylene and $C_{3-4}$alkenylene;

$Y^2$ is —O—, —C(O)—, —S(O)$_f$—, —N(H)— or —N(Alk)-;

q is 1 or 2; and each $R^5$ is the same or different and is independently selected from H, halo, alkyl, alkenyl, cycloalkyl, cycloalkenyl, Ay, Het, oxo, —OR$^6$, —OAy, —C(O)R$^6$, —OC(O)R$^6$, —C(O)Ay, —OC(O)Ay, —C(O)NR$^6$R$^7$, —CO$_2$R$^6$, —CO$_2$Ay, —S(O)$_f$R$^6$, —S(O)$_f$Ay, —S(O)$_2$NR$^6$R$^7$, —C(S)R$^6$, —C(S)NR$^6$R$^7$, —C(S)N(H)Ay, —NR$^6$R$^7$, —N(R$^8$)Ay, —N(R$^8$)Het, —N(R$^6$)—R$^4$R$^7$, —N(R$^6$)—R$^4$—OR$^7$, —N(R$^6$)—R$^4$—S(O)$_f$R$^7$, —N(R$^6$)—R$^4$—CN, —NHC(O)R$^6$, —N(H)S(O)$_2$R$^6$, —C(NH)NR$^6$R$^7$, —N(R$^6$)—C(O)—NR$^6$R$^7$, —N(R$^6$)—S(O)$_2$—NR$^6$R$^7$, —N(R$^6$)—C(O)—R$^4$NR$^6$R$^7$, —N(R$^6$)—S(O)$_2$—R$^4$NR$^6$R$^7$, —CN and —NO$_2$.

In one embodiment, the compounds of formula (I) are defined wherein g is 1, 2, 3 or 4 and m is 0. In another embodiment, wherein m is 1, the group (Alk)$_m$ is preferably C$_{1-3}$alkylene.

In one embodiment, the compounds of formula (I) are defined wherein g is 1, 2, 3 or 4 and n is 0. In one embodiment, wherein n is 1, $Y^2$ is —O, —C(O)— or —N(H)—.

In one particular embodiment, g is 1, 2, 3 or 4, n is 1 and $Y^2$ is —O— or —C(O)—. In one particular embodiment, $Y^2$ is —C(O)—. In another particular embodiment, $Y^2$ is —O—.

In one embodiment, the compounds of formula (I) are defined wherein g is 1, 2, 3 or 4 and p is 0. In another embodiment, wherein p is 1, the group (Alk)$_p$ is preferably C$_{1-3}$alkylene.

In one embodiment, the compounds of formula (I) are defined wherein g is 1, 2, 3 or 4 and q is 1.

In one particular embodiment wherein g is 1, 2, 3 or 4 and q is 1, each $R^5$ is the same or different and is independently selected from H, halo, alkyl, alkenyl, cycloalkyl, Ay, Het, oxo, —OR$^6$, —OAy, —C(O)R$^6$, —OC(O)R$^6$, —C(O)Ay, —C(O)NR$^6$R$^7$, —CO$_2$R$^6$, —S(O)$_f$R$^6$, —S(O)$_2$NR$^6$R$^7$, —C(S)NR$^6$R$^7$, —NR$^6$R$^7$, —N(R$^8$)Ay, —N(R$^8$)Het, —N(R$^6$)—R$^4$R$^7$, —N(R$^6$)—R$^4$—OR$^7$, —N(R$^6$)—R$^4$—S(O)$_f$R$^7$, —N(R$^6$)—R$^4$—CN, —NHC(O)R$^6$, —N(H)S(O)$_2$R$^6$, —C(NH)NR$^6$R$^7$, —N(R$^6$)—C(O)—NR$^6$R$^7$, —N(R$^6$)—S(O)$_2$—NR$^6$R$^7$, —N(R$^6$)—C(O)—R$^4$NR$^6$R$^7$, —CN and —NO$_2$. In one particular embodiment, each $R^5$ is the same or different and is independently selected from H, halo, alkyl, cycloalkyl, Ay, Het, —OR$^6$, —C(O)R$^6$, —OC(O)R$^6$, —C(O)NR$^6$R$^7$, —S(O)$_f$R$^6$, —S(O)$_2$NR$^6$R$^7$, —C(S)NR$^6$R$^7$, —NR$^6$R$^7$, —N(R$^8$)Ay, —N(R$^8$)Het, —N(R$^6$)—R$^4$—OR$^7$, —N(R$^6$)—R$^4$—S(O)$_f$R$^7$, —N(R$^6$)—R$^4$—CN, —NHC(O)R$^6$, —N(H)S(O)$_2$R$^6$, and —CN. In one preferred embodiment, each $R^5$ is the same or different and is independently selected from H, halo, alkyl, cycloalkyl, Ay, Het, —OR$^6$, —C(O)R$^6$, —C(O)NR$^6$R$^7$, —S(O)$_f$R$^6$, —S(O)$_2$NR$^6$R$^7$, —NR$^6$R$^7$, —N(R$^6$)—R$^4$—CN, and —CN.

Each of the individual variables n, $Y^2$, p, q and $R^5$ should be understood to be defined in view of the definition of the other variables comprising moiety Z so as to avoid embodiments which the skilled organic chemist would consider to be obviously inoperative. For example, in those embodiments wherein n is 1 and p is 0 such that Z is the moiety (ii-a)

$$(Alk)_m\text{-}(Y^2)\text{—}(R^5)_q \quad \text{(ii-a)}$$

(wherein all variable are as defined above) the variable $R^5$ should be defined in view of $Y^2$ such that embodiments which the organic chemist of ordinary skill would consider to be obviously inoperative, are avoided. For example, if $Y^2$ is O and p is 0, then $R^5$ is not halo or a group that would result in a peroxide, etc. Accordingly, in one embodiment wherein n is 1 and p is 0; then q is 1 and $R^5$ is a group bound through either carbon or a heteroatom suitable for binding to $Y^2$.

In one particular embodiment, if Z is defined as a moiety wherein:
1) n is 1, $Y^2$ is —O— and p is 0; then q is 1 and $R^5$ is not halo, oxo, nitrile, nitro or a group bound through O or S;
2) n is 1 $Y^2$ is —C(O)— and p is 0; then q is 1 and $R^5$ is not halo, oxo, nitrile, nitro or a group bound through —CO$_2$— or —C(S)—;
3) n is 1 $Y^2$ is —N(H)— or —N(Alk)- and p is 0; then q is 1 and $R^5$ is not halo, oxo, nitrile, or nitro; or
4) n is 1 $Y^2$ is —S(O)$_f$— and p is 0; then q is 1 and $R^5$ is not halo, oxo, nitrile, nitro or a group bound through S.

In one particular embodiment, if Z is defined as a moiety wherein:
1) n is 1, $Y^2$ is —O— and p is 0; then q is 1 and $R^5$ is not: halo, Het bound through a heteroatom, oxo, —OR$^6$, —OAy, —OC(O)R$^6$, —OC(O)Ay, —NR$^6$R$^7$, —N(R$^8$)Ay, —N(R$^8$)Het, —N(R$^6$)—R$^4$R$^7$, —N(R$^6$)—R$^4$—OR$^7$, —N(R$^6$)—R$^4$—S(O)$_f$R$^7$, —N(R$^6$)—R$^4$—CN, —NHC(O)R$^6$, —N(H)S(O)$_2$R$^6$, —C(NH)NR$^6$R$^7$, —N(R$^6$)—C(O)—NR$^6$R$^7$, —N(R$^6$)—S(O)$_2$—NR$^6$R$^7$, —N(R$^6$)—C(O)—R$^4$NR$^6$R$^7$, —N(R$^6$)—S(O)$_2$—R$^4$NR$^6$R$^7$, —CN or —NO$_2$;
2) n is 1 $Y^2$ is —C(O)— and p is 0; then q is 1 and $R^5$ is not: halo, oxo, —C(O)NR$^6$R$^7$, —CO$_2$R$^6$, —CO$_2$Ay, —S(O)$_f$R$^6$, —S(O)$_f$Ay, —S(O)$_2$NR$^6$R$^7$, —C(S)R$^6$, —C(S)NR$^6$R$^7$, —C(S)N(H)Ay, —CN or —NO$_2$;
3) n is 1 $Y^2$ is —N(H)— or —N(Alk)- and p is 0; then q is 1 and $R^5$ is not:
halo, —OC(O)R$^6$, —OC(O)Ay, —N(R$^6$)—C(O)—NR$^6$R$^7$, —N(R$^6$)—S(O)$_2$—NR$^6$R$^7$, —N(R$^6$)—C(O)—R$^4$NR$^6$R$^7$, —N(R$^6$)—S(O)$_2$—R$^4$NR$^6$R$^7$, —CN or —NO$_2$; or
4) n is 1 $Y^2$ is —S(O)$_f$— and p is 0; then q is 1 and $R^5$ is not: halo, oxo, —OR$^6$, —OAy, —OC(O)R$^6$, —OC(O)Ay, —S(O)$_f$R$^6$, —S(O)$_f$Ay, —S(O)$_2$NR$^6$R$^7$, —C(S)R$^6$, —C(S)NR$^6$R$^7$, —C(S)N(H)Ay, —CN or —NO$_2$.

Specific examples of groups defining Z include but are not limited to H (e.g., g is 0)
halo (e.g., F or Cl)
alkyl (e.g., CH$_3$, CF$_3$)
Het (e.g., 5-6 membered heterocycle or heteroaryl having 1 or 2 heteroatoms selected from N, O and S and substituted variants thereof)
OR$^6$ (e.g., OH, OCH$_3$)
CN
C(O)R$^6$ (e.g., C(O)CH$_3$ and C(O)CF$_3$)
C(O)Ay (e.g., C(O)phenyl and substituted variants thereof)
C(O)NR$^6$R$^7$ (e.g., C(O)NH$_2$)
C(O)Het (e.g., C(O)morpholine and substituted variants thereof)
C(O)-Alk-Ay (e.g., C(O)—CH$_2$-phenyl and substituted variants thereof)
SO$_2$R$^6$ (e.g., SO$_2$CH$_3$, SO$_2$CH$_2$CH$_3$, SO$_2$CH$_2$CH$_2$OH)
SO$_2$NR$^6$R$^7$ (e.g., SO$_2$NH$_2$, SO$_2$N(H)CH$_3$ and SO$_2$N(H)cyclopropyl)
Alk-NR$^6$R$^7$ (e.g., —(CH$_2$)$_3$—N(CH$_3$)$_2$)
N(H)C(O)R$^6$ (e.g., NHC(O)CH$_3$)
N(H)-Alk-NR$^6$R$^7$ (e.g., NH—(CH$_2$)$_3$—N(CH$_3$)$_2$)
N(H)C(O)-Alk-NR$^6$R$^7$ (e.g., N(H)C(O)—CH$_2$—NH$_2$)
N(H)-Alk-Het (e.g., NH—(CH$_2$)$_3$-piperazine-N—CH$_3$)
Alk-SO$_2$R$^6$ (e.g., CH$_2$—SO$_2$CH$_3$, CH$_2$—SO$_2$CH$_2$CH$_3$, CH$_2$CH$_3$—SO$_2$CH$_3$ and CH$_2$CH$_3$—SO$_2$CH$_2$CH$_3$)
Alk-SO$_2$NR$^6$R$^7$ (e.g., CH$_2$CH$_3$—SO$_2$NH$_2$)

Alk-Het (e.g., alkyl-morpholine, alkyl-piperidine, alkyl-pyrrolidine, and substituted variants thereof)

O-Alk-OR$^6$ (e.g., O—CH$_2$—OCH$_3$, O—CH$_2$CH$_3$—OCH$_3$)

O-Alk-NR$^6$R$^7$ (e.g., O—(CH$_2$)$_2$—NH$_2$, O—(CH$_2$)$_2$—N(H)CH$_3$, O—(CH$_2$)$_2$—N(CH$_3$)$_2$, O—(CH$_2$)$_2$—N(CH$_2$CH$_3$)$_2$, O—(CH$_2$)$_3$—NH$_2$, O—(CH$_2$)$_3$—N(H)CH$_3$, O—(CH$_2$)$_3$—N(CH$_3$)$_2$, O—(CH$_2$)$_3$—N(CH$_2$CH$_3$)$_2$, O—CH$_2$CH(CH$_3$)—NH$_2$, O—CH$_2$CH(CH$_3$)—N(H)CH$_3$, O—CH$_2$CH(CH$_2$)—N(CH$_3$)$_2$, O—CH$_2$CH(CH$_3$)—N(CH$_2$CH$_3$)$_2$)

O-Alk-Het (e.g., O—(CH$_2$)$_2$-morpholine, O—CH$_2$-pyrrolidine, O—(CH$_2$)$_2$-pyrrolidine, O—CH$_2$-piperidine, O—(CH$_2$)$_2$-piperidine and substituted variants thereof).

It is to be understood that the present invention includes all combinations and subsets of the particular groups defined hereinabove.

Specific examples of compounds of the present invention include those recited in the Examples which follow and pharmaceutically acceptable salts and solvates thereof. Particular compounds of the present invention include N-[3-(3-{2-[(2-Methyl-1,2,3,4-tetrahydro-7-isoquinolinyl)amino]-4-pyrimidinyl}pyrazolo[1,5-a]pyridin-2-yl)phenyl]-2-(2-thienyl)acetamide;

N-[3-(3-{2-[(3-{[2-(1-Pyrrolidinyl)ethyl]oxy}phenyl)amino]-4-pyrimidinyl}pyrazolo[1,5-a]pyridin-2-yl)phenyl]-2-(2-thienyl)acetamide;

N-{5-[3-(2-{[2-(Dimethylamino)-2,3-dihydro-1H-inden-5-yl]amino}pyrimidin-4-yl)pyrazolo[1,5-a]pyridin-2-yl]-2-methoxyphenyl}-2-(2-thienyl)acetamide;

N-[2-Methoxy-5-(3-{2-[(2-methyl-1,2,3,4-tetrahydroisoquinolin-7-yl)amino]pyrimidin-4-yl}pyrazolo[1,5-a]pyridin-2-yl)phenyl]-2-(2-thienyl)acetamide;

N-{3-[3-(2-{[3-(4-methyl-1,3-oxazol-5-yl)phenyl]amino}pyrimidin-4-yl)pyrazolo[1,5-a]pyridin-2-yl]phenyl}-2-(2-thienyl)acetamide;

N-{3-[3-(2-{[2-(Dimethylamino)-2,3-dihydro-1H-inden-5-yl]amino}pyrimidin-4-yl)pyrazolo[1,5-a]pyridin-2-yl]phenyl}-2-(2-thienyl)acetamide;

N-{2-Methyl-5-[3-(2-{[3-(1-pyrrolidinylmethyl)phenyl]amino}-4-pyrimidinyl)pyrazolo[1,5-a]pyridin-2-yl]phenyl}-2-(2-thienyl)acetamide;

N-[5-(3-{2-[(5-{[2-(Dimethylamino)ethyl]oxy}-2-methylphenyl)amino]-4-pyrimidinyl}pyrazolo[1,5-a]pyridin-2-yl)-2-methylphenyl]-2-(2-thienyl)acetamide;

N-[5-(3-{2-[(3-{[2-(Dimethylamino)ethyl]oxy}phenyl)amino]-4-pyrimidinyl}pyrazolo[1,5-a]pyridin-2-yl)-2-methylphenyl]-2-(2-thienyl)acetamide;

N-[2-Methyl-5-(3-{2-[(2-methyl-1,2,3,4-tetrahydro-7-isoquinolinyl)amino]-4-pyrimidinyl}pyrazolo[1,5-a]pyridin-2-yl)phenyl]-2-(2-thienyl)acetamide;

N-[5-(3-{2-[(3-{[2-(Dimethylamino)ethyl]oxy}-2-methylphenyl)amino]-4-pyrimidinyl}pyrazolo[1,5-a]pyridin-2-yl)-2-fluorophenyl]-2-(2-thienyl)acetamide;

N-{2-Fluoro-5-[3-(2-{[3-(1-pyrrolidinylmethyl)phenyl]amino}-4-pyrimidinyl)pyrazolo[1,5-a]pyridin-2-yl]phenyl}-2-(2-thienyl)acetamide;

N-[5-(3-{2-[(5-{[2-(Dimethylamino)ethyl]oxy}-2-methylphenyl)amino]-4-pyrimidinyl}pyrazolo[1,5-a]pyridin-2-yl)-2-fluorophenyl]-2-(2-thienyl)acetamide;

N-[2-Fluoro-5-(3-{2-[(2-methyl-1,2,3,4-tetrahydro-7-isoquinolinyl)amino]-4-pyrimidinyl}pyrazolo[1,5-a]pyridin-2-yl)phenyl]-2-(2-thienyl)acetamide;

N-[5-(3-{2-[(3-{[2-(Dimethylamino)ethyl]oxy}-2-methylphenyl)amino]-4-pyrimidinyl}pyrazolo[1,5-a]pyridin-2-yl)-2-(methyloxy)phenyl]-2-(2-thienyl)acetamide;

N-[5-(3-{2-[(3-{[2-(Dimethylamino)ethyl]oxy}phenyl)amino]-4-pyrimidinyl}pyrazolo[1,5-a]pyridin-2-yl)-2-(methyloxy)phenyl]-2-(2-thienyl)acetamide;

N-[5-(3-{2-[(5-{[2-(Dimethylamino)ethyl]oxy}-2-methylphenyl)amino]-4-pyrimidinyl}pyrazolo[1,5-a]pyridin-2-yl)-2-(methyloxy)phenyl]-2-(2-thienyl)acetamide;

N-{3-[6-Methyl-3-(2-{[3-(1-pyrrolidinylmethyl)phenyl]amino}-4-pyrimidinyl)pyrazolo[1,5-a]pyridin-2-yl]phenyl}-2-(2-thienyl)acetamide;

N-[3-(3-{2-[(3-{[2-(Dimethylamino)ethyl]oxy}phenyl)amino]-4-pyrimidinyl}-6-methylpyrazolo[1,5-a]pyridin-2-yl)phenyl]-2-(2-thienyl)acetamide; and N-{3-[3-(2-{[4-(4-Acetyl-1-piperazinyl)phenyl]amino}-4-pyrimidinyl)-6-methylpyrazolo[1,5-a]pyridin-2-yl]phenyl}-2-(2-thienyl)acetamide, and pharmaceutically acceptable salts and solvates thereof.

It will be appreciated by those skilled in the art that the compounds of the present invention may also be utilized in the form of a pharmaceutically acceptable salt or solvate thereof. The pharmaceutically acceptable salts of the compounds of formula (I) include conventional salts formed from pharmaceutically acceptable (i.e., non-toxic) inorganic or organic acids or bases as well as quaternary ammonium salts. Representative salts include the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, such as oxalic, which are not themselves pharmaceutically acceptable, may be useful in the preparation of salts useful as intermediates in obtaining compounds of this invention and these form a further aspect of the invention.

The term "solvate" as used herein refers to a complex of variable stoichiometry formed by a solute (a compound of formula (I)) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

Processes for preparing pharmaceutically acceptable salts and solvates of compounds such as the compounds of formula (I) are conventional in the art. See, e.g., Burger's Medicinal Chemistry And Drug Discovery 5th Edition, Vol 1: Principles And Practice.

As will be apparent to those skilled in the art, in the processes described below for the preparation of compounds of formula (I), certain intermediates, may be in the form of pharmaceutically acceptable salts or solvates of the compound. Those terms as applied to any intermediate employed in the process of preparing compounds of formula (I) have the same meanings as noted above with respect to compounds of formula (I). Processes for preparing pharmaceutically acceptable salts and solvates of intermediates are known in the art and are analogous to the process for preparing pharmaceutically acceptable salts and solvates of compounds such as the compounds of formula (I).

Certain compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centres are inverted. Certain compounds of formula (I) may be prepared as a mixture of regioisomers. The present invention covers both the mixture of regioisomers as well as the individual compounds. Likewise, it is understood that compounds of formula (I) may exist in tautomeric forms other than that shown in the formula and these are also included within the scope of the present invention.

The compounds of formula (I) and salts and solvates thereof, are believed to have anticancer and antitumor activity. This effect is currently believed to result from inhibition of one or more ErbB family protein kinases and the effect of such inhibition on cell lines whose growth is dependent on ErbB family protein kinase activity. It is well documented in the literature that inhibition of one or more ErbB family protein kinases is believed to result in therapeutic anti-tumor and anticancer effects. See, e.g., Normanno, N., Bianco, C., Strizzi, L., Mancino, M., Maiello, M. R., DeLuca, A., Caponigro, F., Salomon, D. S. *Current Drug Targets*, 2005, 6, 243-257; Hynes, N. E., Lane, H. A. *Nature Reviews Cancer*, 2005, 5, 341-345; and Ben-Baruch, N., Yarden, Y. *Progress in Oncology*, 2004, 46-72.

The compounds of the present invention are typically inhibitors of one or more ErbB family kinases (EGFR, ErbB-2, and/or ErbB-4). The present invention is not limited to compounds of formula (I) which are selective for ErbB family kinase inhibition; rather, the present invention expressly contemplates compounds of formula (I) which may possess activity against kinases other than ErbB family kinases, as well. By "ErbB inhibitor" is meant a compound which exhibits a $pIC_{50}$ of greater than about 6 against at least one ErbB family kinase in the ErbB inhibition enzyme assay described below and/or an $IC_{50}$ of at least about 5 µM potency against at least one cell line that overexpresses at least one ErbB family kinase (e.g., BT474 or HN5) in the methylene blue cellular assay described below. In a more particular embodiment "ErbB inhibitor" refers to a compound which exhibits a $pIC_{50}$ of greater than about 6.5 against at least one ErbB family kinase in the ErbB inhibition enzyme assay described below and/or an $IC_{50}$ of at least 1 µM potency against at least one cell line that overexpresses at least one ErbB family kinase (e.g., BT474 or HN5) in the methylene blue assay described below.

The present invention further provides compounds of formula (I) for use in medical therapy in a mammal, e.g. a human. In particular, the present invention provides compounds of formula (I) for use in the treatment of a condition mediated by at least one ErbB family kinase in a mammal, and more particularly conditions mediated by inappropriate activity of one or more ErbB family kinase in a mammal. In one embodiment, the present invention provides compounds of formula (I) for use in the treatment of a condition mediated by at least two ErbB family kinases, and more particularly conditions mediated by inappropriate activity of one or more ErbB family kinase in a mammal.

The inappropriate ErbB family kinase activity referred to herein is any ErbB kinase activity that deviates from the normal ErbB family kinase activity expected in a particular mammalian subject. The inappropriate activity may arise from one or more of EGFR (ErbB-1), ErbB-2, and ErbB-4. Inappropriate ErbB family kinase activity may take the form of, for instance, an abnormal increase in activity, or an aberration in the timing and/or control of ErbB family kinase activity. Such inappropriate activity may result then, for example, from overexpression or mutation of the protein kinase or ligand leading to inappropriate or uncontrolled activation of the receptor. Furthermore, it is also understood that unwanted ErbB family kinase activity may reside in an abnormal source, such as a malignancy. That is, the level of ErbB family activity does not have to be abnormal to be considered inappropriate, rather the activity derives from an abnormal source.

The present invention also provides compounds of formula (I) for use in the treatment of a susceptible neoplasm.

"Susceptible neoplasm" as used herein refers to neoplasms which are susceptible to treatment with an ErbB inhibitor. Neoplasms which have been associated with inappropriate activity of one or more ErbB family kinases and are therefor susceptible to treatment with an ErbB inhibitor are known in the art, and include both primary and metastatic tumors and cancers. See, Normanno, N.; Bianco, C.; Strizzi, L. Mancino, M.; Maiello, M. R.; DeLuca, A.; Caponigro, F.; Salomon, D. S. *Current Drug Targets*, 2005, 6, 243-257; Hynes, N. E.; Lane, H. A. *Nature Reviews Cancer*, 2005, 5, 341-345; and Ben-Baruch, N.; Yarden, Y. *Progress in Oncology*, 2004, 46-72. For example, susceptible neoplasms within the scope of the present invention include but are not limited to breast cancer, colon cancer, non-small cell lung cancer, prostate cancer, bladder cancer, ovarian cancer, gastric cancer, pancreatic cancer, carcinoma of the head and neck, esophageal carcinoma, melanoma and renal carcinoma.

The present invention provides methods for the treatment of several conditions in a mammal in need thereof, all of which comprise the step of administering a therapeutically effective amount of a compound of formula (I). The mammal in need of treatment with a compound of the present invention is typically a human.

As used herein, the term "treatment" refers to alleviating the specified condition, eliminating or reducing the symptoms of the condition, slowing or eliminating the progression of the condition and preventing or delaying the reoccurrence of the condition in a previously afflicted subject.

As used herein, the term "therapeutically effective amount" means an amount of a compound of formula (I) which is sufficient, in the subject to which it is administered, to elicit the biological or medical response of a cell culture, tissue, system, mammal (including human) that is being sought, for instance, by a researcher or clinician. The term also includes within its scope amounts effective to enhance normal physiological function. For example, a therapeutically effective amount of a compound of formula (I) for the treatment of a condition mediated by inappropriate activity of at least one ErbB family kinase is an amount sufficient to treat the condition in the subject. Similarly, a therapeutically effective amount of a compound of formula (I) for the treatment of a susceptible neoplasm is an amount sufficient to treat the susceptible neoplasm in the subject. In one embodiment of the present invention, a therapeutically effective amount of a compound of formula (I) is an amount sufficient to regulate, modulate, bind or inhibit at least one ErbB family kinase.

The present invention provides a method for treating a condition mediated by at least one ErbB family kinase in a mammal (e.g., a human), which method comprises administering to the mammal a therapeutically effective amount of the compound of formula (I). Conditions which are mediated by at least one ErbB family kinase are known in the art and include but are not limited to neoplasms.

A further aspect of the invention provides a method of treatment of a mammal suffering from a condition mediated by inappropriate activity of one or more ErbB family kinases, which comprises administering to the mammal a therapeutically effective amount of a compound of formula (I). In one embodiment, the condition mediated by inappropriate activity of one or more ErbB family kinases is a susceptible neoplasm.

The present invention also provides a method for treating a susceptible neoplasm (cancer or tumor) in a mammal (e.g., a human) in need thereof, which method comprises administering to the mammal a therapeutically effective amount of the compound of formula (I).

In one particular embodiment, the present invention provides a method for treating breast cancer in a mammal in need thereof comprising administering to the mammal a therapeutically effective amount of the compound of formula (I). In another embodiment, the present invention provides a method for treating colon cancer in a mammal in need thereof comprising administering to the mammal a therapeutically effective amount of the compound of formula (I). In another embodiment, the invention provides a method for treating non-small cell lung cancer in a mammal in need thereof comprising administering to the mammal a therapeutically effective amount of the compound of formula (I).

The precise therapeutically effective amount of the compounds of formula (I) will depend on a number of factors including, but not limited to, the age and weight of the subject being treated, the precise condition requiring treatment and its severity, the nature of the formulation, and the route of administration, and will ultimately be at the discretion of the attendant physician or veterinarian. Typically, the compound of formula (I) will be given for treatment in the range of 0.1 to 200 mg/kg body weight of recipient (mammal) per day and more usually in the range of 1 to 100 mg/kg body weight per day. Acceptable daily dosages, may be from about 0.1 to about 2000 mg/day, and preferably from about 0.1 to about 100 mg/day. Thus, for a 70 kg adult human being treated for a condition mediated by at least one ErbB family kinase, the actual amount per day would usually be from 70 to 700 mg and this amount may be given in a single dose per day or more usually in a number (such as two, three, four, five or six) of sub-doses per day such that the total daily dose is the same. A therapeutically effective amount of a salt or solvate, may be determined as a proportion of the therapeutically effective amount of the compound of formula (I) per se. It is envisaged that similar dosages would be appropriate for treatment of the other conditions referred to above.

The compounds of formula (I) can be used alone in the treatment of each of the foregoing conditions or can be used to provide additive or synergistic effects with certain existing chemotherapies, and/or be used to restore effectiveness of certain existing chemotherapies and radiation.

As one aspect, the present invention provides methods of regulating, modulating, binding, or inhibiting at least one ErbB family kinase for the treatment of conditions mediated by at least one ErbB family kinase, by administering a therapeutically effective amount of a compound of formula (I). "Regulating, modulating, binding or inhibiting at least one ErbB family kinase" refers to regulating, modulating, binding or inhibiting activity of at least one ErbB family kinase (e.g., c-ErbB-2, EGFR, and ErbB-4), as well as regulating, modulating, binding or inhibiting overexpression of at least one ErbB family kinase. Such conditions include certain neoplasms (including cancers and tumors) which have been associated with overexpression of at least one ErbB family kinase.

The present invention also provides the use of a compound of formula (I) for the preparation of a medicament for the treatment of condition mediated by at least one ErbB family kinase in a mammal (e.g., a human) in need thereof. The present invention further provides the use of a compound of formula (I) for the preparation of a medicament for the treatment of a susceptible neoplasm in a mammal. The present invention further provides the use of a compound of formula (I) for the preparation of a medicament for the treatment of breast cancer in a mammal. The present invention further provides the use of a compound of formula (I) for the preparation of a medicament for the treatment of colon cancer in a mammal. The present invention further provides the use of a compound of formula (I) for the preparation of a medicament for the treatment of non-small cell lung cancer in a mammal.

While it is possible that, for use in therapy, a therapeutically effective amount of a compound of formula (I) may be administered as the raw chemical, it is typically presented as the active ingredient of a pharmaceutical composition or formulation. Accordingly, the invention further provides a pharmaceutical composition comprising a compound of the formula (I). The pharmaceutical composition may further comprise one or more pharmaceutically acceptable carriers, diluents, and/or excipients. The carrier(s), diluent(s) and/or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I) with one or more pharmaceutically acceptable carriers, diluents and/or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I), depending on the condition being treated, the route of administration and the age, weight and condition of the patient, or pharmaceutical formulations may be presented in unit dose forms containing a predetermined amount of active ingredient per unit dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages. Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I) can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, to aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations. Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

In the above-described methods of treatment and uses, a compound of formula (I) may be employed alone, in combination with one or more other compounds of formula (I) or in combination with other therapeutic agents. In particular, in methods of treating a condition mediated by at least one ErbB family kinase and methods of treating susceptible neoplasms, combination with other chemotherapeutic, hormonal and/or antibody agents is envisaged as well as combination with surgical therapy and radiotherapy. The term "chemotherapeutic" as used herein refers to any chemical agent having a therapeutic effect on the subject to which it is administered. "Chemotherapeutic" agents include but are not limited to anti-neoplastic agents, analgesics and anti-emetics. Antiemetics include but are not limited to 5HT$_3$ antagonists such as ondensetron, granisetron, and the like; metaclopromide; dexamethasone and neurokinin-1 antagonists. As used herein, "anti-neoplastic agents" include both cytostatic and cytotoxic agents. Combination therapies according to the present invention thus comprise the administration of at least one compound of formula (I) and the use of at least one other treatment method. In one embodiment, combination therapies according to the present invention comprise the administration of at least one compound of formula (I) and at least one other chemotherapeutic agent. In one particular embodiment, the present invention comprises the administration of at least one compound of formula (I) and at least one anti-neoplastic agent. As an additional aspect, the present invention provides the methods of treatment and uses as described above, which comprise administering a compound of formula (I) together with at least one chemotherapeutic agent. In one particular embodiment, the chemotherapeutic agent is an anti-neoplastic agent. In another embodiment, the present invention provides a pharmaceutical composition as described above further comprising at least one other chemotherapeutic agent, more particularly, the chemotherapeutic agent is an anti-neoplastic agent.

The compounds of the formula (I) and at least one additional cancer treatment therapy may be employed in combination concomitantly or sequentially in any therapeutically appropriate combination with such other anti-cancer therapies. In one embodiment, the other anti-cancer therapy is at least one additional chemotherapeutic therapy including administration of at least one anti-neoplastic agent. In another embodiment, the other anti-cancer therapy is at least one additional chemotherapeutic therapy including administration of at least one anti-emetic. The administration in combination of a compound of formula (I) with other anti-neoplastic agents may be in combination in accordance with the invention by administration concomitantly in (1) a unitary pharmaceutical composition including both compounds or (2) separate pharmaceutical compositions each including one of the compounds. The combination may be administered separately in a sequential manner wherein one anti-neoplastic agent is administered first and the other second or vice versa. Such sequential administration may be close in time or remote in time.

When a compound of formula (I) is used in combination with a chemotherapeutic agent, the dose of each compound may differ from that when the compound is used alone. Appropriate doses will be readily appreciated by those skilled in the art. The appropriate dose of the compound(s) of formula (I) and the other therapeutically active agent(s) and the relative timings of administration will be selected in order to achieve the desired combined therapeutic effect, and are within the expertise and discretion of the attendant clinician.

Among the many chemotherapeutic agents which may be used in combination with a compound of the present invention are anti-neoplastic agents. Anti-neoplastic agents may induce anti-neoplastic effects in a cell-cycle specific manner, i.e., are phase specific and act at a specific phase of the cell cycle, or bind DNA and act in a non cell-cycle specific manner, i.e., are non-cell cycle specific and operate by other mechanisms. Both types of anti-neoplastic agents may be employed in combination with the compounds of the present invention.

Typically, any chemotherapeutic agent that has activity versus a susceptible neoplasm being treated may be utilized in combination with the compounds of formula (I), provided that the particular agent is clinically compatible with therapy employing a compound of formula (I). Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphor-ines, alkylsulfonates, nitrosoureas, and triazenes; antibiotic agents such as anthracyclines, actinomycins and bleomycins; topoisomerase II inhibitors such as epipodophyllotoxins; antimetabolites such as purine and pyrimidine analogues and antifolate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids. Examples of diterpenoids include, but are not limited to, paclitaxel and its analog docetaxel. Examples of vinca alkaloids include, but are not limited to, vinblastine, vincristine, and vinorelbine.

Platinum coordination complexes are non-phase specific anti-neoplastic agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Alkylating agents are non-phase anti-neoplastic specific agents and strong electrophiles. Typically, alkylating agents form covalent linkages, by alkylation, to DNA through nucleophilic moieties of the DNA molecule such as phosphate, amino, and hydroxyl groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Antibiotic chemotherapeutic agents are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Topoisomerase II inhibitors include, but are not limited to, epipodophyllotoxins. Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine and thioguanine.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin.

Hormones and hormonal analogues are useful compounds for treating cancers in which there is a relationship between the hormone(s) and growth and/or lack of growth of the cancer. Examples of hormones and hormonal analogues believed to be useful in the treatment of neoplasms include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene and iodoxyfene useful in the treatment of hormone dependent breast carcinoma; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagonists such as goserelin acetate and luprolide.

Signal transduction pathway inhibitors are those inhibitors which block or inhibit a chemical process which evokes an intracellular change. As used herein this change is cell proliferation or differentiation or survival. Signal transduction inhibitors useful in the present invention include inhibitors of receptor tyrosine kinases, non-receptor tyrosine kinases, SH2/SH3 domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Other receptor tyrosine kinases involved in the regulation of cell growth and sometimes termed growth factor receptors, may also be combined with a compound of the present invention. In addition to the epidermal growth factor receptors (EGFr, ErbB2 and ErbB4), other growth factor receptor inhibitors that may be combined with a compound of formula (I) include, for example, platelet derived growth factor receptor (PDGFr), vascular endothelial growth factor receptor (VEGFR), tyrosine kinase with immunoglobulin-like and epidermal growth factor homology domains (TIE-2), insulin growth factor receptor-1 (IGFR-1), macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene and inhibitors of Akt kinases. Several inhibitors of growth factor receptors are under development and include ligand antagonists, antibodies, tyrosine kinase inhibitors, anti-sense oligonucleotides and aptamers. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth Factor Receptors as Targets", New Molecular Targets for Cancer Chemotherapy, Ed. Workman, Paul and Kerr, David, CRC Press 1994, London. In one embodiment, the present invention provides methods of treatment of the various conditions enumerated above comprising administering a compound of formula (I) in combination with a different ErbB inhibitor. In one preferred embodiment, the methods comprise administering a compound of formula (I) in combination with lapatinib.

Tyrosine kinases, which are not growth factor receptor kinases are termed non-receptor tyrosine kinases. Non-receptor tyrosine kinases useful in the present invention, which are targets or potential targets of anti-neoplastic drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual Review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases include Polo-like kinases ("PLK" e.g., PLK1, PLK2 and PLK3) which play critical roles in regulating processes in the cell cycle including the entry into and the exit from mitosis; MAP kinase cascade blockers which include blockers of Raf kinases (Rafk), Mitogen or Extracellular Regulated Kinase (MEKs), and Extracellular Regulated Kinases (ERKs); and Protein kinase C family member blockers including blockers of subtypes of PKCs (alpha, beta, gamma, epsilon, mu, lambda, iota, zeta), IkB kinase family (IKKa, IKKb), PKB family kinases, Akt kinase family members, and TGF beta receptor kinases may also be used in combination with a compound of the present invention. Such Serine/Threonine kinases and inhibitors thereof are described in PCT Publication No. WO04/014899 to GlaxoSmithKline; Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; and Martinez-Iacaci, L., et al, Int. J. Cancer (2000), 88(1), 44-52. In one embodiment, the methods of the present invention comprise administering a compound of formula (I) in combination with a PLK inhibitor, more preferably a compound described in PCT Publication No. WO04/014899.

Inhibitors of Phosphotidyl Inositol-3 Kinase family members including blockers of PI3-kinase, ATM, DNA-PK, and Ku are also useful in combination with the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer Res, (2000) 60(6), 1541-1545.

Also useful in combination with the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC Press 1994, London.

Another group of signal transduction pathway inhibitors useful in combination with the present invention are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block Ras activation in cells containing wild type mutant Ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9(2)99-102; and BioChim. Biophys. Acta, (1989) 1423(3):19-30.

As mentioned above, antibodies to receptor kinase ligand binding may also serve as signal transduction inhibitors. This group of signal transduction pathway inhibitors includes the use of humanized antibodies to the extracellular ligand binding domain of receptor tyrosine kinases. For example, Imclone C225 EGFR specific antibody (see Green, M. C. et al, Monoclonal Antibody Therapy for Solid Tumors, Cancer Treat. Rev., (2000), 26(4), 269-286); Herceptin® ErbB2 antibody (see Tyrosine Kinase Signaling in Breast Cancer: ErbB Family Receptor Tyrosine Kinases, Breast Cancer Res., 2000, 2(3), 176-183); and 2CB VEGFR2 specific antibody (see Brekken, R. A. et al, Selective Inhibition of VEGFR2 Activity by a Monoclonal Anti-VEGF Antibody Blocks Tumor Growth in Mice, Cancer Res. (2000) 60, 5117-5124).

Receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Other inhibitors may be used in combination with the compounds of the present invention. For example, anti-VEGF antibodies, which do not recognize VEGFR (the receptor tyrosine kinase), but bind to the ligand; small molecule inhibitors of integrin (alpha$_v$, beta$_3$) that will inhibit angiogenesis; endostatin and angiostatin (non-RTK) may also prove useful in combination with PLK inhibitors.

Agents used in immunotherapeutic regimens may also be useful in combination with the compounds of formula (I).

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al., J. Clin. Oncol. 18:1812-1823 (2000); and Kitada S et al., Antisense Res. Dev. 4:71-79 (1994).

Cell cycle signaling inhibitors inhibit molecules involved in the control of the cell cycle. Cyclin dependent kinases (CDKs) and their interaction cyclins control progression through the eukaryotic cell cycle. The coordinated activation and inactivation of different cyclin/CDK complexes is necessary for normal progression through the cell cycle. Several inhibitors of cell cycle signaling are under development. For instance, examples of cyclin dependent kinases, including CDK2, CDK4, and CDK6 and inhibitors for the same are described in, for instance, Rosania, et al., *Exp. Opin. Ther. Patents* 10(2):215-230 (2000).

In one embodiment, the methods of the present invention comprise administering to the mammal a compound of formula (I) in combination with a signal transduction pathway inhibitor, particularly erlotinib (TARCEVA®).

Compounds of formula (I) may be prepared using the methods described below. In all of the schemes described below, it is understood that protecting groups may be employed where necessary in accordance with general principles known to those of skill in the art, for example, see T. W. Green and P. G. M. Wuts (1991) Protecting Groups in Organic Synthesis, John Wiley & Sons. These groups may be removed at a convenient stage of the compound synthesis using methods known to those of skill in the art. The selection of processes as well as the reaction conditions and order of their execution shall be consistent with the preparation of compounds of formula (I).

Compounds of formula (I) may be conveniently prepared by the methods outlined in Scheme 1 below.

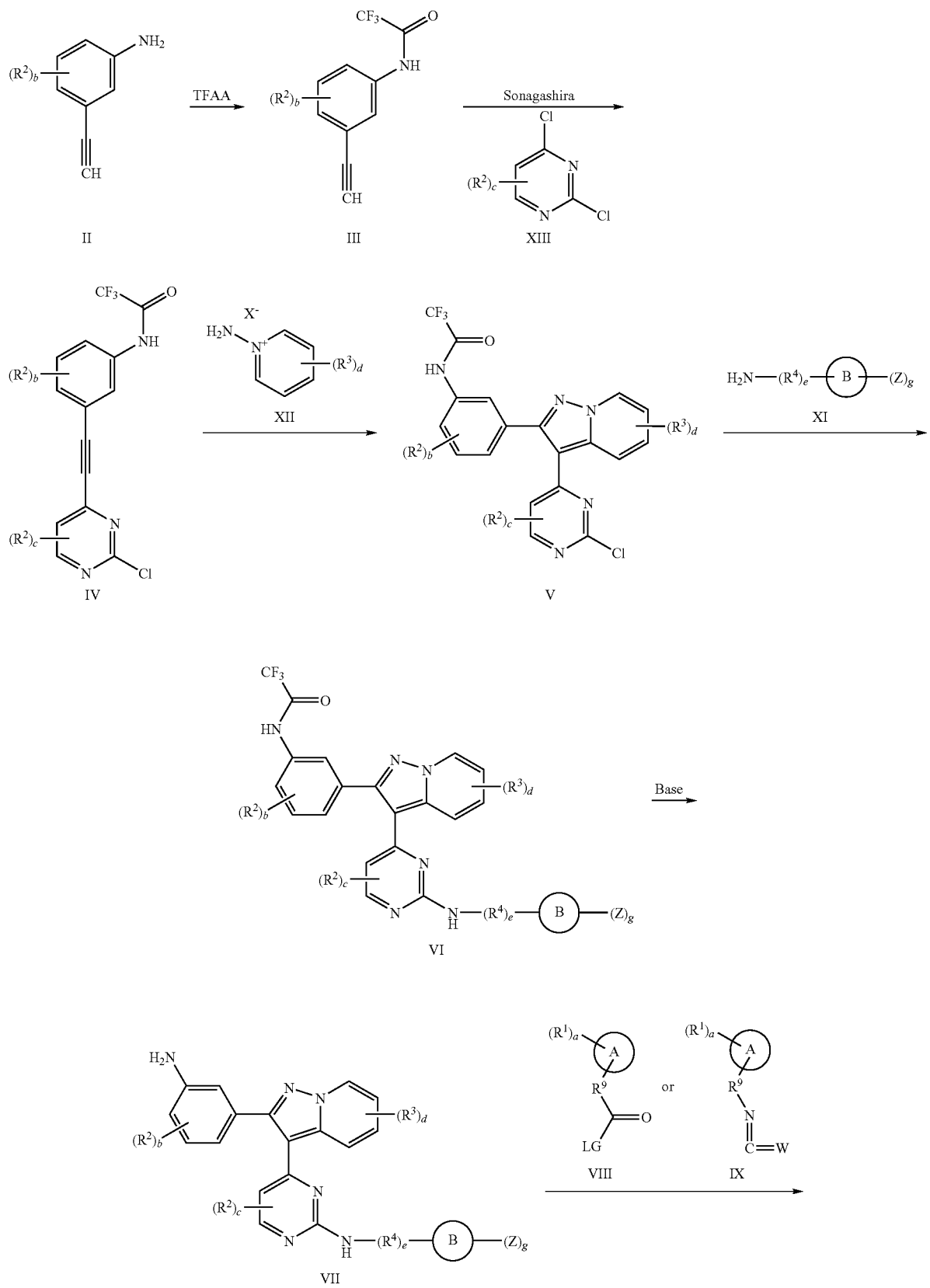

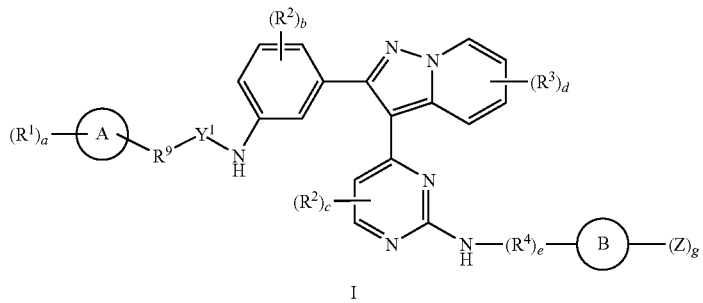

I wherein:
X⁻ is an anion (preferably halide);
LG is a suitable leaving group;
W is O or S; and
and all other variables are as defined above.

Generally, the process for preparing the compounds of formula (I) (all formulas and all variables having been defined above) comprises the steps of:

a) reacting a compound of formula (VII) with a compound of formula (VIII) or a compound of formula (IX) to prepare a compound of formula (I);

b) optionally converting the compound of formula (I) to a pharmaceutically acceptable salt or solvate thereof; and c) optionally converting the compound of formula (I) or a pharmaceutically acceptable salt or solvate thereof to a different compound of formula (I) or a pharmaceutically acceptable salt or solvate thereof.

More specifically, the process for preparing compounds of formula (I) comprises the to steps of:

a) reacting the compound of formula (II) with a trifluoroacetic acid derivative to prepare a compound of formula (III);

b) reacting the compound of formula (III) with a compound of formula (XIII) to prepare a compound of formula (IV);

c) reacting the compound of formula (IV) with a 1-aminopyridinium compound of formula (XII) to prepare a compound of formula (V);

d) reacting the compound of formula (V) with a compound of formula (XI) to prepare a compound of formula (VI);

e) reacting the compound of formula (VI) with a base to prepare a compound of formula (VII);

f) reacting a compound of formula (VII) with a compound of formula (VIII) or a compound of formula (IX) to prepare a compound of formula (I);

g) optionally converting the compound of formula (I) to a pharmaceutically acceptable salt or solvate thereof; and h) optionally converting the compound of formula (I) or a pharmaceutically acceptable salt or solvate thereof to a different compound of formula (I) or a pharmaceutically acceptable salt or solvate thereof.

As will be apparent to those skilled in the art, the order of the foregoing steps is not critical to the process of the present invention, and the process may be carried out using any suitable order of steps.

Compounds of formula (I) wherein $Y^1$ is —C(O)— (i.e., compounds of formula (I-A)) are prepared by reacting a compound of formula (VII) with a compound of formula (VIII).

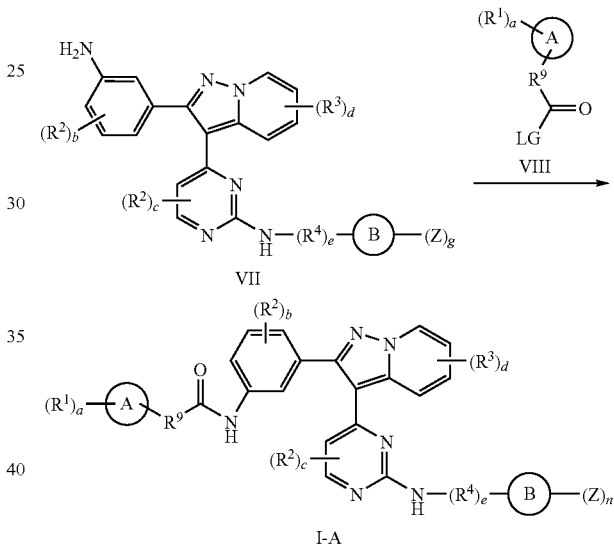

wherein all variables are as defined above.

Suitable leaving groups in the compounds of formula (VIII) will be apparent to those skilled in the art and include, for example, halide and hydroxyl groups. Typically, the reaction is carried out in a suitable solvent such as dichloromethane (DCM) or tetrahydrofuran. It will be understood by those skilled in the art that when LG is hydroxyl, the reaction can be carried out in the presence of an appropriate coupling agent such as dicyclohexylcarbodiimide (DCC) or ethylcarbodiimide hydrochloride (EDC). Compounds of formula (VIII) are commercially available or may be synthesized using techniques conventional in the art. It will be appreciated by those skilled in the art that the compounds of formula (I-A) may be converted to a different compound of formula (I), e.g., a compound of formula (I) wherein $Y^1$ is other than —C(O)—, using the conventional techniques. Representative transformations of compounds of formula (I-A) are described herein below.

Compounds of formula (I) wherein $Y^1$ is —N(H)C(O)— or $Y^1$ is —N(H)C(S)— (i.e., compounds of formula (I-B)), can be prepared by reacting a compound of formula (VII) with a suitable isocyanate or isothiocyanate of formula (I'X).

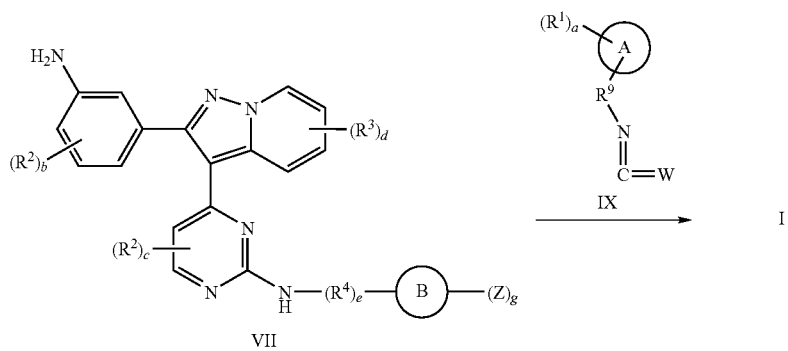

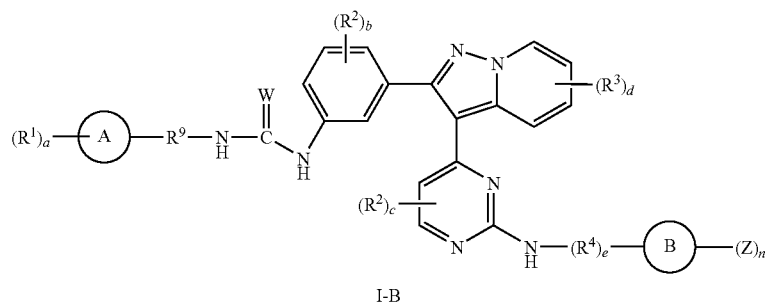

wherein all variables are as defined above.

This reaction may be carried out using conditions conventional in the art for such coupling reactions, including the use of a solvent such as tetrahydrofuran, 1,4-dioxane or DCM at ambient temperature or with heating from about 40 to about 100° C. Compounds of formula (IX) are commercially available or may be synthesized using techniques conventional in the art.

A compound of formula (VII) may be prepared by reacting a compound of formula (VI) with a base.

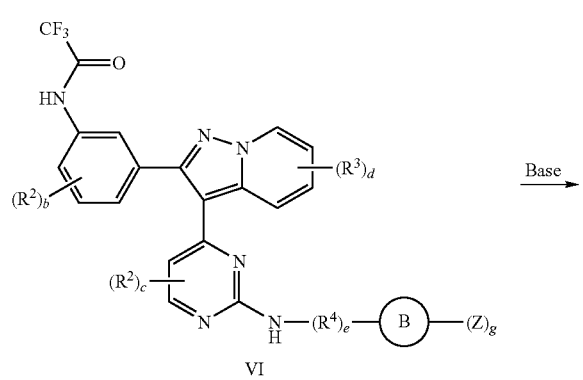

-continued

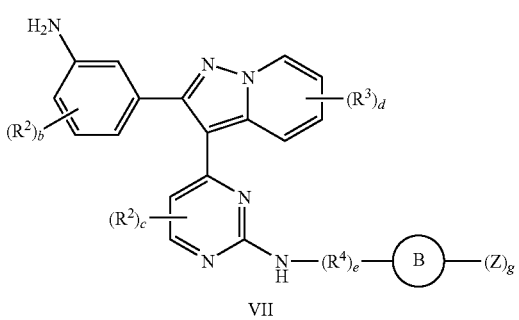

wherein all variables are as defined above.

Suitable bases include lithium hydroxide and sodium hydroxide. This reaction may be carried out in a suitable solvent. Examples of suitable solvents for this reaction include but are not limited to tetrahydrofuran and water. The reaction may be carried out at ambient temperature or with heating from about 40 to about 60° C.

Compounds of formula (VI) may be prepared by reacting a compound of formula (V) with an amine of formula (XI)

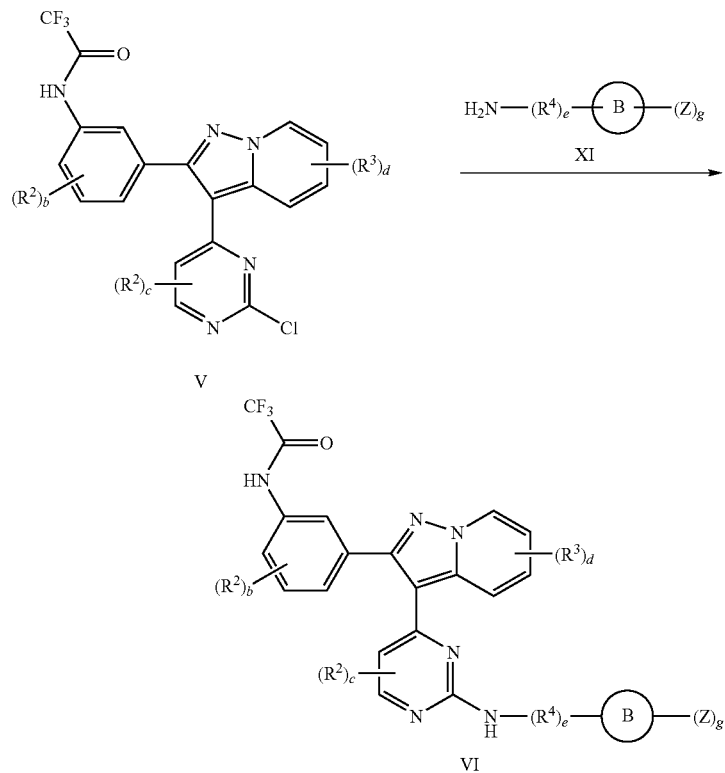

wherein all variables are as defined above.

The reaction may be carried out in a solvent under reflux conditions or in a microwave apparatus at a temperature of from about 100 to about 180° C. in a to suitable vessel. Examples of suitable solvents for this reaction include but are not limited to isopropanol, 1,4-dioxane, ethanol and N,N-dimethylformamide. As will be apparent to those skilled in the art of organic chemistry, it may be desirable to catalyze this reaction for the preparation of certain compounds of formula (VI). For example, for compounds of formula (XI) and (VI), wherein e is 0 and Ring B is aryl, it may be desirable to carry out the reaction in the presence of a catalytic amount of an acid such as hydrochloric acid or hydrobromic acid. As will further be apparent to those skilled in the art, it may also be desirable to install appropriate protecting groups prior to reacting the compound of formula (V) with the compound of formula (XI). For example, in the embodiment, wherein Z is a group containing a primary or secondary amine, the addition is preferably carried out when the amine is protected as, for example, its corresponding trifluoroacetamide. The choice, installation and removal of appropriate protecting groups for reactions such as this are conventional in the art. Compounds of formula (XI) are commercially available or may be synthesized using techniques conventional in the art.

Compounds of formula (V) may be prepared by reacting a compound of formula (IV) with an 1-aminopyridinium compound of formula (XII).

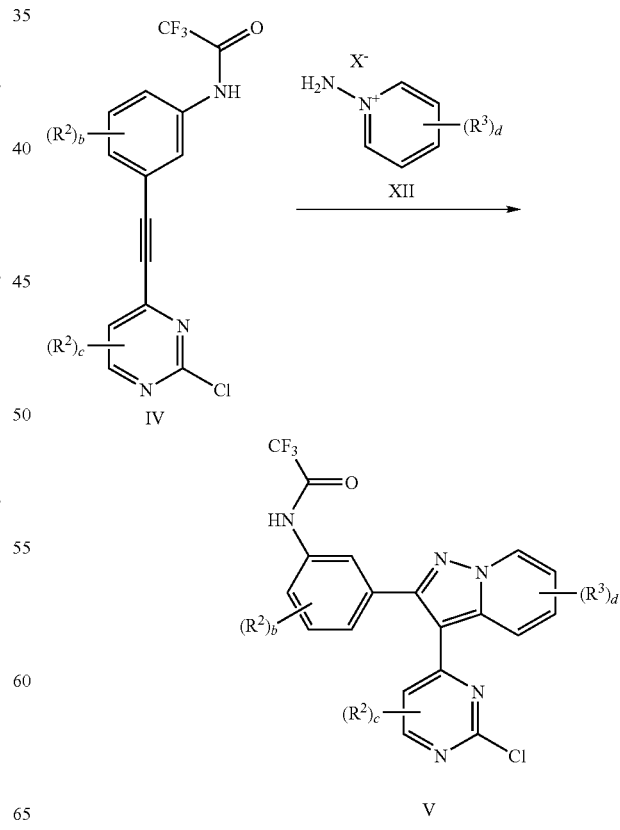

wherein all variables are as defined above.

The reaction is typically carried out in the presence of a base in a suitable solvent. Examples of suitable bases include but are not limited to potassium carbonate and potassium hydroxide. Examples of suitable solvents include dimethyl sulfoxide, dichloromethane, methanol and N,N-dimethylformamide at ambient temperature. Compounds of formula (XII) are commercially available or may be synthesized using to techniques conventional in the art.

Compounds of formula (IV) may be prepared by reacting a compound of formula (III) with a compound of formula (XIII).

catalyzed alkynylation, HANDBOOK OF ORGANOPALLADIUM CHEMISTRY FOR ORGANIC SYNTHESIS 1, 493-529, 2002. Examples of suitable catalysts include palladium catalysts such as dichlorobis(triphenylphosphine)palladium (II). An example of a suitable base is triethylamine. Compounds of formula (XIII) are commercially available or may be synthesized using techniques conventional in the art.

Compounds of formula (III) may be prepared from the corresponding 3-ethynylaniline compound of formula (II) using a trifluoroacetic acid derivative such as trifluoroacetic anhydride under conditions well known to those skilled in the art.

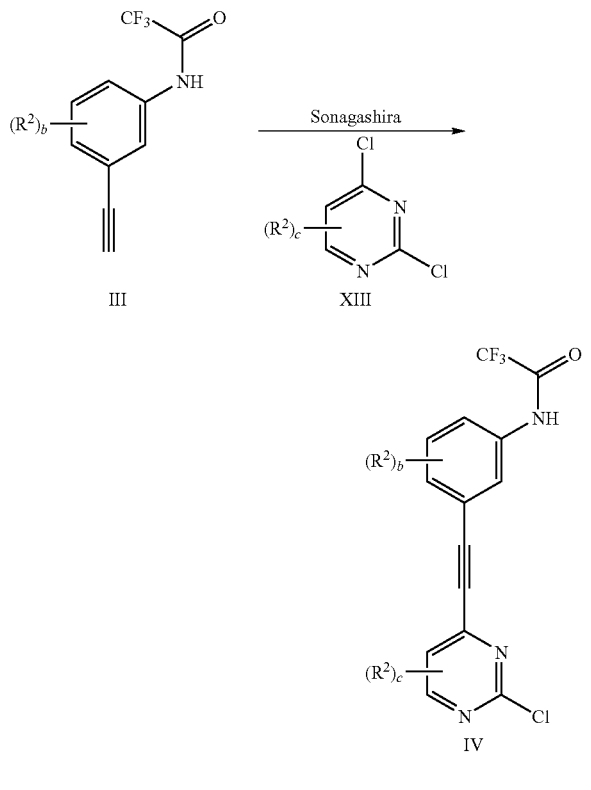

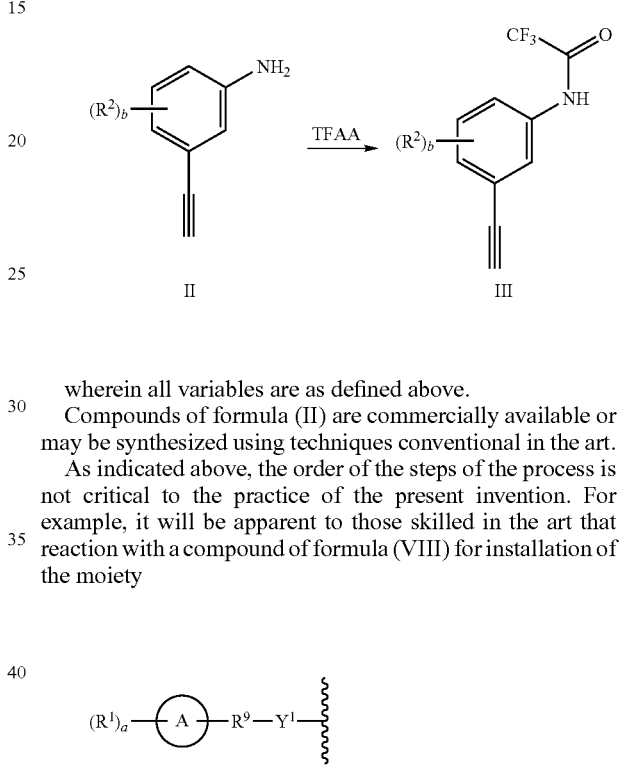

wherein all variables are as defined above.

Compounds of formula (II) are commercially available or may be synthesized using techniques conventional in the art.

As indicated above, the order of the steps of the process is not critical to the practice of the present invention. For example, it will be apparent to those skilled in the art that reaction with a compound of formula (VIII) for installation of the moiety wherein all variables are as defined above.

The reaction is typically carried out using conventional Sonagashira reaction conditions. In particular, the reaction typically is carried out in the presence of a catalyst, copper (I) species and base in a solvent such as tetrahydrofuran according to the method of Sonogashira, Kenkichi. "Palladiumcan be effected prior to reaction with the compound of formula (XI). This process may be carried out by reacting a compound of formula (XIV) with an amine of formula (XI) using standard reaction conditions.

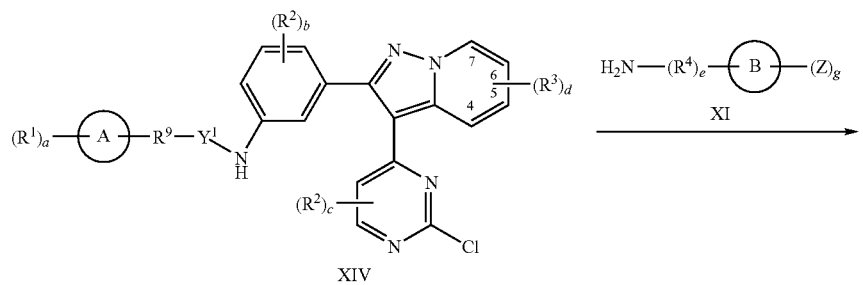

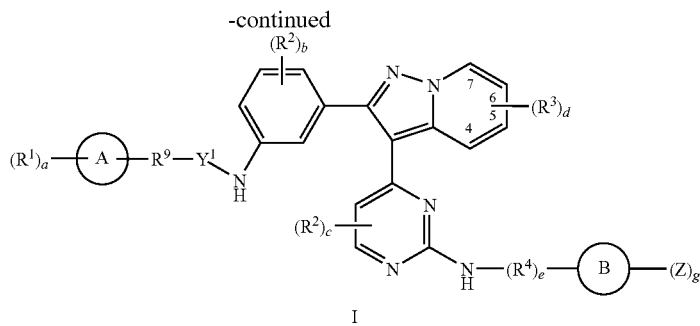

I wherein all variables are as defined above.

The compound of formula (XIV) may conveniently be prepared by removal of the trifluoroacetyl group of a compound of formula (V) and reaction with a compound of formula (VIII) as described above. The removal of trifluoroacetyl group of the compound of formula (V) may be accomplished using techniques well known in the art for the removal of such groups.

According to another process of the present invention, compounds of formula (I) may be prepared as outlined in Scheme 2 below.

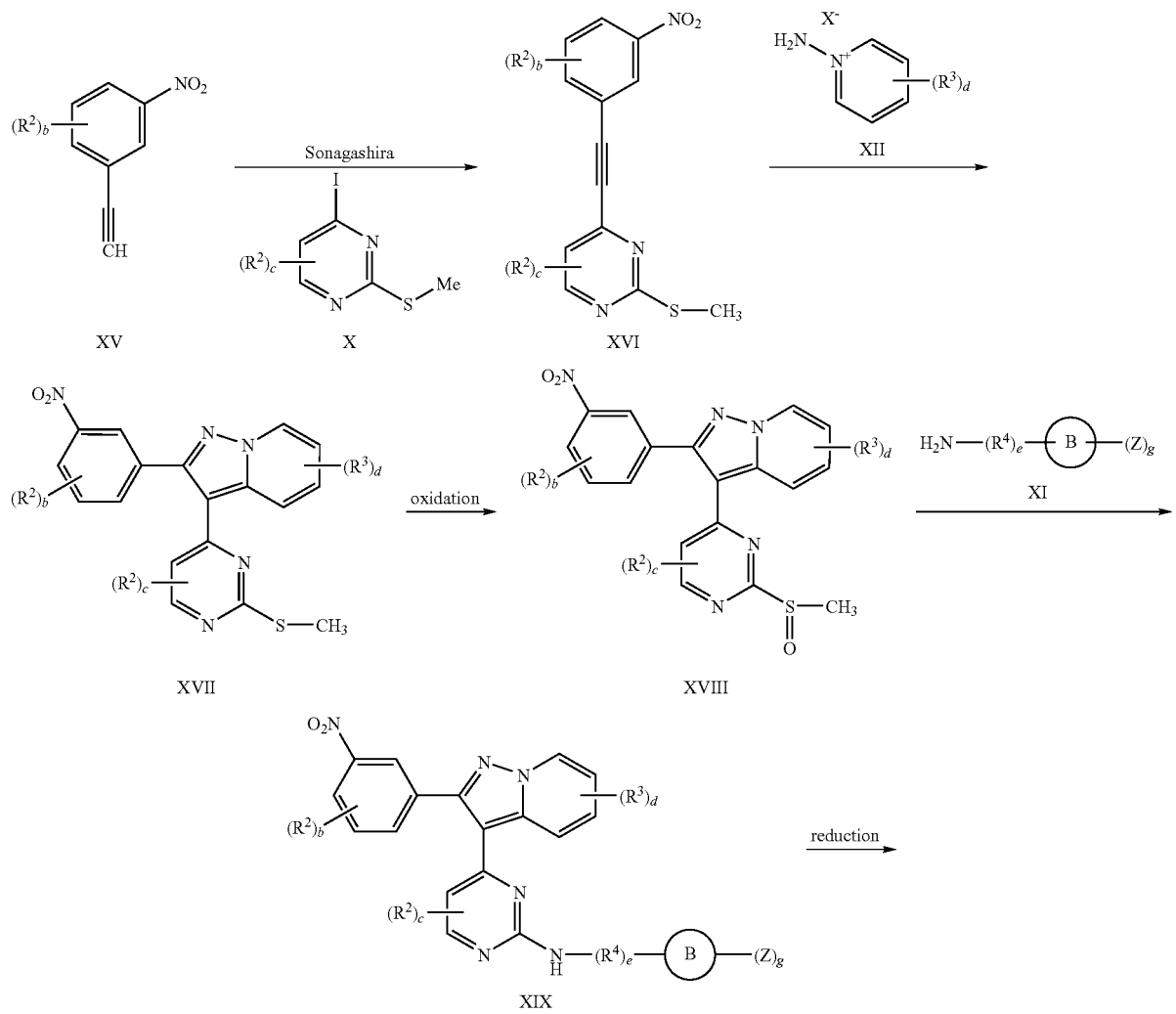

-continued

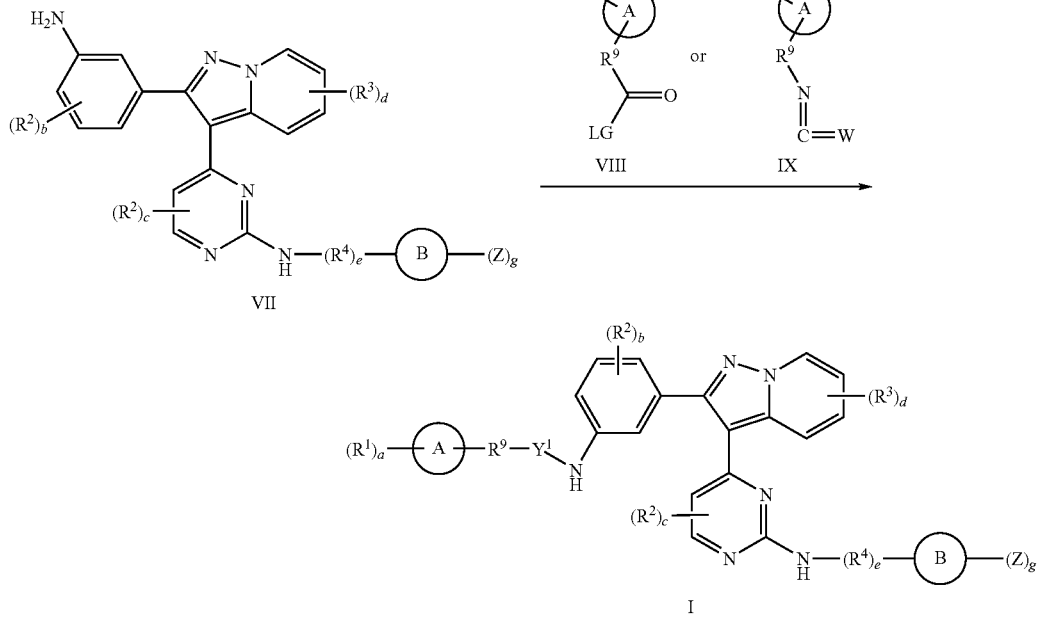

wherein:

Me is —CH₃;

X⁻ is an anion (preferably halide);

LG is a suitable leaving group;

W is O or S; and and all other variables are as defined above.

Generally, the process for preparing the compounds of formula (I) (all formulas and all variables having been defined above) comprises the steps of:

a) reacting the compound of formula (XV) with a compound of formula (X) to prepare a compound of formula (XVI);

b) reacting the compound of formula (XVI) with a 1-aminopyridinium compound of formula (XII) to prepare a compound of formula (XVII);

c) oxidizing the compound of formula (XVII) to prepare a compound of formula (XVIII);

d) reacting the compound of formula (XVIII) with a compound of formula (XI) to prepare a compound of formula (XIX);

e) reducing the compound of formula (XIX) to prepare a compound of formula (VI);

f) reacting a compound of formula (VII) with a compound of formula (VIII) or a compound of formula (IX) to prepare a compound of formula (I);

g) optionally converting the compound of formula (I) to a pharmaceutically acceptable salt or solvate thereof; and h) optionally converting the compound of formula (I) or a pharmaceutically acceptable salt or solvate thereof to a different compound of formula (I) or a pharmaceutically acceptable salt or solvate thereof.

As will be apparent to those skilled in the art, the order of the foregoing steps is not critical to the process of the present invention, and may be varied depending on the nature of the substituents. The process may be carried out using any suitable order of steps.

Methods for reacting a compound of formula (VII) with a compound of formula (VIII) or a compound of formula (IX) to prepare a compound of formula (I) are described above.

According to Scheme 2, the compounds of formula (VII) may be prepared by reducing a compound of formula (XIX).

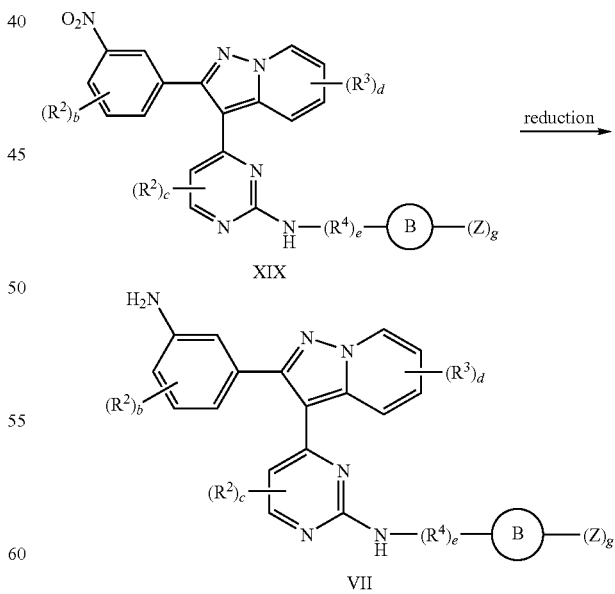

wherein all variables are as defined above.

Conveniently, standard conditions for the reduction of a nitro group may be employed to reduce the nitro group of the compound of formula (XIX) to prepare a compound of formula (VII). An example of suitable reaction conditions for this reduction include, but are not limited to reaction with sodium sulfide nonhydrate in ethanol.

A compound of formula (XIX) may be prepared by reacting a compound of formula (XVIII) with a compound of formula (XI).

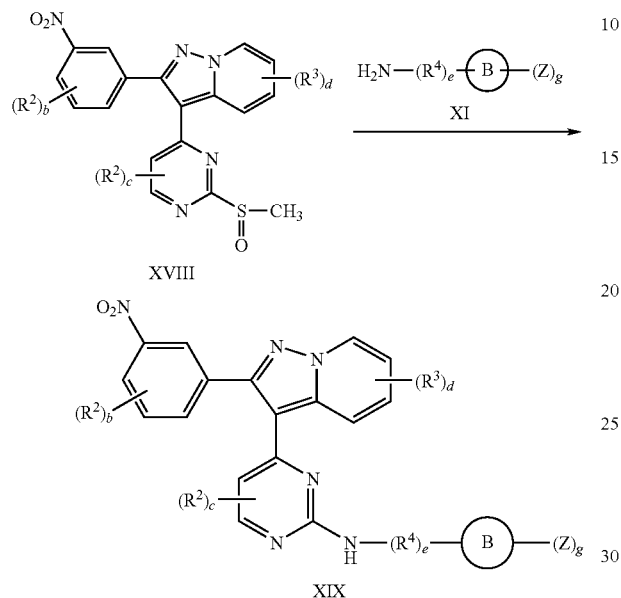

wherein all variables are as defined above.

This reaction is typically carried out by microwave heating of a solution of the compound of formula (XVIII) and a compound of formula (XI) to a temperature of about 120 to 180° C. in a solvent, such as ethanol, with a catalytic amount of an acid, such as hydrochloric acid.

A compound of formula (XVIII) may be prepared by oxidizing a compound of formula (XVII) using standard reagents.

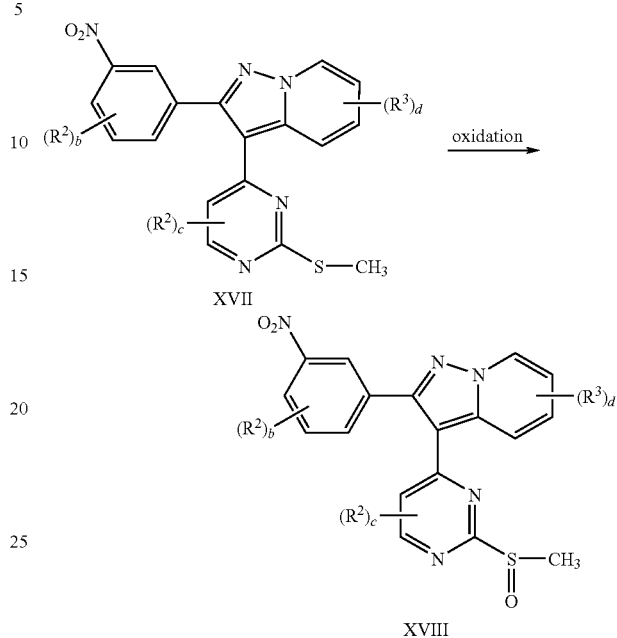

wherein all variables are as defined above.

Examples of suitable oxidation reagents useful for this reaction include but are not limited to 50% meta-chloroperbenzoic acid (mCPBA) in a solvent such as DCM.

The compounds of formula (XVII) may be prepared using procedures analogous to those described above for the preparation of a compound of formula (V).

An alternative method of producing a compound of Formula (I) wherein c is 0 (i.e., a compound of formula (I-D), is shown in Scheme 3, below.

Scheme 3

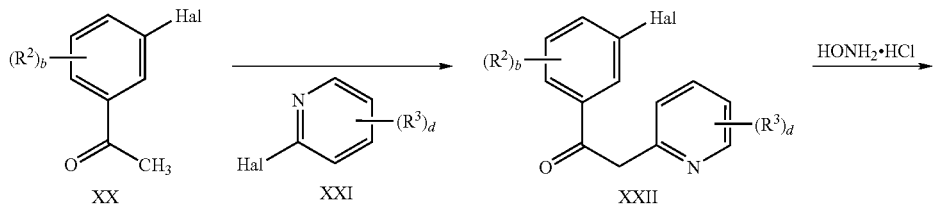

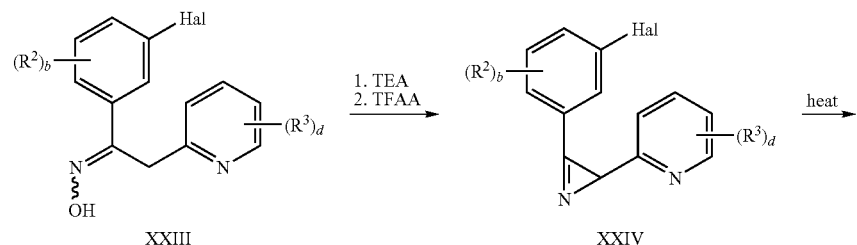

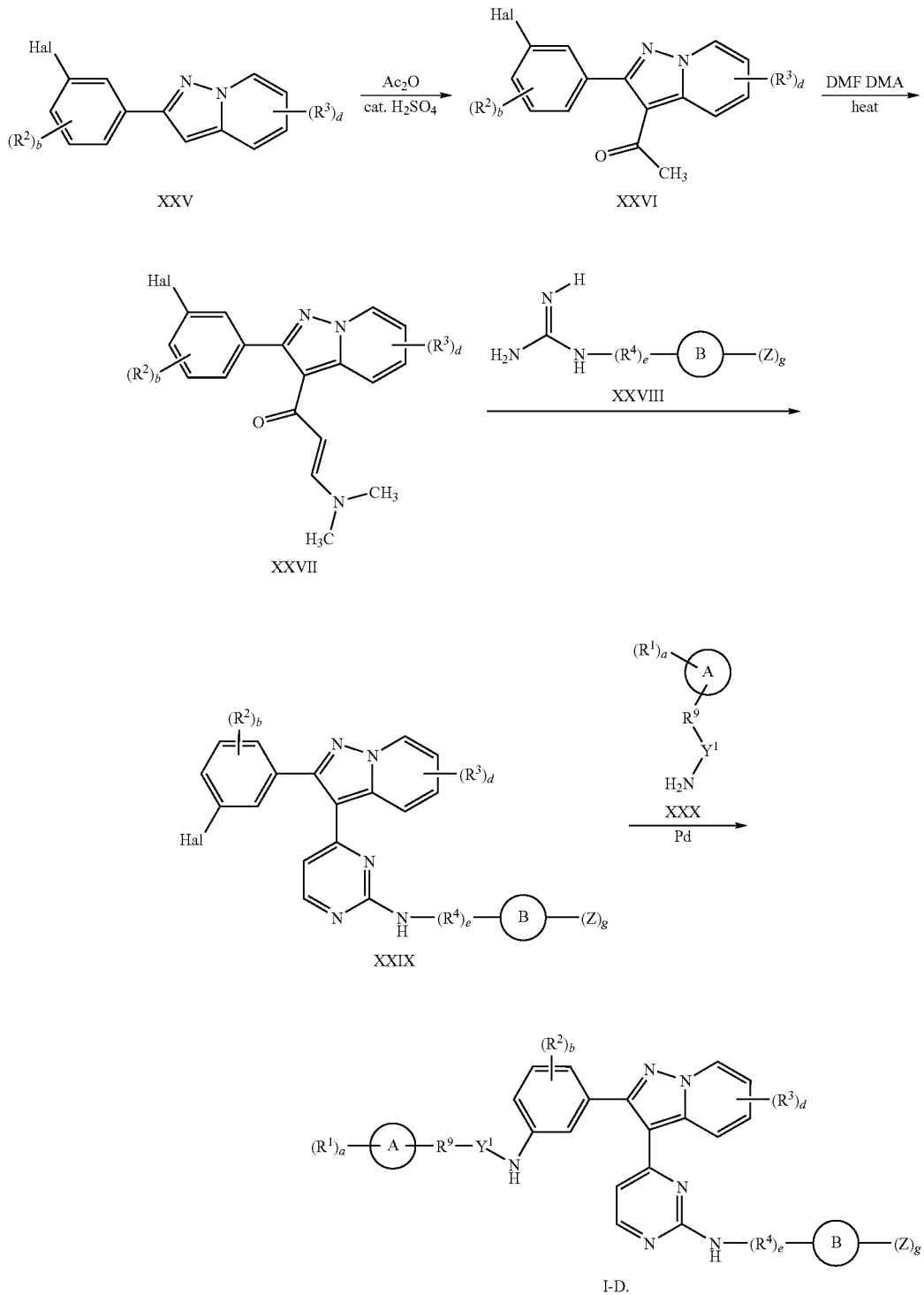

wherein:
each Hal is the same or different halogen; and
all other variables are as defined above.

Generally, the process for preparing the compounds of formula (I) (all formulas and all variables having been defined above) comprises the steps of:

a) reacting the compound of formula (XX) with a compound of formula (XXI) to prepare a compound of formula (XXII);

b) reacting the compound of formula (XXII) with hydroxylamine to prepare a compound of formula (XXIII);

c) reacting the compound of formula (XXIII) with an agent suitable for converting the hydroxylamine to a leaving group in the presence of a base, to prepare a compound of formula (XXIV);

d) heating the compound of formula (XXIV) to prepare a compound of formula (XXV);

e) acetylating the compound of formula (XXV) to prepare a compound of formula (XXVI);

f) reacting the compound of formula (XXVI) with dimethyl formamide dimethyl acetyl to prepare the vinylogous compound of formula (XXVII);

g) reacting with a compound of formula (XXVII) with a compound of formula (XXVIII) with heating to prepare a compound of formula (XXIX);

h) reacting the compound of formula (XXIX) with a compound of formula (XXX) to prepare a compound of formula (I-D);

i) optionally converting the compound of formula (I-D) to a pharmaceutically acceptable salt or solvate thereof; and j) optionally converting the compound of formula (I-D) or a pharmaceutically acceptable salt or solvate thereof to a different compound of formula (I) or a pharmaceutically acceptable salt or solvate thereof.

As will be apparent to those skilled in the art, the order of the foregoing steps is not critical to the process of the present invention, and the process may be carried out using any suitable order of steps. For example, compound of formula (XXVI) may be amidated by a reagent of formula (XXX) prior to formation of the pyrimidine ring through the sequence of reactions outlined in Scheme 3.

More specifically, a compound of formula (I) may be prepared by reacting the compound of formula (XXIX) with a compound of formula (XXX).

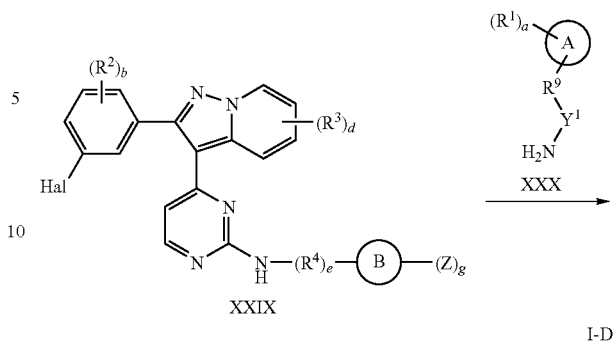

wherein all variables are as defined above.

The reaction is typically carried out by heating a mixture of a compound of formula (XXX) with a compound of formula (XXIX) in the presence of a suitable palladium catalyst such as Pd$_2$dba$_3$ in the presence of a base such as Cs$_2$CO$_3$ with an additive such as Xantphos in a solvent such as 1,4-dioxane. A preferred method of reacting a compound of formula (XXIX) into a compound of formula (XXX) using these conditions is by irradiation in a microwave apparatus at a temperature of at least 150° C.

It will be appreciated by those skilled in the art that a compound of formula (XXX) is an amide derivative such that Y$^1$ contains CO bonded to the amine of the compound in formula (XXX). The reaction may therefore provide a target compound of formula (I) containing an amide such that Y$^1$ is a carbonyl group bonded to the amine.

A compound of formula (XXVI) may be converted to a compound of formula (XXIX) by a two-step procedure of first converting the compound of formula (XXVI) into a vinylogous amide of formula (XXVII) and then reacting the vinylogous amide with a guanidine of formula (XXVIII).

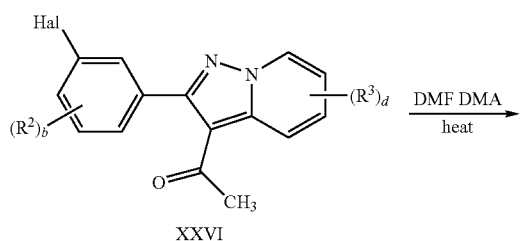

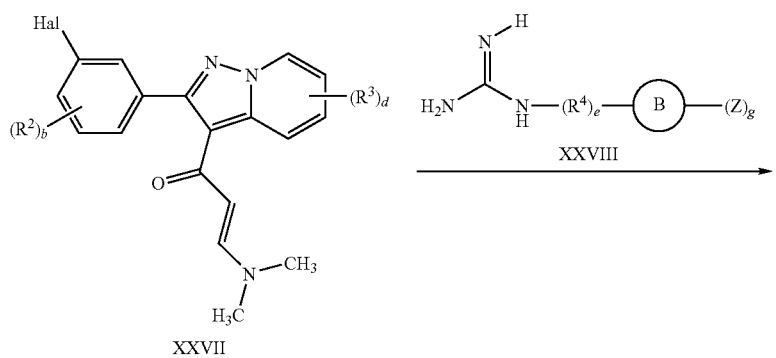

-continued

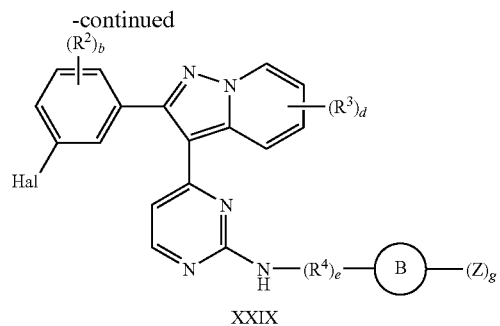

XXIX wherein all variables are as defined above.

The conversion of the compound of formula (XXVI) to the vinylogous amide of formula (XXVII) may be accomplished by heating the compound of formula (XXVI) with a reagent such as dimethylformamide dimethyl acetal at a temperature of around 100° C. Alternative reagents for effecting this transformation include, but are not limited to, dimethylformamide di-tert-butyl acetal.

The reaction of the vinylogous amide of formula (XXVII) with the guanidine of formula (XXVIII) is typically carried out under heating in a solvent such as dioxane in the presence of a base such as triethylamine and potassium carbonate. A preferred method for heating the reaction is irradiating this mixture in a microwave apparatus at a temperature of at least 150° C.

The compound of formula (XXVI) may be prepared by acetylation of a compound of formula (XXV).

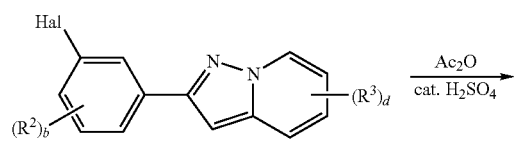

XXV

XXVI wherein all variables are as defined above.

The reaction may be carried out by reacting a compound of formula (XXV) with a suitable acetylating reagent in the presence of an acid catalyst under heating. Preferably, the reaction is heated to a temperature of about 100° C. Examples of suitable acetylating reagents include, but are not limited to acetic anhydride. An example of a suitable acid catalyst is sulfuric acid.

A compound of formula (XXV) may be obtained by heating a compound of formula (XXIV).

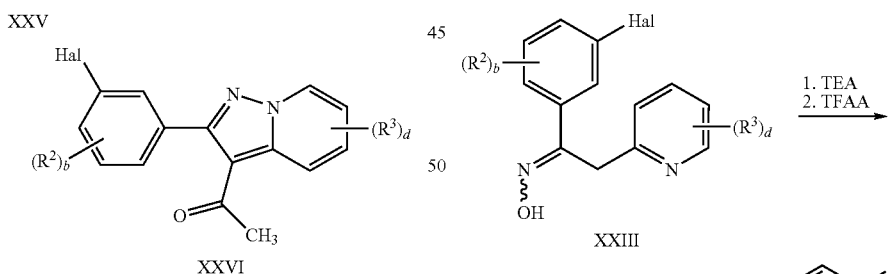

XXIV

XXV

Typically, the reaction is carried out in a solvent such as 1,2-dichloroethane at a temperature of at least 150° C. A useful method of heating a compound of formula (XXIV) to effect this conversion is to use a microwave apparatus.

A compound of formula (XXIV) may be prepared by treatment of a compound of formula (XXIII) with an suitable agent for converting the hydroxylamine moiety into a leaving group in the presence of a base.

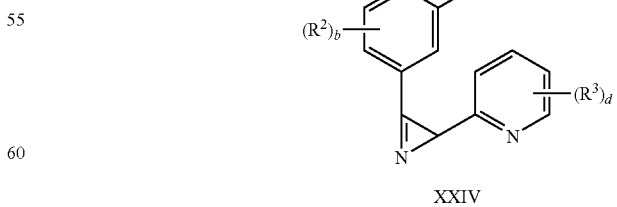

XXIII

XXIV wherein all variables are as defined above.

Suitable agents to affect such a conversion include trifluoroacetic anhydride with a base such as triethylamine in a solvent such as DCM.

A compound of formula (XXIII) may be prepared by reacting a compound of formula (XXII) with hydroxylamine.

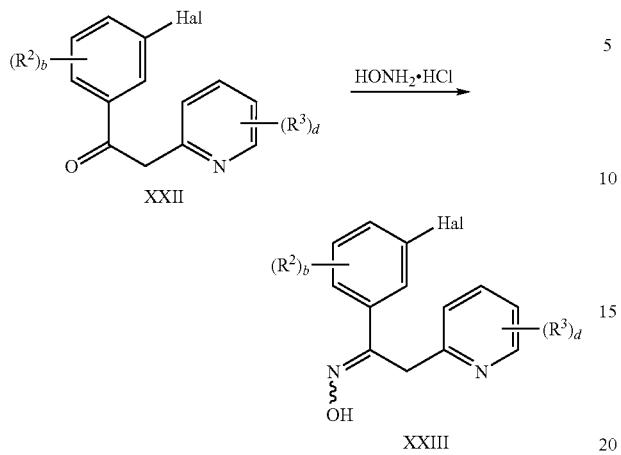

wherein all variables are as defined above.

The reaction may be carried out in a solvent, such as MeOH in the presence of a base, such as sodium hydroxide, and particularly 10% aqueous sodium hydroxide.

The compound of formula (XXII) may be prepared by condensing a compound of formula (XX) with a pyridine compound of formula (XXI).

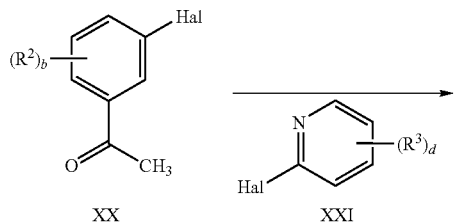

-continued

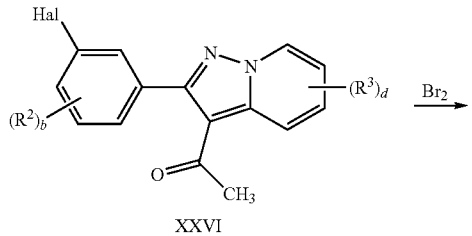

wherein all variables are as defined above.

Suitable conditions for reacting a compound of formula (XX) with a compound of formula (XXI) include, but are not limited to treatment of a compound of formula (XX) with a base such as sodium hydride in a solvent such as tetrahydrofuran and treating this mixture with a compound of formula (XXI). Hal is preferably Br or I in a compound of formula (XX). In a compound of formula (XXI), Hal is preferably Cl.

In a further embodiment of the invention, a compound of formula (I) wherein c is 1 and $R^2$ is F (i.e., a compound of formula (I-E)) may be prepared according to the method shown in Scheme 3a, below. According to this method a compound of formula (XXVI) may be converted into a fluoro derivative of formula (XXXII) via a two-step protocol. The fluoro derivative of formula (XXXII) may be converted to a compound of formula (I-E) using procedures analogous to those described above in Scheme 3.

Scheme 3a

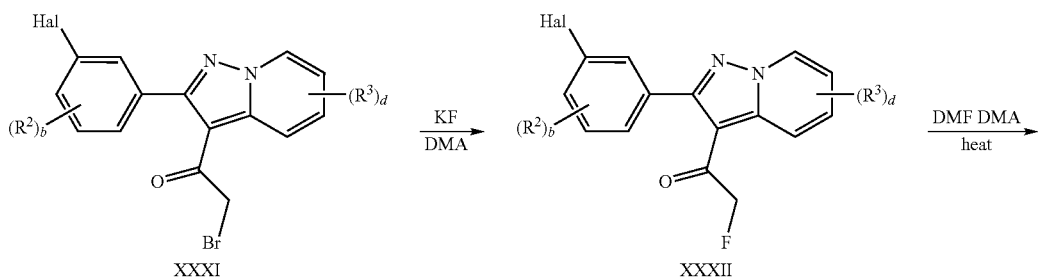

-continued

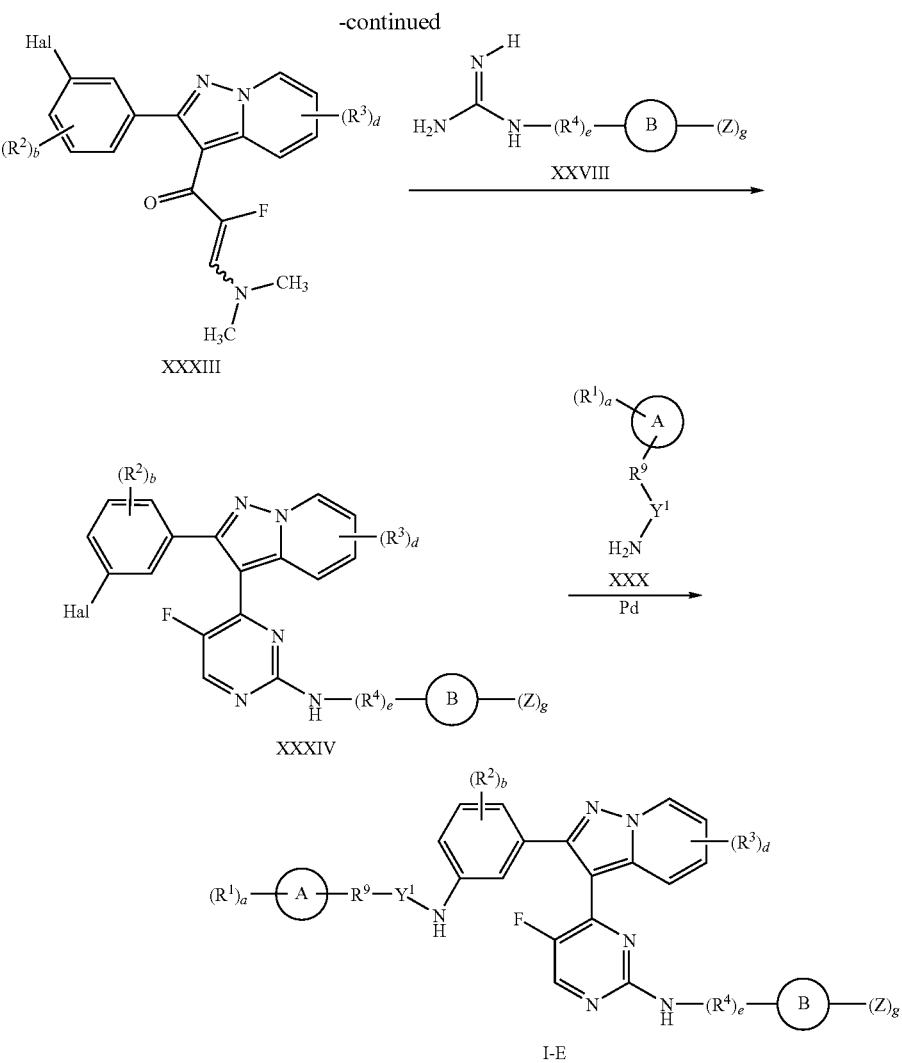

wherein each Hal is the same or different halogen; and all other variables are as defined above.

Generally, the process for preparing the compounds of formula (I) (all formulas and all variables having been defined above) comprises the steps of:

a) brominating the compound of formula (XXVI) to prepare a compound of formula (XXXI);
b) fluorinating the compound of formula (XXXI) to prepare a compound of formula (XXXII);
c) reacting the compound of formula (XXXII) with dimethyl formamide di-tert-butylacetyl to prepare the compound of formula (XXXIII);
d) reacting with a compound of formula (XXXIII) with a compound of formula (XXVIII) with heating to prepare a compound of formula (XXXIV);
e) reacting the compound of formula (XXXIV) with a compound of formula (XXX) to prepare a compound of formula (I-E);
f) optionally converting the compound of formula (I-E) to a pharmaceutically acceptable salt or solvate thereof; and
g) optionally converting the compound of formula (I-E) or a pharmaceutically acceptable salt or solvate thereof to a different compound of formula (I) or a pharmaceutically acceptable salt or solvate thereof.

As will be apparent to those skilled in the art, the order of the foregoing steps is not critical to the process of the present invention, and the process may be carried out using any suitable order of steps.

More specifically, a compound of formula (I-E) may be prepared by reacting the compound of formula (XXXIV) with a compound of formula (XXX) in a manner analogous to the reaction of the compound of formula (XXIX) with a compound of formula (XXX) in Scheme 3 above.

The compound of formula (XXXIV) may be prepared by reacting with a compound of formula (XXXIII) with a compound of formula (XXVIII) with heating in a manner analogous to the reaction of the vinylogous compound of formula (XXVII) with the compound of formula (XXVIII) in Scheme 3 above.

A compound of formula (XXXIII) may be prepared by reacting the compound of formula (XXXII) with dimethyl formamide di-tert-butylacetyl in a manner analogous to the reaction of the compound of formula (XXVI) to prepare the compound of formula (XXVII) in Scheme 3 above.

The compound of formula (XXXII) may be prepared by fluorinating the compound of formula (XXXI).

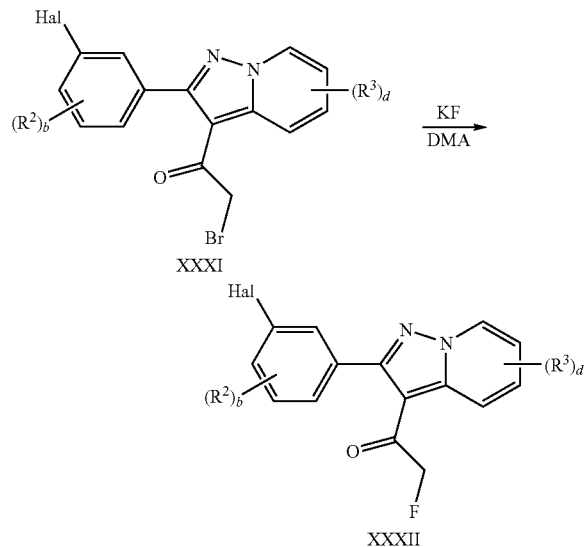

wherein all variables are as defined above.

This reaction may be carried out by treating the bromide compound of formula (XXXI) with a fluorinating reagent such as potassium fluoride in a solvent such as dimethyl acetamide. An example of an appropriate fluorinating reagent includes, but is not limited to potassium fluoride.

The compound of formula (XXXI) may be prepared by brominating the compound of formula (XXVI) with an appropriate brominating agent in a suitable solvent.

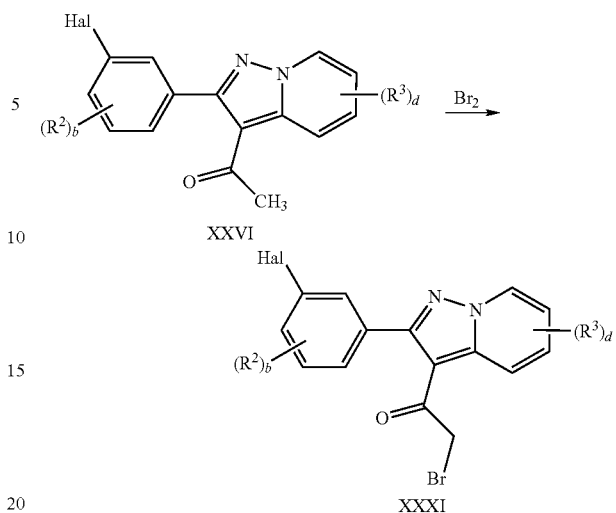

wherein all variables are as defined above.

An example of a brominating agent includes bromine. An example of a suitable solvent is glacial acetic acid.

It will be appreciated by those skilled in the art that choice of the reaction sequence employed to prepare a particular compound of formula (I) may depend upon the specific compound of formula (I) that is desired as well as the availability of starting materials.

As will be apparent to those skilled in the art, a compound of formula (I) may be converted to another compound of formula (I) using techniques well known in the art. For example, one method of converting a compound of formula (I) wherein $Y^1$ is —C(O)— (i.e., a compound of formula (I-A)) to another compound of formula (I) comprises treating a compound of formula (I-A) with Lawesson's reagent.

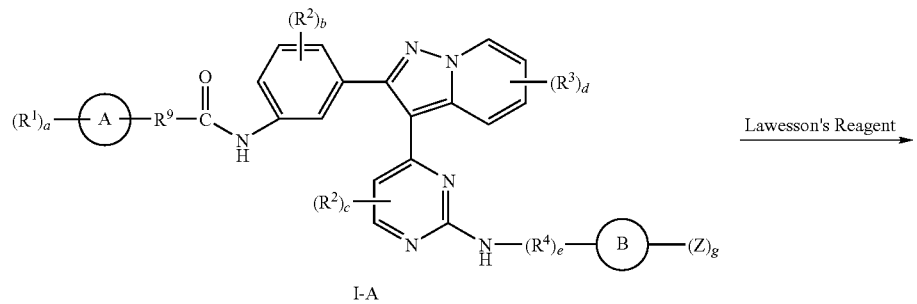

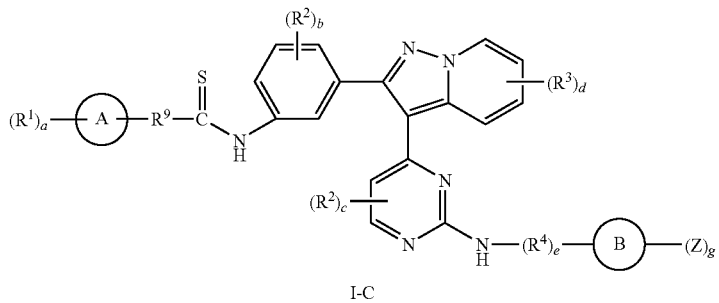

Suitable conditions for this reaction will be apparent to those skilled in the art of organic synthesis.

A compound of formula (I) wherein the moiety Ring B-(Z)$_g$ is a tetrahydroisoquinoline group wherein the tetrahydroisoquinoline amine is a secondary amine may be converted into another compound of formula (I) wherein the amine is a tertiary amine bearing a methyl group. This transformation may be accomplished through a reductive amination procedure. Procedures for reductive amination are well known in the literature and include, for example, stirring the secondary amine bearing compound in a suitable solvent in the presence of aqueous formaldehyde and sodium triacetoxyborohydride and catalytic acid. Examples of suitable solvents include DCM or N,N-dimethylformamide. An example of a suitable acid is acetic acid.

Based upon this disclosure and the examples contained herein one skilled in the art can readily convert a compound of formula (I) or a pharmaceutically acceptable salt or solvate thereof into a different compound of formula (I), or a pharmaceutically acceptable salt or solvate thereof.

The present invention also provides radiolabeled compounds of formula (I) and biotinylated compounds of formula (I) and solid-support-bound versions thereof.

Radiolabeled compounds of formula (I) and biotinylated compounds of formula (I) can be prepared using conventional techniques. For example, radiolabeled compounds of formula (I) can be prepared by reacting the compound of formula (I) with tritium gas in the presence of an appropriate catalyst to produce radiolabeled compounds of formula (I).

In one embodiment, the compounds of formula (I) are tritiated.

The radiolabeled compounds of formula (I) and biotinylated compounds of formula (I) are useful in assays for the identification of compounds which inhibit at least one ErbB family kinase, for the identification of compounds for the treatment of a condition mediated by at least one ErbB family kinase, for the treatment of susceptible neoplasms. Accordingly, the present invention provides an assay method for identifying such compounds, which method comprises the step of specifically binding the radiolabeled compound of formula (I) or the biotinylated compound of formula (I) to the target protein or cellular homogenates. More specifically, suitable assay methods will include competition binding assays. The radiolabeled compounds of formula (I) and biotinylated compounds of formula (I) and solid-support-bound versions thereof, can be employed in assays according to the methods conventional in the art.

The following examples are intended for illustration only and are not intended to limit the scope of the invention in any way, the invention being defined by the claims which follow.

EXAMPLES

As used herein, the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

| | |
|---|---|
| g (grams); | mg (milligrams); |
| L (liters); | mL (milliliters); |
| μL (microliters); | psi (pounds per square inch); |
| M (molar); | mM (millimolar); |
| i.v. (intravenous); | Hz (Hertz); |
| MHz (megahertz); | mol (moles); |
| mmol (millimoles); | rt (room temperature); |
| min (minutes); | h (hours); |
| mp (melting point); | TLC (thin layer chromatography); |
| T$_r$ (retention time); | RP (reverse phase); |
| MeOH (methanol); | i-PrOH (isopropanol); |
| TEA (triethylamine); | TFA (trifluoroacetic acid); |
| TFAA (trifluoroacetic anhydride); | THF (tetrahydrofuran); |
| DMSO (dimethylsulfoxide); | AcOEt (EtOAc); |
| DME (1,2-dimethoxyethane); | DCM (CH$_2$Cl$_2$; dichloromethane); |
| DCE (dichloroethane); | DMF (N,N-dimethylformamide); |
| DMPU (N,N'-dimethylpropyleneurea); | CDI (1,1-carbonyldiimidazole); |
| IBCF (isobutyl CHCl3ate); | HOAc (acetic acid); |
| HOSu (N-hydroxysuccinimide); | HOBT (1-hydroxybenzotriazole); |
| mCPBA (meta-chloroperbenzoic acid); | KOH (potassuim hydroxide); |
| Na$_2$CO$_3$ (sodium carbonate); | NaHCO$_3$ (sodium bicarbonate); |
| LiOH•H$_2$O (lithium hydroxide monohydrate); | K$_2$CO$_3$ (potassium carbonate); |
| CHCl$_3$ (chloroform); | Na$_2$SO$_4$ (sodium sulfate); |
| BOC (tert-butyloxycarbonyl); | Ac (acetyl); |
| DCC (dicyclohexylcarbodiimide); | CBZ (benzyloxycarbonyl); |
| FMOC (9-fluorenylmethoxycarbonyl); | atm (atmosphere); |
| TMSE (2-(trimethylsilyl)ethyl); | TMS (trimethylsilyl); |
| TIPS (triisopropylsilyl); | TBS (t-butyldimethylsilyl); |
| DMAP (4-dimethylaminopyridine); | BSA (bovine serum albumin) |
| ATP (adenosine triphosphate); | HRP (horseradish peroxidase); |
| Ac$_2$O (acetic anhydride); | DMA (dimethyl acetyl); |
| Pd$_2$dba$_3$ (Tris(dibenzylidineacetone)dipalladium (0)); | |
| NaCNBH$_3$ (Sodium cyanoborohydride); | TMSCI (Chlorotrimethylsilane); |
| DMEM (Dulbecco's modified Eagle medium); | |
| HPLC (high pressure liquid chromatography); | |
| BOP (bis(2-oxo-3-oxazolidinyl)phosphinic chloride); | |
| TBAF (tetra-n-butylammonium fluoride); | |
| HBTU (O-Benzotriazole-1-yl-N,N,N',N'-tetramethyluronium hexafluorophosphate); | |
| HEPES (4-(2-hydroxyethyl)-1-piperazine ethane sulfonic acid); | |

DPPA (diphenylphosphoryl azide);
EDC (ethylcarbodiimide hydrochloride); and
EDTA (ethylenediaminetetraacetic acid).

fHNO₃ (fumed HNO₃);

All references to ether are to diethyl ether; brine refers to a saturated aqueous solution of NaCl. Unless otherwise indicated, all temperatures are expressed in ° C. (degrees Centigrade). All reactions are conducted under an inert atmosphere at rt unless otherwise noted.

$^1$H NMR spectra were recorded on a Varian VXR-300, a Varian Unity-300, a Varian Unity-400 instrument, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), br (broad).

Low-resolution mass spectra (MS) were recorded on a JOEL JMS-AX505HA, JOEL SX-102, or a SCIEX-APIiii spectrometer; high resolution MS were obtained using a JOEL SX-102A spectrometer. All mass spectra were taken under electrospray ionization (ESI), chemical ionization (CI), electron impact (EI) or by fast atom bombardment (FAB) methods. Infrared (IR) spectra were obtained on a Nicolet 510 FT-IR spectrometer using a 1-mm NaCl cell. All reactions were monitored by thin-layer chromatography on 0.25 mm E. Merck silica gel plates (60F-254), visualized with UV light, 5% ethanolic phosphomolybdic acid or p-anisaldehyde solution or mass spectrometry (electrospray or AP). Flash column chromatography was performed on silica gel (230-400 mesh, Merck) or using automated silica gel chromatography (Isco, Inc. Sq 16× or 100 sg Combiflash).

Reported HPLC retention times ($T_r$) were obtained on a Waters 2795 instrument attached to a Waters 996 diode array detector reading 210-500 nm. The column used was a Synergi Max-RP (50×2 mm) model #00B-4337-B0. Solvent gradient was 15% MeOH:water to 100% MeOH (0.1% formic acid) over 6 min. Flow rate was 0.8 mL/min. Injection volume was 3 microliters.

Example 1

N-{3-[3-(2-{[3-(1,3-oxazol-5-yl)phenyl]amino}-4-pyrimidinyl)pyrazolo[1,5-a]pyridin-2-yl]phenyl}-2-(2-thienyl)acetamide

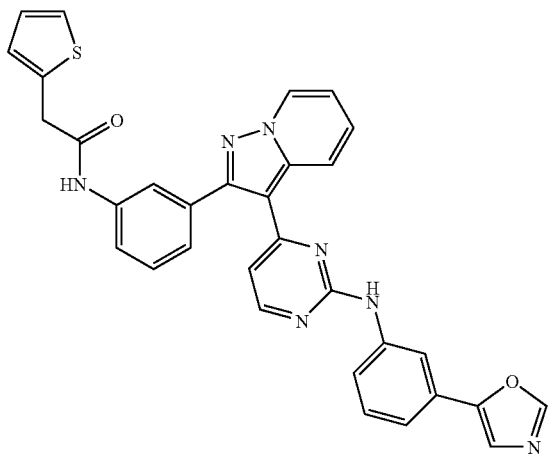

Step A:
N-(3-Ethynyl-phenyl)-2,2,2-trifluoro-acetamide

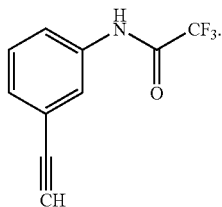

To a solution of 3-ethynyl aniline (10 g, 86 mmol) in DCM cooled to 0° C. was added TEA (17 mL, 128 mmol) and TFAA (14.3 mL, 102 mmol). When TLC showed the reaction to be complete, the solution was diluted with DCM and water. The layers were separated. The organic phase was washed with water and brine, dried over MgSO₄ and concentrated to give the title compound as an off-white solid which was used crude in the next reaction. $^1$H NMR (400 MHz, d₆-DMSO): δ 11.32 (s, 1H), 7.78 (d, J=1.6 Hz, 1H), 7.67 (d, J=8.0 Hz, 1H), 7.41 (t, J=8.0 Hz, 1H), 7.32 (m, 1H), 4.25 (s, 1H) ppm.

Step B: N-[3-(2-Chloro-pyrimidin-4-ylethenyl)-phenyl]-2,2,2-trifluoro-acetamide

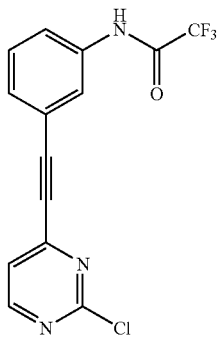

To a mixture of 2,4-dichloropyrimidine (14.5 g, 97.5 mmol), dichlorobis(triphenyl-phosphine)palladium(II) (1.3 g, 2.6 mmol), and copper(I) iodide (25 mg, 0.13 mmol) in degassed THF was added TEA (34 mL, 263 mmol), and the mixture was heated to 50° C. A solution of N-(3-ethynyl-phenyl)-2,2,2-trifluoro-acetamide (14 g, 65 mmol) in THF was added to the mixture over 45 minutes. After several h, the reaction was cooled to rt and diluted with DCM. The organic mixture was washed with water and brine, dried over MgSO₄ and concentrated. The crude material was purified through silica to give the title compound as an off-white solid. $^1$H NMR (400 MHz, d₆-DMSO): δ 11.43 (s, 1H), 8.83 (d, J=4.8 Hz, 1H), 8.00 (s, 1H), 7.80 (d, J=4.8 Hz, 1H), 7.76 (m, 1H), 7.54-7.52 (m, 2H).

Step C: N-{3-[3-(2-Chloro-4-pyrimidinyl)pyrazolo[1,5-a]pyridin-2-yl]phenyl}-2,2,2-trifluoroacetamide

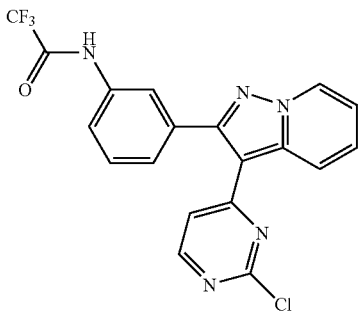

N-[3-(2-Chloro-pyrimidin-4-ylethenyl)-phenyl]-2,2,2-trifluoro-acetamide (9.14 g, 28.1 mmol), N-aminopyridinium iodide (6.24 g, 28.1 mmol), KOH (1.57 g, 28.9 mmol) and K$_2$CO$_3$ (7.76 g) were stirred in DMSO (175 mL) until all starting material was consumed by LC/MS analysis. Reaction was poured into water to yield a precipitate which was filtered off, washed well with water and dried. Crude product was triturated in EtOAc and filtered to yield 7.45 g of the title compound, R$_f$=0.2 (2:1 Hexanes/EtOAc).

Step D: 2,2,2-Trifluoro-N-{3-[3-(2-{[3-(1,3-oxazol-5-yl)phenyl]amino}-4-pyrimidinyl)pyrazolo[1,5-a]pyridin-2-yl]phenyl}acetamide hydrochloride

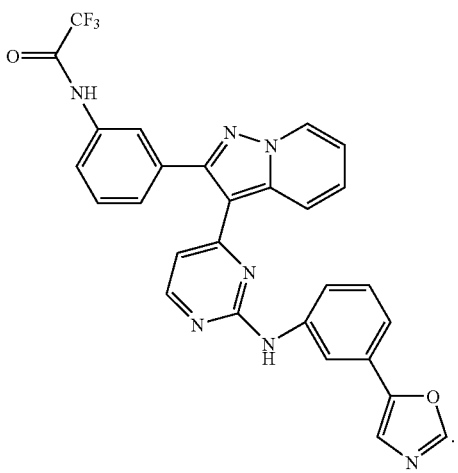

To a mixture of N-{3-[3-(2-chloro-4-pyrimidinyl)pyrazolo[1,5-a]pyridin-2-yl]phenyl}-2,2,2-trifluoroacetamide (0.5 g, 1.2 mmol) in i-PrOH (4 mL) was added 5-(3-aminophenyl)oxazole (0.25 g, 1.56 mmol) and 2 drops of conc. HCl. The reaction was heated in a microwave to 120° C. for 40 min. and allowed to cool to rt. The resulting solid was filtered off, washed with i-PrOH and dried to give the title compound as a tan solid (0.68 g) in 98% yield. ES-LC/MS m/z=542 [M+H]$^+$.

Step E: 4-[2-(3-Aminophenyl)pyrazolo[1,5-a]pyridin-3-yl]-N-[3-(1,3-oxazol-5-yl)phenyl]-2-pyrimidinamine

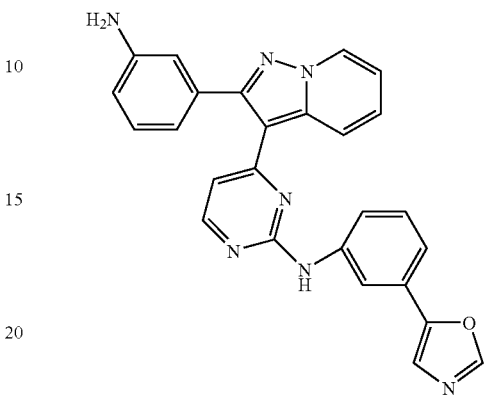

A solution of 2,2,2-trifluoro-N-{3-[3-(2-{[3-(1,3-oxazol-5-yl)phenyl]amino}-4-pyrimidinyl)pyrazolo[1,5-a]pyridin-2-yl]phenyl}acetamide hydrochloride (0.68 g, 1.26 mmol) and LiOH (69 mg, 1.64 mmol) in THF (15 mL) and water (5 mL) was stirred for 6 h at 50° C. The reaction was extracted with DCM. The combined organic phases were dried over MgSO$_4$ and evaporated down to give the title compound as a tan solid, (0.55 g, 98% yield). $^1$H NMR (400 MHz, d$_6$-DMSO): δ 9.73 (s, 1H), 8.82 (d, J=6.7 Hz, 1H), 8.60 (d, J=8.9 Hz, 1H), 8.42 (s, 1H), 8.29 (d, J=5.3 Hz, 1H), 8.24 (s, 1H), 7.76 (d, J=7.7 Hz, 1H), 7.61 (s, 1H), 7.35-7.44 (m, 3H), 7.10-7.19 (m, 2H), 6.83 (s, 1H), 6.69-6.73 (m, 2H), 6.58 (d, J=5.3 Hz, 1H), 5.30 (bs, 2H) ppm. ES-LC/MS m/z=446 [M+H]$^+$.

Step F: N-{3-[3-(2-{[3-(1,3-Oxazol-5-yl)phenyl]amino}-4-pyrimidinyl)pyrazolo[1,5-a]pyridin-2-yl]phenyl}-2-(2-thienyl)acetamide (title compound)

To a stirred solution of 4-[2-(3-aminophenyl)pyrazolo[1,5-a]pyridin-3-yl]-N-[3-(1,3-oxazol-5-yl)phenyl]-2-pyrimidinamine (100 mg, 0.22 mmol) in 1 mL THF was added 2-thiopheneacetyl chloride (40 mg, 0.25 mmol). After 15 min. LC/MS indicated the reaction was complete and several equivalents of PS-trisamine were added and the mixture was stirred for 16 h followed by addition of 25 mg of TEA. The mixture was filtered and the resin washed well with THF. The filtrate was concentrated and the crude purified by HPLC (Agilent, 50-90% gradient over 15 min.) to give the title compound (45 mg, 36% yield). $^1$H NMR (400 MHz, d$_6$-DMSO) δ 10.34 (s, 1H), 9.71 (s, 1H), 8.81 (d, J=6.8 Hz, 1H), 8.49 (d, J=8.6 Hz, 1H), 8.18-8.37 (m, 3H), 7.87 (s, 1H), 7.67-7.72 (m, 2H), 7.54 (s, 1H), 7.24-7.42 (m, 6H), 7.09 (t, J=6.9 Hz, 1H), 6.93-6.95 (m, 2H), 6.49 (d, J=5.3 Hz, 1H), 3.84 (s, 2H) ppm. ES-LC/MS m/z=570 [M+H]$^+$

Example 2

N-[3-(3-{2-[(4-{[3-(Dimethylamino)propyl]amino}-3-fluorophenyl)amino]-4-pyrimidinyl}pyrazolo[1,5-a]pyridin-2-yl)phenyl]-2-(2-thienyl)acetamide

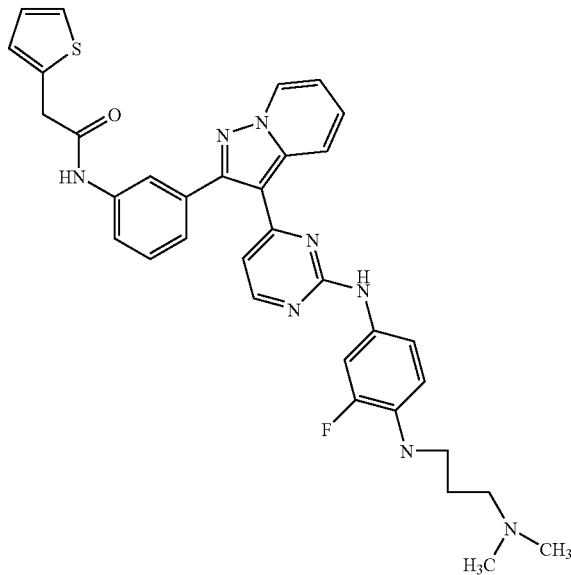

Step A: {3-[3-(2-Chloro-4-pyrimidinyl)pyrazolo[1,5-a]pyridin-2-yl]phenyl}amine

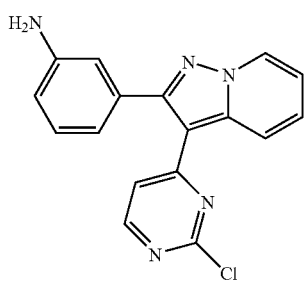

A solution of N-{3-[3-(2-chloro-4-pyrimidinyl)pyrazolo[1,5-a]pyridin-2-yl]phenyl}-2,2,2-trifluoroacetamide (1.0 g, 2.4 mmol) (see Example 1, step C) and LiOH (125 mg, 3.0 mmol) in THF (25 mL) and water (8 mL) was stirred for 2 h at 50° C. The reaction was extracted with DCM. The combined organic phases were dried over MgSO$_4$ and evaporated down to give the title compound as a yellow solid, (0.79 g, 99% yield). $^1$H NMR (400 MHz, d$_6$-DMSO): δ 8.90 (d, J=6.7 Hz, 1H), 8.47 (d, J=5.3 Hz, 1H), 8.45 (s, 1H), 7.66 (t, J=7.9 Hz, 1H), 7.22 (dt, J=1.3, 6.9 Hz, 1H), 7.17 (d, J=7.7 Hz, 1H), 7.08 (d, J=5.5 Hz, 1H), 6.75-6.79 (m, 1H), 6.71 (t, J=7.9 Hz, 2H), 5.32 (bs, 2H) ppm. ES-LC/MS m/z=322, 324 [M+H]$^+$.

Step B: N-{3-[3-(2-Chloro-4-pyrimidinyl)pyrazolo[1,5-a]pyridin-2-yl]phenyl}-2-(2-thienyl)acetamide

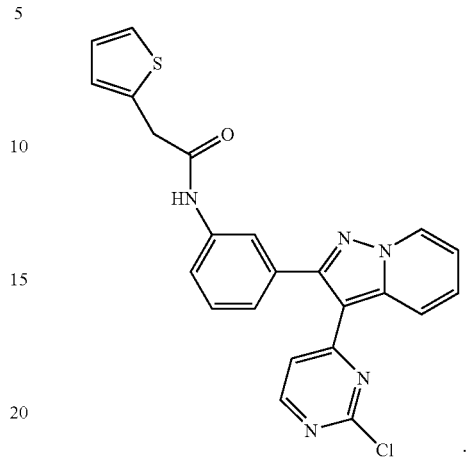

To a stirred solution of {3-[3-(2-chloro-4-pyrimidinyl)pyrazolo[1,5-a]pyridin-2-yl]phenyl}amine (200 mg, 0.62 mmol) and TEA (64 mg, 0.63 mmol) in THF (25 mL) was added dropwise 2-thiopheneacetyl chloride (118 mg, 0.73 mmol). After stirring for 20 min., 15 min. LC/MS analysis indicated the reaction was complete and several equivalents of PS-trisamine were added and the mixture was stirred for 16 h followed by addition of 25 mg of TEA. The mixture was then filtered and the resin washed well with THF. The filtrate was concentrated and the crude partitioned between water and DCM. The layers were separated, and the aqueous was extracted with DCM. The organics were combined, filtered over MgSO$_4$, filtered, reduced in vacuo to yield the title compound (270 mg, 98% yield). $^1$H NMR (400 MHz, d$_6$-DMSO) δ 10.41 (s, 1H), 8.92 (d, J=6.9 Hz, 1H), 8.48 (d, J=5.3 Hz, 1H), 8.43 (d, J=9.0 Hz, 1H), 7.91 (s, 1H), 7.78 (d, J=8.1 Hz, 1H), 7.67 (t, J=7.3 Hz, 1H), 7.49 (t, J=7.9 Hz, 1H), 7.40-7.43 (m, 1H), 7.31 (d, J=6.8 Hz, 1H), 7.24 (dt, J=1.1, 6.8 Hz, 1H), 7.07 (d, J=55 Hz, 1H), 6.99-7.01 (m, 2H), 3.91 (s, 2H) ppm. ES-LC/MS m/z=446, 448 [M+H]$^+$.

Step C: N'-(2-Fluoro-4-nitrophenyl)-N,N-dimethyl-1,3-propanediamine[3-(dimethylamino)propyl](2-fluoro-4-nitrophenyl)amine

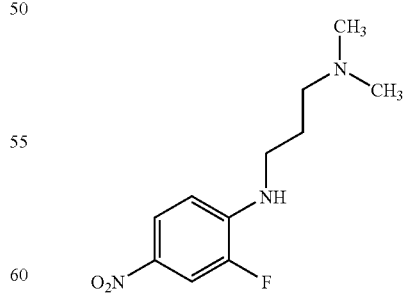

To a solution of 1,2-difluoro-4-nitrobenzene (1 g, 6.28 mmol) in THF (62 mL) was added TEA (1.58 g, 15.7 mmol), followed by N/N-dimethyl-1,3-propanediamine (0.77 g, 7.54 mmol) and the resulting reaction was stirred at rt for 18 h. The reaction was diluted with EtOAc, and quenched with sat aq.

NaHCO$_3$. The layers were separated, and the aqueous was extracted with EtOAc. The organics were combined, filtered over MgSO$_4$, filtered, reduced in vacuo onto silica gel. Purification using ISCO chromatography (hexanes: EtOAc) afforded a yellow solid as the desired product. ES-LC/MS m/z=242 [M+H]$^+$.

Step D: N$^1$-[3-(Dimethylamino)propyl]-2-fluoro-1,4-benzenediamine

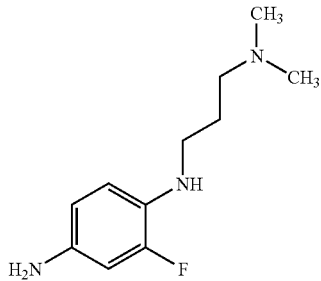

(Dimethylamino)propyl](2-fluoro-4-nitrophenyl)amine hydrochloride (8.2 g, 34 mmol) was dissolved into EtOAc (100 mL) and treated with Pd/C (10%, 1.8 g, 1.7 mmol), placed at RT under 1 atm of H$_2$. The reaction was allowed to stir for 24 h. The reaction was treated with celite, and the resulting slurry was filtered over celite. The filtrate was reduced in vacuo to afford the intermediate aniline as a dark-red oil. This was dissolved into diethyl ether (15 mL) and cooled in ice-water and 1M hydrogen chloride in diethyl ether (34 mL) was added dropwise with stirring. Stirring as continued for 20 min. and the resulting white-grey solid was then filtered off and washed with ether to yield the title compound (6.56 g, 78% yield). $^1$H NMR (400 MHz, d$_6$-DMSO) δ 6.53 (t, J=9.3 Hz, 1H), 6.41 (dd, J=2.1, 13.6 Hz, 1H), 6.32 (d, J=8.5 Hz, 1H), 3.00-3.08 (m, 4H), 2.68 (s, 6H), 1.85-1.92 (m, 2H) ppm. ES-LC/MS m/z=212 [M+H]$^+$.

Step E: N-[3-(3-{2-[(4-{[3-(Dimethylamino)propyl]amino}-3-fluorophenyl)amino]-4-pyrimidinyl}pyrazolo[1,5-a]pyridin-2-yl)phenyl]-2-(2-thienyl)acetamide (title compound)

To a slurry of N-{3-[3-(2-chloro-4-pyrimidinyl)pyrazolo[1,5-a]pyridin-2-yl]phenyl}-2-(2-thienyl)acetamide (100 mg, 0.22 mmol.) in i-PrOH (4 mL) was added N$^1$-[3-(dimethylamino)propyl]-2-fluoro-1,4-benzenediamine (75 mg, 0.30 mmol) and 2 drops of conc. HCl. The reaction was heated in a microwave to 120° C. for 20 min. and allowed to cool to rt. A second batch of N$^1$-[3-(dimethylamino)propyl]-2-fluoro-1,4-benzenediamine (75 mg, 0.30 mmol) was added and the reaction microwaved to 120° C. for 1 h further. The reaction was concentrated and the crude purified by HPLC (Agilent, 50-90% gradient over 15 min.) to give the title compound (50 mg, 36% yield) as an oil which solidified to a dark green solid. $^1$H NMR (400 MHz, d$_6$-DMSO) δ 10.33 (s, 1H), 9.27 (s, 1H), 8.79 (d, J=7.0 Hz, 1H), 8.42 (bd, J=6.8 Hz, 1H), 8.15-8.17 (m, 2H), 7.85 (s, 1H), 7.71 (d, J=8.4 Hz, 1H), 7.51 (d, J=14.3 Hz, 1H), 7.35-7.43 (m, 3H), 7.23 (d, J=7.5 Hz, 1H), 7.18 (d, J=8.6 Hz, 1H), 7.08 (t, J=7.8 Hz, 1H), 6.93-6.95 (m, 2H), 6.60 (t, J=9.4 Hz, 1H), 6.38 (d, J=5.3 Hz, 1H), 3.84 (s, 2H), 3.05 (t, J=7.0 Hz, 2H), 2.37 (t, J=7.0 Hz, 2H), 2.18 (s, 6H), 1.69 (quintet, J=7.0 Hz, 2H) ppm. ES-LC/MS m/z=621 [M+H]$^+$.

Example 3

2-Phenyl-N-(3-{3-[2-(phenylamino)-4-pyrimidinyl]pyrazolo[1,5-a]pyridin-2-yl}phenyl)acetamide

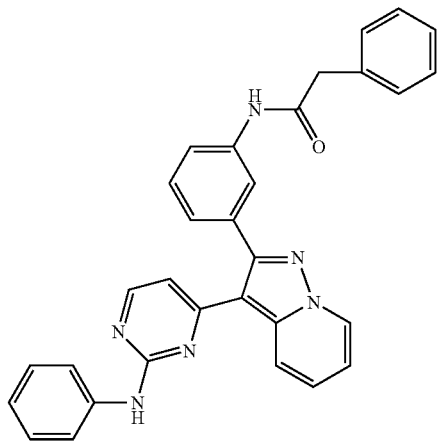

Step A: Trimethyl[(3-nitrophenyl)ethynyl]silane

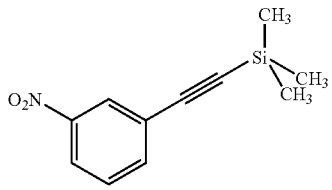

3-Nitroiodebenzene (50 g, 0.201 mol) and diisopropylamine (56.3 mL, 0.402 mol) are dissolved in dry THF (1000 mL) and argon gas was bubbled through the solution for 20 min. Copper (I) iodide (3.83 g, 0.02 mol) and bis(triphenylphosphine)palladium dichloride (7.05 g, 0.01 mol) was added and then trimethylsilylacetylene (31.2 mL, 0.221 mol) was added dropwise over about 30 min with the temperature being maintained at about 25° C. Following complete addition, the mixture was stirred at rt overnight. The mixture was filtered and washed with THF. The filtrate was concentrated under reduced pressure. The residue was purified via silica-gel chromatography with hexane/EtOAc (20/1) to give the title compound (43.22 g) as a pale-brown solid.

Step B: 1-Ethynyl-3-nitrobenzene

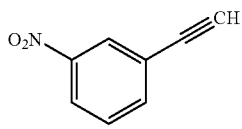

A solution of 1-(3-nitrophenyl)-2-trimethylsilylacetylene (43 g, 0.197 mol) in diethylether (800 mL) was cooled to 0° C. under argon atmosphere. To this solution was added a solution of TBAF (1M in THF, 217 mL, 0.217 mol), dropwise over 30 min, while maintaining the temperature below 10° C.

The reaction mixture was stirred for 30 min at 0° C. The reaction mixture was poured into water and extracted twice with diethyl ether. The organic layers were combined, washed with brine, and dried with $Na_2SO_4$. The solvents were removed under reduced pressure. The residue was purified by silica-gel chromatography with Hexane/EtOAc=20/1 to give the title compound as an orange oil (26 g).

Step C: 4-Iodo-2-(methylthio)pyrimidine

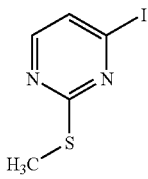

4-Chloro-2-methylthiopyrimidine (40 g, 249 mmol) was added to hydroiodic acid (57% in water, 200 mL). The suspension was vigorously stirred in the absence of light for 72 h at rt. A bright yellow solid formed which was collected by filtration. The solid was added to saturated aqueous $NaHCO_3$ (500 mL) and stirred for 2 min. This was extracted with chloroform (600 mL), the aqueous solution separated and further extracted 2 times with chloroform (350, then 300 mL). The organic extracts were combined, washed with water (100 mL), dried over $MgSO_4$ and filtered. The organic solvent was removed in vacuo to give a colorless oil. Addition of n-hexane and removal of solvent produced the title compound as a white solid (57.9 g, 230 mmol, 92%).

Step D: 2-(Methylthio)-4-[(3-nitrophenyl)ethynyl] pyrimidine

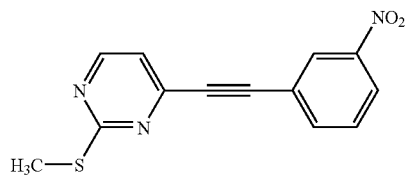

4-Iodo-2-(methylthio)pyrimidine (39.7 g, 0.157 mol) and diisopropylamine (44.2 mL, 0.315 mol) were dissolved in dry THF (720 mL) and argon gas was bubbled through the solution for 20 min. Copper(I) iodide (2.99 g, 14.3 mmol) and bis(triphenylphosphine)palladium dichloride (5.51 g, 7.85 mmol) were added and then 1-ethynyl-3-nitrobenzene (25.4 g, 0.173 mol) in dry THF (100 mL) was added dropwise over about 30 min with the temperature being maintained at about 25° C. Following complete addition, the mixture was stirred at rt overnight. The mixture is filtered and washed with THF. The filtrate is concentrated under reduced pressure. The residue was washed with EtOAc/MeOH to give pale-yellow solid (42 g).

Step E: 3-[2-(Methylthio)-4-pyrimidinyl]-2-(3-nitrophenyl)pyrazolo[1,5-a]pyridine

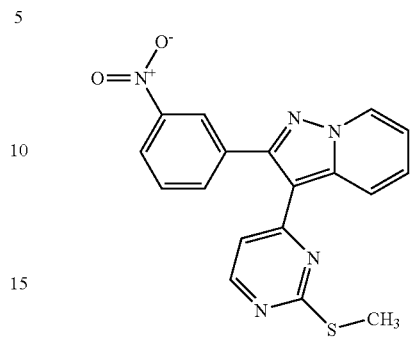

To a 0° C. solution of 2-(methylthio)-4-[(3-nitrophenyl) ethynyl]pyrimidine (4.0 g, 14.7 mmol) and N-aminopyridinium iodide (6.53 g, 29.4 mmol) in DCM (150 mL) was added potassium hydroxide (2.06 g, 36.8 mmol) in water (50 mL). The reaction was allowed to warm to rt and stirred for 16 h. The mixture was diluted with DCM and water. The organic layer was separated and the aqueous layer is extracted with DCM. The combined organic layers were dried over $MgSO_4$, filtered and concentrated to give a dark solid. The residue was dissolved in DCM and MeOH was added until the product formed as a precipitate. The product was collected by filtration and dried to supply the title compound (2.02 g) as an off-white solid. $^1$H NMR (400 MHz, $d_6$-DMSO): δ 11.36 (s, 1H), 8.62 (d, 1H, J=9.2), 8.54 (d, 1H, J=5.6), 7.94 (s, 1H), 7.82 (d, 1H, J=8.8), 7.54 (t, 1H, J=8.0), 7.46 (d, 1H, J=9.2), 7.16 (d, 1H, J=5.2), 2.59 (s, 3H).

Step F: 3-[2-(Methylsulfinyl)-4-pyrimidinyl]-2-(3-nitrophenyl)pyrazolo[1,5-a]pyridine

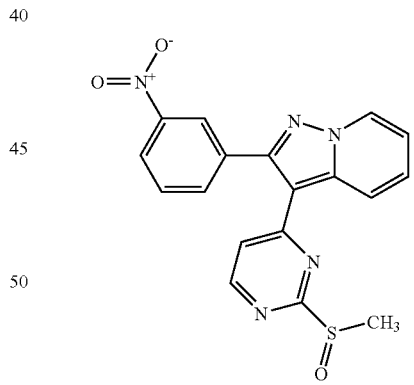

To a solution of 3-[2-(methylthio)-4-pyrimidinyl]-2-(3-nitrophenyl)pyrazolo[1,5-a]pyridine (0.82 g, 2.26 mmol) in DCM (22 mL) was added a solution of 50% mCPBA (818 mg, 2.37 mmol) in DCM (6 mL) through an addition funnel. The reaction was stirred for 10 minutes and saturated aqueous $NaHCO_3$ and the layers were separated. The aqueous layer was extracted with DCM, and the combined organic layers were dried over $MgSO_4$, filtered and concentrated. The residue is purified by silica gel chromatography (50% EtOAC/ hexanes eluant) to provide the product (567 mg) as a yellow solid. $^1$H NMR (400 MHz, $d_6$-DMSO) δ 8.93 (d, 1H, J=6.8), 8.68 (d, 1H, J=5.6), 8.57 (d, 1H, J=8.8), 8.44 (s, 1H, 8.37-8.35

(m, 1H, 8.08 (d, 1H, J=7.6), 7.78 (t, 1H, J=8.0), 7.61-7.65 (m, 1H), 7.21-7.26 (m, 2H), 2.84 (s, 3H).

Step G: 4-[2-(3-Nitrophenyl)pyrazolo[1,5-a]pyridin-3-yl]-N-phenyl-2-pyrimidinamine

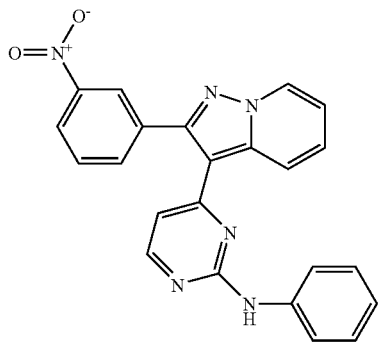

3-[2-(Methylsulfinyl)-4-pyrimidinyl]-2-(3-nitrophenyl) pyrazolo[1,5-a]pyridine (1.5 g, 3.9 mmol) was dissolved in aniline (5 mL). The dark mixture was heated at 100° C. for 5 h. The mixture was cooled and EtOAc (20 mL) and 1N HCl (10 mL) was added. The aqueous layer was extracted with EtOAc (20 mL) and the organic extracts combined, washed with 1N HCl, (15 mL), brine (10 mL), dried over MgSO$_4$ and filtered. The organic solvent was removed in vacuo. The crude material was purified by silica gel chromatography (30-50% EtOAc/hexanes) to give the titled product (830 mg, 52% yield). $^1$H NMR (400 MHz, d$_6$-DMSO) δ 6.58 (d, 1H, J=5.3 Hz), 6.98 (m, 1H), 7.05 (m, 1H), 7.19 (brs, 1H), 7.28-7.36 (m, 3H), 7.57-7.63 (m, 3H), 8.00 (m, 1H), 8.25-8.31 (m, 3H), 8.54 (m, 1H), 8.69 (m, 1H); ES-LC/MS: m/z (M+H)=409.

Step H: 4-[2-(3-Aminophenyl)pyrazolo[1,5-a]pyridin-3-yl]-N-phenyl-2-pyrimidinamine

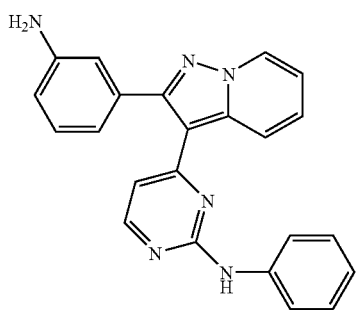

To a solution of 4-[2-(3-nitrophenyl)pyrazolo[1,5-a]pyridin-3-yl]-N-phenyl-2-pyrimidinamine (809 mg, 1.98 mmol) in 1,4-dioxane (16 mL) was added sodium sulfide nonhydrate (1.05 g, 6 mmol) in water (4 mL). The mixture was heated at 90° C. for 5 h, allowed to cool to rt and concentrated in vacuo. The residue was diluted with EtOAc and water. The organic layer was separated and the aqueous layer is extracted with EtOAc. The combined organic layers were dried over MgSO$_4$, filtered and concentrated to give a dark solid. The crude material was purified by silica gel chromatography (hexanes/EtOAc 30-50%) to afford the titled product (462 mg, 62% yield). $^1$H NMR (400 MHz, CDCl$_3$): δ 3.75 (brs, 2H), 6.63 (d, 1H, J=5.3 Hz), 6.78 (m, 1H), 6.91 (m, 1H), 6.96-7.00 (m, 2H), 7.06 (m, 1H), 7.16 (m, 1H), 7.22-7.36 (m, 4H), 7.65 (m, 1H), 8.17 (d, 1H, J=5.3 Hz), 8.42 (m, 1H), 8.52 (m, 1H); ES-LC/MS m/z=379 [M+H]$^+$.

Step I: 2-Phenyl-N-(3-{3-[2-(phenylamino)-4-pyrimidinyl]pyrazolo[1,5-a]pyridin-2-yl}phenyl)acetamide (title compound)

To a solution of 4-[2-(3-aminophenyl)pyrazolo[1,5-a]pyridin-3-yl]-N-phenyl-2-pyrimidinamine (40 mg, 0.1 mmol) in DCM (1.2 mL) was added phenacyl chloride (0.017 mL, 0.11 mmol). When TLC showed the reaction to be complete, the solution was diluted with DCM and washed with a solution of saturated NaHCO$_3$ and with brine. The organic phase was dried over MgSO$_4$ and concentrated. The crude material was purified by silica gel chromatography (hexanes/EtOAc: 30-50%) to give the title compound as a brownish solid (25 mg, 50% yield). $^1$H NMR (400 MHz, DMSO-d6): δ 3.65 (s, 2H), 6.52 (d, 21H, J=5.3 Hz), 6.92 (m, 1H), 7.12 (m, 2H), 7.21-7.26 (m, 4H), 7.30-7.33 (m, 4H), 7.41 (m, 1H), 7.48 (m, 1H), 7.69 (m, 2H), 7.75 (m, 1H), 7.90 (m, 1H), 7.90 (s, 1H), 8.26 (d, 1H, J=5.3 Hz), 8.47 (m, 1H), 8.83 (m, 1H), 9.56 (s, 1H), 10.34 (s, 1H); ES-LC/MS m/z=497 [M+H]$^+$.

Example 4

N-(3-{3-[2-(Phenylamino)-4-pyrimidinyl]pyrazolo[1,5-a]pyridin-2-yl}phenyl)-2-(2-thienyl)acetamide

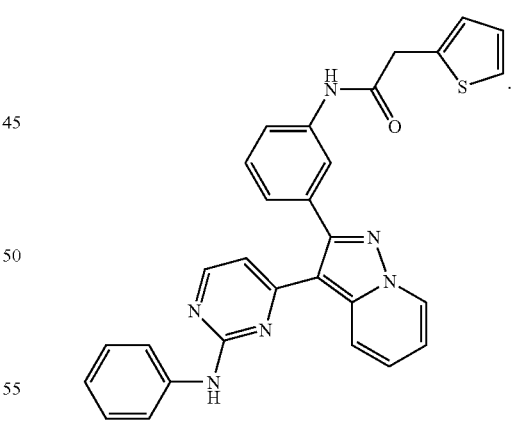

The title compound was synthesized from 4-[2-(3-aminophenyl)pyrazolo[1,5-a]pyridin-3-yl]-N-phenyl-2-pyrimidine and 2-thiopheneacetyl chloride using acylation conditions described in Example 3, Step I above. $^1$H NMR (400 MHz, DMSO-d6): δ 3.88 (s, 2H), 6.53 (d, 1H, J=5.3 Hz), 6.90-6.98 (m, 3H), 7.12 (m, 1H), 7.21-7.28 (m, 3H), 7.38-7.50 (m, 3H), 7.69-7.75 (m, 3H), 7.90 (m, 1H), 8.27 (d, 1H, J=5.3 Hz), 8.47 (m, 1H), 8.84 (d, 1H, J=7.1 Hz), 9.56 (s, 1H), 10.37 (s, 1H); ES-LC/MS m/z=503 [M+H]$^+$.

Example 5

2-(3-Chlorophenyl)-N-(3-{3-[2-(phenylamino)-4-pyrimidinyl]pyrazolo-[1,5-a]pyridin-2-yl}phenyl)acetamide

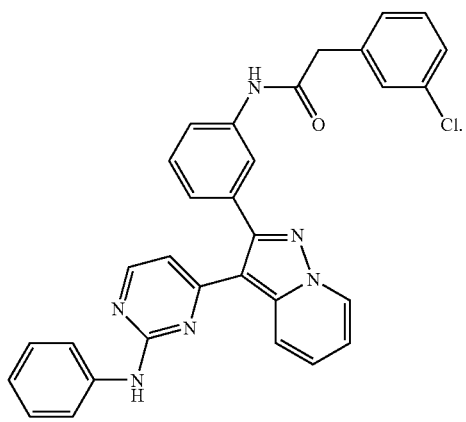

To a solution of 4-[2-(3-aminophenyl)pyrazolo[1,5-a]pyridin-3-yl]-N-phenyl-2-pyrimidine (30 mg, 0.08 mmol) (see Example 3, Step H) in THF (3 mL) was added CDI (14 mg, 0.09 mmol). The resultant mixture was stirred at rt for 1 hour. To the mixture was added (3-chlorophenyl)acetic acid (15 mg, 0.09 mmol) and then stirred at rt for 15 h. Methanol (2 mL) was added and the mixture was concentrated in vacuo. The residue was purified by chromatography on silica gel (hexanes/EtOAc) to give the title compound (25 mg, 60% yield). $^1$H NMR (400 MHz, DMSO-d$_6$): δ 3.68 (s, 2H), 6.53 (d, 1H, J=5.3 Hz), 6.92 (m, 1H), 6.92 (m, 1H), 7.12 (m, 1H), 7.21-7.50 (m, 9H), 7.68-7.76 (m, 3H), 7.89 (m, 1H), 8.26 (d, 1H, J=5.3 Hz), 8.47 (m, 1H), 8.83 (d, 1H, J=6.8 Hz), 9.56 (s, 1H), 10.35 (s, 1H). ES-LC/MS m/z=531 [M+H]$^+$.

Example 6

2-(2,5-Difluorophenyl)-N-(3-{3-[2-(phenylamino)-4-pyrimidinyl]pyrazolo[1,5-a]pyridin-2-yl}phenyl)acetamide

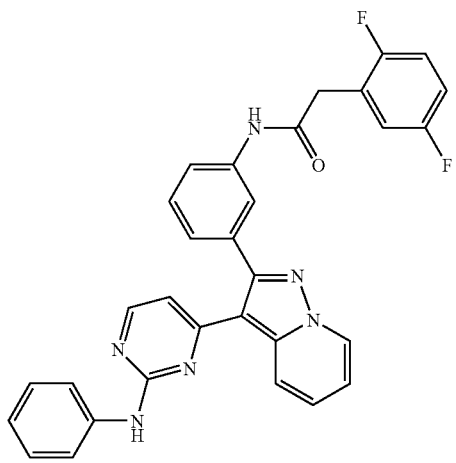

The title compound was synthesized from 4-[2-(3-aminophenyl)pyrazolo[1,5-a]pyridin-3-yl]-N-phenyl-2-pyrimidine (see Example 3, Step H) and (2,5-difluorophenyl)acetic acid using the coupling conditions described in Example 5. $^1$H NMR (400 MHz, DMSO-d6): δ 3.76 (s, 2H), 6.53 (d, 1H, J=5.3 Hz), 6.94 (m, 1H), 7.10-7.27 (m, 7H), 7.41-7.48 (m, 2H), 7.69-7.76 (m, 3H), 7.89 (m, 1H), 8.27 (d, 1H, J=5.3 Hz), 8.48 (m, 1H), 8.83 (m, 1H), 9.56 (s, 1H), 10.39 (s, 1H). ES-LC/MS m/z=533 [M+H]$^+$.

Example 7

N-[3-(3-{2-[(2-Methyl-1,2,3,4-tetrahydro-7-isoquinolinyl)amino]-4-pyrimidinyl}pyrazolo[1,5-a]pyridin-2-yl)phenyl]-2-(2-thienyl)acetamide

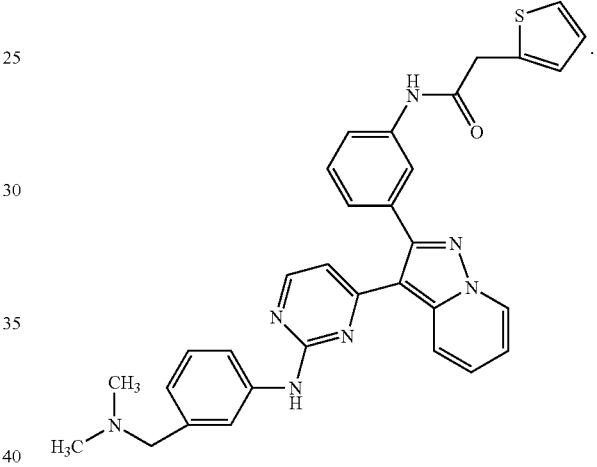

Step A: N-(3-{3-[2-({3-[(Dimethylamino)methyl]phenyl}amino)-4-pyrimidinyl]pyrazolo[1,5-a]pyridin-2-yl}phenyl)-2,2,2-trifluoroacetamide

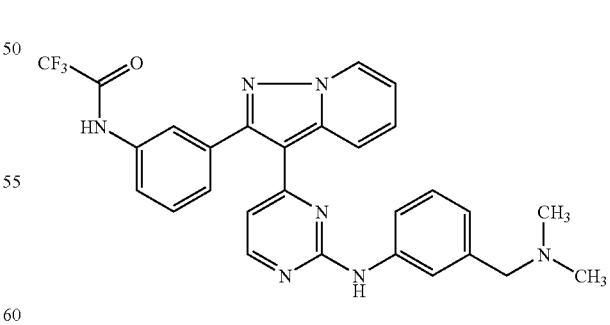

The title compound was prepared from N-{3-[3-(2-chloro-4-pyrimidinyl)pyrazolo[1,5-a]pyridin-2-yl]phenyl}-2,2,2-trifluoroacetamide (see Example 1, Step C) and 3-(dimethylaminomethyl)aniline using displacement conditions described in Example 1, Step D to generate the product in 78% yield. ES-LC/MS m/z=532 [M+H]$^+$.

Step B: 4-[2-(3-Aminophenyl)pyrazolo[1,5-a]pyridin-3-yl]-N-{3-[(dimethylamino)methyl]phenyl}-2-pyrimidinamine

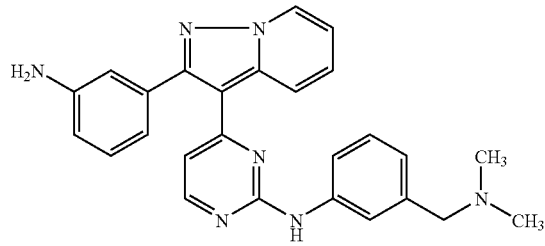

The title compound was prepared from N-(3-{3-[2-({3-[(dimethylamino)methyl]phenyl}amino)-4-pyrimidinyl]pyrazolo[1,5-a]pyridin-2-yl}phenyl)-2,2,2-trifluoroacetamide using hydrolysis conditions described in Example 1, Step E to generate the product in quantitative yield. ES-LC/MS m/z=436 [M+H]$^+$.

Step C: N-(3-{3-[2-({3-[(Dimethylamino)methyl]phenyl}amino)-4-pyrimidinyl]pyrazolo[1,5-a]pyridin-2-yl}phenyl)-2-(2-thienyl)acetamide (title compound)

The title compound was prepared from 4-[2-(3-aminophenyl)pyrazolo[1,5-a]pyridin-3-yl]-N-{3-[(dimethylamino)methyl]phenyl}-2-pyrimidinamine and 2-thiopheneacetyl chloride using acylation conditions described in Example 1, Step F to generate the product in 88% yield. $^1$H NMR (400 MHz, DMSO-d6): δ 2.11 (s, 6H), 3.26 (s, 2H), 3.86 (s, 2H), 6.46 (d, 1H, J=5.3 Hz), 6.85 (d, 1H, J=7.5 Hz), 6.96 (m, 2H), 7.10-7.19 (m, 2H), 7.26 (d, 1H, J=7.9 Hz), 7.36-7.48 (m, 3H), 7.62 (d, 1H, J=8.2 Hz), 7.69 (s, 1H), 7.73 (d, 1H, J=9.1 Hz), 7.89 (s, 1H), 8.23 (d, 1H, J=5.3 Hz), 8.51 (d, 1H, J=8.8 Hz), 8.82 (d, 1H, J=6.9 Hz), 9.52 (s, 1H), 10.35 (s, 1H); ES-LC/MS m/z=560 [M+H]$^+$.

Example 8

N-[3-(3-{(2-[(2-Methyl-1,2,3,4-tetrahydro-7-isoquinolinyl)amino]-4-pyrimidinyl}pyrazolo[1,5-a]pyridin-2-yl)phenyl]-2-(2-thienyl)acetamide

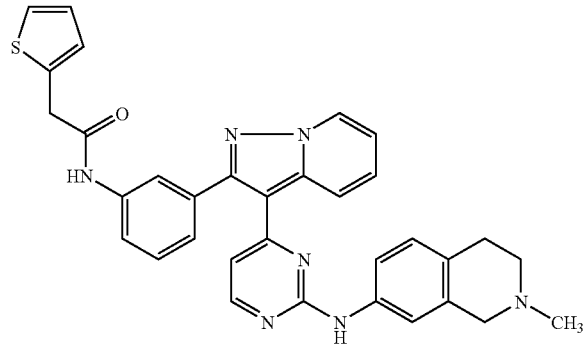

Step A:
2-Methyl-7-nitro-1,2,3,4-tetrahydroisoquinoline

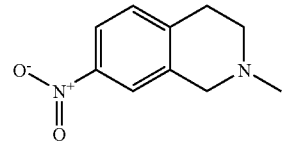

7-Nitro-1,2,3,4-tetrahydroisoquinoline (4.15 g, 23.3 mmol) was combined with paraformaldehyde (3.7 g, 116 mmol), HOAc (6.7 mL, 116 mmol), sodium cyanoborohydride (7.3 g, 116 mmol) in DCE (300 mL) and heated at reflux for 15 h. The reaction was cooled and quenched by stirring with saturated aqueous NaHCO$_3$. The organic layer was dried with MgSO$_4$. The solvent was removed under vacuum and the crude oil was purified by silica gel flash column chromatography (40-100% EtOAc/hexanes). Purification yielded 3.0 g (67%) of the title compound as an oil. $^1$H NMR (400 MHz, DMSO-d$_6$) δ 8.14 (s, 1H), 8.09 (dd, J=8.5, 2.4 Hz, 1H), 7.52 (d, J=8.2 Hz, 1H), 4.22 (s, 2H), 3.29-3.23 (m, 2H), 3.16-3.08 (m, 2H), 2.67 (s, 3H).

Step B:
2-Methyl-1,2,3,4-tetrahydro-7-isoquinolinamine

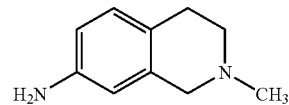

2-Methyl-7-nitro-1,2,3,4-tetrahydroisoquinoline (3.0 g, 15.6 mmol) was dissolved in EtOAc (10 mL) and stirred vigorously with 10% Pd/C (0.3 g) under a hydrogen atmosphere at 55 PSI. The reaction was stirred for 15 h at rt. The reaction was filtered through celite and concentrated to provide 2.2 g (87%) of the desired 2-methyl-1,2,3,4-tetrahydro-7-isoquinolinamine product as a white powder. $^1$H NMR (400 MHz, DMSO-d$_6$) δ 6.83 (d, J=8.3 Hz, 1H), 6.44 (d, J=8.0 Hz, 1H), 6.24 (s, 1H), 4.97 (s, 2H), 3.87 (m, 2H), 3.11 (t, J=6.4 Hz, 2H), 2.85-2.68 (m, 2H), 2.58 (s, 3H).

Step C: 2,2,2-trifluoro-N-[3-(3-{2-[(2-methyl-1,2,3,4-tetrahydro-7-isoquinolinyl)amino]-4-pyrimidinyl}pyrazolo[1,5-a]pyridin-2-yl)phenyl]acetamide

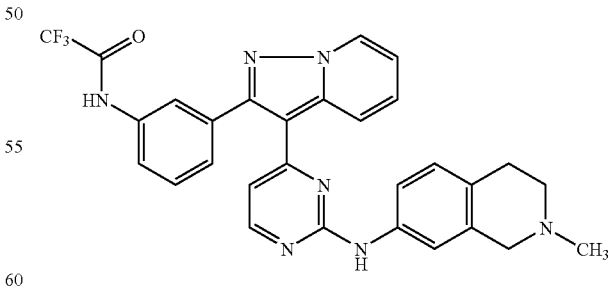

The title compound was prepared from N-{3-[3-(2-chloro-4-pyrimidinyl)pyrazolo[1,5-a]pyridin-2-yl]phenyl}-2,2,2-trifluoroacetamide (see Example 1, Step C) and 2-methyl-1,2,3,4-tetrahydro-7-isoquinolinamine using displacement conditions described in Example 1, Step D to generate the product in 72% yield. ES-LC/MS m/z=544 [M+H]$^+$.

Step D: N-{4-[2-(3-Aminophenyl)pyrazolo[1,5-a]pyridin-3-yl]-2-pyrimidinyl}-2-methyl-1,2,3,4-tetrahydro-7-isoquinolinamine

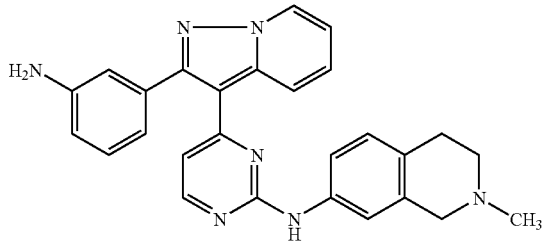

The title compound was prepared from 2,2,2-trifluoro-N-[3-(3-{2-[(2-methyl-1,2,3,4-tetrahydro-7-isoquinolinyl)amino]-4-pyrimidinyl}pyrazolo[1,5-a]pyridin-2-yl)phenyl]acetamide using hydrolysis conditions described in Example 1, Step E to generate the product in quantitative yield. ES-LC/MS m/z=448 [M+H]+.

Step E: N-[3-(3-{2-[(2-Methyl-1,2,3,4-tetrahydro-7-isoquinolinyl)amino]-4-pyrimidinyl}pyrazolo[1,5-a]pyridin-2-yl)phenyl]-2-(2-thienyl)acetamide (title compound)

The title compound was prepared from N-{4-[2-(3-aminophenyl)pyrazolo[1,5-a]pyridin-3-yl]-2-pyrimidinyl}-2-methyl-1,2,3,4-tetrahydro-7-isoquinolinamine and 2-thiopheneacetyl chloride using acylation conditions described in Example 1, Step F to generate the product in 89% yield. $^1$H NMR (400 MHz, DMSO-d6): δ 2.31 (s, 3H), 2.57 (t, 2H, J=5.7 Hz), 2.74 (t, 2H, J=5.6 Hz), 3.38 (s, 2H), 3.88 (s, 2H), 6.47 (d, 1H, J=5.3 Hz), 6.97 (m, 3H), 7.13 (t, 1H, J=6.8 Hz), 7.27 (d, 1H, J=7.5 Hz), 7.38-7.50 (m, 5H), 7.75 (d, 1H, J=8.1 Hz), 7.90 (s, 1H), 8.23 (d, 1H, J=5.3 Hz), 8.46 (d, 1H, J=8.6 Hz), 8.83 (d, 1H, J=7.0 Hz), 9.43 (s, 1H), 10.36 (s, 1H). ES-LC/MS m/z=572 [M+H]+.

Example 9

N-[3-(3-{2-[(3-Fluorophenyl)amino]-4-pyrimidinyl}pyrazolo[1,5-a]pyridin-2-yl)phenyl]-2-(2-thienyl)acetamide

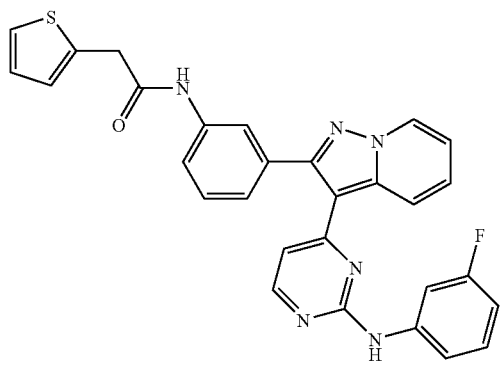

Step A: 2,2,2-Trifluoro-N-[3-(3-{2-[(3-fluorophenyl)amino]-4-pyrimidinyl}pyrazolo-[1,5-a]pyridin-2-yl)phenyl]acetamide

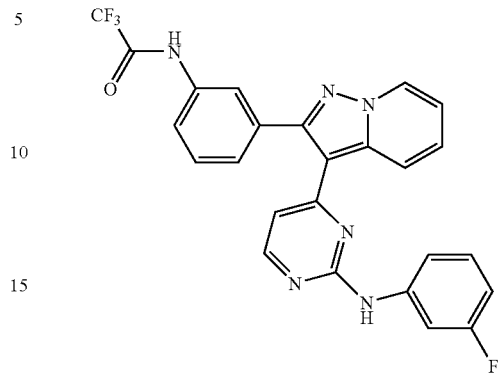

To a mixture of N-{3-[3-(2-chloro-4-pyrimidinyl)pyrazolo[1,5-a]pyridin-2-yl]phenyl}-2,2,2-trifluoroacetamide (see Example 1, Step C) (2.27 g, 5.4 mmol) in EtOH (60 mL) was added 3-fluoroaniline (0.62 mL, 6.48 mmol) and 5 drops of conc. HCl. The reaction was heated to 80° C. for 16 h, allowed to cool to rt and concentrated. The mixture was partitioned between DCM and saturated aq. NaHCO$_3$. The separated aqueous layer was extracted twice with DCM and the combined organic layers were dried over MgSO$_4$, filtered and concentrated to give, after trituration of the residue, the title compound as an off-white solid (2.15 g, 98%). $^1$H NMR (400 MHz, DMSO-d6) δ 11.34 (s, 1H), 9.78 (s, 1H), 8.83 (d, 1H, J=7.2), 8.43 (d, 1H, J=9.2), 8.30 (d, 1H, J=5.2), 7.97 (s, 1H), 7.79-7.72 (m, 2H), 7.52-7.40 (m, 4H), 7.22 (q, 1H, J=7.6), 7.12 (t, 1H, J=6.8), 6.69 (m, 1H), 6.56 (d, 1H, J=5.2).

Step B: 4-[2-(3-Aminophenyl)pyrazolo[1,5-a]pyridin-3-yl]-N-(3-fluorophenyl)-2-pyrimidinamine

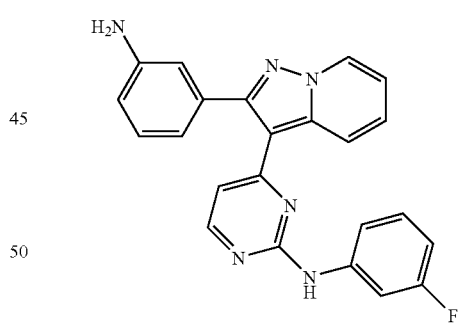

A solution of 2,2,2-trifluoro-N-(3-{3-[2-(3-fluoro-phenylamino)-pyrimidin-4-yl]-pyrazolo[1,5-a]pyridin-2-yl}-phenyl)-acetamide (2.15 g, 4.4 mmol) and LiOH (277 mg, 6.6 mmol) in THF (44 mL) and water (10 mL) was stirred for 16 h. The reaction was extracted with DCM. The combined organic phases were dried over MgSO$_4$ and purified through silica gel to give the title compound as a white solid. $^1$H NMR (400 MHz, d$_6$-DMSO): δ 9.75 (s, 1H), 8.78 (d, J=6.8 Hz, 1H), 8.52 (d, J=9.2 Hz, 1H), 8.25 (d, J=5.6 Hz, 1H), 7.80 (d, J=12.4 Hz, 1H), 7.47-7.43 (m, 2H), 7.29-7.23 (m, 1H), 7.12-7.06 (m, 2H), 6.77 (s, 1H), 6.71 (dt, J=8.4 and 2.4 Hz, 1H), 6.66-6.62 (m, 2H), 6.54 (d, J=5.6 Hz, 1H), 5.21 (s, 2H) ppm. HRMS calculated C$_{23}$H$_{17}$FN$_6$ [M+H]+ 397.1577 found 397.1558.

Step C: N-[3-(3-{2-[(3-Fluorophenyl)amino]-4-pyrimidinyl}pyrazolo[1,5-a]pyridin-2-yl)phenyl]-2-(2-thienyl)acetamide The title compound was prepared from 4-[2-(3-aminophenyl)pyrazolo[1,5-a]pyridin-3-yl]-N-(3-fluorophenyl)-2-pyrimidinamine and 2-thienylacetyl chloride by a procedure analogous to Example 1 step F in 67% yield. $^1$H NMR (300 MHz, DMSO-$d_6$): δ 10.34 (s, 1H), 9.80 (s, 1H), 8.84 (d, 1H), 8.48 (d, 1H), 8.30 (d, 1H), 7.89 (s, 1H), 7.78 (m, 1H), 7.73 (d, 1H), 7.53-7.37 (m, 4H), 7.30-7.22 (m, 2H), 7.12 (m, 1H), 6.96 (m, 2H), 6.71 (m, 1H), 6.55 (d, 1H), 3.86 (s, 2H); HRMS: calc. $C_{29}H_{22}N_6OFS$ (M+H)$^+$ 521.1560 found 521.1548.

Example 10

N-[3-(3-{2-[(3-{[2-(1-Pyrrolidinyl)ethyl]oxy}phenyl)amino]-4-pyrimidinyl}pyrazolo[1,5-a]pyridin-2-yl)phenyl]-2-(2-thienyl)acetamide

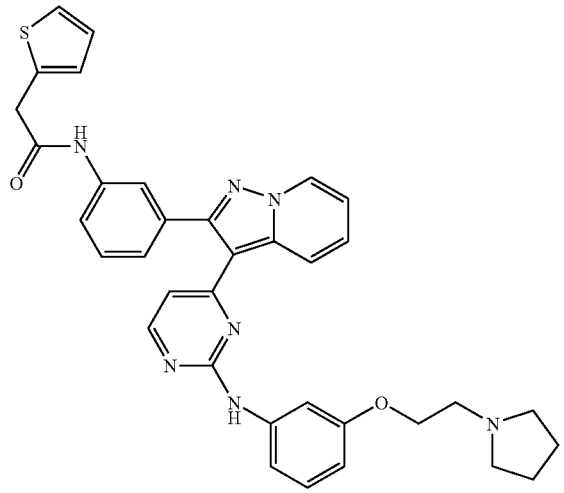

Step A: 2-chloroethyl 3-nitrophenyl ether

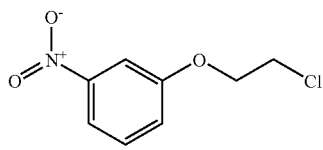

To a mixture of 3-nitrophenol (5.0 g, 36 mmol) and $K_2CO_3$ (7.45 g, 54 mmol), in 2-butanone at 85° C. was added 1-bromo-2-chloroethane (1.7 mL, 71.9 mmol) and the reaction stirred for 24 h. The mixture was cooled to rt and reduced in vacuo. The crude was diluted with EtOAc (200 mL) and water (200 mL) and separated. The aqueous layer was extracted twice with EtOAc (200 mL), the organics were pooled, dried over $MgSO_4$ and reduced in vacuo onto silica gel. Purification was achieved via column chromatography using a gradient of EtOAc/Hexanes to afford a yellow oil that solidified upon standing to afford 4.22 g (58% yield) of titled product as an off-white solid. $^1$H NMR (400 MHz, DMSO-D6) δ ppm 7.8 (m, 1H), 7.7 (t, J=2.4 Hz, 1H), 7.6 (t, J=8.2 Hz, 1H) 7.4 (dd, J=8.2, 2.6 Hz, 1H), 4.4 (m, 2H), 4.0 (m, 2H).

Step B: 3-[(2-Chloroethyl)oxy]aniline

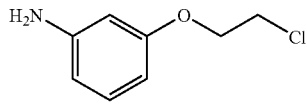

2-Chloroethyl 3-nitrophenyl ether was dissolved in EtOAc (90 mL). To this was added Pt w/sulfide (2.04 g, 0.524 mmol) and then purged with $H_2$ and stirred at RT under 1 atmosphere of $H_2$ overnight. The reaction was filtered through a celite plug and reduced under vacuo to attend 3.4 g (95% yield) of the title compound colorless oil. $^1$H NMR (400 MHz, DMSO-D6) δ ppm 6.9 (t, J=8.0 Hz, 1H), 6.1 (m, 2H), 6.1 (ddd, J=8.1, 2.4, 0.8 Hz, 1H), 5.0 (s, 2H), 4.1 (m, 2H), 3.9 (m, 2H).

Step C: N-(3-{3-[2-({3-[(2-Chloroethyl)oxy]phenyl}amino)-4-pyrimidinyl]pyrazolo[1,5-a]pyridin-2-yl}phenyl)-2,2,2-trifluoroacetamide

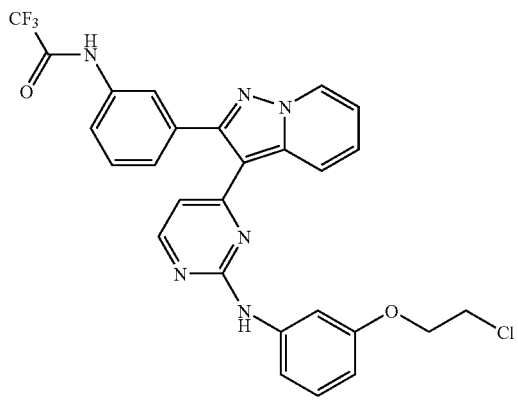

N-{3-[3-(2-Chloro-4-pyrimidinyl)pyrazolo[1,5-a]pyridin-2-yl]phenyl}-2,2,2-trifluoroacetamide (1.0 g, 2.75 mmol) (see Example 1, Step C) was stirred in (20 mL) of i-PrOH and 3-[(2-chloroethyl)oxy]aniline (0.494 g, 2.89 mmol) was added along with 3 drops of conc. HCl and heated to 85° C. for 18 h. The mixture was filtered hot and washed with i-PrOH to yield the titled product as a yellow solid as the HCl salt (1.2 g, 74% yield). ES-LC/MS m/z 553 (M+H).

Step D: 4-[2-(3-Aminophenyl)pyrazolo[1,5-a]pyridin-3-yl]-N-(3-{[2-(1-pyrrolidinyl)ethyl]oxy}phenyl)-2-pyrimidinamine

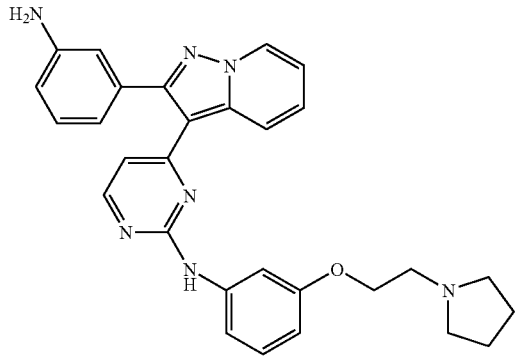

N-(3-{3-[2-({3-[(2-Chloroethyl)oxy]phenyl}amino)-4-pyrimidinyl]pyrazolo[1,5-a]pyridin-2-yl}phenyl)-2,2,2-trifluoroacetamide (0.5 g, 0.85 mmol) was dissolved in pyrrolidine and heated to 50° C. for 18 h. Upon completion the reaction was then cooled and absorbed directly onto silica gel. Purification via column chromatography using a 0-20% gradient of EtOAc/MeOH w/NH₄OH afforded the desired product as a yellow solid, 310 mg, 74% yield. ES-LC/MS m/z 492 [M+H]⁺.

Step E: N-[3-(3-{2-[(3-{[2-(1-Pyrrolidinyl)ethyl]oxy}phenyl)amino]-4-pyrimidinyl}pyrazolo[1,5-a]pyridin-2-yl)phenyl]-2-(2-thienyl)acetamide (title compound)

The title compound was prepared from 4-[2-(3-aminophenyl)pyrazolo[1,5-a]pyridin-3-yl]-N-(3-{[2-(1-pyrrolidinyl)ethyl]oxy}phenyl)-2-pyrimidinamine and 2-thiopheneacetyl chloride using acylation conditions described in Example 1, Step F, and purification via column chromatography using a 0-20% gradient of EtOAc/MeOH w/NH₄OH to generate the product in 44% yield. ¹H NMR (400 MHz, DMSO-D6) δ ppm 1.6 (s, 4H) 2.7 (s, 3H) 3.8 (s, 2H) 4.0 (t, J=6.0 Hz, 2H) 6.5 (m, 2H) 6.9 (m, 2H) 7.1 (m, 3H) 7.2 (m, 2H) 7.4 (m, 2H) 7.4 (m, 1H) 7.5 (t, J=2.3 Hz, 1H) 7.7 (m, 1H) 7.9 (d, J=1.8 Hz, 1H) 8.2 (d, J=5.3 Hz, 1H) 8.5 (s, 1H) 8.8 (d, J=7.0 Hz, 1H) 9.5 (s, 1H) 10.3 (s, 1H). ES-LC/MS m/z 616 [M+H]⁺.

Example 11

N-[3-(3-{2-[3-{[3-(4-Morpholinyl)propyl]oxy}phenylamino]-4-pyrimidinyl}pyrazolo[1,5-a]pyridin-2-yl)phenyl]-2-(2-thienyl)acetamide

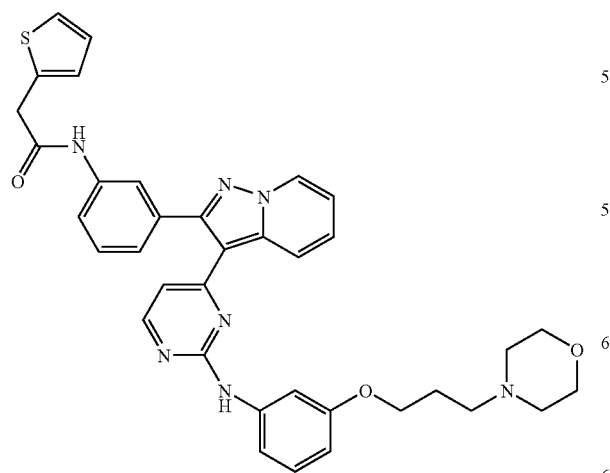

Step A. N-(3-{3-[2-({3-[(3-chloropropyl)oxy]phenyl}amino)-4-pyrimidinyl]pyrazolo[1,5-a]pyridin-2-yl}phenyl)-2,2,2-trifluoroacetamide

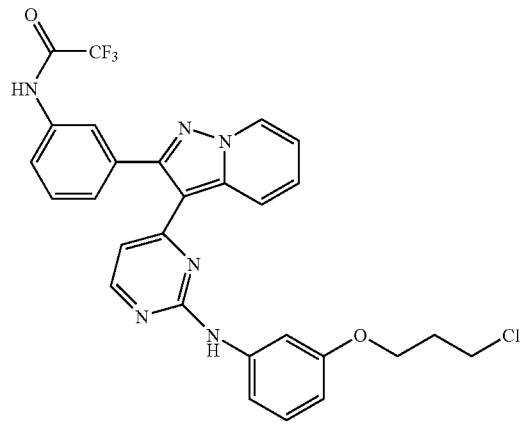

The compound was synthesized from N-{3-[3-(2-chloro-4-pyrimidinyl)-pyrazolo[1,5-a]pyridin-2-yl]phenyl}-2,2,2-trifluoroacetamide (see Example 1, Step C) and 3-[(2-chloropropyl)oxy]aniline as described in Example 10, Step C to afford a dark yellow solid in 81% yield. ES-LCMS m/z 567 [M+H]⁺.

Step B. 4-[2-(3-Aminophenyl)pyrazolo[1,5-a]pyridin-3-yl]-N-(3-{[3-(4-morpholinyl)propyl]oxy}phenyl)-2-pyrimidinamine

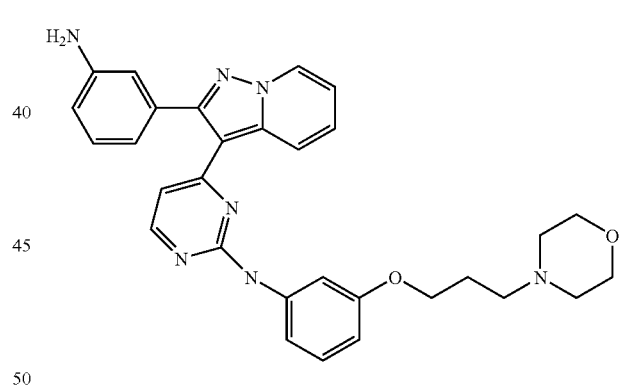

The compound was synthesized from N-(3-{3-[2-({3-[(3-chloropropyl)oxy]-phenyl}amino)-4-pyrimidinyl]pyrazolo[1,5-a]pyridin-2-yl}phenyl)-2,2,2-trifluoroacetamide via chloride displacement with morpholine as described in Example 10, Step D to afford an orange solid in 71% yield. ES-LC/MS m/z 522 [M+H]⁺.

Step C N-[3-(3-{2-[(3-{[3-(4-Morpholinyl)propyl]oxy}phenyl)amino]-4-pyrimidinyl}pyrazolo[1,5-a]pyridin-2-yl)phenyl]-2-(2-thienyl)acetamide (title compound)

The title compound was synthesized from 4-[2-(3-aminophenyl)pyrazolo[1,5-a]pyridin-3-yl]-N-(3-{[3-(4-morpholinyl)propyl]oxy}phenyl)-2-pyrimidinamine using acylation with 2-thienylacetyl chloride as described in Example 10, Step E to yield a light brown solid in 37% yield. $^1$H NMR (400 MHz, DMSO-D6) δ ppm 1.8 (d, J=1.1 Hz, 2H) 2.3 (s, 6H) 3.5 (d, J=4.6 Hz, 4H) 3.9 (s, 2H) 3.9 (m, 2H) 6.5 (m, 2H) 7.0 (m, 2H) 7.1 (m, 2H) 7.3 (dt, J=7.6, 1.4 Hz, 2H) 7.4 (m, 3H) 7.5 (t, J=2.1 Hz, 1H) 7.7 (d, J=1.8 Hz, 1H) 7.9 (t, J=1.8 Hz, 1H) 8.2 (d, J=5.3 Hz, 1H) 8.5 (d, J=8.6 Hz, 1H) 8.8 (m, 1H) 9.5 (s, 1H) 10.3 (s, 1H). ES-LC/MS m/z 646 [M+H]$^+$.

Example 12

N-[3-(3-{2-[(3-{[3-(Dimethylamino)propyl] oxy}phenyl)-amino]-4-pyrimidinyl}pyrazolo[1,5-a] pyridin-2-yl)phenyl]-2-(2-thienyl)acetamide

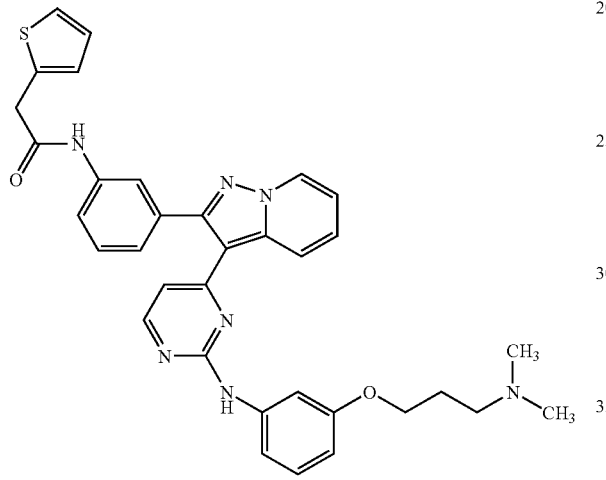

Step A 4-[2-(3-Aminophenyl)pyrazolo[1,5-a]pyridin-3-yl]-N-(3-{[3-(dimethylamino)propyl]oxy}phenyl)-2-pyrimidinamine

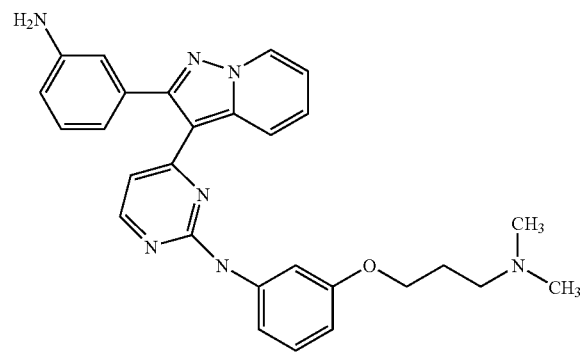

The compound was synthesized from N-(3-{3-[2-({3-[(3-chloropropyl)oxy]-phenyl}amino)-4-pyrimidinyl]pyrazolo[1,5-a]pyridin-2-yl}phenyl)-2,2,2-trifluoroacetamide (see Example 11, Step A) via chloride displacement with dimethylamine as described in Example 10, Step D to afford an orange solid in 87% yield. ES-LC/MS m/z 480 [M+H]$^+$.

Step B N-[3-(3-{2-[(3-{[3-(Dimethylamino)propyl] oxy}phenyl)amino]-4-pyrimidinyl}pyrazolo[1,5-a] pyridin-2-yl)phenyl]-2-(2-thienyl)acetamide (title compound)

The title compound was synthesized from 4-[2-(3-aminophenyl)pyrazolo[1,5-a]pyridin-3-yl]-N-(3-{[3-(dimethylamino)propyl]oxy}phenyl)-2-pyrimidinamine using acylation with 2-thienylacetyl chloride as described in Example 10, Step E to yield a light brown solid in 48% yield. $^1$H NMR (400 MHz, DMSO-D6) δ ppm 1.8 (s, 2H) 2.1 (s, 6H) 2.3 (s, 2H) 3.9 (s, 2H) 3.9 (d, J=6.2 Hz, 2H) 6.5 (m, 2H) 7.0 (m, 2H) 7.1 (m, 2H) 7.3 (s, 2H) 7.4 (m, 2H) 7.5 (m, 2H) 7.7 (m, 1H) 7.9 (d, J=2.2 Hz, 1H) 8.2 (d, J=5.3 Hz, 1H) 8.5 (s, 1H) 8.8 (d, J=7.0 Hz, 1H) 9.5 (s, 1H) 10.3 (s, 1H). ES-LC/MS m/z 604 [M+H]$^+$.

Example 13

N-[3-(3-{2-[(3-{[3-(1-Pyrrolidinyl)propyl] oxy}phenyl)amino]-4-pyrimidinyl}pyrazolo[1,5-a] pyridin-2-yl)phenyl]-2-(2-thienyl)acetamide

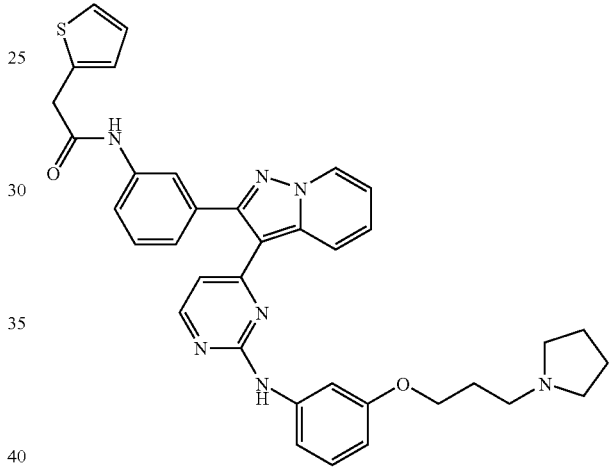

Step A 4-[2-(3-Aminophenyl)pyrazolo[1,5-a]pyridin-3-yl]-N-(3-{[3-(1-pyrrolidinyl)propyl]oxy}phenyl)-2-pyrimidinamine

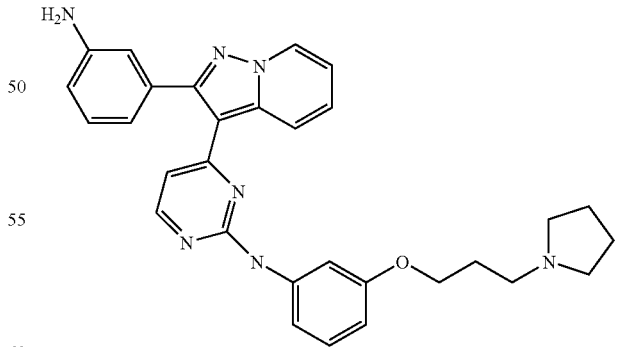

The compound was synthesized from N-(3-{3-[2-({3-[(3-chloropropyl)oxy]phenyl}amino)-4-pyrimidinyl]pyrazolo[1,5-a]pyridin-2-yl}phenyl)-2,2,2-trifluoroacetamide (see Example 11, Step A) via chloride displacement with pyrrolidine as described in Example 10, Step D to afford an orange solid in 87% yield. ES-LC/MS m/z 506 [M+H]$^+$.

Step B N-[3-(3-{2-[(3-{[3-(1-Pyrrolidinyl)propyl]oxy}phenyl)amino]-4-pyrimidinyl}pyrazolo[1,5-a]pyridin-2-yl)phenyl]-2-(2-thienyl)acetamide (title compound)

The title compound was synthesized from 4-[2-(3-aminophenyl)pyrazolo[1,5-a]pyridin-3-yl]-N-(3-{[3-(1-pyrrolidinyl)propyl]oxy}phenyl)-2-pyrimidinamine using acylation with 2-thienylacetyl chloride as described in Example 10, Step E to yield a light brown solid in 51% yield. $^1$H NMR (400 MHz, DMSO-D6) δ ppm 1.6 (s, 4H) 1.8 (s, 2H) 2.4 (s, 4H) 3.9 (s, 2H) 3.9 (d, J=6.2 Hz, 2H) 6.5 (m, 2H) 7.0 (m, 2H) 7.1 (m, 2H) 7.3 (ddd, J=6.3, 1.3, 1.2 Hz, 2H) 7.4 (m, 3H) 7.5 (t, J=2.3 Hz, 1H) 7.7 (m, 1H) 7.9 (d, J=1.8 Hz, 1H) 8.2 (d, J=5.1 Hz, 1H) 8.5 (s, 1H) 8.8 (m, 1H) 9.5 (s, 1H) 10.3 (s, 1H). ES-LC/MS m/z 630 [M+H]$^+$.

Example 14

N-[3-(3-{2-[(3-{[2-(Diethylamino)ethyl]oxy}phenyl)amino]-4-pyrimidinyl}pyrazolo[1,5-a]pyridin-2-yl)phenyl]-2-(2-thienyl)acetamide

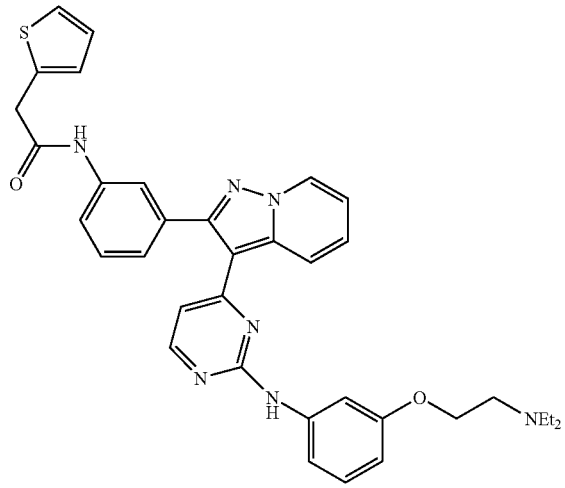

Step A 4-[2-(3-Aminophenyl)pyrazolo[1,5-a]pyridin-3-yl]-N-(3-{[2-(diethylamino)ethyl]oxy}phenyl)-2-pyrimidinamine

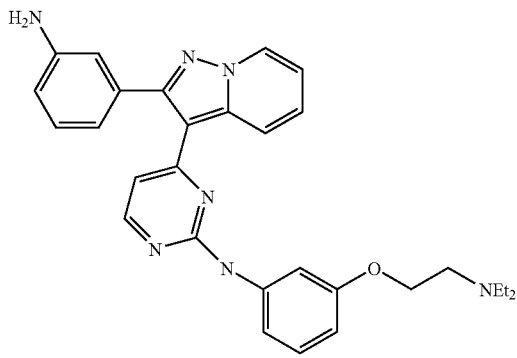

The title compound was synthesized from N-(3-{3-[2-({3-[(2-chloroethyl)oxy]phenyl}amino)-4-pyrimidinyl]pyrazolo[1,5-a]pyridin-2-yl}phenyl)-2,2,2-trifluoroacetamide (see Example 10, Step C) via chloride displacement with diethylamine as described in Example 10, Step D to afford an orange solid in 76% yield. ES-LC/MS m/z 494 [M+H]$^+$.

Step B. N-[3-(3-{2-[(3-{[2-(Diethylamino)ethyl]oxy}phenyl)amino]-4-pyrimidinyl}pyrazolo[1,5-a]pyridin-2-yl)phenyl]-2-(2-thienyl)acetamide (title compound)

The title compound was synthesized from 4-[2-(3-aminophenyl)pyrazolo[1,5-a]pyridin-3-yl]-N-(3-{[2-(diethylamino)ethyl]oxy}phenyl)-2-pyrimidinamine using acylation with 2-thienylacetyl chloride as described in Example 10, Step E to yield a light brown solid in 49% yield. $^1$H NMR (400 MHz, DMSO-D6) δ ppm 1.2 (t, J=7.2 Hz, 6H) 3.2 (s, 4H) 3.5 (s, 2H) 3.9 (s, 2H) 4.3 (s, 2H) 6.5 (d, J=5.3 Hz, 1H) 6.6 (s, 1H) 7.0 (m, 2H) 7.1 (d, J=1.5 Hz, 1H) 7.3 (d, J=5.1 Hz, 1H) 7.4 (m, 2H) 7.5 (m, 1H) 7.6 (s, 1H) 7.7 (s, 1H) 7.9 (s, 1H) 8.2 (d, J=5.3 Hz, 1H) 8.5 (s, 1H) 8.8 (d, J=7.0 Hz, 1H) 9.6 (s, 2H) 10.4 (s, 1H). ES-LC/MS m/z 618 [M+H]$^+$.

Example 15

N-[3-(3-{2-[(3-{[2-(Dimethylamino)ethyl]oxy}phenyl)amino]-4-pyrimidinyl}pyrazolo[1,5-a]pyridin-2-yl)phenyl]-2-(2-thienyl)acetamide

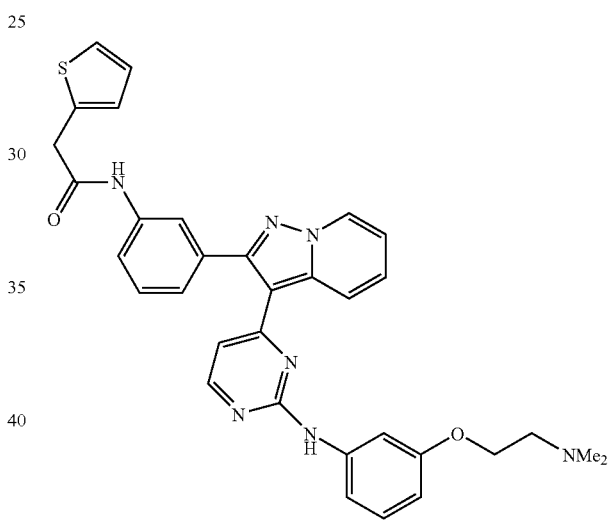

Step A 4-[2-(3-Aminophenyl)pyrazolo[1,5-a]pyridin-3-yl]-N-(3-{[2-(dimethylamino)ethyl]oxy}phenyl)-2-pyrimidinamine

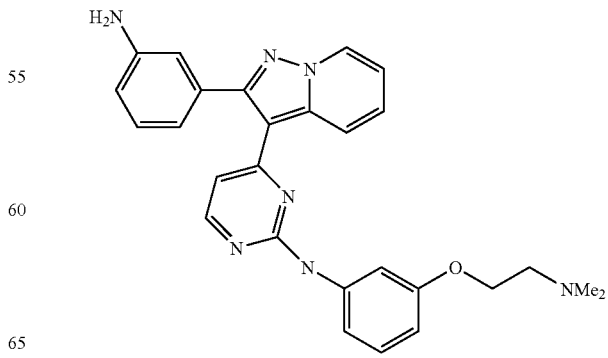

The title compound was synthesized from N-(3-{3-[2-({3-[(2-chloroethyl)oxy]phenyl}amino)-4-pyrimidinyl]pyrazolo[1,5-a]pyridin-2-yl}phenyl)-2,2,2-trifluoroacetamide (see Example 10, Step C) via chloride displacement with dimethylamine as described in Example 10, Step D to afford an orange solid in 85% yield. ES-LC/MS m/z 466 [M+H]+.

Step B N-[3-(3-{2-[(3-{[2-(Dimethylamino)ethyl]oxy}phenyl)amino]-4-pyrimidinyl}pyrazolo[1,5-a]pyridin-2-yl)phenyl]-2-(2-thienyl)acetamide (title compound)

The title compound was synthesized from 4-[2-(3-aminophenyl)pyrazolo[1,5-a]pyridin-3-yl]-N-(3-{[2-(diethylamino)ethyl]oxy}phenyl)-2-pyrimidinamine using acylation with 2-thienylacetyl chloride as described in Example 10, Step E to yield a light brown solid in 57% yield. $^1$H NMR (400 MHz, DMSO-D6) δ ppm 2.8 (s, 5H) 3.8 (d, J=0.9 Hz, 3H) 3.9 (s, 1H) 4.2 (s, 1H) 6.5 (d, J=5.3 Hz, 1H) 6.6 (s, 1H) 6.9 (m, 6H) 7.1 (s, 3H) 7.2 (s, 1H) 7.4 (m, 1H) 7.6 (s, 1H) 7.7 (s, 1H) 7.9 (s, 1H) 8.2 (d, J=5.5 Hz, 1H) 8.5 (s, 1H) 8.8 (m, 1H) 9.6 (s, 1H) 10.4 (s, 1H). ES-LC/MS m/z 590 [M+H]+.

Example 16

N-(3-{3-[2-(1,2,3,4-Tetrahydro-7-isoquinolinylamino)-4-pyrimidinyl]pyrazolo[1,5-a]pyridin-2-yl}phenyl)-2-(2-thienyl)acetamide

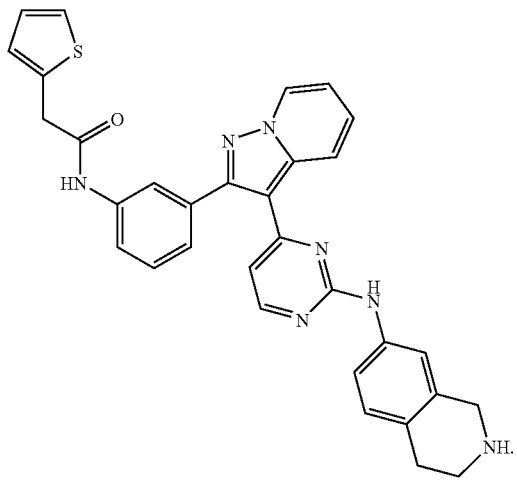

Step A: 2,2,2-Trifluoro-N-[2-(4-nitrophenyl)ethyl]acetamide

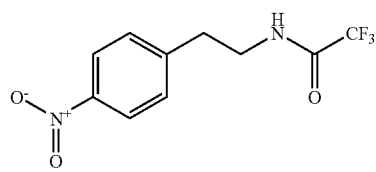

TFAA (17.0 g, 83.4 mmol) was added dropwise to a suspension of [2-(4-nitrophenyl)ethyl]amine hydrochloride and TEA (35 mL, 252.0 mmol) in DCM (500 mL) maintained at 0° C. The reaction was warmed to rt over 1 h. The solvent was removed under vacuum and the residue was partitioned between EtOAc and water. The organic was washed with brine and dried with Na$_2$SO$_4$. The solvent was removed under vacuum, yielding 21.9 g (100%) of the acylated amine. $^1$H NMR (400 MHz, DMSO-d$_6$) δ 9.50 (m, 1H), 8.16 (d, J=8.6 Hz, 2H), 7.49 (d, J=8.7 Hz, 2H), 3.47 (q, J=6.4 Hz, 2H), 2.94 (t, J=7.1 Hz, 2H).

Step B: 7-Nitro-2-(trifluoroacetyl)-1,2,3,4-tetrahydroisoquinoline

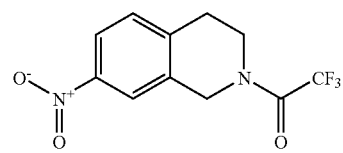

2,2,2-Trifluoro-N-[2-(4-nitrophenyl)ethyl]acetamide (21.9 g, 83.4 mmol) was dissolved in HOAc (80 mL) and sulfuric acid (120 mL) and paraformaldehyde (4.0 g, 125 mmol) were added at rt. The solution was stirred at rt for 24 h. The reaction was poured cautiously into approximately 1 L of ice with stirring. The resulting suspension of brown sludge was extracted into EtOAc. The organic was washed with saturated aqueous NaHCO$_3$, brine and dried over MgSO$_4$. The solvent was removed and the brown solid was triturated with hexanes. The brown solid was dried under vacuum and provided 15 g (66%) of the desired tetrahydroisoquinoline product. $^1$H NMR (400 MHz, DMSO-d$_6$) δ 8.25 (d, J=27.0 Hz, 1H), 8.05 (m, 1H), 7.47 (d, J=8.5 Hz, 1H), 4.88 (d, J=18.1 Hz, 2H), 3.81 (m, 2H), 3.06-2.97 (m, 2H).

Step C: 2-(Trifluoroacetyl)-1,2,3,4-tetrahydro-7-isoquinolinamine

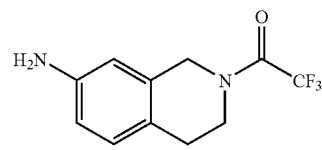

7-Nitro-2-(trifluoroacetyl)-1,2,3,4-tetrahydroisoquinoline (15 g, 54.7 mmol) was stirred vigorously in EtOAc (50 mL) with 5% Pd/C (1.5 g) under hydrogen gas (1 atmosphere) for 15 h and then filtered through celite. The filtrate was concentrated under vacuum and yielded 11.2 g (84%) of the tan solid 2-(trifluoroacetyl)-1,2,3,4-tetrahydro-7-isoquinolinamine. $^1$H NMR (400 MHz, DMSO-d$_6$) δ 6.84-6.79 (m, 1H), 6.46-6.40 (m, 1H), 6.35 (m, 1H), 4.95 (s, 2H), 4.56 (s, 2H), 3.76-3.68 (m, 2H), 2.74-2.66 (m, 2H).

Step D: 2-(2-Thienyl)-N-{3-[3-(2-{[1-(trifluoro-acetyl)-1,2,3,4-tetrahydro-7-isoquinolinyl]amino}-4-pyrimidinyl)pyrazolo[1,5-a]pyridin-2-yl]phenyl}acetamide

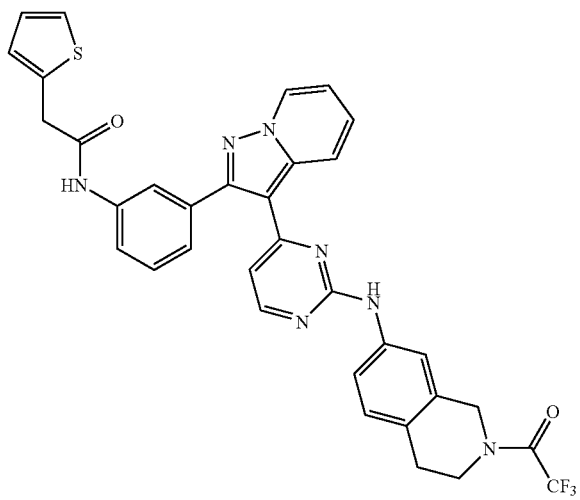

The compound was synthesized from N-{3-[3-(2-chloro-4-pyrimidinyl)pyrazolo-[1,5-a]pyridin-2-yl]phenyl}-2-(2-thienyl)acetamide (see Example 2, Step B) via chloride displacement with 2-(trifluoroacetyl)-1,2,3,4-tetrahydro-7-isoquinolinamine as described in Example 2, Step E (microwave at 160° C. for 10 min.). Purification via column chromatography using a 0-30% gradient of EtOAc/MeOH generated the product as a light tan solid in 31% yield. $^1$H NMR (400 MHz, DMSO-$d_6$) δ 10.38 (s, 1H), 9.68 (s, 1H), 8.84 (d, 1H), 8.47 (m, 1H), 8.24 (d, 1H), 7.90 (s, 1H), 7.74 (s, 2H), 7.44 (m, 4H), 7.29 (d, 1H), 7.13 (m, 2H), 6.97 (s, 2H), 6.50 (d, 1H), 4.69 (s, 2H), 3.88 (s, 2H), 3.38 (m, 2H), 2.88 (m, 2H). ES-LC/MS m/z=654 [M+H]$^+$.

Step E: N-(3-{3-[2-(1,2,3,4-Tetrahydro-7-isoquinolinylamino)-4-pyrimidinyl]pyrazolo[1,5-a]pyridin-2-yl}phenyl)-2-(2-thienyl)acetamide (title compound)

A solution of 2-(2-thienyl)-N-{3-[3-(2-{[1-(trifluoro-acetyl)-1,2,3,4-tetrahydro-7-quinolinyl]amino}-4-pyrimidinyl)pyrazolo[1,5-a]pyridin-2-yl]phenyl}acetamide (0.075 g, 0.11 mmol) and LiOH (50 mg, 1.2 mmol) in MeOH (10 mL) was stirred for 30 min. The reaction mixture was evaporated down and the crude taken up in DCM and washed with brine. Purification via column chromatography using a 0-30% gradient of EtOAc/MeOH generated the product as a yellow solid in 42% yield. $^1$H NMR (400 MHz, $d_6$-DMSO): δ 10.36 (s, 1H), 9.41 (s, 1H), 8.83 (d, 1H), 8.48 (d, 1H), 8.22 (d, 1H), 7.89 (s, 1H), 7.75 (d, 2H), 7.43 (m, 5H), 7.28 (d, 1H), 7.12 (t, 1H), 6.97 (m, 3H), 6.44 (d, 1H), 3.88 (s, 2H), 3.77 (s, 2H), 2.93 (t, 2H), 2.62 (m, 2H). ES-LC/MS m/z=558 [M+H]$^+$.

Example 17

N-{3-[3-(2-{[3-(1,3-Oxazol-5-yl)phenyl]amino}-4-pyrimidinyl)pyrazolo[1,5-a]pyridin-2-yl]phenyl}-2-(3-thienyl)acetamide

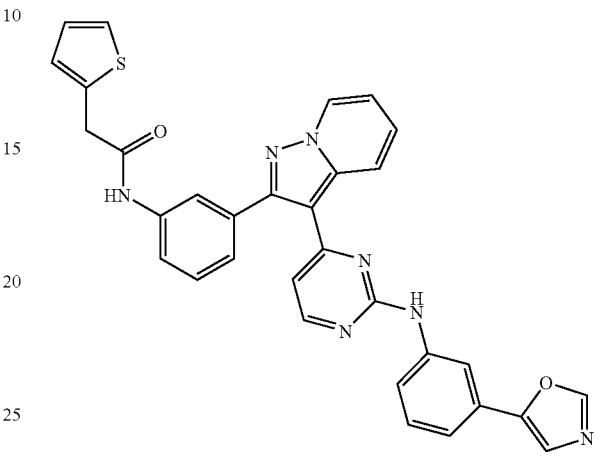

Step A. 2,2,2-Trifluoro-N-{3-[3-(2-{[3-(1,3-oxazol-5-yl)phenyl]amino}-4-pyrimidinyl)pyrazolo[1,5-a]pyridin-2-yl]phenyl}acetamide

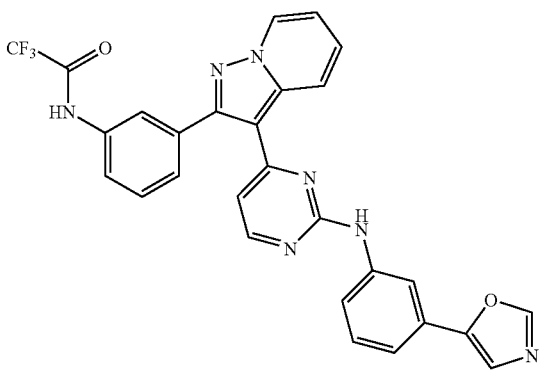

To a solution of N-{3-[3-(2-chloro-4-pyrimidinyl)pyrazolo[1,5-a]pyridin-2-yl]phenyl}-2,2,2-trifluoroacetamide (1.0 g, 0.002 mol) (see Example 1, Step C) in 1,4-dioxane (25 mL) and i-PrOH (5 mL) was added 3-(1,3-oxazol-5-yl)aniline (1.15 g, 0.007 mols) followed by catalytic 12M HCl. After heating overnight at 90° C., the reaction was quenched with saturated NaHCO$_3$ (25 mL), the solvent was removed by rotary evaporation, the aqueous layer extracted with DCM (25 mL), the organic layer concentrated, and purified by column chromatography (5-50% EtOAc in hexanes then 100% EtOAc) to provide the product (0.89 g, 69%) as an off-white solid. ES-LC/MS m/z=542 [M+H]$^+$.

Step B. Preparation of 4-[2-(3-aminophenyl)pyrazolo[1,5-a]pyridin-3-yl]-N-[3-(1,3-oxazol-5-yl)phenyl]-2-pyrimidinamine

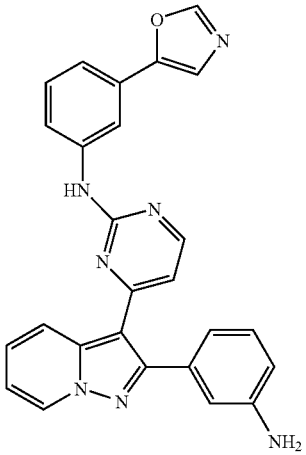

A solution of 2,2,2-trifluoro-N-{3-[3-(2-{[3-(1,3-oxazol-5-yl)phenyl]amino}-4-pyrimidinyl)pyrazolo[1,5-a]pyridin-2-yl]phenyl}acetamide (0.89 g, 0.002 mols) and 1M LiOH (8.22 mL, 0.008 mols) in 10:1 THF:water (20 mL) was heated at 60° C. for 5 h. The reaction was washed with brine (25 mL), organic layer separated, aqueous layer extracted with EtOAc (25 mL), organic layers combined, filtered through a cotton plug, and solvent removed by rotary evaporation. The crude product was purified by column chromatography (5%-75% EtOAc in hexanes then 100% EtOAc) to provide the aniline (0.70 g, 96%) as a pale yellow foam. ES-LC/MS m/z=446 [M+H]$^+$.

Step C. Preparation of N-{3-[3-(2-{[3-(1,3-oxazol-5-yl)phenyl]amino}-4-pyrimidinyl)pyrazolo[1,5-a]pyridin-2-yl]phenyl}-2-(3-thienyl)acetamide (title compound)

To a solution of 4-[2-(3-aminophenyl)pyrazolo[1,5-a]pyridin-3-yl]-N-[3-(1,3-oxazol-5-yl)phenyl]-2-pyrimidinamine (50 mg, 0.112 mmol) in 5:1 THF:DMA (2 mL) was added HOBT (46 mg, 0.34 mmol), 0.28 g polystyrene-bound carbodiimide resin (280 mg, 0.34 mmol), and 3-thienylacetic acid (48 mg, 0.34 mmol). After stirring at rt for 48 h, excess Dowex 550A OH anion-exchange resin was added and the resulting mixture was allowed to stir overnight. The solids were then removed by vacuum filtration and rinsed with THF (25 mL) and MeOH (25 mL). The filtrate was concentrated under reduced pressure and purified by mass-guided prep LC (C18, 15% H$_2$0 (with 0.1% formic acid)/CH$_3$OH to 100% CH$_3$OH gradient) to afford the title compound (30 mg, 47%). 1H NMR (400 MHz, DMSO-d$_6$) δ 3.65 (s, 2H), 6.51 (d, 1H, J=5.37 Hz), 7.07-7.12 (m, 2H), 7.23-7.48 (m, 7H), 7.55 (s, 1H), 7.68-7.76 (m, 2H), 7.89 (s, 1H), 8.20 (s, 1H), 8.27 (d, 1H, J=5.37 Hz), 8.38 (s, 1H), 8.50-8.51 (m, 1H), 8.81 (d, 1H, J=6.84 Hz), 9.73 (s, 1H), 10.28 (s, 1H). ES-LC/MS m/z=570 [M+H]$^+$.

Example 18

2-(1H-Indol-3-yl)-N-{3-[3-(2-{[3-(1,3-oxazol-5-yl)phenyl]amino}-4-pyrimidinyl)pyrazolo[1,5-a]pyridin-2-yl]phenyl}acetamide

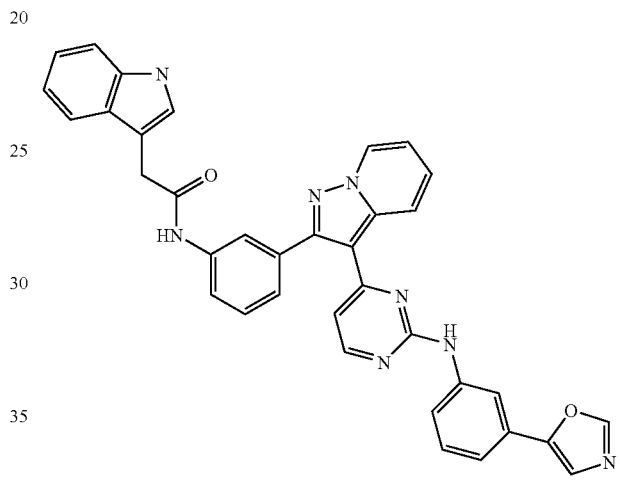

To a solution of 4-[2-(3-aminophenyl)pyrazolo[1,5-a]pyridin-3-yl]-N-[3-(1,3-oxazol-5-yl)phenyl]-2-pyrimidinamine (50 mg, 0.112 mmol) (see Example 17, Step B) in 5:1 THF:DMA (2 mL) was added HOBT (46 mg, 0.34 mmol), 0.28 g polystyrene-bound carbodiimide resin (280 mg, 0.34 mmol), and 1H-indol-3-ylacetic acid (59 mg, 0.34 mmol). After stirring at rt for 48 h, excess Dowex 550A OH anion-exchange resin was added and the resulting mixture was allowed to stir overnight. The solids were then removed by vacuum filtration and rinsed with THF (25 mL) and MeOH (25 mL). The filtrate was concentrated under reduced pressure and purified by mass-guided prep LC (C18, 15% H$_2$O (with 0.1% formic acid)/CH$_3$OH to 100% CH$_3$OH gradient) to afford the title compound (34.5 mg, 51%). $^1$H NMR (400 MHz, DMSO-d$_6$) δ 3.72 (s, 2H), 6.50 (d, 1H, J=5.37 Hz), 6.95-6.98 (m, 1H), 7.04-7.11 (m, 2H), 7.22-7.41 (m, 5H), 7.55 (s, 1H), 7.59 (d, 1H, J=7.81 Hz), 7.68-7.69 (m, 1H), 7.74-7.76 (m, 1H), 7.90 (s, 1H), 8.19 (s, 1H), 8.25 (d, 1H, J=5.37 Hz), 8.38 (s, 1H), 8.49-8.51 (m, 1H), 8.81 (d, 1H, J=6.84 Hz), 9.72 (s, 1H), 10.26 (s, 1H), 10.90 (s, 1H). ES-LC/MS m/z=603 [M+H]$^+$.

Example 19

2-(3-Methyl-5-isoxazolyl)-N-{3-[3-(2-{[3-(1,3-oxazol-5-yl)phenyl]amino}-4-pyrimidinyl)pyrazolo[1,5-a]pyridin-2-yl]phenyl}acetamide

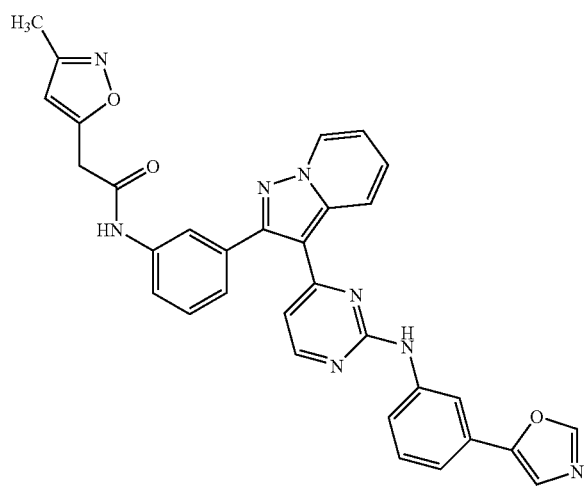

To a solution of 4-[2-(3-aminophenyl)pyrazolo[1,5-a]pyridin-3-yl]-N-[3-(1,3-oxazol-5-yl)phenyl]-2-pyrimidinamine (50 mg, 0.112 mmol) (see Example 17, Step B) in 5:1 THF:DMA (2 mL) was added HOBT (46 mg, 0.34 mmol), 0.28 g polystyrene-bound carbodiimide resin (280 mg, 0.34 mmol), and (3-methyl-5-isoxazolyl)acetic acid (48 mg, 0.34 mmol). After stirring at rt for 48 h, excess Dowex 550A OH anion-exchange resin was added and the resulting mixture was allowed to stir overnight. The solids were then removed by vacuum filtration and rinsed with THF (25 mL) and MeOH (25 mL). The filtrate was concentrated under reduced pressure and purified by mass-guided prep LC (C18, 15% $H_2O$ (with 0.1% formic acid)/$CH_3OH$-100% $CH_3OH$ gradient) to afford the title compound (39 mg, 61%). $^1H$ NMR (400 MHz, DMSO-$d_6$) δ 2.19 (s, 3H), 3.88 (s, 2H), 6.25 (s, 1H), 6.50 (d, 1H, J=5.37 Hz), 7.09-7.12 (m, 1H), 7.29-7.45 (m, 5H), 7.55 (s, 1H), 7.69-7.73 (m, 2H), 7.87 (s, 1H), 8.19 (s, 1H), 8.27 (d, 1H, J=5.37 Hz), 8.38 (s, 1H), 8.50-8.51 (m, 1H), 8.81 (d, 1H, J=7.32 Hz), 9.73 (s, 1H), 10.44 (s, 1H). ES-LC/MS m/z=569 [M+H]$^+$.

Example 20

2-(2,6-Difluorophenyl)-N-{3-[3-(2-{[3-(1,3-oxazol-5-yl)phenyl]amino}-4-pyrimidinyl)pyrazolo[1,5-a]pyridin-2-yl]-phenyl}acetamide

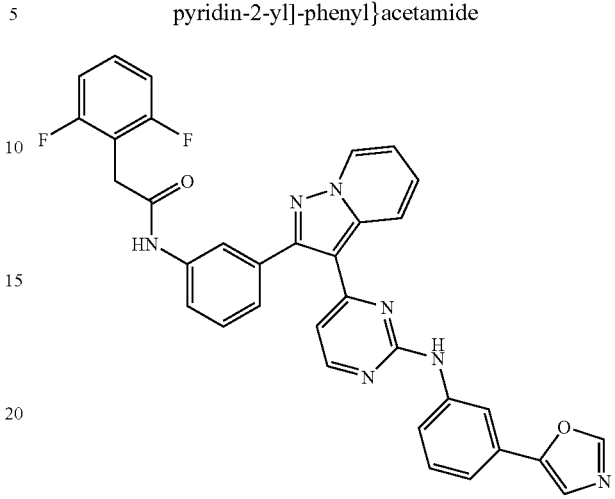

To a solution of 4-[2-(3-aminophenyl)pyrazolo[1,5-a]pyridin-3-yl]-N-[3-(1,3-oxazol-5-yl)phenyl]-2-pyrimidinamine (50 mg, 0.112 mmol) (see Example 17, Step B) in 5:1 THF:DMA (2 mL) was added HOBT (46 mg, 0.34 mmol), 0.28 g polystyrene-bound carbodiimide resin (280 mg, 0.34 mmol), and (2,6-difluorophenyl)acetic acid (58 mg, 0.34 mmol). After stirring at rt for 48 h, excess Dowex 550A OH anion-exchange resin was added and the resulting mixture was allowed to stir overnight. The solids were then removed by vacuum filtration and rinsed with THF (25 mL) and MeOH (25 mL). The filtrate was concentrated under reduced pressure and purified by mass-guided prep LC (C18, 15% $H_2O$ (with 0.1% formic acid)/$CH_3OH$ to 100% $CH_3OH$ gradient) to afford the title compound (44.5 mg, 66%). $^1H$ NMR (400 MHz, DMSO-$d_6$) δ 3.77 (s, 2H), 6.51 (d, 1H, J=5.37 Hz), 7.07-7.11 (m, 3H), 7.26-7.43 (m, 6H), 7.56 (s, 1H), 7.69-7.74 (m, 2H), 7.87 (s, 1H), 8.20 (s, 1H), 8.27 (d, 1H, J=5.37 Hz), 8.38 (s, 1H), 8.51-8.53 (m, 1H), 8.81 (d, 1H, J=6.84 Hz), 9.73 (s, 1H), 10.44 (s, 1H). ES-LC/MS m/z=600 [M+H]$^+$.

Example 21

N-{3-[3-(2-{[3-(1,3-Oxazol-5-yl)phenyl]amino}-4-pyrimidinyl)pyrazolo[1,5-a]pyridin-2-yl]phenyl}-2-(3-pyridinyl)acetamide

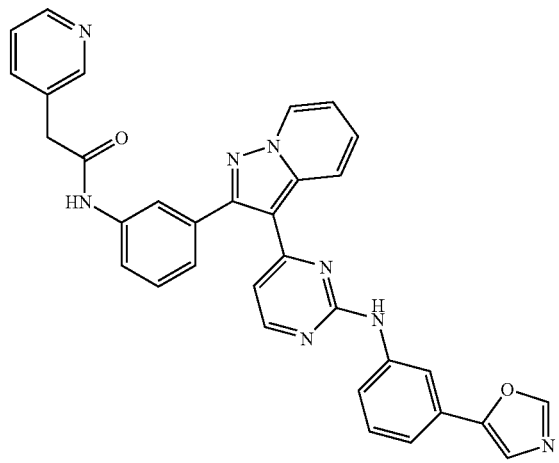

To a solution of 4-[2-(3-aminophenyl)pyrazolo[1,5-a]pyridin-3-yl]-N-[3-(1,3-oxazol-5-yl)phenyl]-2-pyrimidinamine (50 mg, 0.112 mmol) (see Example 17, Step B) in 5:1 THF:DMA (2 mL) was added HOBT (46 mg, 0.34 mmol), 0.28 g polystyrene-bound carbodiimide resin (280 mg, 0.34 mmol), and 3-pyridinylacetic acid (46 mg, 0.34 mmol). After stirring at rt for 48 h, excess Dowex 550A OH anion-exchange resin was added and the resulting mixture was allowed to stir overnight. The solids were then removed by vacuum filtration and rinsed with THF (25 mL) and MeOH (25 mL). The filtrate was concentrated under reduced pressure and purified by mass-guided prep LC (C18, 15% $H_2O$ (with 0.1% formic acid)/$CH_3OH$ to 100% $CH_3OH$ gradient) to afford the title compound (27.8 mg, 44%). $^1$H NMR (400 MHz, DMSO-$d_6$) δ 3.70 (s, 2H), 6.50 (d, 1H, J=5.37 Hz), 7.09-7.11 (m, 1H), 7.26 (d, 1H, J=7.32 Hz), 7.30-7.43 (m, 5H), 7.55 (s, 1H), 7.69-7.74 (m, 3H), 7.88 (s, 1H), 8.19 (s, 1H), 8.27 (d, 1H, J=5.37 Hz), 8.38 (s, 1H), 8.43-8.44 (m, 1H), 8.51 (s, 2H), 8.81 (d, 1H, J=6.84 Hz), 9.73 (s, 1H), 10.39 (s, 1H). ES-LC/MS m/z=565 [M+H]$^+$.

Example 22

N-{3-[3-(2-{[3-(1,3-Oxazol-5-yl)phenyl]amino}-4-pyrimidinyl)pyrazolo[1,5-a]pyridin-2-yl]phenyl}-2-(4-pyridinyl)acetamide

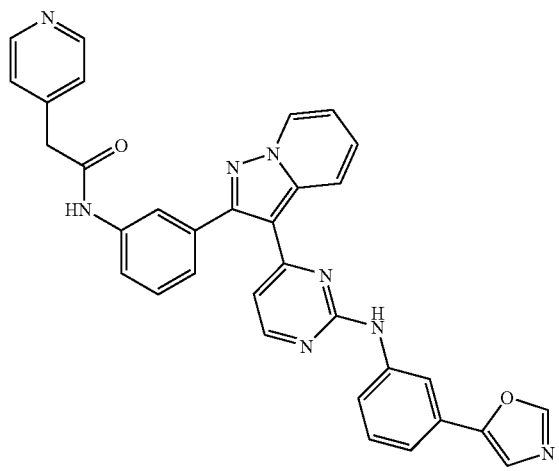

To a solution of 4-[2-(3-aminophenyl)pyrazolo[1,5-a]pyridin-3-yl]-N-[3-(1,3-oxazol-5-yl)phenyl]-2-pyrimidinamine (50 mg, 0.112 mmol) (see Example 17, Step B) in 5:1 THF:DMA (2 mL) was added HOBT (46 mg, 0.34 mmol), 0.28 g polystyrene-bound carbodiimide resin (280 mg, 0.34 mmol), and 4-pyridinylacetic acid (46 mg, 0.34 mmol). After stirring at rt for 48 h, excess Dowex 550A OH anion-exchange resin was added and the resulting mixture was allowed to stir overnight. The solids were then removed by vacuum filtration and rinsed with THF (25 mL) and MeOH (25 mL). The filtrate was concentrated under reduced pressure and purified by mass-guided prep LC (C18, 15% water (with 0.1% formic acid)/$CH_3OH$ to 100% $CH_3OH$ gradient) to afford the title compound (36.3 mg, 57%). $^1$H NMR (400 MHz, DMSO-$d_6$) δ 3.70 (s, 2H), 6.51 (d, 1H, J=5.37 Hz), 7.09-7.11 (m, 1H), 7.27-7.43 (m, 7H), 7.55 (s, 1H), 7.68-7.73 (m, 2H), 7.89 (s, 1H), 8.19 (s, 1H), 8.27 (d, 1H, J=5.37 Hz), 8.38 (s, 1H), 8.48-8.51 (m, 3H), 8.81 (d, 1H, J=6.84 Hz), 9.73 (s, 1H), 10.40 (s, 1H). ES-LC/MS m/z=565 [M+H]$^+$.

Example 23

N-{3-[3-(2-{[3-(1,3-Oxazol-5-yl)phenyl]amino}-4-pyrimidinyl)pyrazolo[1,5-a]pyridin-2-yl]phenyl}-2-(2-pyridinyl)acetamide

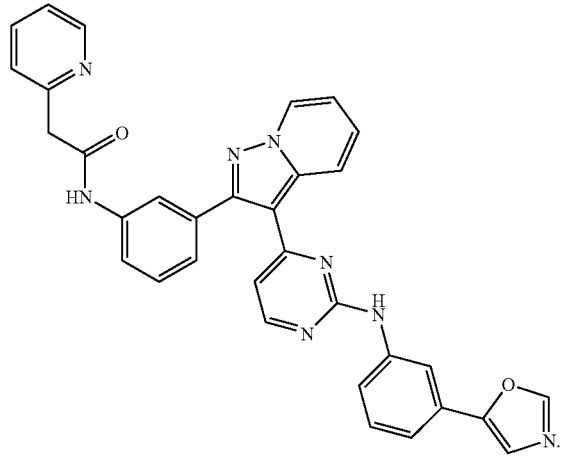

To a solution of 4-[2-(3-aminophenyl)pyrazolo[1,5-a]pyridin-3-yl]-N-[3-(1,3-oxazol-5-yl)phenyl]-2-pyrimidinamine (50 mg, 0.112 mmol) (see Example 17, Step B) in 5:1 THF:DMA (2 mL) was added HOBT (46 mg, 0.34 mmol), 0.28 g polystyrene-bound carbodiimide resin (280 mg, 0.34 mmol), and 2-pyridinylacetic acid (46 mg, 0.34 mmol). After stirring at rt for 48 h, excess Dowex 550A OH anion-exchange resin was added and the resulting mixture was allowed to stir overnight. The solids were then removed by vacuum filtration and rinsed with THF (25 mL) and MeOH (25 mL). The filtrate was concentrated under reduced pressure and purified by mass-guided prep LC (C18, 15% water (with 0.1% formic acid)/$CH_3OH$ to 100% $CH_3OH$ gradient) to afford the title compound (20.7 mg, 33%). $^1$H NMR (400 MHz, DMSO-$d_6$) δ 3.84 (s, 2H), 6.51 (d, 1H, J=5.37 Hz), 7.10 (t, 1H, J=6.84 Hz), 7.24-7.43 (m, 7H), 7.56 (s, 1H), 7.69-7.76 (m, 3H), 7.91 (s, 1H), 8.20 (s, 1H), 8.27 (d, 1H, J=4.88 Hz), 8.38 (s, 1H), 8.48-8.53 (m, 2H), 8.81 (d, 1H, J=6.84 Hz), 9.73 (s, 1H), 10.40 (s, 1H). ES-LC/MS m/z=565 [M+H]$^+$.

Example 24

N-(3-{3-[2-({3-[(Dimethylamino)methyl]phenyl}amino)-4-pyrimidinyl]pyrazolo[1,5-a]pyridin-2-yl}phenyl)-2-(3-thienyl)acetamide

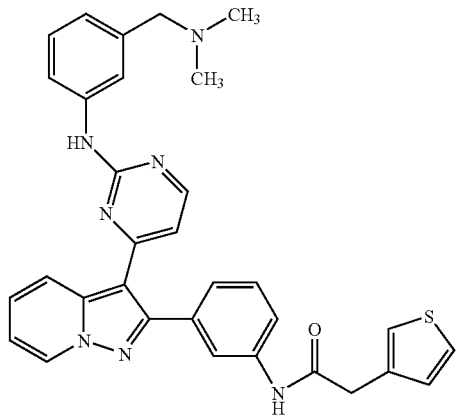

Step A. 4-[2-(3-Aminophenyl)pyrazolo[1,5-a]pyridin-3-yl]-N-{3-[(dimethylamino)methyl]phenyl}-2-pyrimidinamine

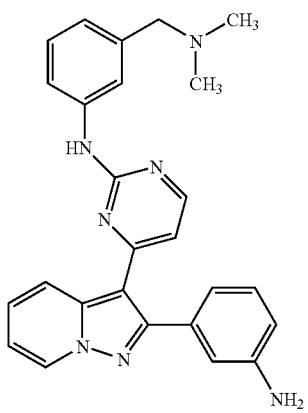

To a solution of N-{3-[3-(2-chloro-4-pyrimidinyl)pyrazolo[1,5-a]pyridin-2-yl]phenyl}-2,2,2-trifluoroacetamide (3.0 g, 0.007 mols) (see Example 1, Step C) in 1,4-dioxane (60 mL) and i-PrOH (60 mL) was added 3-[(dimethylamino)methyl]aniline (1.61 g, 0.011 mol) followed by catalytic 12M HCl. After heating four days at 90° C., reaction was quenched with saturated NaHCO$_3$ (100 mL), solvent removed by rotary evaporation, aqueous layer extracted with DCM (3×200 mL), organic layers concentrated, and purified by column chromatography (0-100% 9:1:0.1 DCM:MeOH:NH$_4$OH) to provide the product (1.25 g, 40%) as tan foam. ES-LC/MS m/z=436 [M+H]$^+$.

Step B. N-(3-{3-[2-({3-[(Dimethylamino)methyl]phenyl}amino)-4-pyrimidinyl]pyrazolo[1,5-a]pyridin-2-yl}phenyl)-2-(3-thienyl)acetamide (title compound)

To a solution of 4-[2-(3-aminophenyl)pyrazolo[1,5-a]pyridin-3-yl]-N-{3-[(dimethylamino)methyl]phenyl}-2-pyrimidinamine (50 mg, 0.115 mmol) in 5:1 THF:DMA (2 mL) was added HOBT (46 mg, 0.34 mmol), 0.28 g polystyrene-bound carbodiimide resin (280 mg, 0.34 mmol), and 3-thienylacetic acid (48 mg, 0.34 mmol). After stirring at rt for 48 h, excess Dowex 550A OH anion-exchange resin was added and the resulting mixture was allowed to stir overnight. The solids were then removed by vacuum filtration and rinsed with THF (25 mL) and MeOH (25 mL). The filtrate was concentrated under reduced pressure and purified by column chromatography (0-100% 9:1:0.1 DCM:MeOH:NH$_4$OH) to afford the title compound (32 mg, 50%). $^1$H NMR (400 MHz, CDCl$_3$) δ 2.27 (s, 6H), 3.46 (s, 2H), 3.78 (s, 2H), 6.54 (d, 1H, J=5.31 Hz), 6.90 (dd, 1H, J=1.47, 6.96 Hz), 6.99-7.00 (m, 1H), 7.06 (dd, 1H, J=1.28, 4.94 Hz), 7.22-7.38 (m, 8H), 7.53-7.56 (m, 2H), 7.61-7.63 (m, 1H), 7.77-7.80 (m, 1H), 8.16 (d, 1H, J=5.31 Hz), 8.32-8.35 (m, 1H), 8.46-8.48 (m, 1H). ES-LC/MS m/z=560 [M+H]$^+$.

Example 25

2-(2,6-Difluorophenyl)-N-(3-{3-[2-({3-[(dimethylamino)methyl]-phenyl}amino)-4-pyrimidinyl]pyrazolo[1,5-a]pyridin-2-yl}phenyl)acetamide

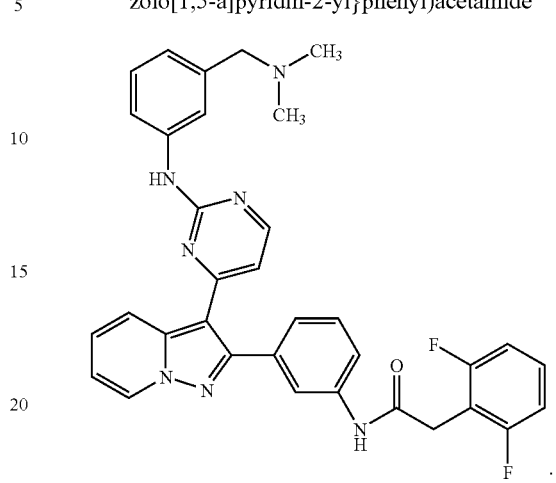

To a solution of 4-[2-(3-aminophenyl)pyrazolo[1,5-a]pyridin-3-yl]-N-{3-[(dimethylamino)methyl]phenyl}-2-pyrimidinamine (50 mg, 0.115 mmol) (see Example 24, Step A) in 5:1 THF:DMA (2 mL) was added HOBT (46 mg, 0.34 mmol), 0.28 g polystyrene-bound carbodiimide resin (280 mg, 0.34 mmol), and (2,6-difluorophenyl)acetic acid (59 mg, 0.34 mmol). After stirring at rt for 48 h, excess Dowex 550A OH anion-exchange resin was added and the resulting mixture was allowed to stir overnight. The solids were then removed by vacuum filtration and rinsed with THF (25 mL) and MeOH (25 mL). The filtrate was concentrated under reduced pressure and purified by column chromatography (DCM: 0-100% 90:9:1 DCM:MeOH:NH$_4$OH)$_{(aq)}$ to afford the title compound (37.7 mg, 56%). $^1$H NMR (400 MHz, DMSO-d$_6$) δ 2.11 (s, 6H), 3.31 (s, 2H), 3.76 (s, 2H), 6.45 (d, 1H, J=5.31 Hz), 6.84 (d, 1H, J=7.33 Hz), 7.04-7.19 (m, 4H), 7.24 (d, 1H, J=7.87 Hz), 7.31-7.46 (m, 3H), 7.61 (d, 1H, J=7.14 Hz), 7.68 (s, 1H), 7.70-7.73 (m, 1H), 7.85-7.86 (m, 1H), 8.22 (d, 1H, J=5.31 Hz), 8.49-8.51 (m, 1H), 8.79 (d, 1H, J=6.96 Hz), 9.51 (s, 1H), 10.42 (s, 1H). ES-LC/MS m/z=590 [M+H]$^+$.

Example 26

N-(3-{3-[2-({3-[(Dimethylamino)methyl]phenyl}amino)-4-pyrimidinyl]pyrazolo[1,5-a]pyridin-2-yl}phenyl)-2-(3-pyridinyl)acetamide

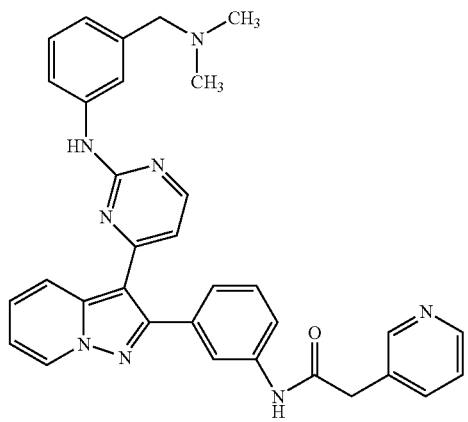

To a solution of 4-[2-(3-aminophenyl)pyrazolo[1,5-a]pyridin-3-yl]-N{3-[(dimethylamino)methyl]phenyl}-2-pyrimidinamine (50 mg, 0.115 mmol) (see Example 24, Step A) in 5:1 THF:DMA (2 mL) was added HOBT (46 mg, 0.34 mmol), 0.28 g polystyrene-bound carbodiimide resin (280 mg, 0.34 mmol), and 3-pyridinylacetic acid (47 mg, 0.34 mmol). After stirring at rt for 48 h, excess Dowex 550A OH anion-exchange resin was added and the resulting mixture was allowed to stir overnight. The solids were then removed by vacuum filtration and rinsed with THF (25 mL) and MeOH (25 mL). The filtrate was concentrated under reduced pressure and purified by column chromatography (DCM: 0-100% 90:9:1 DCM:MeOH:NH$_4$OH$_{(aq)}$) to afford the title compound (43.8 mg, 69%). $^1$H NMR (400 MHz, DMSO-d$_6$) δ 2.12 (s, 6H), 3.34 (s, 2H), 3.68 (s, 2H), 6.45 (d, 1H, J=5.31 Hz), 6.85 (d, 1H, J=7.51 Hz), 7.10 (dd, 1H, J=1.28, 6.78 Hz), 7.14-7.18 (m, 1H), 7.23-7.25 (m, 1H), 7.30-7.34 (m, 1H), 7.37-7.46 (m, 2H), 7.61-7.62 (m, 1H), 7.68-7.74 (m, 3H), 7.86-7.87 (m, 1H), 8.22 (d, 1H, J=5.31 Hz), 8.42-8.43 (m, 1H), 8.48-8.50 (m, 2H), 8.80 (d, 1H, J=6.96 Hz), 9.52 (s, 1H), 10.37 (s, 1H). ES-LC/MS m/z=555 [M+H]$^+$.

Example 27

N-(3-{3-[2-({3-[(Dimethylamino)methyl]phenyl}amino)-4-pyrimidinyl]pyrazolo[1,5-a]pyridin-2-yl}phenyl)-2-(2-pyridinyl)acetamide

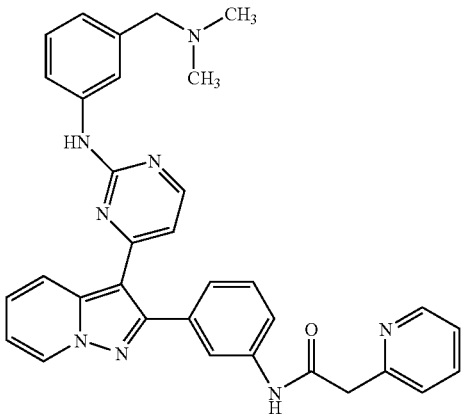

To a solution of 4-[2-(3-aminophenyl)pyrazolo[1,5-a]pyridin-3-yl]-N-{3-[(dimethylamino)methyl]phenyl}-2-pyrimidinamine (50 mg, 0.115 mmol) (see Example 24, Step A) in 5:1 THF:DMA (2 mL) was added HOBT (46 mg, 0.34 mmol), 0.28 g polystyrene-bound carbodiimide resin (280 mg, 0.34 mmol), and 2-pyridinylacetic acid (47 mg, 0.34 mmol). After stirring at rt for 48 h, excess Dowex 550A OH anion-exchange resin was added and the resulting mixture was allowed to stir overnight. The solids were then removed by vacuum filtration and rinsed with THF (25 mL) and MeOH (25 mL). The filtrate was concentrated under reduced pressure and purified by column chromatography (DCM: 0-100% 90:9:1 DCM:MeOH:NH$_4$OH$_{(aq)}$) to afford the title compound (35.2 mg, 55%). $^1$H NMR (400 MHz, DMSO-d$_6$) δ 2.13 (s, 6H), 3.34 (s, 2H), 3.84 (s, 2H), 6.46 (d, 1H, J=5.31 Hz), 6.86 (d, 1H, J=6.95 Hz), 7.10 (dd, 1H, J=1.28, 6.77 Hz), 7.16-7.20 (m, 1H), 7.24-7.27 (m, 2H), 7.37-7.48 (m, 3H), 7.62-7.64 (m, 1H), 7.70-7.77 (m, 3H), 7.90-7.91 (m, 1H), 8.22 (d, 1H, J=5.31 Hz), 8.47-8.53 (m, 2H), 8.81 (d, 1H, J=6.95 Hz), 9.53 (s, 1H), 10.39 (s, 1H). ES-LC/MS m/z=555 [M+H]$^+$.

Example 28

N-(3-{3-[2-({3-[(Dimethylamino)methyl]phenyl}amino)-4-pyrimidinyl]pyrazolo[1,5-a]pyridin-2-yl}phenyl)-2-(3-methyl-5-isoxazolyl)acetamide

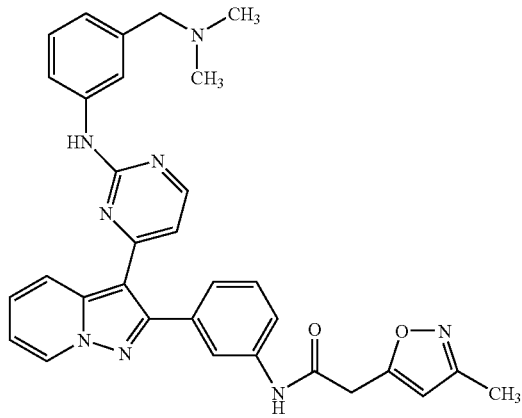

To a solution of 4-[2-(3-aminophenyl)pyrazolo[1,5-a]pyridin-3-yl]-N-{3-[(dimethylamino)methyl]phenyl}-2-pyrimidinamine (50 mg, 0.115 mmol) (see Example 24, Step A) in 5:1 THF:DMA (2 mL) was added HOBT (46 mg, 0.34 mmol), 0.28 g polystyrene-bound carbodiimide resin (280 mg, 0.34 mmol), and (3-methyl-5-isoxazolyl)acetic acid (49 mg, 0.34 mmol). After stirring at rt for 48 h, excess Dowex 550A OH anion-exchange resin was added and the resulting mixture was allowed to stir overnight. The solids were then removed by vacuum filtration and rinsed with THF (25 mL) and MeOH (25 mL). The filtrate was concentrated under reduced pressure and purified by column chromatography (DCM: 0-100% 90:9:1 DCM:MeOH:NH$_4$OH$_{(aq)}$) to afford the title compound (43.5 mg, 68%). $^1$H NMR (400 MHz, DMSO-d$_6$) δ 2.13 (s, 6H), 2.19 (s, 3H), 3.34 (s, 2H), 3.88 (s, 2H), 6.25 (s, 1H), 6.47 (d, 1H, J=5.31 Hz), 6.87 (d, 1H, J=7.32 Hz), 7.10-7.20 (m, 2H), 7.28-7.30 (m, 1H), 7.41-7.48 (m, 2H), 7.62-7.64 (m, 1H), 7.69-7.74 (m, 2H), 7.86-7.87 (m, 1H), 8.24 (d, 1H, J=5.31 Hz), 8.50-8.52 (m, 1H), 8.82 (d, 1H, J=6.77 Hz) 9.53 (s, 1H), 10.43 (s, 1H). ES-LC/MS m/z=559 [M+H]$^+$.

Example 29

N-(3-{3-[2-({3-[(Dimethylamino)methyl]phenyl}amino)-4-pyrimidinyl]pyrazolo[1,5-a]pyridin-2-yl}phenyl)-2-(5-methyl-2-phenyl-1,3-thiazol-4-yl)acetamide

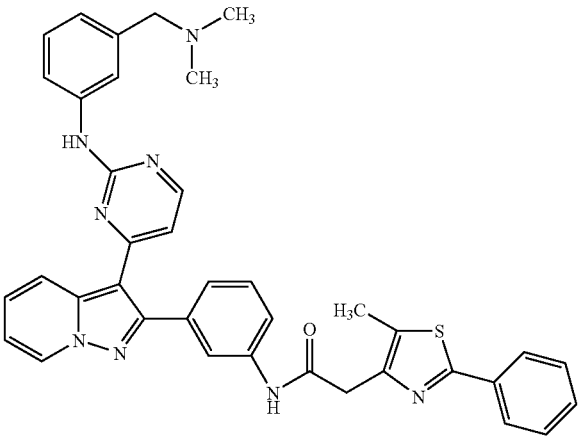

To a solution of 4-[2-(3-aminophenyl)pyrazolo[1,5-a]pyridin-3-yl]-N-{3-[(dimethylamino)methyl]phenyl}-2-pyrimidinamine (50 mg, 0.115 mmol) (see Example 24, Step A) in 5:1 THF:DMA (2 mL) was added HOBT (46 mg, 0.34 mmol), 0.28 g polystyrene-bound carbodiimide resin (280 mg, 0.34 mmol), and (5-methyl-2-phenyl-1,3-thiazol-4-yl) acetic acid (80 mg, 0.34 mmol). After stirring at rt for 48 h, excess Dowex 550A OH anion-exchange resin was added and the resulting mixture was allowed to stir overnight. The solids were then removed by vacuum filtration and rinsed with THF (25 mL) and MeOH (25 mL). The filtrate was concentrated under reduced pressure and purified by column chromatography (DCM: 0-100% 90:9:1 DCM:MeOH:NH$_4$OH$_{(aq)}$) to afford the title compound (50.1 mg, 67%). $^1$H NMR (400 MHz, DMSO-d$_6$) δ 2.11 (s, 6H), 2.43 (s, 3H), 3.31 (s, 2H), 3.81 (s, 2H), 6.45 (d, 1H, J=5.31 Hz), 6.84 (d, 1H, J=6.96 Hz), 7.08-7.11 (m, 1H), 7.14-7.18 (m, 1H), 7.23-7.25 (m, 1H), 7.38-7.46 (m, 5H), 7.59-7.62 (m, 1H), 7.68 (s, 1H), 7.75-7.81 (m, 3H), 7.89 (s, 1H), 8.21 (d, 1H, J=5.49 Hz), 8.48-8.51 (m, 1H), 8.79 (d, 1H, J=6.96 Hz) 9.50 (s, 1H), 10.35 (s, 1H). ES-LC/MS m/z=651 [M+H]$^+$.

Example 30

N-[3-(4-fluoro-3-{2-[(2-methyl-1,2,3,4-tetrahydro-7-isoquinolinyl)amino]-4-pyrimidinyl}pyrazolo[1,5-a]pyridin-2-yl)phenyl]-2-(2-thienyl)acetamide

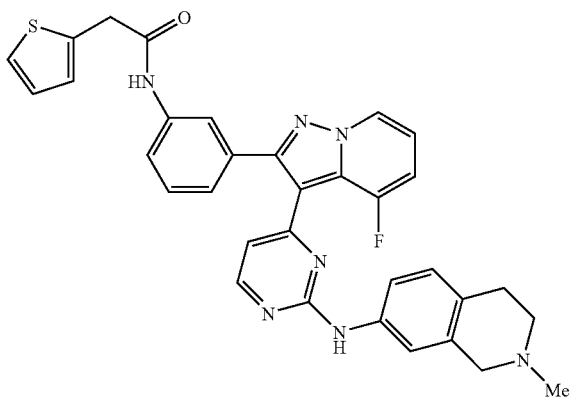

Step A: 1-Amino-3-fluoropyridinium nitrate

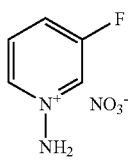

To the solution of barium oxide (7.1 g) and barium nitrate (8.1 g) in water (50 mL) was added 3-fluoropyridine (8.0 g). Hydroxylamine sulphonic acid (8.2 g) in water (20 mL) was added into the solution dropwise over 5 min. The reaction was heated to 90° C. for 12 h. Filtration removed the precipitates and the filtrate was concentrated to give a crude brown sticky solid (7.0 g, 77% yield). The crude 1-amino-3-fluoropyridinium nitrate was carried to next step without further purification.

Step B: N-{3-[3-(2-Chloro-4-pyrimidinyl)-4-fluoropyrazolo[1,5-a]pyridin-2-yl]phenyl}-2,2,2-trifluoroacetamide and N-{3-[3-(2-chloro-4-pyrimidinyl)-6-fluoropyrazolo[1,5-a]pyridin-2-yl]phenyl}-2,2,2-trifluoroacetamide

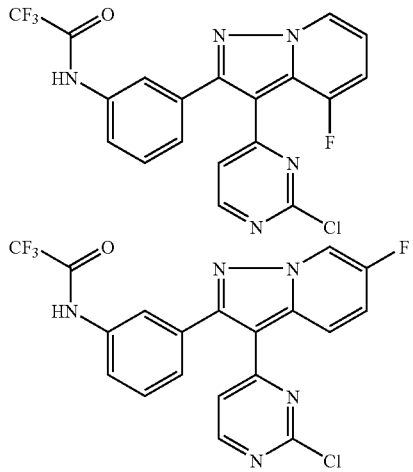

To a solution of N-[3-(2-chloro-pyrimidin-4-ylethenyl)-phenyl]-2,2,2-trifluoro-acetamide (See Example 1, step B) (5.0 g) in DMF (40 mL) were added 1-amino-3-fluoropyridinium nitrate (5.4 g) and K$_2$CO$_3$ (6.0 g). The reaction was kept stirring at RT for 1.5 h. The DMF solution was poured into 5% LiCl solution (60 mL) and extracted with EtOAc (2×30 mL). The combined organic phase were dried (Na$_2$SO$_4$) and concentrated. The crude products were separated through silica gel column chromatography to afford two products. The first to elute was N-{3-[3-(2-chloro-4-pyrimidinyl)-6-fluoropyrazolo[1,5-a]pyridin-2-yl]phenyl}-2,2,2-trifluoroacetamide (2.0 g, 30% yield). $^1$H NMR (400 MHz, DMSO-d$_6$) δ ppm 7.08 (d, 1H, J=5.49 Hz), 7.45 (d, J=7.68 Hz), 7.55 (t, 1H, J=7.96 Hz), 7.73-7.79 (m, 1H), 7.83 (d, 1H, J=0.91 Hz), 7.95 (t, 1H, J=1.74 Hz), 8.41 (dd, 1H, J=9.97, 5.76 Hz), 8.49 (d, 1H, J=5.49 Hz), 9.27 (dd, 1H, J=4.30, 2.29 Hz). ES-LC/MS m/z=436 [M+H]$^+$.

The second to elute was N-{3-[3-(2-chloro-4-pyrimidinyl)-4-fluoropyrazolo[1,5-a]pyridin-2-yl]phenyl}-2,2,2-trifluoroacetamide (2.67 g, 40% yield). $^1$H NMR (400 MHz, DMSO-d$_6$) δ ppm 7.09-7.15 (m, 1H), 7.32-7.41 (m, 2H), 7.45 (t, 1H, J=7.96 Hz), 7.55 (dd, 1H, J=5.12, 2.56 Hz), 7.68-7.74 (m, 1H), 7.92 (t, 1H, J=1.83 Hz), 8.72 (d, 1H, J=5.12 Hz), 8.78 (d, 1H, J=6.77 Hz), 11.31 (s, 1H). ES-LC/MS m/z=436 [M+H]$^+$.

Step C: 3-[3-(2-Chloro-4-pyrimidinyl)-4-fluoropyrazolo[1,5-a]pyridin-2-yl]aniline

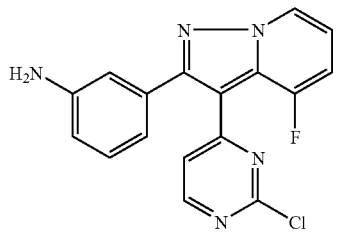

To the solution of N-{3-[3-(2-chloro-4-pyrimidinyl)-4-fluoropyrazolo[1,5-a]pyridin-2-yl]phenyl}-2,2,2-trifluoroacetamide (0.40 g) in THF (27 mL) and water (3 mL) was added 5% LiOH solution (2.3 mL). The reaction was kept stirring at RT for 15 h and was worked up with sat. NaHCO₃ solution (20 mL) and extracted with EtOAc (2×20 mL). The organic phase was dried (Na₂SO₄) and concentrated to afford the crude 3-[3-(2-chloro-4-pyrimidinyl)-4-fluoropyrazolo[1,5-a]pyridin-2-yl]aniline (0.30 g, 95% yield) as yellow solid. ES-LC/MS m/z=340 [M+H]⁺.

Step D: N-{3-[3-(2-chloro-4-pyrimidinyl)-4-fluoro-pyrazolo[1,5-a]pyridin-2-yl]phenyl}-2-(2-thienyl)acetamide

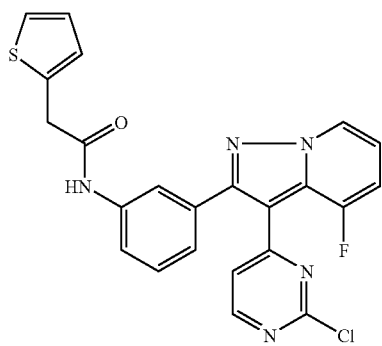

To the solution of 3-[3-(2-chloro-4-pyrimidinyl)-4-fluoropyrazolo[1,5-a]pyridin-2-yl]aniline (0.28 g) in THF (15 mL) was added 2-thienylacetyl chloride (0.16 g). The reaction was kept stirring at RT for 0.5 h and worked up with sat. NaHCO₃ solution (8 mL). After extraction with EtOAc (2×10 mL), drying with Na₂SO₄, and concentration, the crude mixture was purified through silica gel column chromatography to afford N-{3-[3-(2-chloro-4-pyrimidinyl)-4-fluoropyrazolo[1,5-a]pyridin-2-yl]phenyl}-2-(2-thienyl)acetamide as a yellow solid (0.36 g, 95%). ES-LC/MS m/z=464 [M+H]⁺.

Step E: N-[3-(4-fluoro-3-{2-[(2-methyl-1,2,3,4-tetrahydro-7-isoquinolinyl)amino]-4-pyrimidinyl}pyrazolo[1,5-a]pyridin-2-yl)phenyl]-2-(2-thienyl)acetamide (title compound)

To the solution of N-{3-[3-(2-chloro-4-pyrimidinyl)-4-fluoropyrazolo[1,5-a]pyridin-2-yl]phenyl}-2-(2-thienyl)acetamide (0.080 g) in i-PrOH (5 mL) was added 2-methyl-1,2,3,4-tetrahydro-7-isoquinolinamine (0.041 g) and 2 drops of concentrate hydrochloric acid. The reaction was microwaved in a sealed tube at 180° C. for 10 min. The i-PrOH was removed by rotary evaporation and the residue was treated with sat. NaHCO₃ (5 mL), extracted with EtOAc (2×5 mL), and dried (Na₂SO₄). Concentration and purification with column chromatography afforded the title compound as a white solid (0.060 g, 60% yield). ¹H NMR (400 MHz, DMSO-d₆) δ 2.25 (s, 3H), 2.63 (s, 2H), 3.17 (s, 2H), 3.84 (s, 2H), 6.80 (s, 1H), 6.89 (dd, 1H, J=4.94, 3.11 Hz), 6.95 (d, 2H, J=3.66 Hz), 6.99-7.05 (m, 1H), 7.08 (d, 1H, J=7.68 Hz), 7.18 (s, 1H), 7.24-7.30 (m, 2H), 7.35-7.37 (m, 1H), 7.58 (d, 1H, J=1.10 Hz), 8.05 (t, 1H, J=1.83 Hz), 8.44 (d, 1H, J=5.12 Hz), 8.72 (d, 1H, J=6.95 Hz), 9.39 (s, 1H), 10.32 (s, 1H). ES-LC/MS m/z=590 [M+H]⁺.

Example 31

N-[3-(3-{2-[(3-{[2-(dimethylamino)ethyl]oxy}phenyl)amino]-4-pyrimidinyl}-4-fluoropyrazolo[1,5-a]pyridin-2-yl)phenyl]-2-(2-thienyl)acetamide

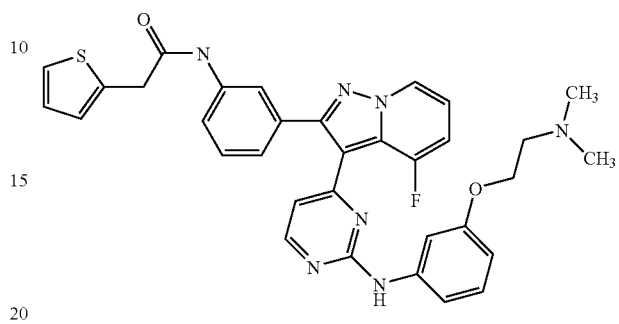

The title compound was synthesized from N-{3-[3-(2-chloro-4-pyrimidinyl)-4-fluoropyrazolo[1,5-a]pyridin-2-yl]phenyl}-2-(2-thienyl)acetamide (see Example 30, step D) (0.080 g) and 3-{[2-(dimethylamino)ethyl]oxy}aniline (0.062 g) using the procedure described in Example 30, step E. The title compound was isolated as a white solid (0.056 g, 55% yield). ¹H NMR (400 MHz, DMSO-d₆) δ 2.13 (s, 6H), 2.52 (t, 2H, J=6.13 Hz), 3.83 (s, 2H), 3.87 (t, 2H, J=6.13 Hz), 6.42 (d, 1H, J=8.17 Hz), 6.85 (dd, 1H, J=4.74, 2.26 Hz), 6.95 (m, 2H), 7.01 (m, 3H), 7.12 (m, 1H), 7.28 (m, 2H), 7.35 (m, 1H), 7.40 (s, 1H), 7.56 (m, 1H), 7.98 (s, 1H), 8.45 (d, 1H, J=4.94 Hz), 8.72 (d, 1H, J=6.95 Hz), 9.55 (s, 1H), 10.29 (s, 1H). ES-LC/MS m/z=608 [M+H]⁺.

Example 32

N-[3-(4-fluoro-3-{2-[(3-fluorophenyl)amino]-4-pyrimidinyl}pyrazolo[1,5-a]pyridin-2-yl)phenyl]-2-(2-thienyl)acetamide

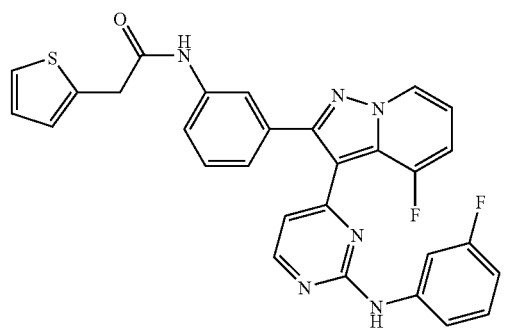

The title compound was synthesized from N-{3-[3-(2-chloro-4-pyrimidinyl)-4-fluoropyrazolo[1,5-a]pyridin-2-yl]phenyl}-2-(2-thienyl)acetamide (see Example 30, step D) (0.080 g) and 3-fluoroaniline (0.041 g) using the procedure described in Example 30, step E. The title compound was isolated as a white solid (0.059 g, 65% yield). ¹H NMR (400 MHz, DMSO-d₆) δ 3.83 (s, 2H), 6.60 (m, 1H), 6.94 (m, 2H), 7.01-7.12 (m, 3H), 7.21-7.31 (m, 3H), 7.49-7.58 (m, 2H), 7.97 (s, 1H), 8.50 (d, 1H, J=5.03 Hz), 8.73 (d, 1H, J=6.70 Hz), 9.78 (s, 1H), 10.27 (s, 1H). ES-LC/MS m/z=539 [M+H]⁺.

Example 33

N-[3-(6-fluoro-3-{2-[(3-fluorophenyl)amino]-4-pyrimidinyl}pyrazolo[1,5-a]pyridin-2-yl)phenyl]-2-(2-thienyl)acetamide

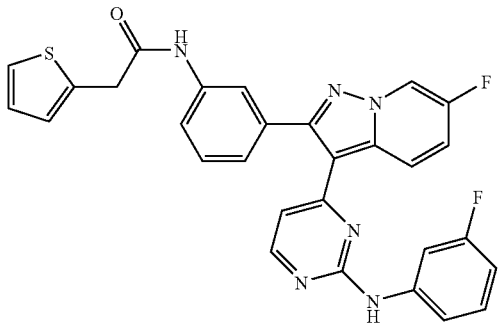

Step A: 3-[3-(2-chloro-4-pyrimidinyl)-6-fluoropyrazolo[1,5-a]pyridin-2-yl]aniline

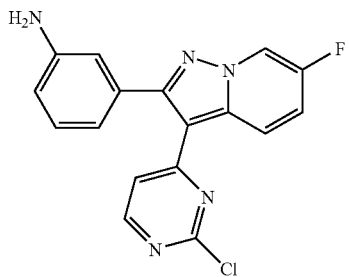

The title compound was synthesized from N-{3-[3-(2-chloro-4-pyrimidinyl)-6-fluoropyrazolo[1,5-a]pyridin-2-yl]phenyl}-2,2,2-trifluoroacetamide (see Example 30, step B) (0.32 g) using the procedure described in Example 30, step C. The crude 3-[3-(2-chloro-4-pyrimidinyl)-6-fluoropyrazolo[1,5-a]pyridin-2-yl]aniline was isolated as a yellow solid (0.24 g, 96% yield). ES-LC/MS m/z=340 [M+H]$^+$.

Step B: N-{3-[3-(2-chloro-4-pyrimidinyl)-6-fluoropyrazolo[1,5-a]pyridin-2-yl]phenyl}-2-(2-thienyl)acetamide

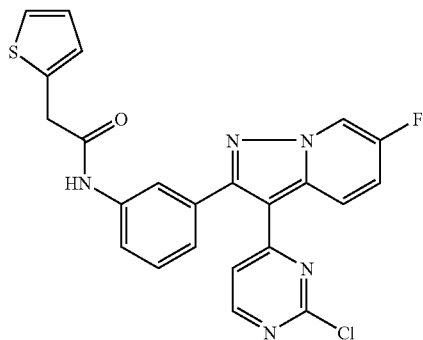

The title compound was synthesized from 3-[3-(2-chloro-4-pyrimidinyl)-6-fluoropyrazolo[1,5-a]pyridin-2-yl]aniline (0.20 g) using the procedure described in Example 30, step D, as a yellow solid (0.26 g, 96% yield). ES-LC/MS m/z=464 [M+H]$^+$.

Step C: N-[3-(6-fluoro-3-{2-[(3-fluorophenyl)amino]-4-pyrimidinyl}pyrazolo[1,5-a]pyridin-2-yl)phenyl]-2-(2-thienyl)acetamide (title compound)

The title compound was synthesized from N-{3-[3-(2-chloro-4-pyrimidinyl)-6-fluoropyrazolo[1,5-a]pyridin-2-yl]phenyl}-2-(2-thienyl)acetamide (0.070 g) and 3-fluoroaniline (0.033 g) using the procedure described in Example 30, step E. The title compound was isolated as a white solid (0.048 g, 66% yield). $^1$H NMR (400 MHz, DMSO-d$_6$) δ 3.84 (s, 2H), 6.54 (d, 1H, J=5.52 Hz), 6.70 (m, 1H), 6.94 (m, 2H), 7.24 (m, 2H), 7.34-7.45 (m, 3H), 7.60 (m, 1H), 7.68-7.77 (m, 2H), 7.87 (s, 1H), 8.29 (d, 1H, J=5.52 Hz), 8.51 (m, 1H), 9.16 (m, 1H), 9.81 (s, 1H), 10.32 (s, 1H). ES-LC/MS m/z=539 [M+H]$^+$.

Example 34

N-[3-(3-{2-[(3-{[2-(dimethylamino)ethyl]oxy}phenyl)amino]-4-pyrimidinyl}-6-fluoropyrazolo[1,5-a]pyridin-2-yl)phenyl]-2-(2-thienyl)acetamide

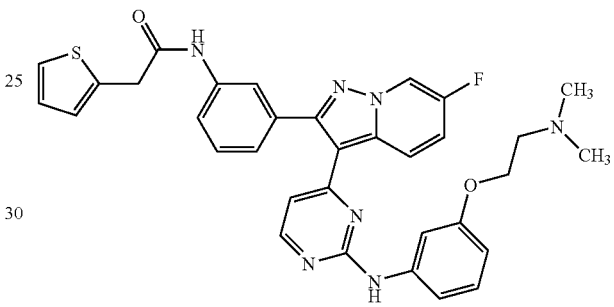

The title compound was synthesized from N-{3-[3-(2-chloro-4-pyrimidinyl)-6-fluoropyrazolo[1,5-a]pyridin-2-yl]phenyl}-2-(2-thienyl)acetamide (Example 33, step B) (0.070 g) and 3-{[2-(dimethylamino)ethyl]oxy}aniline (0.057 g) using the procedure described in Example 30, step E. The title compound was isolated as a white solid (0.050 g, 55% yield). $^1$H NMR (400 MHz, DMSO-d$_6$) δ 2.15 (s, 6H), 2.56 (t, 2H, J=6.08 Hz), 3.84 (s, 2H), 3.95 (t, 2H, J=6.08 Hz), 6.46 (d, 1H, J=5.69 Hz), 6.51 (m, 1H), 6.95 (m, 1H), 7.12 (t, 1H, J=8.85 Hz), 7.23 (m, 2H), 7.35 (m, 1H), 7.40 (t, 1H, J=7.90 Hz), 7.50 (s, 1H), 7.59 (m, 1H), 7.71 (m, 1H), 7.86 (s, 1H), 8.24 (d, 1H, J=5.69 Hz), 8.53 (m, 1H), 9.15 (m, 1H), 9.56 (s, 1H), 10.32 (s, 1H). ES-LC/MS m/z=608 [M+H]$^+$.

Example 35

N-[3-(6-fluoro-3-{2-[(2-methyl-1,2,3,4-tetrahydro-7-isoquinolinyl)amino]-4-pyrimidinyl}pyrazolo[1,5-a]pyridin-2-yl)phenyl]-2-(2-thienyl)acetamide

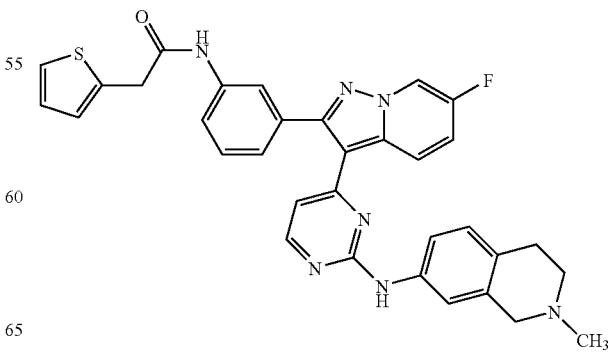

The title compound was synthesized from N-{3-[3-(2-chloro-4-pyrimidinyl)-6-fluoropyrazolo[1,5-a]pyridin-2-yl]phenyl}-2-(2-thienyl)acetamide (Example 33, step B) (0.070 g) and 2-methyl-1,2,3,4-tetrahydro-7-isoquinolinamine (0.036 g) using the procedure described in Example 30, step E. The title compound was isolated as a white solid (0.048 g, 55% yield). $^1$H NMR (400 MHz, DMSO-$d_6$) δ 2.28 (s, 3H), 2.55 (m, 2H), 2.71 (m, 2H), 3.11 (m, 1H), 3.35 (s, 1H), 3.84 (s, 2H), 6.18 (s, 1H), 6.31 (m, 1H), 6.44 (d, 1H, J=5.50 Hz), 6.94 (m, 2H), 7.23 (m, 1H), 7.34-7.45 (m, 2H), 7.55 (m, 1H), 7.71 (d, 1H, J=8.79 Hz), 7.87 (s, 1H), 8.21 (d, 1H, J=5.41 Hz), 8.48 (s, 1H), 9.14 (m, 1H), 9.43 (s, 1H), 10.34 (s, 1H). ES-LC/MS m/z=590 [M+H]$^+$.

Example 36

N-(5-{3-[2-({3-[(dimethylamino)methyl]phenyl}amino)-4-pyrimidinyl]pyrazolo[1,5-a]pyridin-2-yl}-2-fluorophenyl)-2-(2-thienyl)acetamide

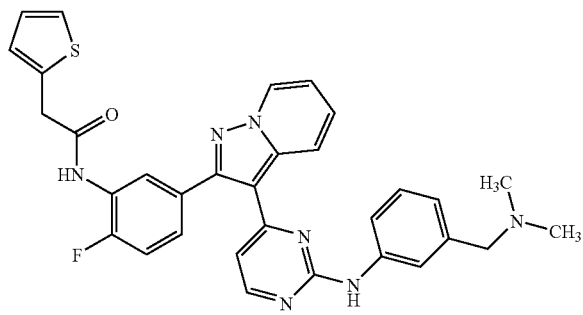

Step A: N-(5-bromo-2-fluorophenyl)-2,2,2-trifluoroacetamide

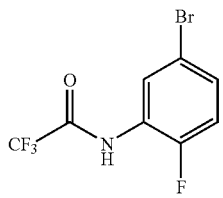

To a solution of 4-fluoro-3-nitrobromobenzene (5.0 g, 23 mmol) in absolute EtOH (500 mL) was added SnCl$_2$ dihydrate (31 g, 136 mmol) and the resulting mixture was allowed to stir overnight at rt. The solvent was removed under reduced pressure, and the residue was suspended in EtOAc, washed with 1 N NaOH, and filtered through a celite pad. The organic layer was concentrated by rotary evaporation, and dissolved in DCM (500 mL). To this solution were added TEA (26 mL, 184 mmol) and TFAA (6.5 mL, 46 mmol). After overnight stirring, the reaction was washed with 1 N HCl, dried over Na$_2$SO$_4$, concentrated and purified by column chromatography to yield the title compound (5.6 g, 87%) as a white solid. ES-LC/MS m/z=287 [M+H]$^+$.

Step B: 2,2,2-trifluoro-N-{2-fluoro-5-[(trimethylsilyl)ethynyl]phenyl}acetamide

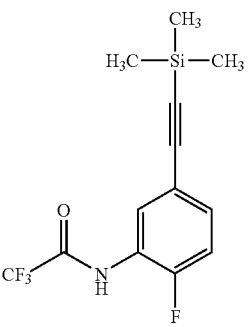

To an oven-dried flask under N$_2$ was added N-(5-bromo-2-fluorophenyl)-2,2,2-trifluoroacetamide (5.6 g, 20 mmol), anhydrous degassed THF (200 mL), dichlorobis(triphenylphosphine)palladium(II) (1.7 g, 2.5 mmol), copper(I) iodide (0.28 g, 1.5 mmol), and trimethylsilylacetylene (7.0 mL, 50 mmol). Next, TEA (27 mL, 197 mmol) was added dropwise and the resulting mixture was heated at 60° C. overnight. The crude reaction mixture was adsorbed to silica gel and purified by column chromatography to afford the desired product (5.3 g, 89%) as an off white solid. ES-LC/MS m/z=302 [M−H]$^-$.

Step C: N-(5-ethynyl-2-fluorophenyl)-2,2,2-trifluoroacetamide

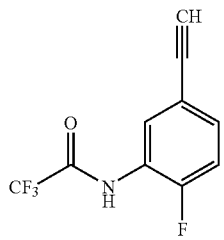

A solution of 2,2,2-trifluoro-N-{2-fluoro-5-[(trimethylsilyl)ethynyl]phenyl}acetamide (5.3 g, 17 mmol) in THF (400 mL) was cooled to 0° C., and a 1.0 M solution of TBAF in THF (17 mL, 17 mmol) was added dropwise. The resulting mixture was stirred for 10 min. at 0° C. The reaction was quenched with water (150 mL), concentrated under reduced pressure, and extracted with DCM. The combined organic layers were concentrated under reduced pressure, and the crude solid was used in the next reaction without further purification. ES-LC/MS m/z=230 [M−H]$^-$.

Step D: N-{5-[(2-chloro-4-pyrimidinyl)ethynyl]-2-fluorophenyl}-2,2,2-trifluoroacetamide

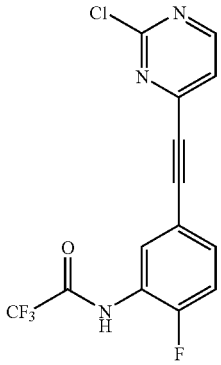

To an oven-dried flask under $N_2$ was added 2,4-dichloropyrimidine (5.1 g, 34 mmol), anhydrous degassed THF (250 mL), dichlorobis(triphenylphosphine)-palladium(II) (595 mg, 0.85 mmol), copper(I) iodide (97 mg, 0.5 mmol), and TEA (9.5 mL, 68 mmol), and the resulting suspension was heated to 60° C. A solution of N-(5-ethynyl-2-fluorophenyl)-2,2,2-trifluoroacetamide (3.9 g, 17 mmol) in THF (100 mL) was added dropwise, and the resulting mixture stirred overnight at 60° C. After 16 h, the crude reaction mixture was filtered through celite, adsorbed to silica gel, and purified by column chromatography to afford the desired product (4.6 g, 78%) as an off white solid. $^1$H NMR (400 MHz, CDCl$_3$): δ 8.65 (d, J=5.1 Hz, 1H), 8.58 (d, J=7.3 Hz, 1H), 7.49 (m, 1H), 7.41 (d, J=5.0 Hz, 1H), 7.24 (m, 1H). ES-LC/MS m/z ~344 [M+H]$^+$.

Step E: N-{5-[3-(2-chloro-4-pyrimidinyl)pyrazolo[1,5-a]pyridin-2-yl]-2-fluorophenyl}-2,2,2-trifluoroacetamide

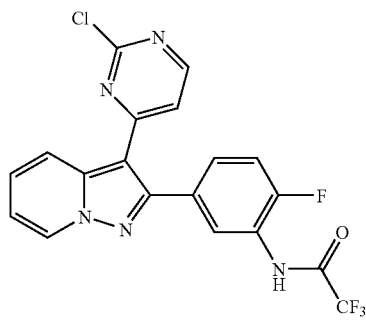

To a solution of N-{5-[(2-chloro-4-pyrimidinyl)ethynyl]-2-fluorophenyl}-2,2,2-trifluoroacetamide (4.6 g, 13 mmol) in DMF (100 mL) was added aminopyridinium iodide (5.9 g, 27 mmol) and $K_2CO_3$ (5.5 g, 40 mmol). After stirring 2 h at rt, the reaction mixture was diluted with diethyl ether (250 mL) and EtOAc (250 mL), and washed with water. The organic layer was adsorbed to silica gel and purified by column chromatography to afford the desired product (3.2 g, 55%) as a tan solid. $^1$H NMR (400 MHz, CDCl$_3$): δ 8.57 (m, 2H), 8.31 (d, J=5.5 Hz, 1H), 8.14 (s, 1H), 7.47 (m, 2H), 7.31 (t, J=9.4 Hz, 1H), 7.04 (t, J=6.8 Hz), 6.99 (d, J=5.3 Hz, 1H). ES-LC/MS m/z=436 [M+H]$^+$.

Step F: N-(5-{3-[2-({3-[(dimethylamino)methyl]phenyl}amino)-4-pyrimidinyl]pyrazolo[1,5-a]pyridin-2-yl}-2-fluorophenyl)-2,2,2-trifluoroacetamide

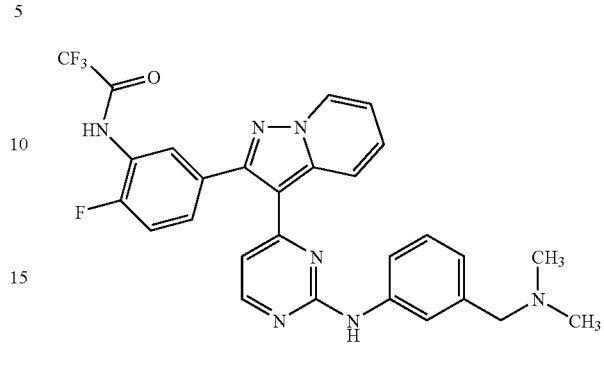

A suspension of N-{5-[3-(2-chloro-4-pyrimidinyl)pyrazolo[1,5-a]pyridin-2-yl]-2-fluorophenyl}-2,2,2-trifluoroacetamide (0.20 g, 0.46 mmol) and 3-[(dimethylamino)methyl]aniline (86 mg, 0.57 mmol) in i-PrOH (6 mL) and 12 N HCl (6 drops) was heated in a microwave for 20 min. at 180° C. The reaction mixture was diluted with DCM (50 mL) and washed with 5% aqueous $Na_2CO_3$. The aqueous layer was extracted with 20% MeOH/DCM, and the combined organic phases were dried over $MgSO_4$ and concentrated. The crude product was purified by column chromatography to give the title compound (0.16 g, 65% yield). $^1$H NMR (400 MHz, d$_6$-DMSO): δ 10.8 (bs, 1H), 9.57 (s, 1H), 8.84 (d, J=6.8 Hz, 1H), 8.50 (d, J=9.0 Hz, 1H), 8.29 (d, J=5.3 Hz, 1H), 7.82 (dd, J=7.3, 2.0 Hz, 1H), 7.70 (s, 1H), 7.65 (d, J=8.0 Hz, 1H), 7.57-7.59 (m, 1H), 7.44-7.51 (m, 2H), 7.20 (t, J=7.9 Hz, 1H), 7.15 (t, J=6.9 Hz, 1H), 6.88 (d, J=7.5 Hz, 1H), 6.51 (d, J=5.3 Hz, 1H), 3.99 (s, 2H), 2.15 (s, 6H). ES-LC/MS m/z=550 [M+H]$^+$.

Step G: 4-[2-(3-amino-4-fluorophenyl)pyrazolo[1,5-a]pyridin-3-yl]-N-{3-[(dimethylamino)methyl]phenyl}-2-pyrimidinamine

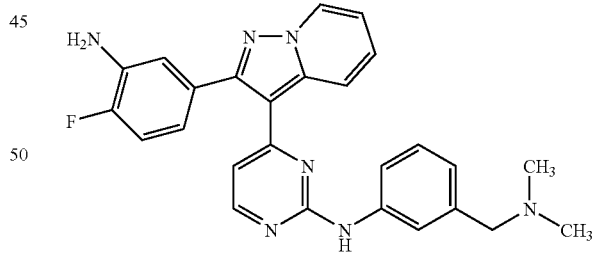

A solution of N-(5-{3-[2-({3-[(dimethylamino)methyl]phenyl}amino)-4-pyrimidinyl]pyrazolo[1,5-a]pyridin-2-yl}-2-fluorophenyl)-2,2,2-trifluoroacetamide (0.16 g, 0.3 mmol) and LiOH (25 mg, 0.6 mmol) in THF (8 mL) and water (1 mL) was stirred for 3 h at 60° C. The reaction mixture was diluted with EtOAc (50 mL) and washed with 1 N NaOH and brine. The organic phase was dried over $MgSO_4$ and purified by column chromatography to give the title compound, (0.12 g, 85% yield). $^1$H NMR (400 MHz, d$_6$-DMSO): δ 9.51 (s, 1H), 8.80 (d, J=7.0 Hz, 1H), 8.54 (d, J=8.9 Hz, 1H), 8.25 (d, J=5.4 Hz, 1H), 7.71 (s, 1H), 7.67 (d, J=8.1 Hz, 1H), 7.45 (t, J=7.7 Hz, 1H), 7.21 (t, J=7.8 Hz, 1H), 7.07-7.12 (m, 2H), 7.02

(dd, J=8.8, 2.0 Hz, 1H), 6.88 (d, J=7.5 Hz, 1H), 6.69-6.73 (m, 1H), 6.50 (d, J=5.3 Hz, 1H), 5.31 (s, 2H), 3.36 (s, 2H), 2.14 (s, 6H). ES-LC/MS m/z=454 [M+H]⁺.

Step H: N-(5-{3-[2-({3-[(dimethylamino)methyl]phenyl}amino)-4-pyrimidinyl]pyrazolo[1,5-a]pyridin-2-yl}-2-fluorophenyl)-2-(2-thienyl)acetamide (title compound)

To a stirred solution of 4-[2-(3-amino-4-fluorophenyl)pyrazolo[1,5-a]pyridin-3-yl]-N-{3-[(dimethylamino)methyl]phenyl}-2-pyrimidinamine (58 mg, 0.13 mmol) in THF (3 mL) was added TEA (27 µL, 0.19 mmol) and 2-thiopheneacetyl chloride (17 µL, 0.13 mmol). After 20 h, the reaction mixture was diluted with EtOAc (20 mL), adsorbed onto silica gel, and purified by column chromatography to give the title compound (58 mg, 77% yield). ¹H NMR (400 MHz, d₆-DMSO) δ10.15 (s, 1H), 9.54 (s, 1H), 8.83 (d, J=7.0 Hz, 1H), 8.48 (d, J=8.8 Hz, 1H), 8.26-8.29 (m, 2H), 7.69 (s, 1H), 7.63 (d, J=8.2 Hz, 1H), 7.47 (t, J=7.9 Hz, 1H), 7.36-7.39 (m, 2H), 7.18 (t, J=7.8 Hz, 1H), 7.13 (t, J=6.9 Hz), 6.96-6.98 (m, 2H), 6.87 (d, J=7.1 Hz, 1H), 6.52 (d, J=5.3 Hz, 1H), 3.99 (s, 2H), 3.32 (s, 2H), 2.15 (s, 6H). ES-LC/MS m/z=578 [M+H]⁺.

Example 37

N-{5-[3-(2-{[2-(dimethylamino)-2,3-dihydro-1H-inden-5-yl]amino}-4-pyrimidinyl)pyrazolo[1,5-a]pyridin-2-yl]-2-fluorophenyl}-2-(2-thienyl)acetamide

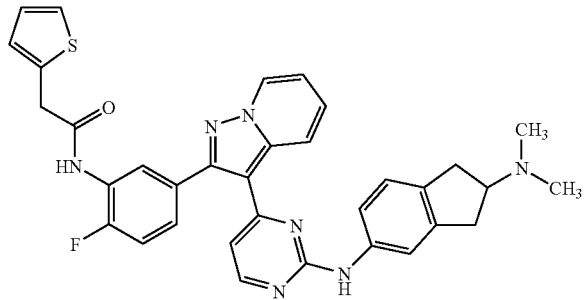

Step A: N-{5-[3-(2-{[2-(dimethylamino)-2,3-dihydro-1H-inden-5-yl]amino}-4-pyrimidinyl)pyrazolo[1,5-a]pyridin-2-yl]-2-fluorophenyl}2,2,2-trifluoroacetamide

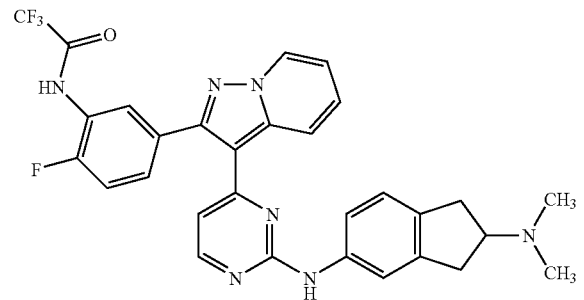

The title compound was prepared from N-{5-[3-(2-chloro-4-pyrimidinyl)pyrazolo[1,5-a]pyridin-2-yl]-2-fluorophenyl}-2,2,2-trifluoroacetamide (see Example 36, Step E) and N²,N²-dimethyl-2,3-dihydro-1H-indene-2,5-diamine (see Example 53, Step B) using displacement conditions described in Example 36, Step F to generate the title compound in 83% yield. ES-LC/MS m/z=576 [M+H]⁺.

Step B: {4-[2-(3-amino-4-fluorophenyl)pyrazolo[1,5-a]pyridin-3-yl]-2-pyrimidinyl}[2-(dimethylamino)-2,3-dihydro-1H-inden-5-yl]amine

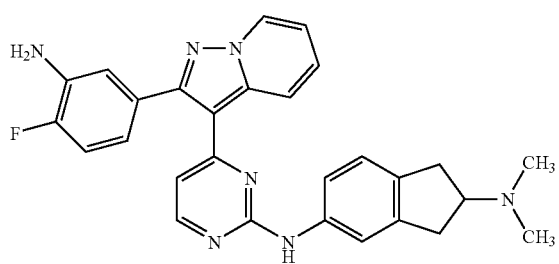

The title compound was prepared from N-{5-[3-(2-{[2-(dimethylamino)-2,3-dihydro-1H-inden-5-yl]amino}-4-pyrimidinyl)pyrazolo[1,5-a]pyridin-2-yl]-2-fluorophenyl}-2,2,2-trifluoroacetamide and LiOH using hydrolysis conditions described in Example 36, Step G to generate the desired product in 88% yield. ¹H NMR (400 MHz, d₆-DMSO): δ 9.40 (s, 1H), 8.79 (d, J=7.0 Hz, 1H), 8.48 (d, J=9.0 Hz, 1H), 8.23 (d, J=5.4 Hz, 1H), 7.66 (s, 1H), 7.39-7.46 (m, 2H), 7.01-7.11 (m, 4H), 6.70-6.72 (m, 1H), 6.48 (d, J=5.4 Hz, 1H), 5.31 (s, 2H), 2.91-2.98 (m, 3H), 2.68-2.72 (m, 2H), 2.20 (s, 6H). ES-LC/MS m/z=480 [M+H]⁺.

Step C: N-{5-[3-(2-{[2-(dimethylamino)-2,3-dihydro-1H-inden-5-yl]amino}-4-pyrimidinyl)pyrazolo[1,5-a]pyridin-2-yl]-2-fluorophenyl}-2-(2-thienyl)acetamide (title compound)

The title compound was prepared from {4-[2-(3-amino-4-fluorophenyl)pyrazolo[1,5-a]pyridin-3-yl]-2-pyrimidinyl}[2-(dimethylamino)-2,3-dihydro-1H-inden-5-yl]amine and 2-thiopheneacetyl chloride using acylation conditions described in Example 36, Step H to generate the desired product in 76% yield. ¹H NMR (400 MHz, d₆-DMSO) δ 10.14 (s, 1H), 9.42 (s, 1H), 8.83 (d, J=6.9 Hz, 1H), 8.42 (d, J=8.7 Hz, 1H), 8.29 (d, J=6.6 Hz, 1H), 8.25 (d, J=5.4 Hz, 1H), 7.61 (s, 1H), 7.35-7.47 (m, 5H), 7.03-7.13 (m, 4H), 6.52 (d, J=5.4 Hz, 1H), 3.99 (s, 2H), 2.87-2.99 (m, 3H), 2.66-2.72 (m, 2H), 2.21 (s, 6H). ES-LC/MS m/z=604 [M+H]⁺.

Example 38

N-[5-(3-{2-[(3-{[2-(dimethylamino)ethyl]oxy}phenyl)amino]-4-pyrimidinyl}pyrazolo[1,5-a]pyridin-2-yl)-2-fluorophenyl]-2-(2-thienyl)acetamide

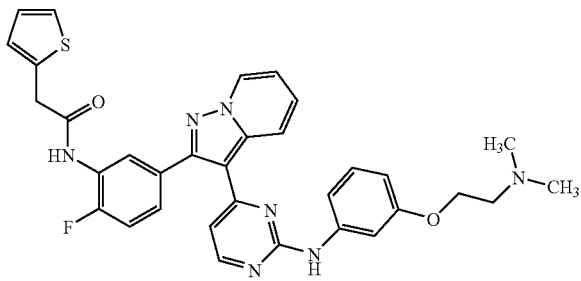

Step A: N-[5-(3-{2-[(3-{[2-(dimethylamino)ethyl]oxy}phenyl)amino]-4-pyrimidinyl}pyrazolo[1,5-a]pyridin-2-yl)-2-fluorophenyl]-2,2,2-trifluoroacetamide

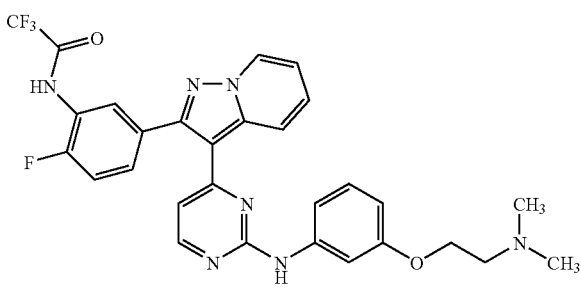

The title compound was prepared from N-{5-[3-(2-chloro-4-pyrimidinyl)pyrazolo[1,5-a]pyridin-2-yl]-2-fluorophenyl}-2,2,2-trifluoroacetamide (see Example 36, Step E) and 3-{[2-(dimethylamino)ethyl]oxy}aniline using displacement conditions described in Example 36, Step F to generate the title compound in 77% yield. $^1$H NMR (400 MHz, $d_6$-DMSO): δ 11.3 (bs, 1H), 9.58 (s, 1H), 8.84 (d, J=6.9 Hz, 1H), 8.49 (d, J=9.0 Hz, 1H), 8.30 (d, J=5.3 Hz, 1H), 7.82 (dd, J=7.3, 2.2 Hz, 1H), 7.44-7.52 (m, 4H), 7.28 (d, J=8.9 Hz, 1H), 7.14 (t, J=7.9 Hz, 1H), 6.52-6.55 (m, 2H), 4.00 (t, J=5.7 Hz, 2H), 2.63 (t, J=5.7 Hz, 2H), 2.21 (s, 6H). ES-LC/MS m/z=580 [M+H]$^+$.

Step B: 4-[2-(3-amino-4-fluorophenyl)pyrazolo[1,5-a]pyridin-3-yl]-N-(3-{[2-(dimethylamino)ethyl]oxy}phenyl)-2-pyrimidinamine

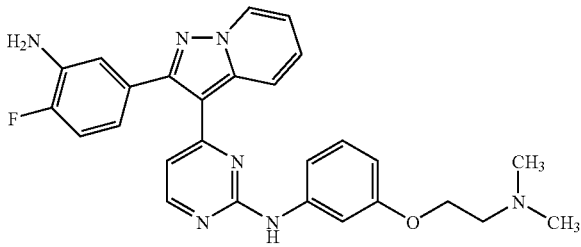

The title compound was prepared from N-[5-(3-{2-[(3-{[2-(dimethylamino)ethyl]oxy}phenyl)amino]-4-pyrimidinyl}pyrazolo[1,5-a]pyridin-2-yl)-2-fluorophenyl]-2,2,2-trifluoroacetamide and LiOH using the hydrolysis conditions described in Example 36, Step G to generate the desired product in 97% yield. $^1$H NMR (400 MHz, $d_6$-DMSO): δ 9.53 (s, 1H), 8.80 (d, J=6.9 Hz, 1H), 8.52 (d, J=9.2 Hz, 1H), 8.27 (d, J=5.3 Hz, 1H), 7.53 (s, 1H), 7.46 (t, J=7.9 Hz, 1H), 7.29 (d, J=9.1 Hz, 1H), 7.07-7.18 (m, 3H), 7.02 (dd, J=8.8, 2.0 Hz, 1H), 6.70-6.72 (m, 1H), 6.54 (dd, J=8.1, 2.4 Hz, 1H), 6.50 (d, J=5.3 Hz, 1H), 5.31 (s, 2H), 4.02 (t, J=5.9 Hz, 2H), 2.61 (t, J=5.9 Hz, 2H), 2.22 (s, 6H). ES-LC/MS m/z=484 [M+H]$^+$.

Step C: N-[5-(3-{2-[(3-{[2-(dimethylamino)ethyl]oxy}phenyl)amino]-4-pyrimidinyl}pyrazolo[1,5-a]pyridin-2-yl)-2-fluorophenyl]-2-(2-thienyl)acetamide (title compound)

The title compound was prepared 4-[2-(3-amino-4-fluorophenyl)pyrazolo[1,5-a]pyridin-3-yl]-N-(3-{[2-(dimethylamino)ethyl]oxy}phenyl)-2-pyrimidinamine and 2-thiopheneacetyl chloride using the acylation conditions described in Example 36, Step H to generate, after HPLC purification, the desired product as a TFA salt in 37% yield. $^1$H NMR (400 MHz, $d_6$-DMSO) δ 10.15 (s, 1H), 9.62 (s, 1H), 8.85 (d, J=6.8 Hz, 1H), 8.49 (d, J=8.7 Hz, 1H), 8.27 (d, J=5.5 Hz, 2H), 7.61 (s, 1H), 7.49 (t, J=7.9 Hz, 1H), 7.30-7.39 (m, 3H), 7.19 (t, J=8.0 Hz, 2H), 7.13 (t, J=6.9 Hz, 2H), 6.96-6.98 (m, 1H), 6.60 (d, J=6.1 Hz, 1H), 6.55 (d, J=5.3 Hz, 1H), 4.25-4.26 (m, 2H), 3.99 (s, 2H), 3.50 (m, 2H), 2.85 (s, 6H). ES-LC/MS m/z=608 [M+H]$^+$.

Example 39

N-[3-(3-{2-[(3-{[2-(dimethylamino)ethyl]oxy}phenyl)amino]-4-pyrimidinyl}pyrazolo[1,5-a]pyridin-2-yl)phenyl]-2-(3-thienyl)acetamide

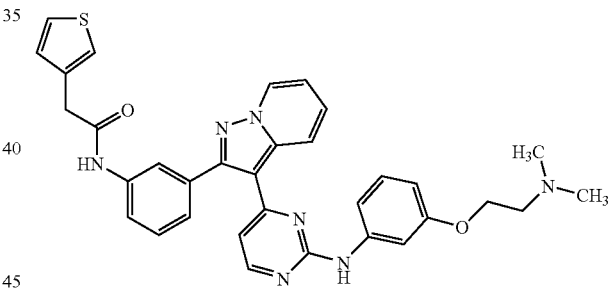

Step A: N-[3-(3-{2-[(3-{[2-(Dimethylamino)ethyl]oxy}phenyl)amino]-4-pyrimidinyl}pyrazolo[1,5-a]pyridin-2-yl)phenyl]-2,2,2-trifluoroacetamide

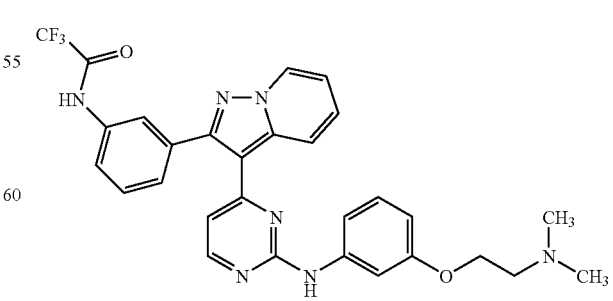

To a suspension of N-{3-[3-(2-chloro-4-pyrimidinyl)pyrazolo[1,5-a]pyridin-2-yl]phenyl}-2,2,2-trifluoroacetamide (150 mg, 0.36 mmol) (see Example 1, Step C) in i-PrOH (4 mL) were added 3-{[2-(dimethylamino)ethyl]oxy}aniline (80 mg, 0.45 mmol) and 12 N HCl (3 drops). The reaction was stirred overnight at 80° C. The crude reaction mixture was diluted with DCM and extracted with saturated aqueous NaHCO$_3$. The organic layer was dried over Na$_2$SO$_4$, filtered, and purified by column chromatography to generate the title compound in 84% yield. $^1$H NMR (400 MHz, d$_6$-DMSO): δ 11.4 (bs, 1H), 9.58 (s, 1H), 8.85 (d, J=7.0 Hz, 1H), 8.50 (d, J=9.0 Hz, 1H), 8.28 (d, J=5.3 Hz, 1H), 8.00 (s, 1H), 7.83 (d, J=8.5 Hz, 1H), 7.45-7.57 (m, 4H), 7.28 (d, J=9.4 Hz, 1H), 7.10-7.15 (m, 2H), 6.51-6.56 (m, 2H), 4.00 (t, J=5.7 Hz, 2H), 2.7 (bs, 2H), 2.35 (s, 6H). ES-LC/MS m/z=562 [M+H]$^+$.

Step B: 4-[2-(3-aminophenyl)pyrazolo[1,5-a]pyridin-3-yl]-N-(3-{[2-(dimethylamino)ethyl]oxy}phenyl)-2-pyrimidinamine

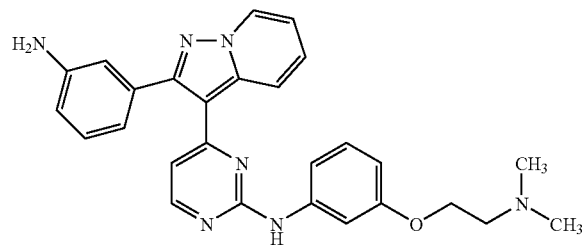

The compound was prepared from N-[3-(3-{2-[(3-{[2-(dimethylamino)ethyl]oxy}-phenyl)amino]-4-pyrimidinyl}pyrazolo[1,5-a]pyridin-2-yl)phenyl]-2,2,2-trifluoroacetamide and LiOH using the hydrolysis conditions described in Example 36, Step G to generate the desired product in quantitative yield. $^1$H NMR (400 MHz, d$_6$-DMSO): δ 9.51 (s, 1H), 8.80 (d, J=7.1 Hz, 1H), 8.56 (d, J=8.8 Hz, 1H), 8.24 (d, J=5.3 Hz, 1H), 7.54 (s, 1H), 7.46 (t, J=7.8 Hz, 1H), 7.30 (d, J=8.1 Hz, 1H), 7.08-7.18 (m, 3H), 6.80 (s, 1H), 6.68 (t, J=7.9 Hz, 2H), 6.51-6.55 (m, 2H), 5.24 (s, 2H), 3.99 (t, J=5.8 Hz, 2H), 2.59 (t, J=5.9 Hz, 2H), 2.18 (s, 6H). ES-LC/MS m/z=466 [M+H]$^+$.

Step C: N-[3-(3-{2-[(3-{[2-(dimethylamino)ethyl]oxy}phenyl)amino]-4-pyrimidinyl}pyrazolo[1,5-a]pyridin-2-yl)phenyl]-2-(3-thienyl)acetamide (title compound)

To a solution of 4-[2-(3-aminophenyl)pyrazolo[1,5-a]pyridin-3-yl]-N-(3-{[2-(dimethylamino)ethyl]oxy}phenyl)-2-pyrimidinamine (140 mg, 0.3 mmol) in THF were added 3-thienylacetic acid (51 mg, 0.36 mmol), TEA (125 μL, 0.9 mmol), and O-(7-azabenzotriazol-1-yl)-N,N,N',N'-tetramethyluronium hexafluorophosphate (136 mg, 0.36 mmol). The reaction was stirred overnight at rt, after which the reaction mixture was diluted with DCM, washed with 5% aqueous Na$_2$CO$_3$, dried over Na$_2$SO$_4$, and adsorbed onto silica gel. The crude product was purified by column chromatography and lyophilized to generate the title compound in 72% yield. $^1$H NMR (400 MHz, d$_6$-DMSO) δ 10.27 (s, 1H), 9.55 (s, 1H), 8.83 (d, J=6.7 Hz, 1H), 8.51 (d, J=8.8 Hz, 1H), 8.26 (d, J=5.1 Hz, 1H), 7.89 (s, 1H), 7.76 (d, J=8.1 Hz, 1H), 7.40-7.53 (m, 4H), 7.26-7.31 (m, 3H), 7.08-7.18 (m, 3H), 6.53 (d, J=8.2 Hz, 1H), 6.48 (d, J=5.3 Hz, 1H), 3.99 (t, J=5.7 Hz, 2H), 3.66 (s, 2H), 2.58 (t, J=5.9 Hz, 2H), 2.18 (s, 6H). ES-LC/MS m/z=588 [M+H]$^+$.

Example 40

N-{3-[3-(2-{[3-({[2-(dimethylamino)ethyl]amino}methyl)phenyl]-amino}-4-pyrimidinyl)pyrazolo[1,5-a]pyridin-2-yl]phenyl}-2-(2-thienyl)acetamide

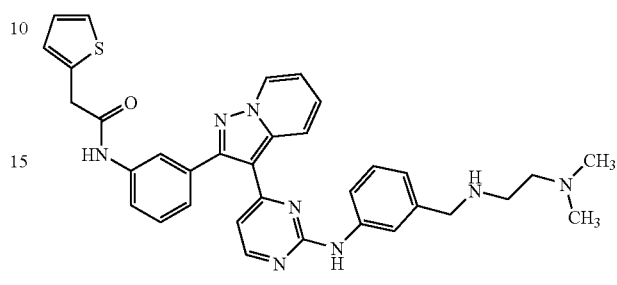

Step A: [2-(Dimethylamino)ethyl][(3-nitrophenyl)methyl]amine

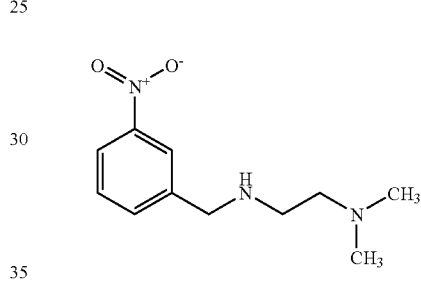

A solution of 3-nitrobenzaldehyde (127 mg, 0.84 mmol), N,N-dimethylethylenediamine (184 μL, 1.7 mmol), and HOAc (5 drops) in DCM (10 mL) was stirred at rt for 6 h and then heated to 40° C. for 1 hour. The reaction was cooled to 0° C., and sodium cyanoborohydride (360 mg, 1.7 mmol) was added in one portion. The reaction was stirred overnight at rt. After 16 h, the reaction mixture was washed with 4 N NaOH, dried over Na$_2$SO$_4$, and concentrated. The crude product was used in the next reaction without further purification. ES-LC/MS m/z=224 [M+H]$^+$.

Step B: N-[2-(dimethylamino)ethyl]-2,2,2-trifluoro-N-[(3-nitrophenyl)methyl]-acetamide

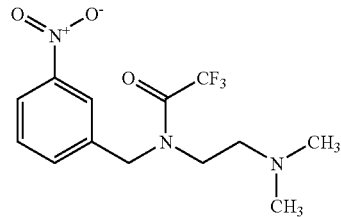

To a solution of [2-(dimethylamino)ethyl][(3-nitrophenyl)methyl]amine (180 mg, 0.8 mmol) in DCM was added TEA (167 μL, 1.2 mmol) and TFAA (135 μL, 0.96 mmol). After 3 h at rt, the reaction mixture was diluted with DCM, washed with 2 N NaOH, dried over Na$_2$SO$_4$, and adsorbed onto silica gel. The product was purified by column chromatography to generate the title compound in 76% yield over two steps. $^1$H NMR (400 MHz, CDCl$_3$) δ 8.18 (s, 1H), 8.12 (d, J=8.2 Hz, 1H), 7.74 (d, J=7.5 Hz, 1H), 7.52 (t, J=7.9 Hz, 1H), 4.70 (s, 2H), 3.13 (t, J=6.0 Hz, 2H), 3.00 (t, J=5.9 Hz, 2H), 2.78 (s, 6H). ES-LC/MS m/z=320 [M+H]$^+$.

Step C: N-[(3-aminophenyl)methyl]-N-[2-(dimethylamino)ethyl]-2,2,2-trifluoroacetamide

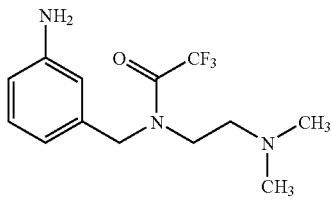

To a solution of N-[2-(dimethylamino)ethyl]-2,2,2-trifluoro-N-[(3-nitrophenyl)methyl]acetamide (204 mg, 0.64 mmol) in i-PrOH was added 10% Pd/C (20 mg, 0.02 mmol). A balloon charged with H$_2$ was installed, and the reaction was stirred at rt under a hydrogen atmosphere. After 17 h, the reaction mixture was filtered through celite and adsorbed onto silica gel. The crude product was purified by column chromatography to generate the title compound in 62% yield. $^1$H NMR (400 MHz, CDCl$_3$) δ 7.10 (t, J=7.9 Hz, 1H), 6.69-6.70 (m, 2H), 6.58 (d, J=7.9 Hz, 1H), 3.76 (s, 2H), 2.75 (t, J=6.0 Hz, 2H), 2.49 (t, J=6.0 Hz, 2H), 2.24 (s, 6H). ES-LC/MS m/z=290 [M+H]$^+$.

Step D: N-{3-[3-(2-{[3-({[2-(Dimethylamino)ethyl]amino}methyl)phenyl]amino}-4-pyrimidinyl)pyrazolo[1,5-a]pyridin-2-yl]phenyl}-2-(2-thienyl)acetamide (title compound)

A suspension of N-[(3-aminophenyl)methyl]-N-[2-(dimethylamino)ethyl]-2,2,2-trifluoroacetamide (61 mg, 0.21 mmol) and N-{3-[3-(2-chloro-4-pyrimidinyl)pyrazolo[1,5-a]pyridin-2-yl]phenyl}-2-(2-thienyl)acetamide (75 mg, 0.17 mmol) (see Example 2, Step B) in i-PrOH (3 mL) was acidified with 3 drops of 12 N HCl and heated in a microwave for 25 min. at 180° C. The reaction mixture was then diluted with DCM, washed with 2 N NaOH, dried over Na$_2$SO$_4$, and adsorbed onto silica gel. The crude product was purified by column chromatography to generate the title compound in 66% yield. $^1$H NMR (400 MHz, CDCl$_3$) δ 8.47 (d, J=6.8 Hz, 1H), 8.36 (d, J=8.8 Hz, 1H), 8.16 (d, J=5.1 Hz, 1H), 7.80 (d, J=7.2 Hz, 1H), 7.73 (s, 1H), 7.53-7.61 (m, 3H), 7.32-7.45 (m, 4H), 7.01 (s, 2H), 6.90 (t, J=6.6 Hz, 1H), 6.55 (d, J=5.1 Hz, 1H), 3.94 (s, 2H), 3.79 (s, 2H), 2.70 (t, J=5.8 Hz, 2H), 2.42 (t, J=5.9 Hz, 2H), 2.18 (s, 6H). ES-LC/MS m/z=603 [M+H]$^+$.

Example 41

N-{3-[3-(2-{[3-({[2-(Methylsulfonyl)ethyl]amino}methyl)phenyl]-amino}-4-pyrimidinyl)pyrazolo[1,5-a]pyridin-2-yl]phenyl}-2-(2-thienyl)acetamide

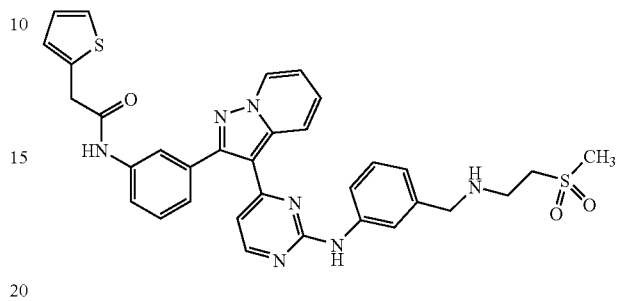

Step A: [2-(Methylsulfonyl)ethyl][(3-nitrophenyl)methyl]amine

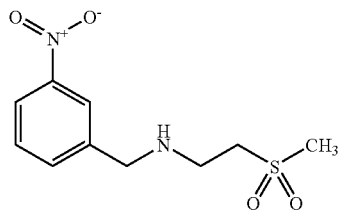

A solution of 3-nitrobenzylamine hydrochloride (1.0 g, 5.3 mmol) in DCM was converted to the free base by treating with 2 N NaOH. The organic layer was separated and concentrated, and the residue was redissolved in MeOH. To this solution was added methylvinylsulfone (232 μL, 2.6 mmol), and the reaction was stirred at rt. After 5 h, the crude reaction mixture was adsorbed onto silica gel and purified by column chromatography to generate the title compound in quantitative yield. $^1$H NMR (400 MHz, CDCl$_3$) δ 8.21 (s, 1H), 8.13 (d, J=8.2 Hz, 1H), 7.67 (d, J=7.5 Hz, 1H), 7.51 (t, J=7.9 Hz, 1H), 3.93 (s, 2H), 3.16-3.24 (m, 4H), 3.01 (s, 3H). ES-LC/MS m/z=259 [M+H]$^+$.

Step B: 2,2,2-Trifluoro-N-[2-(methylsulfonyl)ethyl]-N-[(3-nitrophenyl)methyl]-acetamide

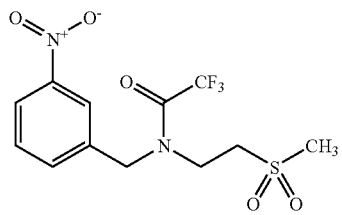

To a solution of [2-(methylsulfonyl)ethyl][(3-nitrophenyl)methyl]amine (0.70 g, 2.7 mmol) in DCM (25 mL) was added diisopropylethylamine (0.71 mL, 4.0 mmol) and TFAA (0.42 mL, 3.0 mmol). After 1 hour at rt, the reaction mixture was diluted with DCM and extracted with saturated aqueous NaHCO₃. The organic layer was dried over Na₂SO₄, adsorbed onto silica gel, and purified by column chromatography to generate the title compound as a clear oil (0.88 g, 92% yield). $^1$H NMR (400 MHz, CDCl₃) δ 8.24 (d, J=8.8 Hz, 1H), 8.11 (s, 1H), 7.58-7.63 (m, 2H), 4.91 (s, 2H), 3.78 (t, J=6.4 Hz, 2H), 3.36 (t, J=6.3 Hz, 2H), 2.99 (s, 3H). ES-LC/MS m/z=355 [M+H]$^+$.

Step C: N-[(3-Aminophenyl)methyl]-2,2,2-trifluoro-N-[2-(methylsulfonyl)ethyl]-acetamide

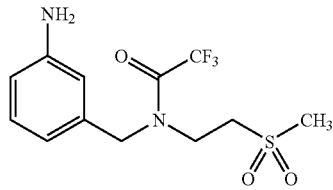

To a suspension of 2,2,2-trifluoro-N-[2-(methylsulfonyl)ethyl]-N-[(3-nitrophenyl)methyl]acetamide (0.88 g, 2.5 mmol) in i-PrOH was added 10% Pd/C (80 mg, 0.08 mmol). A balloon filled with hydrogen gas was installed, and the reaction was stirred vigorously at rt. After 64 h, the reaction mixture was filtered through celite, adsorbed onto silica gel, and purified by column chromatography to generate the title compound in 93% yield. $^1$H NMR (400 MHz, CDCl₃) δ 7.17 (t, J=7.5 Hz, 1H), 6.60-6.67 (m, 2H), 6.53 (s, 1H), 4.62 (s, 2H), 3.73 (t, J=6.9 Hz, 2H), 3.18 (t, J=6.8 Hz, 2H), 2.92 (s, 3H). ES-LC/MS m/z=324 [M+H]$^+$.

Step D: 2,2,2-Trifluoro-N-[2-(methylsulfonyl)ethyl]-N-[(3-{[4-(2-{3-[(2-thienylacetyl)amino]phenyl}pyrazolo[1,5-a]pyridin-3-yl)-2-pyrimidinyl]amino}phenyl)methyl]acetamide

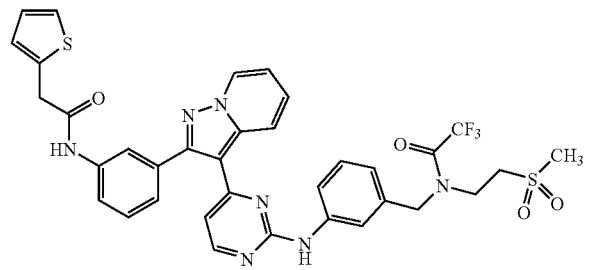

A suspension of N-[(3-aminophenyl)methyl]-2,2,2-trifluoro-N-[2-(methylsulfonyl)ethyl]acetamide (68 mg, 0.21 mmol) and N-{3-[3-(2-chloro-4-pyrimidinyl)pyrazolo[1,5-a]pyridin-2-yl]phenyl}-2-(2-thienyl)acetamide (75 mg, 0.17 mmol) (see Example 2, Step B) in i-PrOH (3 mL) was acidified with 2 drops of 12 N HCl and heated in a microwave for 15 min. at 180° C. The reaction mixture was then diluted with EtOAc, washed with saturated aqueous NaHCO₃, dried over Na₂SO₄, and adsorbed onto silica gel. The crude product was purified by column chromatography to generate the title compound in 63% yield. $^1$H NMR (400 MHz, CDCl₃) δ 8.51 (d, J=6.8 Hz, 1H), 8.31 (d, J=8.6 Hz, 1H), 8.22 (d, J=5.3 Hz, 1H), 7.67-7.80 (m, 2H), 7.56 (d, J=8.0 Hz, 1H), 7.26-7.39 (m, 4H), 7.17 (t, J=7.7 Hz, 1H), 7.05 (s, 1H), 6.94 (d, J=6.9 Hz, 1H), 6.88 (d, J=8.4 Hz, 1H), 6.62-6.64 (m, 2H), 6.53 (s, 1H), 4.68 (s, 2H), 3.96 (s, 2H), 3.72-3.75 (m, 2H), 3.16-3.24 (m, 2H), 2.90 (s, 3H). ES-LC/MS m/z=734 [M+H]$^+$.

Step E: N-{3-[3-(2-{[3-({[2-(methylsulfonyl)ethyl]amino}methyl)phenyl]amino}-4-pyrimidinyl)pyrazolo[1,5-a]pyridin-2-yl]phenyl}-2-(2-thienyl)acetamide (title compound)

To a solution of 2,2,2-trifluoro-N-[2-(methylsulfonyl)ethyl]-N-[(3-{[4-(2-{3-[(2-thienylacetyl)amino]phenyl}pyrazolo[1,5-a]pyridin-3-yl)-2-pyrimidinyl]amino}phenyl)methyl]acetamide (79 mg, 0.11 mmol) in THF (3 mL) was added LiOH hydrate (10 mg, 0.21 mmol) in water (0.5 mL). The solution was heated to 50° C. for 2 h, and then diluted with EtOAc, washed with 1N Na₂CO₃, dried over Na₂SO₄, and concentrated to generate the title compound in 62% yield. $^1$H NMR (400 MHz, d₆-DMSO) δ 10.36 (s, 1H), 9.55 (s, 1H), 8.84 (d, J=6.8 Hz, 1H), 8.52 (d, J=8.9 Hz, 1H), 8.24 (d, J=5.4 Hz, 1H), 7.90 (s, 1H), 7.74-7.76 (m, 2H), 7.59 (d, J=8.1 Hz, 1H), 7.38-7.50 (m, 2H), 7.28 (d, J=7.7 Hz, 1H), 7.20 (t, J=7.8 Hz, 1H), 7.13 (t, J=6.8 Hz, 1H), 6.92-6.98 (m, 3H), 6.44-6.51 (m, 2H), 3.88 (s, 2H), 3.66 (s, 2H), 3.23 (t, J=6.3 Hz, 2H), 3.01 (s, 3H), 2.91 (t, J=6.1 Hz). ES-LC/MS m/z=638 [M+H]$^+$.

Example 42

N-{3-[3-(2-{[3-(Aminomethyl)phenyl]amino}-4-pyrimidinyl)pyrazolo[1,5-a]pyridin-2-yl]phenyl}-2-(2-thienyl)acetamide

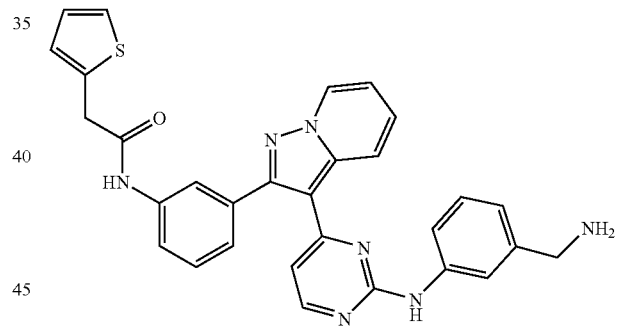

Step A:
2,2,2-Trifluoro-N-[(3-nitrophenyl)methyl]acetamide

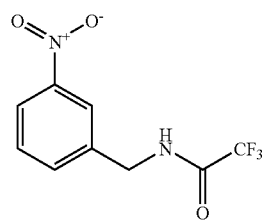

To a suspension of 3-nitrobenzylamine hydrochloride (10.2 g, 54 mmol) in DCM was added TEA (37.6 mL, 270 mmol). After 5 min., the solution became clear, and TFAA (11.4 mL, 81 mmol) was added dropwise over 30 min. and the reaction was stirred at rt. After 16 h, the crude reaction mixture was washed with 1 N HCl, dried over $Na_2SO_4$, adsorbed onto silica gel and purified by column chromatography to generate the title compound in 92% yield. $^1$H NMR (400 MHz, $CDCl_3$) δ 8.15-8.19 (m, 2H), 7.65 (d, J=7.7 Hz, 1H), 7.56 (t, J=7.9 Hz, 1H), 6.7 (bs, 1H), 4.64 (s, 2H).

Step B:
N-[(3-aminophenyl)methyl]-2,2,2-trifluoroacetamide

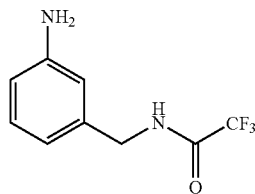

To a solution of 2,2,2-trifluoro-N-[(3-nitrophenyl)methyl]acetamide (0.5 g, 2.0 mmol) in i-PrOH was added 10% Pd/C (40 mg, 0.04 mmol). A balloon filled with hydrogen gas was installed, and the reaction was stirred vigorously at rt. After 15 h, the reaction mixture was filtered through celite, adsorbed onto silica gel, and purified by column chromatography to generate the title compound in 85% yield. $^1$H NMR (400 MHz, $CDCl_3$) δ 7.14-7.27 (m, 1H), 6.59-6.68 (m, 3H), 4.43 (s, 2H), 3.74 (s, 2H). ES-LC/MS m/z=219 [M+H]$^+$.

Step C: 2,2,2-Trifluoro-N-[(3-{[4-(2-{3-[(2-thienylacetyl)amino]phenyl}-pyrazolo[1,5-a]pyridin-3-yl)-2-pyrimidinyl]amino}phenyl)methyl]acetamide

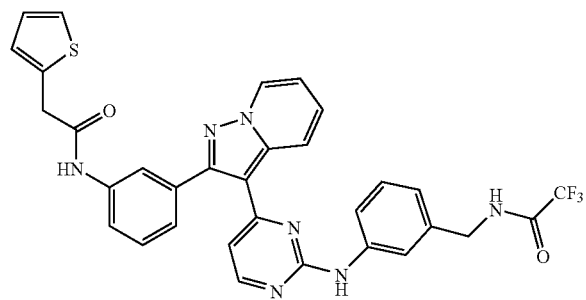

A suspension of N-[(3-aminophenyl)methyl]-2,2,2-trifluoroacetamide (46 mg, 0.21 mmol) and N-{3-[3-(2-chloro-4-pyrimidinyl)pyrazolo[1,5-a]pyridin-2-yl]phenyl}-2-(2-thienyl)acetamide (75 mg, 0.17 mmol) (see Example 2, Step B) in i-PrOH (3 mL) was acidified with 2 drops of 12 N HCl and heated in a microwave for 15 min. at 180° C. The reaction mixture was then diluted with DCM, washed with saturated aqueous $NaHCO_3$, dried over $Na_2SO_4$, and adsorbed onto silica gel. The crude product was purified by column chromatography to generate the title compound in 67% yield. $^1$H NMR (400 MHz, $CDCl_3$) δ 8.51 (d, J=6.8 Hz, 1H), 8.31 (d, J=9.1 Hz, 1H), 8.22 (d, J=5.2 Hz, 1H), 7.72-7.75 (m, 2H), 7.63 (s, 1H), 7.46 (d, J=8.3 Hz, 1H), 7.26-7.38 (m, 7H), 7.04 (s, 1H), 6.94 (m, 1H), 6.63 (d, J=5.4 Hz, 1H), 4.48 (d, J=5.7 Hz, 2H), 3.96 (s, 2H). ES-LC/MS m/z=628 [M+H]$^+$.

Step D: N-{3-[3-(2-{[3-(Aminomethyl)phenyl]amino}-4-pyrimidinyl)pyrazolo[1,5-a]pyridin-2-yl]phenyl}-2-(2-thienyl)acetamide (title compound)

To a solution of 2,2,2-trifluoro-N-[(3-{[4-(2-{3-[(2-thienylacetyl)amino]phenyl}-pyrazolo[1,5-a]pyridin-3-yl)-2-pyrimidinyl]amino}phenyl)methyl]acetamide (71 mg, 0.11 mmol) in THF (3 mL) was added LiOH hydrate (10 mg, 0.21 mmol) in water (0.5 mL). The solution was heated to 50° C. for 2 h, and then diluted with DCM, washed with 1N $Na_2CO_3$, dried over $Na_2SO_4$, and concentrated to generate the title compound in 94% yield. $^1$H NMR (400 MHz, $d_6$-DMSO) 610.37 (s, 1H), 9.51 (s, 1H), 8.83 (d, J=6.8 Hz, 1H), 8.53 (d, J=8.8 Hz, 1H), 8.24 (d, J=5.4 Hz, 1H), 7.90 (s, 1H), 7.74-7.76 (m, 2H), 7.55 (d, J=8.1 Hz, 1H), 7.38-7.50 (m, 3H), 7.28 (d, J=7.5 Hz, 1H), 7.19 (t, J=7.8 Hz, 1H), 7.12 (t, J=6.8 Hz, 1H), 6.94-6.98 (m, 3H), 6.46 (d, J=5.3 Hz, 1H), 3.88 (s, 2H), 3.67 (s, 2H). ES-LC/MS m/z=532 [M+H]$^+$.

Example 43

N-{3-[3-(2-{[3-(Aminomethyl)phenyl]amino}-4-pyrimidinyl)pyrazolo[1,5-a]pyridin-2-yl]phenyl}-2-(3-thienyl)acetamide

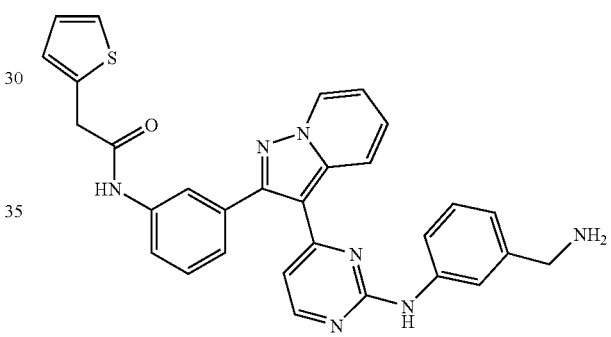

Step A: N-{3-[3-(2-Chloro-4-pyrimidinyl)pyrazolo[1,5-a]pyridin-2-yl]phenyl}-2-(3-thienyl)acetamide

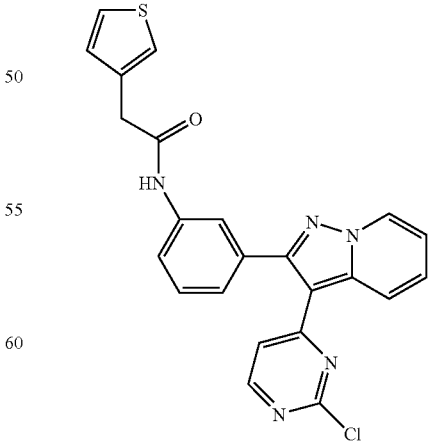

To solution of {3-[3-(2-chloro-4-pyrimidinyl)pyrazolo[1,5-a]pyridin-2-yl]phenyl}amine (125 mg, 0.4 mmol) (see Example 2, step A) in THF (5 mL) were added 3-thienylacetic acid (67 mg, 0.47 mmol), 1-(3-dimethylaminopropyl)-3-ethylcarbodiimide hydrochloride (90 mg, 0.47 mmol), N-hydroxybenzotriazole (63 mg, 0.47 mmol), and diisopropylethylamine (200 µL, 1.2 mmol). After 20 h at rt, the reaction mixture was diluted with DCM, washed with water, dried over Na$_2$SO$_4$, filtered, and adsorbed onto silica gel. The crude product was purified by column chromatography to generate the title compound in 69% yield. ES-LC/MS m/z=446 [M+H]$^+$.

Step B: 2,2,2-Trifluoro-N-[(3-{[4-(2-{3-[(3-thienylacetyl)amino]phenyl}pyrazolo-[1,5-a]pyridin-3-yl)-2-pyrimidinyl]amino}phenyl)methyl]acetamide

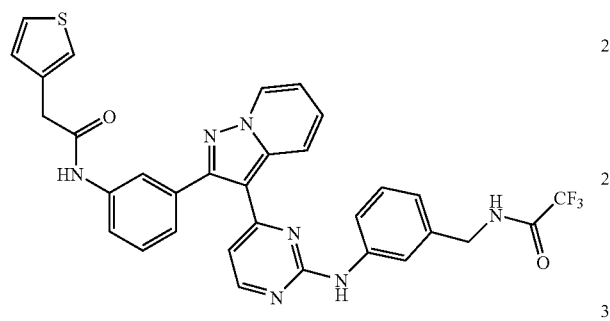

A suspension of N-[(3-aminophenyl)methyl]-2,2,2-trifluoroacetamide (73 mg, 0.34 mmol) and N-{3-[3-(2-chloro-4-pyrimidinyl)pyrazolo[1,5-a]pyridin-2-yl]phenyl}-2-(3-thienyl)acetamide (120 mg, 0.27 mmol) in i-PrOH (4 mL) was acidified with 3 drops of 12 N HCl and stirred at 80° C. overnight. After 16 h, the reaction mixture was diluted with DCM, washed with saturated aqueous NaHCO$_3$, dried over Na$_2$SO$_4$, and adsorbed onto silica gel. The crude product was purified by column chromatography to generate the title compound in 53% yield. $^1$H NMR (400 MHz, d$_6$-DMSO) δ 10.28 (s, 1H), 9.98 (t, 1H), 9.63 (s, 1H), 8.83 (d, J=6.9 Hz, 1H), 8.52 (d, J=9.0 Hz, 1H), 8.24 (d, J=5.1 Hz, 1H), 7.90 (s, 1H), 7.63 (s, 1H), 7.75 (d, J=9.0 Hz, 1H), 7.71 (s, 1H), 7.67 (d, J=8.2 Hz, 1H), 7.47-7.49 (m, 2H), 7.42 (t, J=7.9 Hz, 1H), 7.32 (d, J=2.2 Hz, 1H), 7.26 (d, J=9.1 Hz, 1H), 7.22 (d, J=7.9 Hz, 1H), 7.08-7.13 (m, 2H), 6.85 (d, J=7.7 Hz, 1H), 6.51 (d, J=5.1 Hz, 1H), 4.35 (d, J=5.9 Hz, 2H), 3.66 (s, 2H). ES-LC/MS m/z=628 [M+H]$^+$.

Step D: N-{3-[3-(2-{[3-(aminomethyl)phenyl]amino}-4-pyrimidinyl)pyrazolo[1,5-a]pyridin-2-yl]phenyl}-2-(3-thienyl)acetamide (title compound)

To a solution of 2,2,2-trifluoro-N-[(3-{[4-(2-{3-[(3-thienylacetyl)amino]phenyl}-pyrazolo[1,5-a]pyridin-3-yl)-2-pyrimidinyl]amino}phenyl)methyl]acetamide (87 mg, 0.14 mmol) in THF (2 mL) was added LiOH hydrate (12 mg, 0.28 mmol) in water (0.5 mL). The solution was heated to 50° C. for 1.5 h, and then diluted with DCM, washed with 1N Na$_2$CO$_3$, dried over Na$_2$SO$_4$, and concentrated to generate the title compound in 83% yield. $^1$H NMR (400 MHz, d$_6$-DMSO) δ10.29 (s, 1H), 9.50 (s, 1H), 8.83 (d, J=6.8 Hz, 1H), 8.53 (d, J=8.8 Hz, 1H), 8.24 (d, J=5.2 Hz, 1H), 7.89 (s, 1H), 7.74-7.77 (m, 2H), 7.40-7.56 (m, 4H), 7.08-7.32 (m, 5H), 6.95 (d, J=7.5 Hz, 1H), 6.46 (d, J=5.1 Hz, 1H), 3.67 (s, 2H), 3.66 (s, 2H). ES-LC/MS m/z=532 [M+H]$^+$.

Example 44

N-[3-(3-{2-[(4-chloro-3-{[2-(1-pyrrolidinyl)ethyl]oxy}phenyl)amino]-4-pyrimidinyl}pyrazolo[1,5-a]pyridin-2-yl)phenyl]-2-(2-thienyl)acetamide

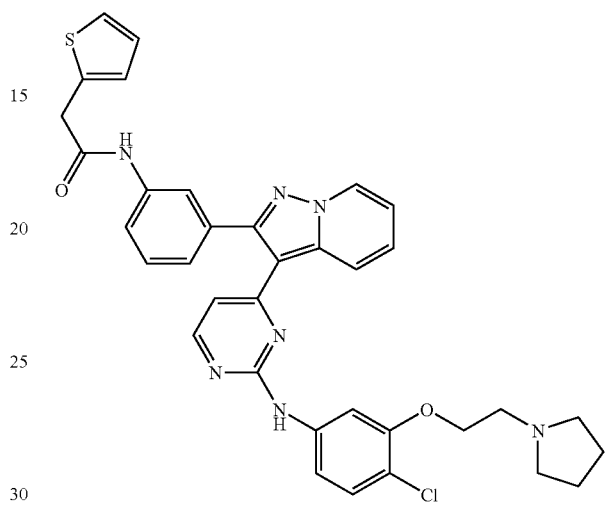

Step A:
1-Chloro-2-[(2-chloroethyl)oxy]-4-nitrobenzene

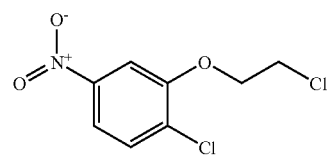

The compound was synthesized from 2-chloro-5-nitrophenol following procedure described in Example 10, Step A, to give product as an oil in 53% yield. ES-LC/MS m/z 235 (M+H).

Step B: 4-Chloro-3-[(2-chloroethyl)oxy]aniline

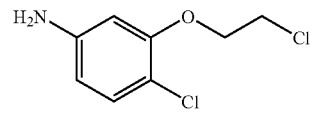

The compound was synthesized from 1-chloro-2-[(2-chloroethyl)oxy]-4-nitrobenzene following procedure described in Example 10, step B, to give product as a dark oil in 61% yield. $^1$H NMR (400 MHz, DMSO-D6) δ ppm 3.9 (m, 2H) 4.2 (t, J=5.2 Hz, 2H) 5.2 (s, 2H) 6.1 (dd, J=8.4, 2.4 Hz, 1H) 6.3 (d, J=2.2 Hz, 1H) 7.0 (d, J=8.6 Hz, 1H). ES-LC/MS m/z 206 (M+H).

Step C: N-(3-{3-[2-({4-Chloro-3-[(2-chloroethyl)oxy]phenyl}amino)-4-pyrimidinyl]pyrazolo[1,5-a]pyridin-2-yl}phenyl)-2,2,2-trifluoroacetamide

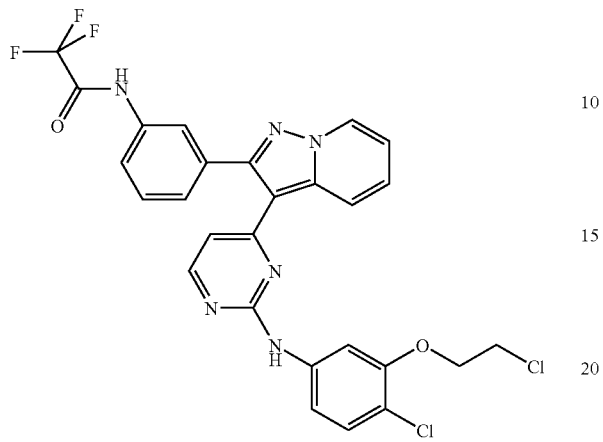

The compound was synthesized from N-{3-[3-(2-chloro-4-pyrimidinyl)-pyrazolo[1,5-a]pyridin-2-yl]phenyl}-2,2,2-trifluoroacetamide (see Example 1, Step C) and 1-chloro-2-[(2-chloroethyl)oxy]-4-nitrobenzene as described in Example 10, Step C to afford a dark yellow solid in 34% yield. ES-LC/MS m/z 587 [M+H]$^+$.

Step D: 4-[2-(3-Aminophenyl)pyrazolo[1,5-a]pyridin-3-yl]-N-(4-chloro-3-{[2-(1-pyrrolidinyl)ethyl]oxy}phenyl)-2-pyrimidinamine

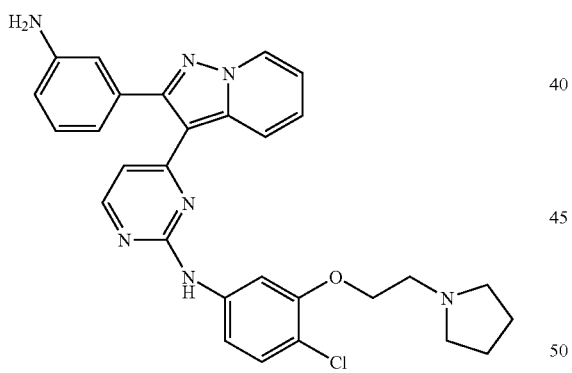

The compound was synthesized from N-(3-{3-[2-({4-chloro-3-[(2-chloroethyl)oxy]phenyl}amino)-4-pyrimidinyl]pyrazolo[1,5-a]pyridin-2-yl}phenyl)-2,2,2-trifluoroacetamide and pyrrolidine using procedure outlined in Example 10, Step D, to afford a solid in 50% yield. ES-LC/MS m/z 526-[M+H]$^+$.

Step E: N-[3-(3-{2-[(4-chloro-3-{[2-(1-pyrrolidinyl)ethyl]oxy}phenyl)amino]-4-pyrimidinyl}pyrazolo[1,5-a]pyridin-2-yl)phenyl]-2-(2-thienyl)acetamide (title compound)

The title compound was prepared from 4-[2-(3-aminophenyl)pyrazolo[1,5-a]pyridin-3-yl]-N-(4-chloro-3-{[2-(1-pyrrolidinyl)ethyl]oxy}phenyl)-2-pyrimidinamine and 2-thiopheneacetyl chloride using acylation conditions described in Example 1, Step F, and purification via column chromatography using a 0-20% gradient of EtOAc/MeOH w/NH$_4$OH to generate the product in 71% yield. $^1$H NMR (400 MHz, DMSO-D6) δ ppm 1.7 (s, 4H) 3.8 (s, 3H) 4.0 (s, 3H) 6.5 (s, 1H) 6.9 (d, J=4.4 Hz, 2H) 7.1 (t, J=6.9 Hz, 2H) 7.2 (t, J=9.0 Hz, 2H) 7.4 (m, 3H) 7.5 (m, 2H) 7.7 (s, 2H) 7.9 (s, 1H) 8.2 (d, J=0.9 Hz, 1H) 8.4 (s, 1H) 8.8 (d, J=1.3 Hz, 1H) 9.7 (s, 1H) 10.3 (s, 1H). ES-LC/MS m/z 650 [M+H]$^+$.

Example 45

N-[3-{2-[(4-Chloro-3-{[2-(dimethylamino)ethyl]oxy}phenyl)amino]-4-pyrimidinyl}pyrazolo[1,5-a]pyridin-2-yl)phenyl]-2-(2-thienyl)acetamide

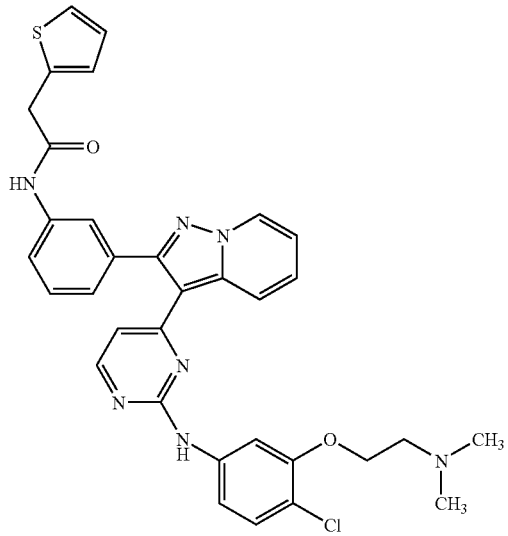

Step A: 4-[2-(3-Aminophenyl)pyrazolo[1,5-a]pyridin-3-yl]-N-(4-chloro-3-{[2-(dimethylamino)ethyl]oxy}phenyl)-2-pyrimidinamine

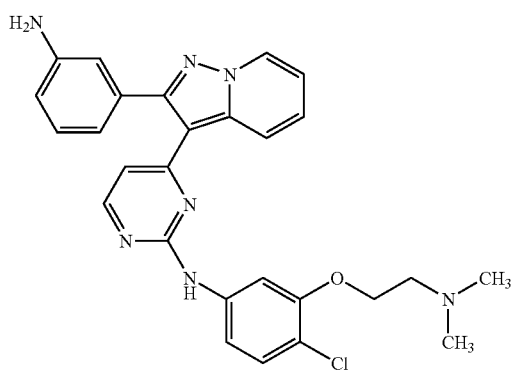

The compound was synthesized from N-(3-{3-[2-({4-chloro-3-[(2-chloroethyl)oxy]phenyl}amino)-4-pyrimidinyl]pyrazolo[1,5-a]pyridin-2-yl}phenyl)-2,2,2-trifluoroacetamide (see Example 44, Step C) via chloride displacement with dimethylamine as described in Example 10, Step D to afford a solid in 78% yield. ES-LC/MS m/z 500 [M+H]⁺.

Step B: N-[3-(3-{2-[(4-Chloro-3-{[2-(dimethylamino)ethyl]oxy}phenyl)amino]-4-pyrimidinyl}pyrazolo[1,5-a]pyridin-2-yl)phenyl]-2-(2-thienyl)acetamide (title compound)

The title compound was synthesized from 4-[2-(3-aminophenyl)pyrazolo[1,5-a]pyridin-3-yl]-N-(4-chloro-3-{[2-(dimethylamino)ethyl]oxy}phenyl)-2-pyrimidinamine using 2-thienylacetyl chloride as described in Example 10, Step E to give a yellow solid in 70% yield. ¹H NMR (300 MHz, DMSO-D6) δ ppm 2.2 (s, 6H) 2.6 (t, J=5.8 Hz, 2H) 3.9 (s, 2H) 4.0 (t, J=6.0 Hz, 2H) 6.6 (d, J=5.2 Hz, 1H) 7.0 (d, J=4.2 Hz, 2H) 7.2 (m, 1H) 7.3 (m, 1H) 7.4 (m, 2H) 7.5 (s, 1H) 7.6 (s, 1H) 7.8 (m, 2H) 7.9 (s, 1H) 8.3 (d, J=5.2 Hz, 1H) 8.5 (d, J=9.7 Hz, 1H) 8.9 (d, J=6.7 Hz, 2H) 9.7 (s, 1H) 10.4 (s, 1H). ES-LC/MS m/z 624 [M+H]⁺.

Example 46

N-{3-[3-(2-{[4-Chloro-3-({2-[methyl(1-methyl-3-pyrrolidinyl)amino]-ethyl}oxy)phenyl]amino}-4-pyrimidinyl)pyrazolo[1,5-a]pyridin-2-yl]phenyl}-2-(2-thienyl)acetamide

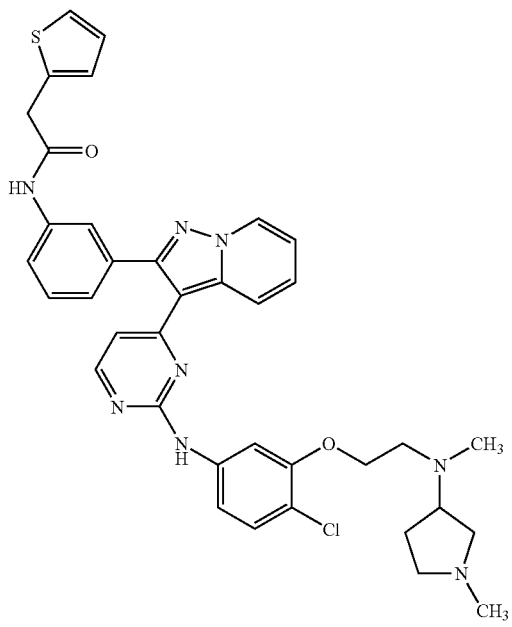

Step A: 4-[2-(3-Aminophenyl)pyrazolo[1,5-a]pyridin-3-yl]-N-[4-chloro-3-({2-[methyl(1-methyl-3-pyrrolidinyl)amino]ethyl}oxy)phenyl]-2-pyrimidinamine

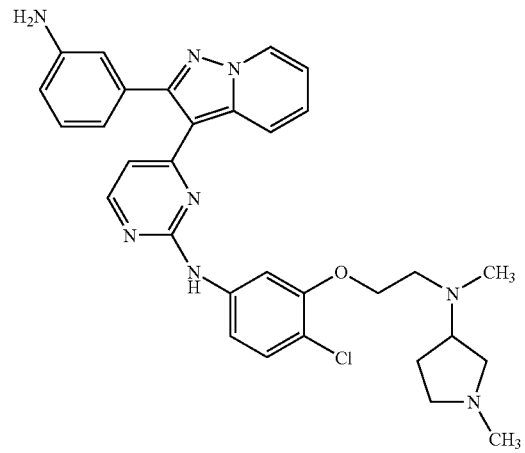

The compound was synthesized from N-(3-{3-[2-({4-chloro-3-[(2-chloroethyl)oxy]phenyl}amino)-4-pyrimidinyl]pyrazolo[1,5-a]pyridin-2-yl}phenyl)-2,2,2-trifluoroacetamide (see Example 44, Step C) via chloride displacement with N,1-dimethyl-3-pyrrolidinamine as described in Example 10, Step D to afford a solid in 62% yield. ES-LC/MS m/z 569 [M+H]⁺.

Step B: N-{3-[3-(2-{[4-Chloro-3-({2-[methyl(1-methyl-3-pyrrolidinyl)amino]ethyl}-oxy)phenyl]amino}-4-pyrimidinyl)pyrazolo[1,5-a]pyridin-2-yl]phenyl}-2-(2-thienyl)acetamide (title compound)

The title compound was synthesized from 4-[2-(3-aminophenyl)pyrazolo[1,5-a]pyridin-3-yl]-N-[4-chloro-3-({2-[methyl(1-methyl-3-pyrrolidinyl)amino]ethyl}oxy)phenyl]-2-pyrimidinamine using 2-thienylacetyl chloride as described in Example 10, Step E to give a brown solid in 55% yield. ¹H NMR (400 MHz, DMSO-D6) δ ppm 2.7 (s, 2H) 2.8 (m, 5H) 3.0 (d, J=14.5 Hz, 4H) 3.1 (s, 2H) 3.8 (s, 1H) 3.9 (s, 1H) 3.9 (s, 2H) 4.0 (s, 1H) 6.5 (d, J=5.3 Hz, 1H) 6.9 (s, 2H) 6.9 (s, 3H) 7.1 (m, 2H) 7.2 (m, 3H) 7.4 (m, 2H) 7.5 (d, J=8.6 Hz, 1H) 7.7 (d, J=20.0 Hz, 1H) 7.9 (s, 1H) 8.3 (d, J=5.1 Hz, 1H) 8.8 (d, J=6.4 Hz, 1H) 9.7 (s, 1H) 10.4 (s, 1H). ES-LC/MS m/z 693 [M+H]⁺.

Example 47

N-[3-(3-{2-[(4-(Methyloxy)-3-{4-[2-(methylsulfonyl)ethyl]-1-piperazinyl}phenyl)amino]-4-pyrimidinyl}pyrazolo[1,5-a]pyridin-2-yl)phenyl]-2-(2-thienyl)acetamide

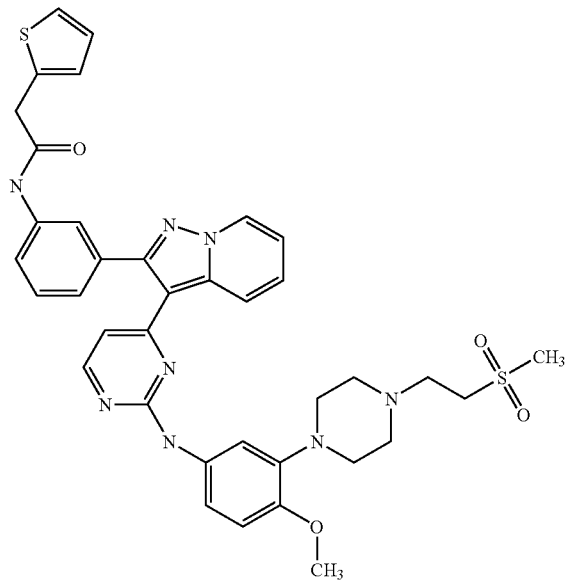

Step A: 1-[2-(Methyloxy)-5-nitrophenyl]piperazine

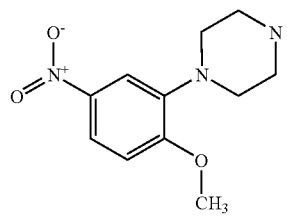

To 1-[2-(methyloxy)phenyl]piperazine (11.0 g, 50.7 mmol) was added concentrated $H_2SO_4$ (60 mL) dropwise to and stirred for 4 h at 0° C. $KNO_3$ (7.2 g, 71.2 mmol) was then added and the mixture stirred overnight while allowing to warm to rt. Reaction was then quenched with ice and then 2N NaOH (100 mL) added and extracted three times with EtOAc. Combined organic phases were dried over $MgSO_4$ and loaded directly onto silica gel. Purified by silica gel chromatography in 0-20% MeOH/$NH_4OH$ in EtOAc. Yield 5.7 g, 42% yield, of an orange solid. $^1$H NMR (400 MHz, DMSO-D6) δ ppm 2.8 (m, 4H) 2.9 (m, 4H) 3.1 (m, 1H) 3.9 (s, 3H) 7.1 (d, J=9.1 Hz, 1H) 7.6 (d, J=2.7 Hz, 1H) 7.9 (dd, J=9.0, 2.7 Hz, 1H).

Step B: 1-[2-(Methyloxy)-5-nitrophenyl]-4-[2-(methylsulfonyl)ethyl]piperazine

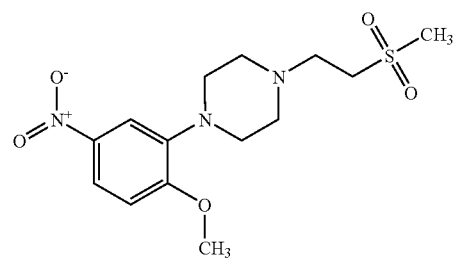

The compound was synthesized by heating a solution of 1-[2-(methyloxy)-5-nitrophenyl]piperazine (0.5 g, 2.11 mmol) and methyl vinyl sulfone (0.336 g, 3.16 mmol) in iPrOH (25 mL) to reflux overnight. Reaction was cooled to rt and dried directly onto silica gel. Purified by silica gel chromatography 0-20% MeOH/$NH_4OH$ in EtOAc to obtain 0.5 g (69% yield) of the desired compound as a solid. $^1$H NMR (400 MHz, DMSO-D6) δ ppm 2.6 (m, 4H) 2.7 (t, J=6.8 Hz, 2H) 3.0 (m, 8H) 3.9 (s, 3H) 7.1 (d, J=9.0 Hz, 1H) 7.6 (d, J=2.7 Hz, 1H) 7.9 (dd, J=9.1, 2.8 Hz, 1H).

Step C: 4-(Methyloxy)-3-{4-[2-(methylsulfonyl)ethyl]-1-piperazinyl}aniline

To a solution of 0.5 g of 1-[2-(methyloxy)-5-nitrophenyl]-4-[2-(methylsulfonyl)ethyl]piperazine (0.5 g, 1.46 mmol) in EtOH (15 mL) was added 10% Pd/C (0.05 g) and reaction stirred under $H_2$ for 18 h. Reaction was then filtered through celite and the solvent removed in vacuo to give the desired product as yellow oil, 0.36 g (55% yield). $^1$H NMR (400 MHz, DMSO-D6) δ ppm 2.5 (m, 3H) 2.7 (t, J=6.4 Hz, 3H) 2.9 (d, J=1.8 Hz, 2H) 2.9 (d, J=11.4 Hz, 2H) 3.0 (s, 4H) 3.3 (d, J=6.4 Hz, 3H) 3.6 (s, 3H) 6.1 (dd, J=8.3, 2.5 Hz, 1H) 6.2 (d, J=2.4 Hz, 1H) 6.6 (d, J=8.8 Hz, 1H).

Step D: 2,2,2-Trifluoro-N-[3-(3-{2-[(4-(methyloxy)-3-{4-[2-(methylsulfonyl)ethyl]-1-piperazinyl}phenyl)amino]-4-pyrimidinyl}pyrazolo[1,5-a]pyridin-2-yl)phenyl]acetamide

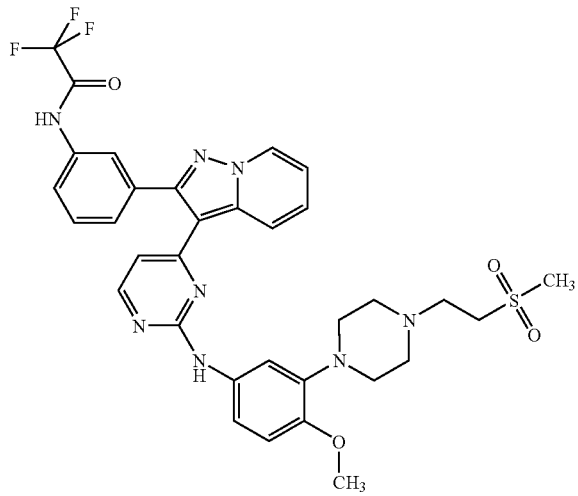

The compound was synthesized from N-{3-[3-(2-chloro-4-pyrimidinyl)-pyrazolo[1,5-a]pyridin-2-yl]phenyl}-2,2,2-trifluoroacetamide (see Example 1, Step C) and 4-(methyloxy)-3-{4-[2-(methylsulfonyl)ethyl]-1-piperazinyl}aniline to afford a yellow solid in 42% yield. ES-LC/MS m/z 695 [M+H]+.

Step E: 4-[2-(3-Aminophenyl)pyrazolo[1,5-a]pyridin-3-yl]-N-(4-(methyloxy)-3-{4-[2-(methylsulfonyl)ethyl]-1-piperazinyl}phenyl)-2-pyrimidinamine

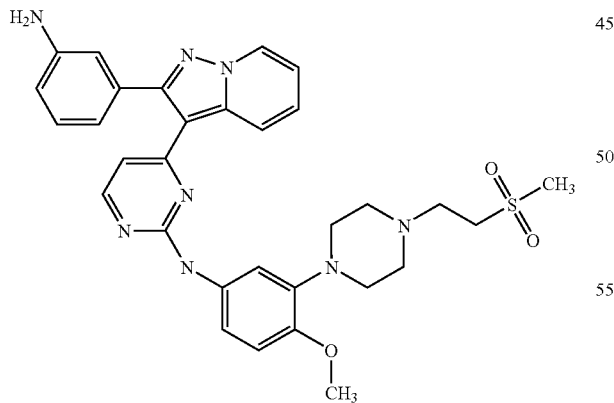

The compound was synthesized from 2,2,2-trifluoro-N-[3-(3-{2-[(4-(methyloxy)-3-{4-[2-(methylsulfonyl)ethyl]-1-piperazinyl}phenyl)amino]-4-pyrimidinyl}pyrazolo[1,5-a]pyridin-2-yl)phenyl]acetamide as described in Example 1, Step E to afford a tan solid in 98% yield. ES-LC/MS m/z 599 [M+H]+.

Step F: N-[3-(3-{2-[(4-(Methyloxy)-3-{4-[2-(methylsulfonyl)ethyl]-1-piperazinyl}phenyl)amino]-4-pyrimidinyl}pyrazolo[1,5-a]pyridin-2-yl)phenyl]-2-(2-thienyl)acetamide (title compound)

The title compound was synthesized from 4-[2-(3-aminophenyl)pyrazolo[1,5-a]pyridin-3-yl]-N-(4-(methyloxy)-3-{4-[2-(methylsulfonyl)ethyl]-1-piperazinyl}phenyl)-2-pyrimidinamine using 2-thienylacetyl chloride as described in Example 10, Step E to give a light brown solid in 47% yield. $^1$H NMR (400 MHz, DMSO-D6) δ ppm 2.5 (m, 4H) 2.7 (m, 3H) 2.9 (m, 4H) 3.0 (s, 3H) 3.7 (s, 3H) 3.9 (s, 2H) 6.4 (d, J=5.1 Hz, 1H) 6.8 (d, J=9.1 Hz, 1H) 7.0 (d, J=4.6 Hz, 2H) 7.1 (t, J=6.6 Hz, 1H) 7.3 (m, 3H) 7.4 (d, J=10.4 Hz, 1H) 7.4 (m, 2H) 7.7 (d, J=8.1 Hz, 1H) 7.9 (s, 1H) 8.2 (d, J=5.5 Hz, 1H) 8.8 (d, J=7.0 Hz, 1H) 9.3 (s, 1H) 10.3 (s, 1H). ES-LC/MS m/z 723 [M+H]+.

Example 48

N-{5-[3-(2-{[2-(Dimethylamino)-2,3-dihydro-1H-inden-5-yl]amino}pyrimidin-4-yl)pyrazolo[1,5-a]pyridin-2-yl]-2-methoxyphenyl}-2-(2-thienyl)acetamide

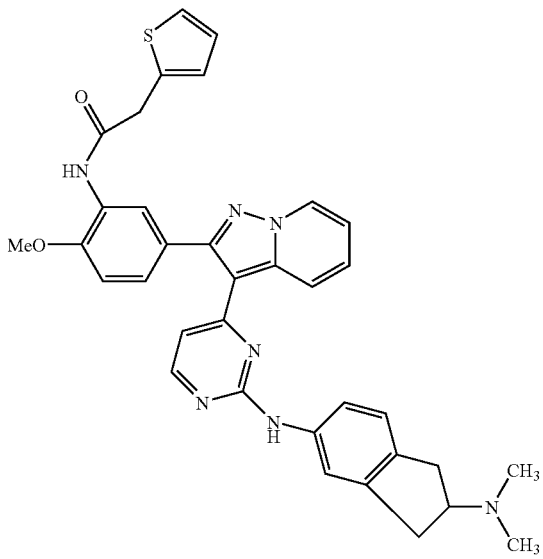

Step A: N-[5-Bromo-2-(methyloxy)phenyl]-2,2,2-trifluoroacetamide

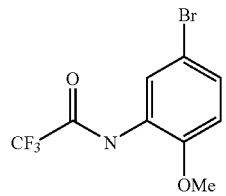

To a solution of 4-bromo-2-nitroanisole (2.0 g, 0.009 mol) in absolute EtOH (100 mL) was added SnCl$_2$.2H$_2$O (11.68 g, 0.051 mol) and the resulting mixture was allowed to stir overnight at rt. The solvent was removed under reduced pressure, residue suspended in EtOAc (100 mL), washed with 1M NaOH (100 mL), and filtered through a celite pad. The organic layer was removed, concentrated by rotary evaporation, and dried under high vacuum. The resulting residue was then dissolved in DCM (150 mL) followed by the addition of TEA (5.19 g, 0.051 mol) and TFAA (4.52 g, 0.022 mol). After overnight stirring, the reaction was washed with 1M HCl (50 mL), organic layer concentrated and purified by column chromatography (1-10% gradient of EtOAc in hexanes) to yield the title compound (1.53 g, 60%) as a white solid. ES-LC/MS m/z=297 [M−H]+.

Step B: 2,2,2-Trifluoro-N-{2-(methyloxy)-5-[(trimethylsilyl)ethynyl]phenyl}-acetamide

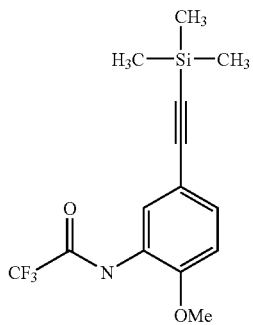

To an oven-dried flask under N₂ was added N-[5-bromo-2-(methyloxy)phenyl]-2,2,2-trifluoroacetamide (1.53 g, 0.005 mol), anhydrous degassed THF (100 mL), dichlorobis(triphenylphosphine)palladium(II) (0.45 mg, 0.6 mmol), copper(I) iodide (73 mg, 0.38 mmol), and trimethylsilylacetylene (1.26 g, 0.013 mol). Next, TEA (5.19 g, 0.05 mol) was added dropwise and the resulting mixture was heated at 60° C. overnight. The crude reaction mixture was adsorbed to silica gel and purified by column chromatography (0-10% EtOAc in hexanes) to afford the desired product (0.68 g, 42%) as an off white solid. ES-LC/MS m/z=314 [M−H]+.

Step C: N-[5-Ethynyl-2-(methyloxy)phenyl]-2,2,2-trifluoroacetamide

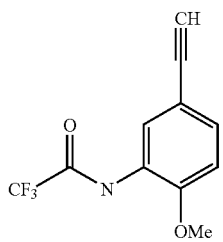

To a solution of 2,2,2-trifluoro-N-{2-(methyloxy)-5-[(trimethylsilyl)ethynyl]phenyl}-acetamide (680 mg, 2.16 mmol) in THF (50 mL) was added dropwise 1.0 M TBAF in THF (2.59 mL, 2.59 mmol) and the resulting mixture was stirred for 30 min at rt. The reaction was quenched with water (50 mL), concentrated under reduced pressure, and the aqueous layer was extracted with DCM (2×50 mL). The organic layers were combined, solvent removed under reduced pressure, and purified by column chromatography (5-25% EtOAc in hexanes) to give the title compound (500 mg, 96%) as an off white solid. ¹H NMR (400 MHz, CDCl₃) δ 3.00 (s, 1H), 3.93 (s, 3H), 6.86 (d, 1H, J=8.42 Hz), 7.31 (dd, 1H, J=8.42 Hz, 2.01 Hz), 8.46 (d, 1H, J=2.01 Hz).

Step D: N-[5-[(2-Chloro-4-pyrimidinyl)ethynyl]-2-(methyloxy)phenyl]-2,2,2-trifluoroacetamide

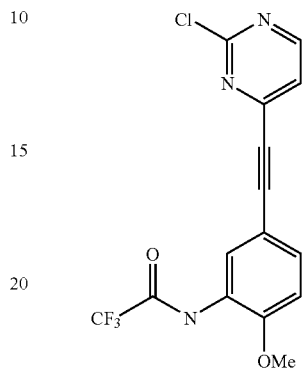

To an oven-dried flask under N₂ was added 2,4-dichloropyrimidine (860 mg, 5.76 mmol), anhydrous degassed THF (100 mL), dichlorobis(triphenylphosphine)-palladium(II) (81 mg, 0.12 mmol), copper(I) iodide (13 mg, 0.07 mmol), and TEA (1.26 g, 0.013 mol). After heating the reaction at 60° C. for 30 min, N-[5-ethynyl-2-(methyloxy)phenyl]-2,2,2-trifluoroacetamide (560 mg, 2.30 mmol) was added dropwise as a solution in THF (10 mL) and the resulting mixture was allowed to heat overnight. The crude reaction mixture was adsorbed to silica gel and purified by column chromatography (0-10% EtOAc in hexanes) to afford the desired product (0.68 g, 42%) as an off white solid. ES-LC/MS m/z=356 [M+H]+.

Step E: N-[5-[3-(2-Chloro-4-pyrimidinyl)pyrazolo[1,5-a]pyridin-2-yl]-2-(methyloxy)phenyl]-2,2,2-trifluoroacetamide

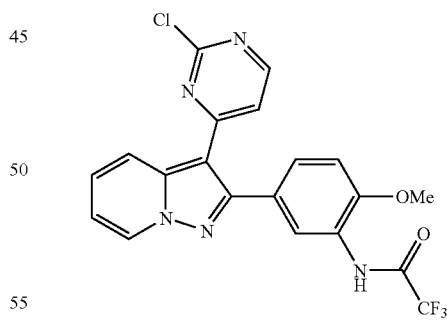

A solution of N-[5-[(2-chloro-4-pyrimidinyl)ethynyl]-2-(methyloxy)phenyl]-2,2,2-trifluoroacetamide (534 mg, 1.50 mmol), aminopyridinium iodide (670 mg, 3.01 mmol), and K₂CO₃ (620 mg, 4.51 mmol) in DMF (10 mL) was stirred at rt for 3 h. The solvent was removed by rotary evaporation and the residue was redissolved in DCM (50 mL) and washed with water (50 mL). The organic layer was adsorbed to silica gel and purified by column chromatography (5-50% EtOAc in hexanes) to afford the pyrazolopyridine (370 mg, 55%) as a tan solid. ES-LC/MS m/z=448 [M+H]+.

Step F: N-{5-[3-(2-Chloropyrimidin-4-yl)pyrazolo[1,5-a]pyridin-2-yl]-2-methoxyphenyl}-2-(2-thienyl)acetamide

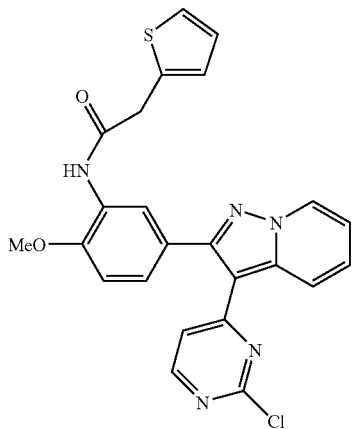

A solution of N-[5-[3-(2-chloro-4-pyrimidinyl)pyrazolo[1,5-a]pyridin-2-yl]-2-(methyloxy)phenyl]-2,2,2-trifluoroacetamide (250 mg, 0.56 mmol) and 1M LiOH (1.30 mL, 1.39 mmol) in 10:1 THF:H$_2$O (5 mL) was heated at 50° C. overnight. After removal of THF by rotary evaporation, the reaction mixture was redissolved in EtOAc and washed with water (25 mL) and brine (25 mL). The organic layer was dried over MgSO$_4$. Following filtration, the solvent was removed by rotary evaporation. After high vacuum removal of the residual solvent, the crude mixture was dissolved in THF (5 mL) and to this was added thiophene-2-acetylchloride (0.10 mL, 0.84 mmol). After overnight stirring, water (0.5 mL) was added and THF removed by rotary evaporation. The reaction mixture was redissolved in DCM (25 mL) washed with saturated NaHCO$_3$ (10 mL), water (10 mL) and brine (10 mL). Organics were dried over MgSO$_4$, filtered and filtrate concentrated under reduced pressure to afford the desired amide (210 mg, 79%) as an off-white solid. ES-LC/MS m/z=476 [M+H]$^-$.

Step H: N-{5-[3-(2-{[2-(Dimethylamino)-2,3-dihydro-1H-inden-5-yl]amino}pyrimidin-4-yl)pyrazolo[1,5-a]pyridin-2-yl]-2-methoxyphenyl}-2-(2-thienyl)acetamide (title compound)

To a solution of N-{5-[3-(2-chloropyrimidin-4-yl)pyrazolo[1,5-a]pyridin-2-yl]-2-methoxyphenyl}-2-(2-thienyl)acetamide (90 mg, 0.19 mmol) in anhydrous i-PrOH (3 mL) was added N$^2$,N$^2$-dimethylindane-2,5-diamine (37 mg, 0.21 mmol) followed by catalytic 12M HCl. After heating for 10 min. in the microwave at 180° C., the reaction was quenched with saturated NaHCO$_3$ (25 mL) and the solvent was removed by rotary evaporation. The aqueous layer was extracted with DCM (25 mL), the organic layer-concentrated, and purified by column chromatography (1-10% MeOH in DCM) to provide the product (27 mg, 24%) as a yellow solid. $^1$H NMR (400 MHz, CDCl$_3$) δ 2.18 (s, 6H), 2.65-2.71 (m, 2H), 2.88-2.97 (m, 2H), 3.89 (s, 3H), 3.98 (s, 2H), 6.51 (d, 1H, J=5.3 Hz), 6.94-6.96 (m, 2H), 7.02-7.14 (m, 3H), 7.26-7.28 (m, 1H), 7.35-7.43 (m, 3H), 7.63 (s, 1H), 8.20 (d, 1H, J=5.3 Hz), 8.31 (s, 1H), 8.43 (d, 1H, J=8.9 Hz), 8.79 (d, 1H, J=7.0 Hz) 9.38 (s, 1H), 9.45 (s, 1H) ppm. ES-LC/MS m/z=616 [M+H]$^+$.

Example 49

N-[2-Methoxy-5-(3-{2-[(2-methyl-1,2,3,4-tetrahydroisoquinolin-7-yl)amino]pyrimidin-4-yl}pyrazolo[1,5-a]pyridin-2-yl)phenyl]-2-(2-thienyl)acetamide

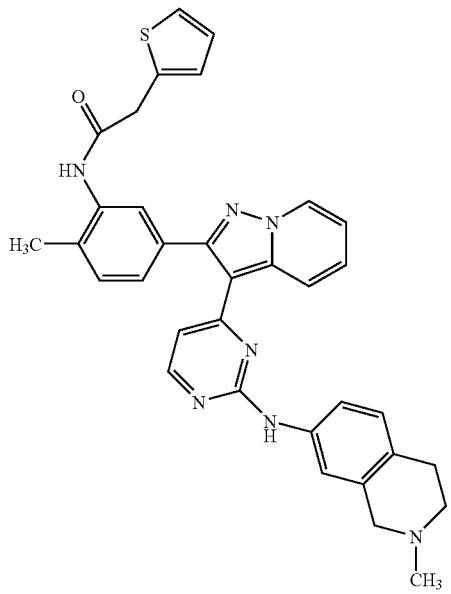

To a solution of N-{5-[3-(2-chloropyrimidin-4-yl)pyrazolo[1,5-a]pyridin-2-yl]-2-methoxyphenyl}-2-(2-thienyl)acetamide (110 mg, 0.23 mmol) (see Example 48, step F) in anhydrous i-PrOH (3 mL) was added 2-methyl-1,2,3,4-tetrahydroisoquinolin-7-amine (39 mg, 0.24 mmol), followed by catalytic 12M HCl. After heating for 10 min in the microwave at 180° C., the reaction was quenched with saturated NaHCO$_3$ (25 mL), the solvent removed by rotary evaporation, and the aqueous layer extracted with DCM (25 mL). The organic layer was concentrated and purified by column chromatography (1-10% MeOH in DCM) to provide the product (74 mg, 53%) as a yellow solid. $^1$H NMR (400 MHz, CDCl$_3$) δ 2.28 (s, 3H), 2.53-2.55 (m, 2H), 2.70-2.72 (m, 2H), 3.36 (s, 2H), 3.87 (s, 3H), 3.97 (s, 2H), 6.49 (d, 1H, J=5.1 Hz), 6.94-6.95 (m, 2H), 7.05-7.13 (m, 2H), 7.25-7.27 (d, 1H, J=8.1 Hz), 7.35-7.43 (m, 3H), 7.48 (s, 1H), 8.19 (d, 1H, J=5.3 Hz), 8.31 (s, 1H), 8.43 (d, 1H, J=8.6 Hz), 8.78 (d, 1H, J=6.8 Hz) 9.38 (s, 1H), 9.45 (s, 1H) ppm. ES-LC/MS m/z=602 [M+H]$^+$.

Example 50

N-[4-(3-{2-[(3-{[2-(Dimethylamino)ethyl]oxy}phenyl)amino]-4-pyrimidinyl}pyrazolo[1,5-a]pyridin-2-yl)phenyl]-2-phenylacetamide

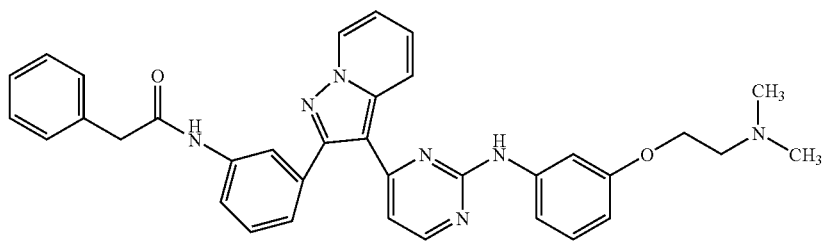

To a stirred solution of 4-[2-(3-aminophenyl)pyrazolo[1,5-a]pyridin-3-yl]-N-(4-{[2-(dimethylamino)ethyl]oxy}phenyl)-2-pyrimidinamine (50 mg, 0.11 mmol) (see Example 15, step A) in DCM (5 mL) was added phenylacetyl chloride (20 mg, 0.12 mmol). After 1.5 h LC/MS indicated the reaction was complete. The solution was washed with saturated NaHCO₃ solution (20 mL), the organic layer was separated and purified by LC (0%-20% MeOH/DCM) to afford the title compound (30 mg, 48%) as a white solid. ¹H NMR (400 MHz, d₆-DMSO) δ 10.31 (s, 1H), 9.54 (s, 1H), 8.80-8.82 (m, 1H), 8.49 (d, J=8.78 Hz, 1H), 8.25 (d, J=5.31 Hz, 1H), 7.87-7.88 (m, 1H), 7.73-7.76 (m, 1H), 7.38-7.52 (m, 3H), 7.20-7.31 (m, 7H), 7.09-7.14 (m, 2H), 6.49-6.52 (m, 1H), 6.45 (d, J=5.31 Hz, 1H), 3.96 (t, J=5.85 Hz, 2H), 3.63 (s, 2H), 2.57 (t, J=5.85 Hz, 2H), 2.16 (s, 1H) ppm. ES-LC/MS m/z=584 [M+H]⁺.

Example 51

2,6-Difluoro-N-[3-(3-{5-fluoro-2-[(2-methyl-1,2,3,4-tetrahydro-7-isoquinolinyl)amino]-4-pyrimidinyl}pyrazolo[1,5-a]pyridin-2-yl)phenyl]benzamide

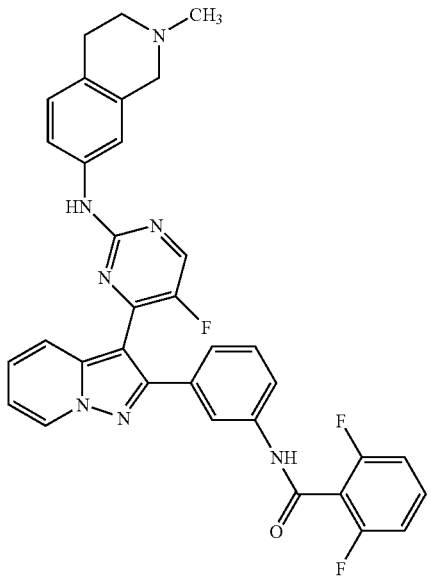

Step A: N-{3-[(2-Chloro-5-fluoro-4-pyrimidinyl)ethynyl]phenyl}-2,2,2-trifluoroacetamide

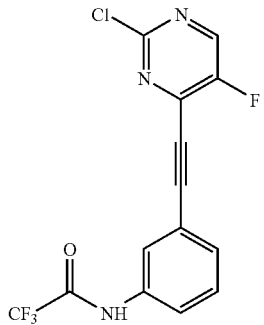

To an oven-dried flask under N₂ was added 2,4-dichloro-5-fluoropyrimidine (1.56 g, 9.4 mmol), anhydrous, degassed THF (100 mL), dichlorobis(triphenyl-phosphine)palladium (II) (62 mg, 0.09 mmol), copper(I) iodide (10 mg, 0.05 mmol), and TEA (0.164 g, 0.23 mmol). After heating the reaction at 60° C. for 30 min. N-(3-ethynylphenyl)-2,2,2-trifluoroacetamide (1.0, 4.69 mmol) was added dropwise as a solution in THF (25 mL) and the resulting mixture was allowed to heat overnight. The crude reaction mixture was adsorbed onto silica gel and purified by column chromatography (2-10% EtOAc in hexanes) to afford the desired product (1.25 g, 78%) as an off white solid. ES-LC/MS m/z=344 [M+H]⁺.

Step B: N N-{3-[3-(2-Chloro-5-fluoro-4-pyrimidinyl)pyrazolo[1,5-a]pyridin-2-yl]phenyl}-2,2,2-trifluoroacetamide

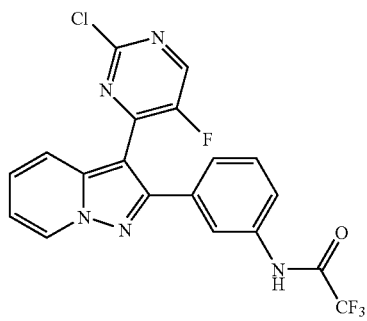

A solution of N-{3-[(2-chloro-5-fluoro-4-pyrimidinyl)ethynyl]phenyl}-2,2,2-trifluoroacetamide (1.25 g, 3.64 mmol), aminopyridinium iodide (163 g, 7.34 mmol), and K₂CO₃ (1.52 g, 11 mmol) in DMF (50 mL) was stirred at rt for 2 h followed by solvent removal. The residue was suspended in water (50 mL) and extracted twice with EtOAc (100 mL). The organic layer was adsorbed onto silica gel and purified by column chromatography (10-50% EtOAc in hexanes) to afford the pyrazolopyridine (1.34 g, 85%) as an off-white solid. ES-LC/MS m/z=436 [M+H]⁺.

Step C: 2,2,2-Trifluoro-N-[3-(3-{5-fluoro-2-[(2-methyl-1,2,3,4-tetrahydro-7-isoquinolinyl)amino]-4-pyrimidinyl}pyrazolo[1,5-a]pyridin-2-yl)phenyl]acetamide

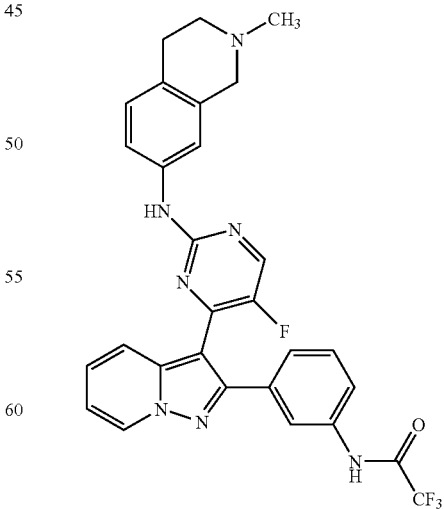

A solution N N-{3-[3-(2-chloro-5-fluoro-4-pyrimidinyl)pyrazolo[1,5-a]pyridin-2-yl]phenyl}-2,2,2-trifluoroacetamide (20 mg, 0.05 mmol), Pd₂(dba)₃ (8.4 mg, 0.009 mmol), xantphos (8.0 mg, 0.013 mmol), cesium carbonate (67 mg, 0.21 mmol), and 2-methyl-1,2,3,4-tetrahydro-6-isoquinolinamine (22.3 mg, 0.14 mmol) in anhydrous 1,4-dioxane, that had been previously degassed with nitrogen, was heated at 100° C. for 48 h. At this time, the crude reaction was adsorbed onto silica gel and purified by LC (DCM to 10% MeOH/DCM) to afford the product (13 mg, 50%) as a tan solid. ES-LC/MS m/z=562 [M+H]⁺.

Step D: N-{4-[2-(3-Aminophenyl)pyrazolo[1,5-a]pyridin-3-yl]-5-fluoro-2-pyrimidinyl}-2-methyl-1,2,3,4-tetrahydro-7-isoquinolinamine

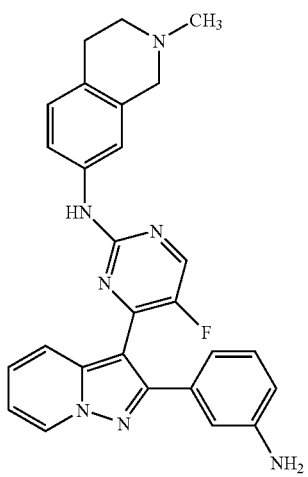

To a solution of 2,2,2-trifluoro-N-[3-(3-{5-fluoro-2-[(2-methyl-1,2,3,4-tetrahydro-7-isoquinolinyl)amino]-4-pyrimidinyl}pyrazolo[1,5-a]pyridin-2-yl)phenyl]acetamide (13 mg, 0.023 mmol) in 5:1 THF:H₂O (6 mL) was added 1M LiOH (0.14 mL, 0.14 mmol) and the reaction mixture was stirred overnight at rt. The reaction was washed with brine (10 mL), the organic layer separated and adsorbed onto silica gel and purified by column chromatography (0-10% MeOH/DCM+1% NH₄OH) to afford the title compound (8.6 mg, 80%) as an off-white solid. ES-LC/MS m/z=466 [M+H]⁺.

Step E: 2,6-Difluoro-N-[3-(3-{5-fluoro-2-[(2-methyl-1,2,3,4-tetrahydro-7-isoquinolinyl)amino]-4-pyrimidinyl}pyrazolo[1,5-a]pyridin-2-yl)phenyl]benzamide (title compound)

To a solution of N-{4-[2-(3-aminophenyl)pyrazolo[1,5-a]pyridin-3-yl]-5-fluoro-2-pyrimidinyl}-2-methyl-1,2,3,4-tetrahydro-7-isoquinolinamine (50 mg, 0.11 mmol) in THF (5 mL) was added 2,6-difluorobenzoyl chloride (20 mg, 0.11 mmol) and the reaction mixture stirred at rt for 20 min. The reaction was diluted with MeOH, adsorbed onto silica gel, and purified by column chromatography (0-10% MeOH/DCM+1% NH₄OH) to afford the title compound (15.4 mg, 24%) as a pale yellow solid. ¹H NMR (400 MHz, DMSO-d₆) δ 10.86 (s, 1H), 9.52 (s, 1H), 8.86 (d, J=7.69 Hz, 1H), 8.45-8.46 (m, 1H), 8.06 (s, 1H), 7.89 (d, J=8.61 Hz, 1H), 7.71-7.73 (m, 1H), 7.54-7.58 (m, 1H), 7.30-7.47 (m, 4H), 7.20-7.24 (m, 3H), 7.08-7.12 (m, 1H), 6.86 (d, J=8.42 Hz, 1H), 3.26 (s, 2H), 2.66-2.69 (m, 2H), 2.49-2.51 (m, 2H), 2.26 (s, 3H). ES-LC/MS m/z=606 [M+H]⁺.

Example 52

N-{3-[3-(2-{[3-(4-methyl-1,3-oxazol-5-yl)phenyl]amino}pyrimidin-4-yl)pyrazolo[1,5-a]pyridin-2-yl]phenyl}-2-(2-thienyl)acetamide

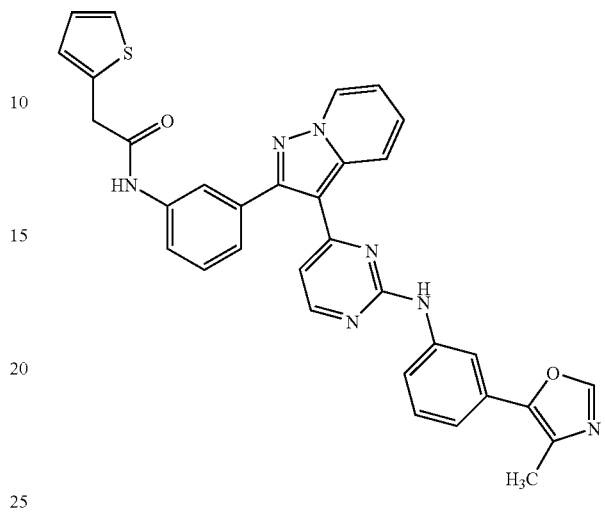

Step A: {1-[(3-Aminophenyl)sulfonyl]ethyl}formamide

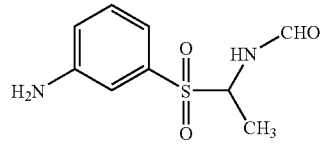

A stirred mixture of dry acetonitrile (500 mL) and dry toluene (500 mL) was cooled to −30° C., followed by the addition of formamide (50.7 g, 1.1 mol), acetaldehyde (37 g, 0.85 mol) and TMS-CI (106.4 g, 0.98 mol) at −30° C. under nitrogen atmosphere. The reaction mixture was stirred at rt for 1 h and warmed to 55° C., then para-toluene sulphonic acid was added and stirred the reaction mixture at this temperature overnight. The reaction mixture was cooled to 0° C., followed by the addition of tert-butyl ether (300 mL) and stirred for 1 h. The white precipitate formed was filtered off and dried. The crude product (110 g) was taken onto the next step without further purification.

Step B: 3-{[1-(Isocyanoethyl)ethyl]sulfonyl}aniline

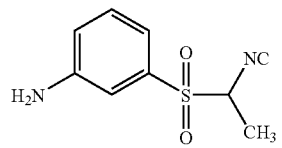

To cooled (0° C.) solution of {1-[(3-aminophenyl)sulfonyl]ethyl}formamide (11 g, 0.484 mol) in dry THF (1 L), was added slowly phosphorus oxychloride (148.4 g, 0.968 mol) and the reaction stirred for 30 min. TEA (293.8 g, 2.9 mol) was them added dropwise over 30 min. and the reaction stirred for 2 h further at 0° C. After no starting material was observed by TLC the reaction mixture was quenched with water and extracted with EtOAc (3×350 mL). The combined organic layers were washed with brine, water, dried over anhydrous $Na_2SO_4$ and concentrated. The crude product (60 g) was taken onto the next step without further purification.

Step C: 4-Methyl-5-(3-nitrophenyl)-1,3-oxazole

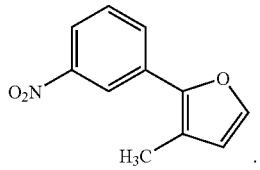

To a cooled (0° C.) solution of 3-{[1-(isocyanoethyl)ethyl]sulfonyl}aniline (60 g, 0.287 mol) in dry MeOH (800 mL), was added dry powdered $K_2CO_3$ and stirred at rt for 1 h. The reaction mixture was re-cooled to 0° C. and 3-nitro benzaldehyde (43 g, 0.287 mol) added. The reaction mixture was warmed to rt, followed by heating at 55° C. overnight with stirring. The excess solvent was removed under reduced pressure, the residue was dissolved in water (100 mL) and extracted with EtOAc (3×350 mL). The combined organic layers were washed with brine, water, dried over anhydrous $Na_2SO_4$ and concentrated. The crude product was purified by silica get (60-120 mesh) column chromatograph using 15% EtOAc in petroleum-ether to yield product as yellow solid. Yield 50 g (86%).

Step D: 3-(4-Methyl-1,3-oxazol-5-yl)aniline

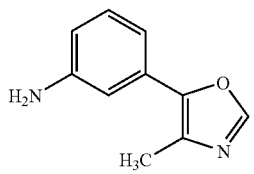

Pd/C (5 g) was transferred carefully to a solution of 4-methyl-5-(3-nitrophenyl)-1,3-oxazole (50 g) in MeOH (600 mL) in a Parr-shaker bottle and hydrogenated at 3.5 kg pressure for 20 h. The reaction mixture was filtered over a celite bed and the filtrate concentrated. The residue was purified by silica gel column chromatograph using 40% EtOAc in petroleum-ether to get a yellow solid. Yield 18 g (42%). $^1$H NMR (400 MHz, DMSO-$d_6$) δ 8.23 (s, 1H), 7.08 (t, J=8.0 Hz, 1H), 6.82 (s, 1H), 6.71 (d, J=7.9 Hz, 1H), 6.52 (d, J=8.2 Hz, 1H), 5.24 (s, 2H), 2.29 (s, 3H).

Step E: N-{3-[3-(2-{[3-(4-Methyl-1,3-oxazol-5-yl)phenyl]amino}pyrimidin-4-yl)pyrazolo[1,5-a]pyridin-2-yl]phenyl}-2-(2-thienyl)acetamide (title compound)

The title compound was synthesized from N-{3-[3-(2-chloro-4-pyrimidinyl)pyrazolo[1,5-a]pyridin-2-yl]phenyl}-2-(2-thienyl)acetamide (see Example 2, step B) and 3-(4-methyl-1,3-oxazol-5-yl)aniline following the protocol described in Example 2, step E. The reaction formed a suspension on cooling to rt. The suspension was filtered and provided the title compound in 81% yield.

$^1$H NMR (400 MHz, DMSO-$d_6$) δ 10.37 (s, 1H), 9.85 (s, 1H), 8.83 (d, J=6.9 Hz, 1H), 8.47 (d, J=9.0 Hz, 1H), 8.28 (s, 1H), 8.26 (d, J=5.3 Hz, 1H), 8.13 (m, 1H), 7.90 (m, 1H), 7.72 (m, 2H), 7.44-7.35 (m, 4H), 7.27 (d, J=7.6 Hz, 1H), 7.21 (d, J=7.8 Hz, 1H), 7.11 (m, 1H), 6.96 (s, 1H), 6.95 (t, J=3.3 Hz, 1H), 6.52 (d, J=5.4 Hz, 1H), 3.87 (s, 2H), 2.32 (s, 3H). ES-LC/MS m/z=585 [M+H]$^+$.

Example 53

N-{3-[3-(2-{[2-(Dimethylamino)-2,3-dihydro-1H-inden-5-yl]amino}pyrimidin-4-yl)pyrazolo[1,5-a]pyridin-2-yl]phenyl}-2-(2-thienyl)acetamide

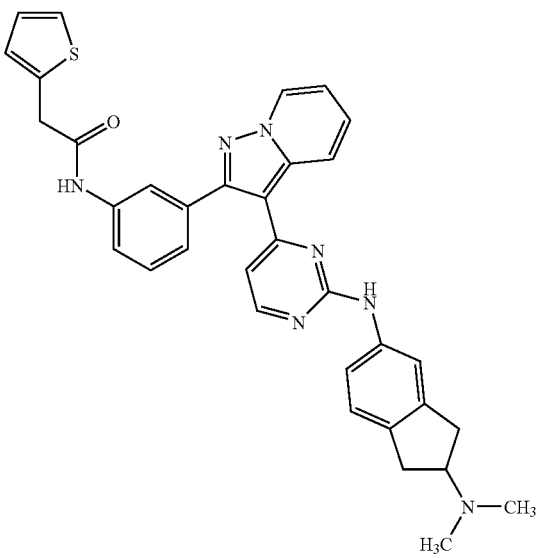

Step A:
N,N-Dimethyl-5-nitro-2,3-dihydro-1H-inden-2-amine

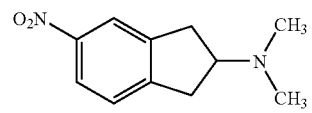

(5-Nitro-2,3-dihydro-1H-inden-2-yl)amine hydrochloride (5.52 g, 26 mmol), paraformaldehyde (4.1 g, 128 mmol), sodium cyanoborohydride (8.1 g, 128 mmol), and HOAc (7.4 mL, 128 mmol) were combined in DCE (200 mL) and the suspension was heated to reflux for 15 h. The reaction was cooled and quenched with saturated aqueous NaHCO₃. The organic layer was separated, washed with brine and dried with MgSO₄ and concentrated to an oil. The crude material was purified by silica gel flash column chromatography (0-100% (90% DCM/9% MeOH/1% NH₄OH)/DCM) to yield 2.7 g (52%) of a yellow oil that crystallized while stored on the bench top. ¹H NMR (400 MHz, CDCl₃) δ 8.07 (m, 2H), 7.36 (d, J=8.1 Hz, 1H), 4.13 (m, 1H), 3.34 (m, 4H), 2.74 (s, 6H).

Step B:
(5-Amino-2,3-dihydro-1H-inden-2-yl)dimethylamine

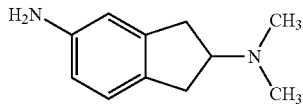

Dimethyl(5-nitro-2,3-dihydro-1H-inden-2-yl)amine (1.5 g, 7.3 mmol)) was dissolved in MeOH and stirred vigorously with of 5% Pd/C (250 mg) under a 55 PSI atmosphere of hydrogen for 15 h. The reaction was filtered through celite and the solvent was removed under vacuum. The reaction produced 1.2 g (94%) of the white powder (5-amino-2,3-dihydro-1H-inden-2-yl)dimethylamine. ¹H NMR (400 MHz, DMSO-d₆) δ 6.84 (d, J=8.2 Hz, 1H), 6.41 (s, 1H), 6.38-6.36 (m, 1H), 4.88 (s, 2H), 3.86 (quint, J=8.8 Hz, 1H), 3.16-2.88 (m, 4H), 2.60 (s, 6H).

Step C: N-{3-[3-(2-{[2-(Dimethylamino)-2,3-dihydro-1H-inden-5-yl]amino}pyrimidin-4-yl)pyrazolo[1,5-a]pyridin-2-yl]phenyl}-2-(2-thienyl)acetamide (title compound)

The title compound was synthesized by combining N-{3-[3-(2-chloro-4-pyrimidinyl)pyrazolo[1,5-a]pyridin-2-yl]phenyl}-2-(2-thienyl)acetamide (147 mg, 0.33 mmol) (see Example 2, step B) and (5-amino-2,3-dihydro-1H-inden-2-yl)dimethylamine (70 mg, 0.40 mmol) in i-PrOH (2 mL) and adding 1M hydrochloric acid in diethyl ether (33 uL, 0.03 mmol). The reaction was heated to 180° C. in the microwave for 20 min. repeatedly until LC/MS analysis of the reaction mixture showed consumption of starting material. The reaction product was concentrated to a residue, partitioned between chloroform and saturated aqueous NaHCO₃ and the organic fraction was washed with brine. The crude organic solution was dried with Na₂SO₄ and concentrated. The crude product was purified by silica gel flash column chromatography (DCM: 0-100% 90:9:1 DCM:MeOH:NH₄OH₍ₐq₎). Purification yielded 43 mg (22%) of a brown powder. ¹H NMR (400 MHz, DMSO-d₆) δ 10.34 (s, 1H), 9.41 (s, 1H), 8.81 (d, J=6.9 Hz, 1H), 8.46 (m, 1H), 8.21 (dd, J=5.2, 4.1 Hz, 1H), 7.90-7.87 (m, 1H), 7.73 (d, J=8.0 Hz, 1H), 7.64 (d, J=15.4 Hz, 1H), 7.48-7.35 (m, 4H), 7.25 (d, J=7.7 Hz, 1H), 7.11 (t, J=7.0 Hz, 1H), 7.06-7.02 (m, 1H), 6.97-6.94 (m, 1H), 6.45 (dd, J=8.6, 5.4 Hz, 1H), 3.86 (s, 2H), 3.30 (s, 6H), 3.02-2.86 (m, 2H), 2.70-2.63 (m, 1H), 2.17 (s, 2H). ES-LC/MS m/z=586 [M+H]⁺.

Example 54

N-[3-(3-{2-[(2-Amino-2,3-dihydro-1H-inden-5-yl)amino]-4-pyrimidinyl}pyrazolo[1,5-a]pyridin-2-yl)phenyl]-2-(2-thienyl)acetamide

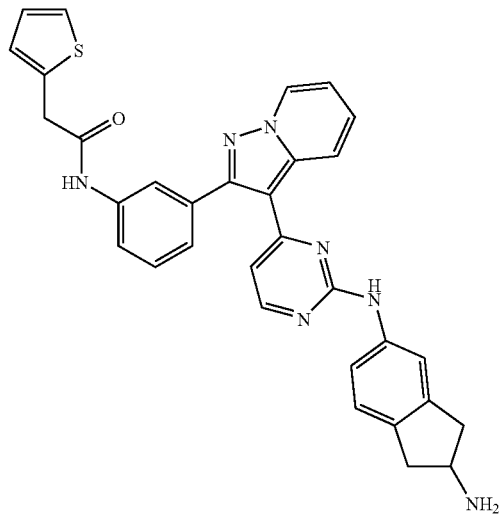

Step A: 2,2,2-Trifluoro-N-(5-nitro-2,3-dihydro-1H-inden-2-yl)acetamide

TFAA (361 μL, 2.6 mmol) was added dropwise to a solution of (5-nitro-2,3-dihydro-1H-inden-2-yl)amine hydrochloride (500 mg, 2.3 mmol), TEA (327 μL, 2.3 mmol) and DCM (20 mL) stirring at 0° C. The ice bath was allowed to warm and the reaction stirred at rt for 15 h. The reaction was washed in a separatory funnel with saturated aqueous NaHCO₃ followed by brine and then dried over Na₂SO₄. The solvent was removed under vacuum and the residue was purified by silica gel flash column chromatography (DCM: 0-100% 90:9:1 DCM:MeOH:NH₄OH₍ₐq₎). Purification yielded 476 mg (84%) of product as a white powder. ¹H NMR (400 MHz, DMSO-d₆) δ 9.75 (d, J=6.8 Hz, 1H), 8.10 (s, 1H), 8.06 (dd, J=8.3, 2.2 Hz, 1H), 7.49 (d, J=8.2 Hz, 1H), 4.67-4.58 (m, 1H), 3.35 (dd, J=16.8, 8.1 Hz, 2H), 3.01 (dd, J=16.5, 5.7 Hz, 2H).

Step B: N-(5-Amino-2,3-dihydro-1H-inden-2-yl)-2,2,2-trifluoroacetamide

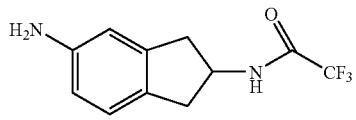

2,2,2-Trifluoro-N-(5-nitro-2,3-dihydro-1H-inden-2-yl)acetamide (245 mg, 0.89 mmol) was dissolved in EtOAc and stirred vigorously for 15 h. with 5% Pd/C (70 mg) under hydrogen atmosphere (1 atm). The reaction was filtered through celite and the solvent was removed under vacuum. Filtration yielded 214 mg (98%) of the desired amine as a brown powder. ¹H NMR (400 MHz, DMSO-d₆) δ 9.60 (d, J=7.1 Hz, 1H), 6.81 (d, J=8.0 Hz, 1H), 6.39 (s, 1H), 6.34 (d, J=8.1 Hz, 1H), 4.83 (s, 2H), 4.43 (m, 1H), 3.01 (m, 2H), 2.71 (m, 2H); ES-LC/MS (M+H)⁺=245.11.

141

Step C: 2,2,2-Trifluoro-N-(5-{[4-(2-{3-[(2-thienylacetyl)amino]phenyl}pyrazolo-[1,5-a]pyridin-3-yl)-2-pyrimidinyl]amino}-2,3-dihydro-1H-inden-2-yl)acetamide

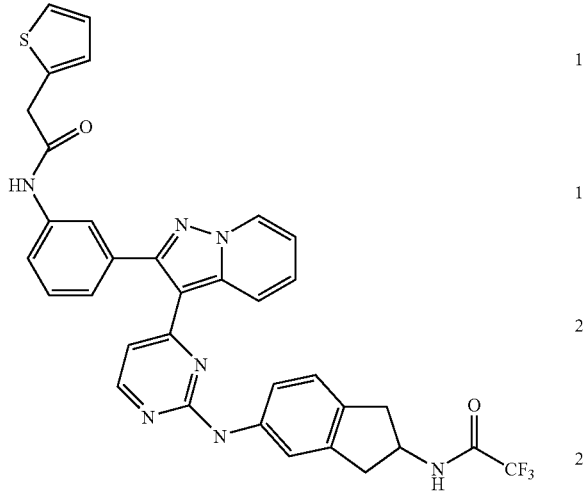

N-{3-[3-(2-Chloro-4-pyrimidinyl)pyrazolo[1,5-a]pyridin-2-yl]phenyl}-2-(2-thienyl)acetamide (109 mg, 0.25 mmol) (see Example 2, step B) and N-(5-amino-2,3-dihydro-1H-inden-2-yl)-2,2,2-trifluoroacetamide (72 mg, 0.30 mmol) were combined in i-PrOH (2 mL) and 1M hydrochloric acid in diethyl ether (25 µL, 0.025 mmol) and heated at 180° C. in the microwave reactor for 20 min. The reaction product was concentrated and purified directly by silica gel flash column chromatography (30-100% EtOAc in hexanes). Purification yielded 61 mg (38%) of a brown oil. ES-LC/MS m/z=654 [M+H]$^+$.

Step D: N-[3-(3-{2-[(2-Amino-2,3-dihydro-1H-inden-5-yl)amino]-4-pyrimidinyl}pyrazolo[1,5-a]pyridin-2-yl)phenyl]-2-(2-thienyl)acetamide (title compound)

2,2,2-Trifluoro-N-(5-{[4-(2-{3-[(2-thienylacetyl)amino]phenyl}pyrazolo[1,5-a]pyridin-3-yl)-2-pyrimidinyl]amino}-2,3-dihydro-1H-inden-2-yl)acetamide (61 mg, 0.09 mmol) was stirred with LiOH (20 mg, 0.47 mmol) in MeOH (5 mL) at rt. After 24 h. additional LiOH (20 mg, 0.47 mmol) was added and the reaction stirred until complete conversion was indicated by LC/MS analysis. The MeOH was removed under vacuum and the residue partitioned between EtOAc and water. The organic was washed with brine and dried with MgSO$_4$. The solvent was removed and the crude product was purified by silica gel flash column chromatography (DCM: 0-100% 90:9:1 DCM:MeOH:NH$_4$OH$_{(aq)}$) and yielded 40 mg (77%) of the title compound. $^1$H NMR (400 MHz, DMSO-d$_6$) δ 10.32 (s, 1H), 9.37 (s, 1H), 8.79 (d, J=7.0 Hz, 1H), 8.45 (d, J=8.6 Hz, 1H), 8.19 (d, J=5.3 Hz, 1H), 7.86 (s, 1H), 7.72 (d, J=8.1 Hz, 1H), 7.62 (s, 1H), 7.46-7.32 (m, 4H), 7.24 (d, J=7.6 Hz, 1H), 7.09 (t, J=6.9 Hz, 1H), 7.01 (d, J=8.0 Hz, 1H), 6.95 (m, 1H), 6.42 (d, J=5.3 Hz, 1H), 3.85 (s, 2H), 3.65 (m, 1H), 2.94 (dd, J=15.5, 6.8 Hz, 2H), 2.47 (m, 2H), 1.83 (s, 2H). ES-LC/MS m/z=558 [M+H]$^+$.

142

Example 55

N-[3-(3-{2-[(7-Amino-5,6,7,8-tetrahydro-2-naphthalenyl)amino]-4-pyrimidinyl}pyrazolo[1,5-a]pyridin-2-yl)phenyl]-2-(2-thienyl)acetamide

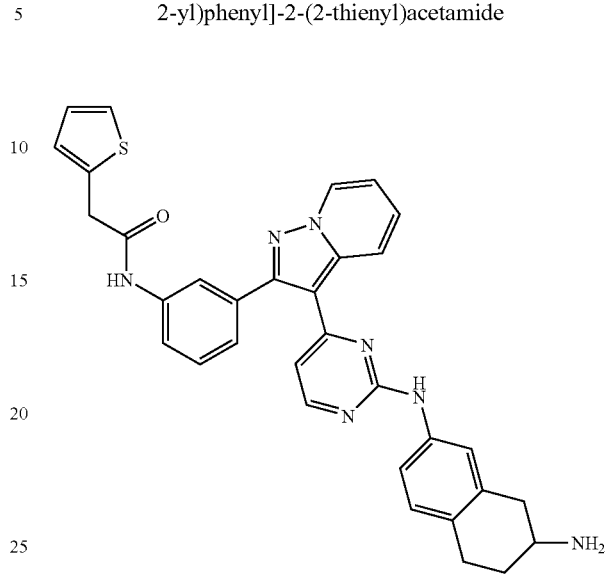

Step A: 7-Nitro-1,2,3,4-tetrahydro-1-naphthalenol

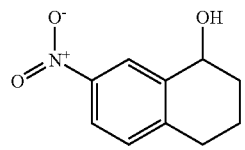

7-Nitro-3,4-dihydro-1(2H)-naphthalenone (5.0 g, 26.1 mmol) was stirred with 2M borane-dimethylsulfide in THF (14.4 mL, 28.8 mmol) in THF (200 mL) at rt for 15 h. The reaction was cooled to 0° C. and quenched with MeOH. The solvent and reaction byproducts were removed under vacuum and afforded 5.0 g (99%) of the desired alcohol as a brown powder. $^1$H NMR (400 MHz, DMSO-d$_6$) δ 8.25 (d, J=2.6 Hz, 1H), 7.98 (dd, J=8.5, 2.6 Hz, 1H), 7.34 (d, J=8.5 Hz, 1H), 5.55 (d, J=5.7 Hz, 1H), 4.63 (m, 1H), 2.87-2.73 (m, 2H), 2.00-1.83 (m, 2H), 1.75-1.60 (m, 2H).

Step B:
6-Nitro-1a,2,3,7b-tetrahydronaphtho[1,2-b]oxirene

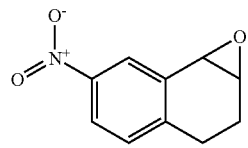

7-Nitro-1,2,3,4-tetrahydro-1-naphthalenol (4.0 g, 20.9 mmol) was treated with Amberlyst-15 (5.0 g) in toluene (100 mL) at 100° C. for 15 h. The reaction was cooled and the Amberlyst was removed by filtration. The filtrate was concentrated under vacuum to afford 3.33 g (92%) of the desired alkene as a brown oil. The 6-nitro-1,2-dihydronaphthalene (3.3 g, 18.9 mmol) was combined with 3-chloroperoxybenzoic acid (5.1 g, 22.6 mmol) in chloroform (60 mL) and heated to reflux for 15 h. The reaction was cooled, diluted with EtOAc and washed three times with 5% aqueous $K_2CO_3$. The organic was dried with $Na_2SO_4$, concentrated to a residue and purified by silica gel flash column chromatography (0-50% EtOAc in hexanes). Purification yielded 1.3 g (36%) of the epoxide as a white solid. $^1$H NMR (400 MHz, DMSO-$d_6$) δ 8.44 (d, J=2.6 Hz, 1H), 8.12 (dd, J=8.1, 2.4 Hz, 1H), 7.41 (d, J=8.5 Hz, 1H), 4.16 (d, J=4.4 Hz, 1H), 3.78 (m, 1H), 2.75-2.55 (m, 2H), 2.39-2.33 (m, 1H), 1.75-1.67 (m, 1H).

Step C: 7-Nitro-3,4-dihydro-2(1H)-naphthalenone

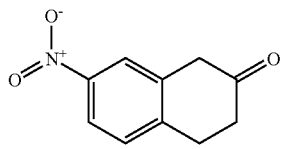

6-Nitro-1a,2,3,7b-tetrahydronaphtho[1,2-b]oxirene (1.3 g, 6.8 mmol) was combined with anhydrous zinc iodide powder (1.0 g, 3.1 mmol) in benzene and stirred at rt under nitrogen in a dark vessel for 15 h. The reaction mixture was filtered and the filtrate concentrated under vacuum. The crude residue was purified by silica gel flash column chromatography (10-50% EtOAc/hexanes) to yield 750 mg (58%) of the desired ketone as a yellow powder. $^1$H NMR (400 MHz, DMSO-$d_6$) δ 8.09 (d, J=2.1 Hz, 1H), 8.06 (dd, J=8.2, 2.4 Hz, 1H), 7.55 (d, J=8.3 Hz, 1H), 3.75 (s, 2H), 3.15 (t, J=6.7 Hz, 2H), 2.50-2.43 (m, 4H).

Step D: 7-Nitro-1,2,3,4-tetrahydro-2-naphthalenamine

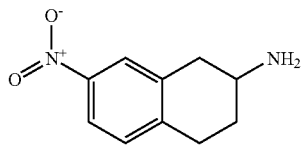

7-Nitro-3,4-dihydro-2(1H)-naphthalenone (200 mg, 1.1 mmol) was combined with ammonium acetate (807 mg, 10.5 mmol), sodium cyanoborohydride (86 mg, 1.4 mmol) and MeOH (5 mL) and heated to 50° C. for 15 h. The reaction was cooled and concentrated under vacuum and the residue was partitioned between EtOAc and water. The organic layer was washed with 5% aqueous $K_2CO_3$, brine and dried over $Na_2SO_4$. The crude was concentrated under vacuum and purified by silica gel flash column chromatography (0-100% (90% DCM/9% MeOH/1% $NH_4OH$)/DCM). Purification provided 130 mg (65%) of the desired amine as a brown oil. $^1$H NMR (400 MHz, DMSO-$d_6$) δ 7.90-7.89 (m, 2H), 7.31 (d, J=8.5 Hz, 1H), 3.06-2.88 (m, 3H), 2.84-2.72 (m, 1H), 2.54-2.44 (m, 2H), 1.81 (d, J=35.2 Hz, 2H), 1.51-1.42 (m, 1H).

Step E: N-(7-Amino-1,2,3,4-tetrahydro-2-naphthalenyl)-2,2,2-trifluoroacetamide

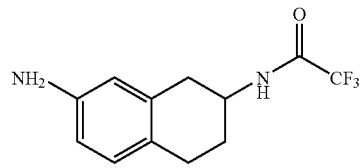

7-Nitro-1,2,3,4-tetrahydro-2-naphthalenamine was acylated with TFAA as described in Example 54, Step A in 90% yield, and subsequently reduced to the corresponding aniline as described in Example 54, Step B in 99% yield. $^1$H NMR (400 MHz, DMSO-$d_6$) δ 9.39 (d, J=7.7 Hz, 1H), 6.70 (d, J=7.8 Hz, 1H), 6.33 (dd, J=8.1, 2.4 Hz, 1H), 6.23 (s, 1H), 4.78 (s, 2H), 3.97-3.87 (m, 1H), 2.79-2.58 (m, 4H), 1.91-1.84 (m, 1H), 1.69-1.59 (m, 1H). ES-LC/MS m/z=259 [M+H]$^+$.

Step F: 2,2,2-Trifluoro-N-(7-{[4-(2-{3-[(2-thienylacetyl)amino]phenyl}pyrazolo[1,5-a]pyridin-3-yl)-2-pyrimidinyl]amino}-1,2,3,4-tetrahydro-2-naphthalenyl)acetamide

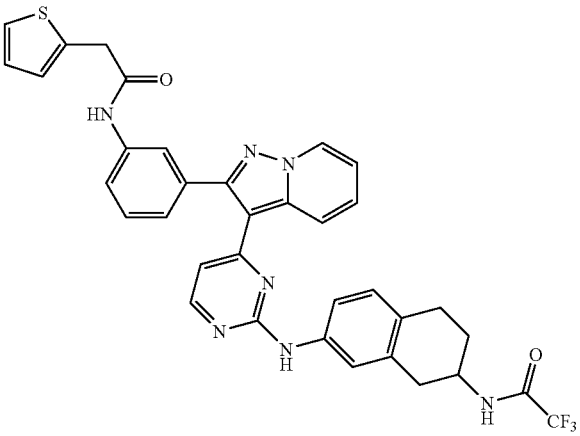

N-{3-[3-(2-Chloro-4-pyrimidinyl)pyrazolo[1,5-a]pyridin-2-yl]phenyl}-2-(2-thienyl)acetamide (99 mg, 0.22 mmol) (see Example 2, Step B) and N-(7-amino-1,2,3,4-tetrahydro-2-naphthalenyl)-2,2,2-trifluoroacetamide (69 mg, 0.26 mmol) following the protocol outlined in Example 54, Step C. Purification provided 60 mg (41%) of the coupled adduct as an oil. ES-LC/MS m/z=668 [M+H]$^+$.

Step G: N-[3-(3-{2-[(7-Amino-5,6,7,8-tetrahydro-2-naphthalenyl)amino]-4-pyrimidinyl}pyrazolo[1,5-a]pyridin-2-yl)phenyl]-2-(2-thienyl)acetamide (title compound)

The title compound was prepared by treating 2,2,2-trifluoro-N-(7-{[4-(2-{3-[(2-thienylacetyl)amino]phenyl}pyrazolo[1,5-a]pyridin-3-yl)-2-pyrimidinyl]amino}-1,2,3,4-tetrahydro-2-naphthalenyl)acetamide (60 mg, 0.09 mmol) with LiOH in MeOH as described in Example 54, Step D. Purification yielded 50 mg (51%) of the desired amine. ¹H NMR (400 MHz, DMSO-d₆) δ 10.32 (s, 1H), 9.34 (s, 1H), 8.80 (d, J=6.8 Hz, 1H), 8.46 (d, J=8.8 Hz, 1H), 8.18 (d, J=5.4 Hz, 1H), 7.86 (s, 1H), 7.72 (d, J=8.1 Hz, 1H), 7.48-7.34 (m, 4H), 7.24 (d, J=7.6 Hz, 1H), 7.09 (t, J=6.7 Hz, 1H), 6.95-6.89 (m, 3H), 6.41 (d, J=5.2 Hz, 1H), 3.85 (s, 2H), 2.96 (m, 1H), 2.79-2.60 (m, 3H), 2.41-2.31 (m, 1H), 1.90-1.74 (m, 3H), 1.46-1.33 (m, 1H). ES-LC/MS m/z=572 [M+H]⁺.

Example 56

N-{2-Methyl-5-[3-(2-{[3-(1-pyrrolidinylmethyl)phenyl]amino}-4-pyrimidinyl)pyrazolo[1,5-a]pyridin-2-yl]phenyl}-2-(2-thienyl)acetamide

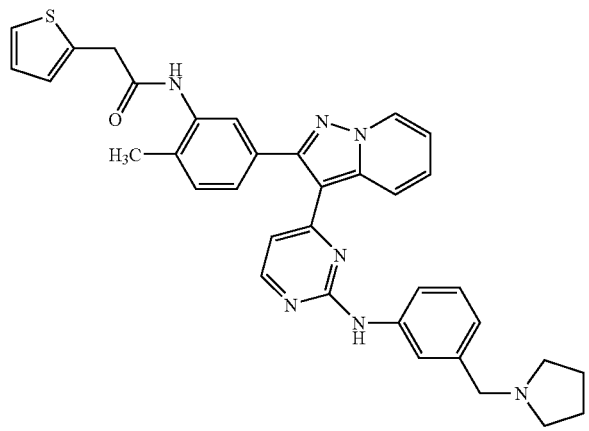

Step A: N-(5-Bromo-2-methylphenyl)-2,2,2-trifluoroacetamide

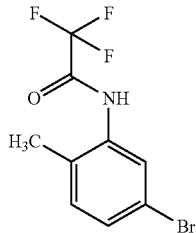

To a solution of 5-bromo-2-methylaniline (10 g, 54 mmol) in DCM (500 mL) was added TEA (11 mL, 81 mmol) and TFAA (9 mL, 65 mmol). After 1 h, the reaction was diluted with water. The organic phase was washed two times with water, dried over MgSO₄ and concentrated to give the desired product (15 g, 99%) as a pale yellow solid. ¹H NMR (400 MHz, d₆-DMSO) δ 11.02 (s, 1H), 7.49 (d, J=2.0 Hz, 1H), 7.43 (dd, J=8.0 and 2.0 Hz, 1H), 7.26 (d, J=8.0 Hz, 1H), 2.13 (s, 3H) ppm.

Step B: 2,2,2-Trifluoro-N-{2-methyl-5-[(trimethylsilyl)ethynyl]phenyl}acetamide

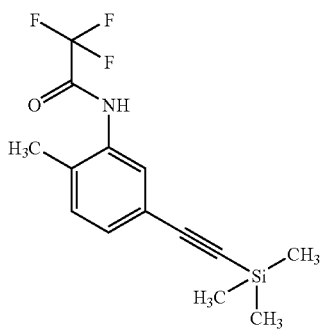

To a solution of N-(5-bromo-2-methylphenyl)-2,2,2-trifluoroacetamide (15 g, 54 mmol) in THF (300 mL) was added Pd(PPh₃)₂Cl₂ (3.79 g, 5.4 mmol), CuI (513 mg, 2.7 mmol) and TEA (23 mL, 162 mmol). The solution was heated to 60° C. A solution of trimethylsilylacetylene (11.5 mL, 81 mmol) in THF (200 mL) was added dropwise through an addition funnel over about 60 min. After 16 h, the reaction was concentrated onto silica gel and purified by column chromatography to give the desired product (10.92 g, 67%). ¹H NMR (400 MHz, d₆-DMSO) δ 10.97 (s, 1H), 7.35-7.30 (m, 3H), 2.18 (S, 3H), 0.21 (s, 9H) ppm.

Step C: N-(5-Ethynyl-2-methylphenyl)-2,2,2-trifluoroacetamide

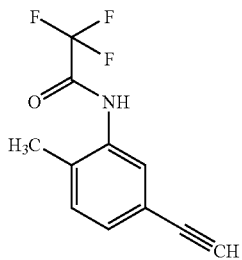

To a solution of 2,2,2-trifluoro-N-{2-methyl-5-[(trimethylsilyl)ethynyl]phenyl}-acetamide (10.9 g, 36 mmol) in THF (350 mL) cooled to 0° C. was added a 1M solution of tetrabutylammonium fluoride in THF (40 mmol, 40 mL). The reaction was diluted with water and extracted two times with EtOAc. The combined organic extractions were washed with water, dried over MgSO₄ and concentrated onto silica gel. The crude material was purified by column chromatography to give the desired product (6.4 g, 78%). ¹H NMR (400 MHz, d₆-DMSO) δ 11.00 (s, 1H), 7.36-7.30 (m, 3H), 4.19 (s, 1H), 2.17 (s, 3H) ppm.

Step D: N-{5-[(2-Chloro-4-pyrimidinyl)ethynyl]-2-methylphenyl}-2,2,2-trifluoroacetamide

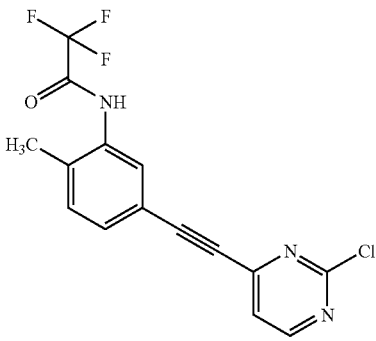

To a solution of 2,4-dichloropyrimidine (3.8 g, 25.5 mmol) in THF (175 mL) was added Pd(PPh$_3$)$_2$Cl$_2$ (1.8 g, 2.6 mmol), CuI (247 mg, 1.3 mmol), and TEA (10.7 mL, 76.5 mmol) and the mixture was heated to 60° C. A solution of N-(5-ethynyl-2-methylphenyl)-2,2,2-trifluoroacetamide (6.4 g, 28 mmol) in THF (75 mL) was added through an addition funnel over 60 min. After 16 h, the dark reaction was concentrated onto silica gel and purified by column chromatography. Fractions containing product were concentrated and the impurity was triturated with DCM. The remaining liquid was purified again by column chromatography to give the desired product (2.7 g, 31%). $^1$H NMR (400 MHz, d$_6$-DMSO) δ 11.09 (s, 1H), 8.83 (d, J=4.8 Hz, 1H), 7.77 (d, J=5.2 Hz, 1H), 7.62 (s, 1H), 7.58 (dd, J=8.0 and 1.6 Hz, 1H), 7.45 (d, J=8.0 Hz, 1H), 2.24 (s, 3H) ppm.

Step E: N-{5-[3-(2-Chloro-4-pyrimidinyl)pyrazolo[1,5-a]pyridin-2-yl]-2-methylphenyl}-2,2,2-trifluoroacetamide

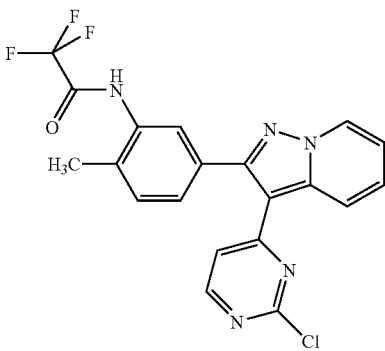

To a solution of N-{5-[(2-chloro-4-pyrimidinyl)ethynyl]-2-methylphenyl}-2,2,2-trifluoroacetamide (2.7 g, 8 mmol) in DMF (50 mL) was added N-aminopyridinium iodide (3.6 g, 16 mmol) and K$_2$CO$_3$ (3.3 g, 24 mmol). After 3 h, the reaction was diluted with water and extracted with DCM. The combined organic solutions were dried over MgSO$_4$ and concentrated onto silica gel. The crude material was purified by column chromatography. Fractions containing product were concentrated and the solid triturated with DCM and hexanes to give 1.92 g of the desired product (56%). $^1$H NMR (400 MHz, d$_6$-DMSO) δ 11.07 (s, 1H), 8.89 (d, J=6.8 Hz, 1H), 8.45 (d, J=6.8 Hz, 1H), 8.40 (d, J=8.8 Hz, 1H), 7.65-7.61 (m, 1H), 7.55 (s, 1H), 7.52-7.49 (m, 1H), 7.45 (d, J=8.0 Hz, 1H), 7.22-7.19 (m, 1H), 7.08 (d, J=5.6 Hz, 1H), 2.27 (s, 3H) ppm.

Step F: 5-[3-(2-Chloro-4-pyrimidinyl)pyrazolo[1,5-a]pyridin-2-yl]-2-methylaniline

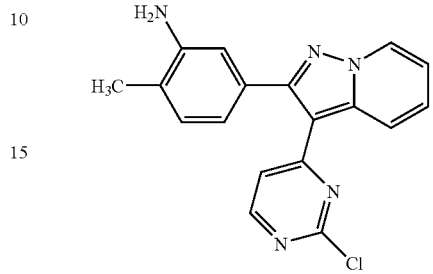

A solution of N-{5-[3-(2-chloro-4-pyrimidinyl)pyrazolo[1,5-a]pyridin-2-yl]-2-methylphenyl}-2,2,2-trifluoroacetamide (1.92 g, 4.45 mmol) and 1M aqueous lithium hydroxide in THF (36 mL) and water (4 mL) was stirred at 50° C. When starting material was consumed the reaction was diluted with water. The resulting solid was filtered and dried to give the title compound (2.1 g, 100%). $^1$H NMR 400 MHz, d$_6$-DMSO) δ 8.83 (d, J=7.2 Hz, 1H), 8.42-8.38 (m, 2H), 7.59 (t, J=8.0 Hz, 1H), 7.15 (m, 1H), 7.05-7.02 (m, 2H), 6.80 (d, J=1.2 Hz, 1H), 6.63-6.61 (m, 1H), 5.03 (s, 2H), 2.10 (s, 3H) ppm.

Step G: N-{5-[3-(2-Chloro-4-pyrimidinyl)pyrazolo[1,5-a]pyridin-2-yl]-2-methylphenyl}-2-(2-thienyl)acetamide

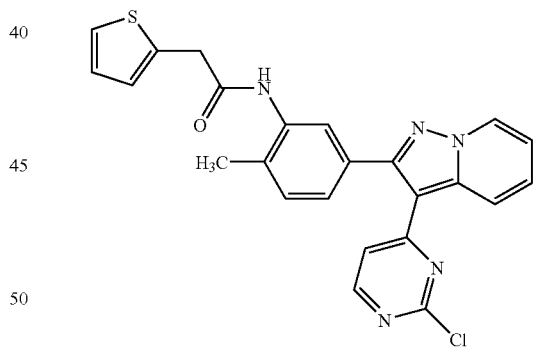

To a solution of 5-[3-(2-chloro-4-pyrimidinyl)pyrazolo[1,5-a]pyridin-2-yl]-2-methylaniline (856 mg, 2.55 mmol) in THF (25 mL) was added thiophene-2-acetyl chloride (0.33 mL, 2.68 mmol). When TLC showed the reaction to be complete, PS-trisamine was added. After 16 h, TEA was added and the mixture was filtered. The filtrate was diluted with DCM and washed with water. The organic phase was dried over MgSO$_4$ and concentrated onto silica gel. The crude material was purified by column chromatography to give of the desired product (1.13 g, 97%). $^1$H NMR (400 MHz, d$_6$-DMSO) δ 9.63 (s, 1H), 8.87 (d, J=7.2 Hz, 1H), 8.43-8.39 (m, 2H), 7.70 (s, 1H), 7.62 (t, J=8.0 Hz, 1H), 7.38-7.30 (m, 3H), 7.20 (m, 1H), 7.18 (d, J=6.8 Hz, 1H), 7.09-6.95 (m, 2H), 3.91 (s, 2H), 2.28 (s, 3H) ppm.

Step H: N-{2-Methyl-5-[3-(2-{[3-(1-pyrrolidinylmethyl)phenyl]amino}-4-pyrimidinyl)pyrazolo[1,5-a]pyridin-2-yl]phenyl}-2-(2-thienyl)acetamide (Title Compound)

N-{5-[3-(2-Chloro-4-pyrimidinyl)pyrazolo[1,5-a]pyridin-2-yl]-2-methylphenyl}-2-(2-thienyl)acetamide (100 mg, 0.22 mmol), 3-(1-pyrrolidinylmethyl)aniline (78 mg, 0.44 mmol) and catalytic conc. HCl in iPrOH (4 mL) were heated in a microwave at 180° C. for 10 min. The reaction was concentrated and the residue was dissolved in DCM. The organic solution was washed with saturated $NaHCO_3$ $_{(aq)}$ and water, dried over $MgSO_4$ and concentrated onto silica gel. The crude material was purified by column chromatography. Fractions containing pure product were concentrated, taken up in MeOH and neutralized with MP-carbonate. The mixture was filtered and the filtered concentrated and triturated with DCM and hexanes to give the title compound (28 mg, 21%). $^1$H NMR (400 MHz, $d_6$-DMSO) δ 9.62 (s, 1H), 9.50 (s, 1H), 8.80 (d, J=6.8 Hz, 1H), 8.50 (d, J=9.2 Hz, 1H), 8.21 (d, J=5.6 Hz, 1H), 7.73 (s, 1H), 7.68 (s, 1H), 7.63 (d, J=8.4 Hz, 1H), 7.45-7.41 (m, 1H), 7.36 (m, 1H), 7.32-7.28 (m, 2H), 7.16 (t, J=7.8 Hz, 1H), 7.11-7.07 (m, 1H), 6.98-6.95 (m, 2H), 6.87 (d, J=7.2 Hz, 1H), 6.50 (d, J=5.6 Hz, 1H), 3.91 (s, 2H), 3.50 (s, 2H), 2.39 (m, 4H), 2.26 (s, 3H), 1.65-1.64 (m, 4H) ppm. ES-LC/MS m/z=600 [M+H]$^+$.

Example 57

N-[5-(3-{2-[(5-{[2-(Dimethylamino)ethyl]oxy}-2-methylphenyl)amino]-4-pyrimidinyl}pyrazolo[1,5-a]pyridin-2-yl)-2-methylphenyl]-2-(2-thienyl)acetamide

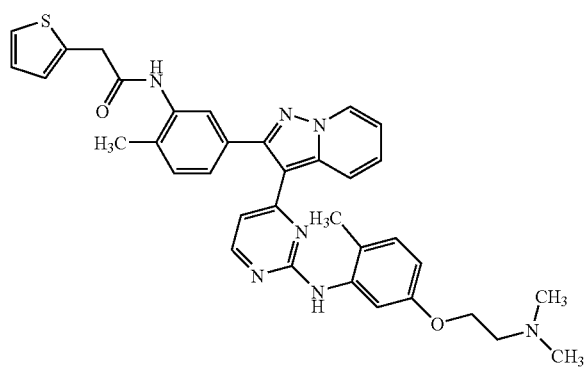

N-{5-[3-(2-chloro-4-pyrimidinyl)pyrazolo[1,5-a]pyridin-2-yl]-2-methylphenyl}-2-(2-s thienyl)acetamide (100 mg, 0.22 mmol) and 5-{[2-(dimethylamino)ethyl]oxy}-2-methylaniline hydrochloride (102 mg, 0.44 mmol) were coupled according to the procedure of Example 56, Step H to give the title compound (45 mg, 33%). $^1$H NMR (400 MHz, $d_6$-DMSO) δ 9.61 (s, 1H), 8.74 (d, J=6.8 Hz, 1H), 8.66 (s, 1H), 8.25 (d, J=9.2 Hz, 1H), 8.08 (d, J=5.2 Hz, 1H), 7.67 (s, 1H), 7.35 (d, J=4.8 Hz, 1H), 7.32-7.25 (m, 3H), 7.16 (d, J=2.8 Hz, 1H), 7.12 (d, J=8.8 Hz, 1H), 7.05-7.01 (m, 1H), 6.96-6.93 (m, 2H), 6.68 (dd, J=8.4 and 2.4 Hz, 1H), 6.38 (d, J=5.6 Hz, 1H), 3.96 (m, 2H), 3.89 (s, 2H), 2.56 (m, 2H), 2.15 (s, 3H), 2.14 (s, 6H) ppm. ES-LC/MS m/z=618 [M+H]$^+$.

Example 58

N-[5-(3-{2-[(3-{[2-(Dimethylamino)ethyl]oxy}phenyl)amino]-4-pyrimidinyl}pyrazolo[1,5-a]pyridin-2-yl)-2-methylphenyl]-2-(2-thienyl)acetamide

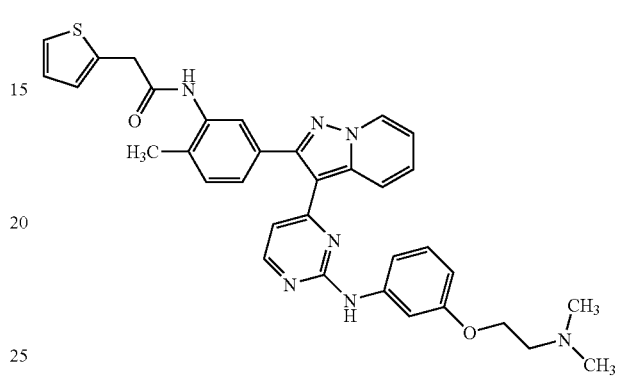

N-{5-[3-(2-chloro-4-pyrimidinyl)pyrazolo[1,5-a]pyridin-2-yl]-2-methylphenyl}-2-(2-thienyl)acetamide (100 mg, 0.22 mmol) and 3-{[2-(dimethylamino)ethyl]oxy}-aniline dihydrochloride (112 mg, 0.44 mmol) were coupled according to the procedure of Example 56, Step H to give 25 mg of the title compound (19%). $^1$H NMR (400 MHz, $d_6$-DMSO) δ 9.63 (s, 1H), 9.53 (s, 1H), 8.81 (d, J=7.2 Hz, 1H), 8.49 (d, J=9.2 Hz, 1H), 8.23 (d, J=5.6 Hz, 1H), 7.72 (s, 1H), 7.52 (s, 1H), 7.47-7.43 (m, 1H), 7.36 (d, J=4.8 Hz, 1H), 7.30-7.25 (m, 3H), 7.14-7.08 (m, 2H), 6.97-6.95 (m, 2H), 6.52-6.50 (m, 2H), 3.97 (m, 2H), 3.90 (s, 2H), 2.58 (t, J=5.6 Hz, 2H), 2.26 (s, 3H), 2.17 (s, 6H) ppm. ES-LC/MS m/z=604 [M+H]$^+$.

Example 59

N-[2-Methyl-5-(3-{2-[(2-methyl-1,2,3,4-tetrahydro-7-isoquinolinyl)amino]-4-pyrimidinyl}pyrazolo[1,5-a]pyridin-2-yl)phenyl]-2-(2-thienyl)acetamide

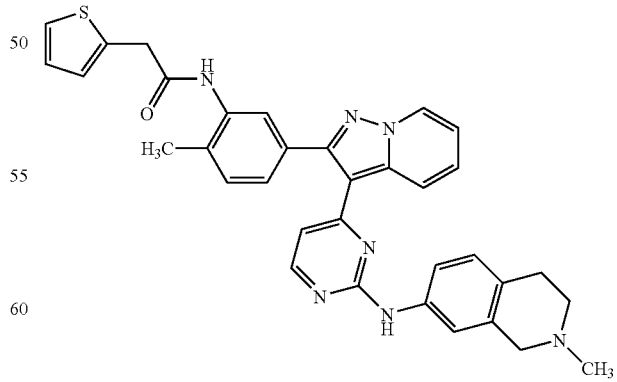

N-{5-[3-(2-Chloro-4-pyrimidinyl)pyrazolo[1,5-a]pyridin-2-yl]-2-methylphenyl}-2-(2-thienyl)acetamide (100 mg, 0.22 mmol) and 2-methyl-1,2,3,4-tetrahydro-7-isoquinolinamine (72 mg, 0.44 mmol) were coupled according to the procedure of Example 56, Step H, to give 31 mg of the title compound (24%). $^1$H NMR (400 MHz, d$_6$-DMSO) δ 9.63 (s, 1H), 9.41 (s, 1H), 8.80 (d, J=6.8 Hz, 1H), 8.45 (d, J=8.8 Hz, 1H), 8.20 (d, J=5.2 Hz, 1H), 7.73 (s, 1H), 7.50-7.49 (m, 1H), 7.45-7.36 (m, 3H), 7.32-7.27 (m, 2H), 7.11-7.07 (m, 1H), 6.97-6.96 (m, 3H), 6.48 (d, J=5.2 Hz, 1H), 3.90 (s, 2H), 3.37 (s, 2H), 2.75-2.72 (m, 2H), 2.57-2.54 (m, 2H), 2.29 (s, 3H), 2.26 (s, 3H) ppm. ES-LC/MS m/z 586 [M+H]$^-$.

Example 60

N-[5-(3-{2-[(3-{[2-(Dimethylamino)ethyl]oxy}-2-methylphenyl)amino]-4-pyrimidinyl}pyrazolo[1,5-a]pyridin-2-yl)-2-fluorophenyl]-2-(2-thienyl)acetamide

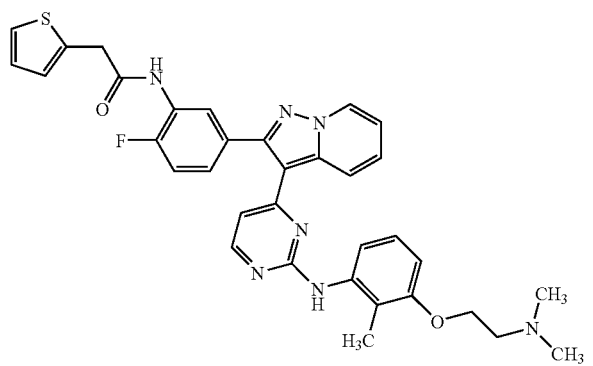

Step A: N-(5-Bromo-2-fluorophenyl)-2,2,2-trifluoroacetamide

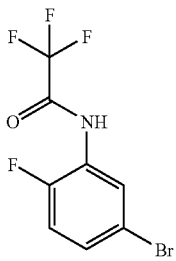

To a solution of 4-bromo-1-fluoro-2-nitrobenzene (10 g, 45 mmol) in EtOH (400 mL) was added tin (II) chloride (34 g, 180 mmol) and the reaction was heated to 60° C. After 16 h, the reaction was cooled and neutralized with NaOH$_{(aq)}$. Ethyl acetate was added and the liquid was decanted away from the solid several times. The combined organics were dried over MgSO$_4$ and concentrated to an orange residue. The residue was dissolved in DCM (400 mL). Triethylamine (12.5 mL, 90 mmol) and TFAA (7.5 mL, 54 mmol) were added. After 30 min, the reaction was concentrated directly onto silica gel The crude material was purified by column chromatography and the product was triturated with hexanes to give of the desired product (8.04 g, 62%). $^1$H NMR (400 MHz, d$_6$-DMSO) δ 11.39 (s, 1H), 7.76-7.73 (m, 1H), 7.59-7.55 (m, 1H), 7.38-7.33 (m, 1H) ppm.

Step B: 2,2,2-Trifluoro-N-{2-fluoro-5-[(trimethylsilyl)ethynyl]phenyl}acetamide

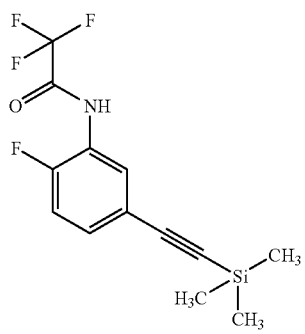

N-(5-Bromo-2-fluorophenyl)-2,2,2-trifluoroacetamide (8.04 g, 28 mmol) and (trimethylsilyl)acetylene (6 mL, 42 mmol) were coupled according to the procedure of Example 56, Step B to give the desired product (6.66 g, 78%). $^1$H NMR (400 MHz, d$_6$-DMSO) δ 11.32 (s, 1H), 7.62-7.60 (m, 1H), 7.47-7.44 (m, 1H), 7.39-7.33 (m, 1H), 0.21 (s, 9H) ppm.

Step C: N-(5-Ethynyl-2-fluorophenyl)-2,2,2-trifluoroacetamide

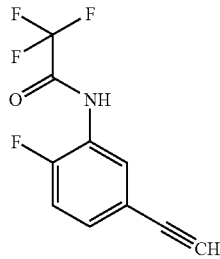

2,2,2-Trifluoro-N-{2-fluoro-5-[(trimethylsilyl)ethynyl]phenyl}acetamide (6.66 g, 22 mmol) was desilylated according to the procedure of Example 56, Step C to give the desired product (5.32 g, 100%). Product was used as such without purification. ES-LC/MS m/z=230 [M−H]$^-$.

Step D: N-{5-[(2-Chloro-4-pyrimidinyl)ethynyl]-2-fluorophenyl}-2,2,2-trifluoroacetamide

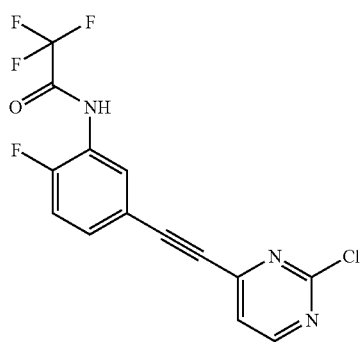

N-(5-Ethynyl-2-fluorophenyl)-2,2,2-trifluoroacetamide (5.32 g, 22 mmol) and 1,4-dichloropyrimidine (3.13 g, 0.21 mmol) were coupled according to the procedure of Example 56, Step D to give the desired product (2.06 g, 29%). ¹H NMR (400 MHz, d₆-DMSO) δ 11.47 (s, 1H), 8.84 (d, J=5.2 Hz, 1H), 7.88 (dd, J=7.2 and 2.0 Hz, 1H), 7.79 (d, J=5.2 Hz, 1H), 7.75-7.71 (m, 1H), 7.54-7.50 (m, 1H) ppm.

Step E: N-{5-[3-(2-Chloro-4-pyrimidinyl)pyrazolo[1,5-a]pyridin-2-yl]-2-fluorophenyl}-2,2,2-trifluoroacetamide

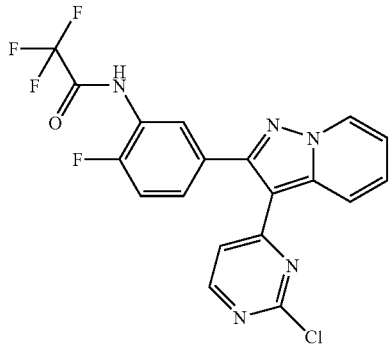

N-{5-[(2-Chloro-4-pyrimidinyl)ethynyl]-2-fluorophenyl}-2,2,2-trifluoroacetamide (2.06 g, 6 mmol) was subjected to cyclization according to the procedure of Example 56, Step E to give the desired product (1.78 g, 68%). ¹H NMR (400 MHz, d₆-DMSO) δ 11.41 (s, 1H), 8.89 (d, J=6.8 Hz, 1H), 8.49 (d, J=5.2 Hz, 1H), 8.38 (d, J=9.2 Hz, 1H), 7.79 (dd, J=7.2 and 2.0 Hz, 1H), 7.66-7.61 (m, 2H), 7:53-7.48 (m, 1H), 7.23-7.20 (m, 1H), 7.10 (d, J=5.6 Hz, 1H) ppm.

Step F: 5-[3-(2-Chloro-4-pyrimidinyl)pyrazolo[1,5-a]pyridin-2-yl]-2-fluoroaniline

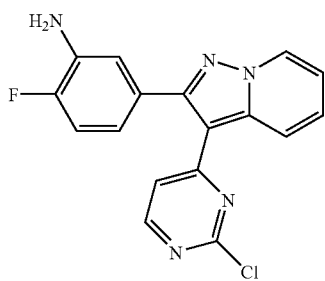

N-{5-[3-(2-Chloro-4-pyrimidinyl)pyrazolo[1,5-a]pyridin-2-yl]-2-fluorophenyl}-2,2,2-trifluoroacetamide (1.78 g) was deprotected according to the procedure of Example 56, Step F to give the desired product (1.34 g, 97%). ¹H NMR (400 MHz, d₆-DMSO) δ 8.84 (d, J=6.8 Hz, 1H), 8.44 (d, J=5.2 Hz, 1H), 8.38 (d, J=8.8 Hz, 1H), 7.60 (t, J=7.8 Hz, 1H), 7.17 (t, J=6.8 Hz, 1H), 7.12-7.07 (m, 1H), 7.02 (d, J=5.6 Hz, 1H), 6.95 (dd, J=8.8 and 2.0 Hz, 1H), 6.69-6.65 (m, 1H), 5.34 (s, 2H) ppm.

Step G: N-{5-[3-(2-Chloro-4-pyrimidinyl)pyrazolo[1,5-a]pyridin-2-yl]-2-fluorophenyl}-2-(2-thienyl)acetamide 5-[3-(2-Chloro-4-pyrimidinyl)pyrazolo[1,5-a]pyridin-2-yl]-2-fluoroaniline (690 mg, 2.0 mmol) and thiophene-2-acetyl chloride (0.26 mL, 2.1 mmol) were coupled according to the procedure of Example 56, Step G to give the desired product (858 mg, 92%). ¹H NMR (400 MHz, d₆-DMSO) δ 10.21 (s, 1H), 8.93 (d, J=9.2 Hz, 1H), 8.49 (d, J=7.6 Hz, 1H), 8.44 (d, J=12.0 Hz, 1H), 8.29-8.27 (m, 1H), 7.70-7.65 (m, 1H), 7.49-7.41 (m, 3H), 7.27-7.22 (m, 1H), 7.13 (d, J=7.2 Hz, 1H), 7.02-6.98 (m, 2H), 4.02 (s, 2H) ppm.

Step H: N-[5-(3-{2-[(3-{([2-(Dimethylamino)ethyl]oxy}-2-methylphenyl)amino]-4-pyrimidinyl}pyrazolo[1,5-a]pyridin-2-yl)-2-fluorophenyl]-2-(2-thienyl)acetamide (Title Compound)

N-{5-[3-(2-Chloro-4-pyrimidinyl)pyrazolo[1,5-a]pyridin-2-yl]-2-fluorophenyl}-2-(2-thienyl)acetamide (100 mg, 0.22 mmol) and 3-{[2-(dimethylamino)ethyl]oxy}-2-methylaniline hydrochloride (102 mg, 0.44 mmol) were coupled according to the procedure of Example 56, Step H to give the title compound (31 mg, 23%). ¹H NMR (400 MHz, d₆-DMSO) δ 10.14 (s, 1H), 8.80 (s, 1H), 8.75 (d, J=6.8 Hz, 1H), 8.20-8.15 (m, 2H), 8.10 (d, J=5.2 Hz, 1H), 7.39-7.25 (m, 4H), 7.13-6.94 (m, 5H), 6.81 (d, J=8.4 Hz, 1H), 6.36 (d, J=5.2 Hz, 1H), 4.06 (t, J=5.6 Hz, 2H), 3.97 (s, 2H), 2.65 (t, J=5.6 Hz, 2H), 2.21 (s, 6H), 2.04 (s, 3H) ppm. ES-LC/MS m/z=622 [M+H]⁺.

Example 61

N-{2-Fluoro-5-[3-(2-{[3-(1-pyrrolidinylmethyl)phenyl]amino}-4-pyrimidinyl)pyrazolo[1,5-a]pyridin-2-yl]phenyl}-2-(2-thienyl)acetamide

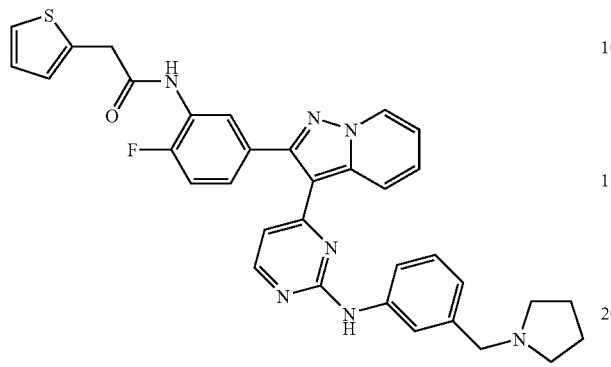

N-{5-[3-(2-Chloro-4-pyrimidinyl)pyrazolo[1,5-a]pyridin-2-yl]-2-fluorophenyl}-2-(2-thienyl)acetamide (100 mg, 0.22 mmol) and 3-(1-pyrrolidinylmethyl)aniline (78 mg, 0.44 mmol) were coupled according to the procedure of Example 56, Step H to give of the title compound (35 mg, 26%). $^1$H NMR (400 MHz, $d_6$-DMSO) δ 10.11 (s, 1H), 9.49 (s, 1H), 8.80 (d, J=6.8 Hz, 1H), 8.44 (d, J=8.8 Hz, 1H), 8.26-8.22 (m, 2H), 7.64 (s, 1H), 7.59 (d, J=8.0 Hz, 1H), 7.43 (t, J=7.8 Hz, 1H), 7.37-7.32 (m, 3H), 7.16-7.07 (m, 2H), 6.95-6.93 (m, 2H), 6.85 (d, J=7.2 Hz, 1H), 6.49 (d, J=4.8 Hz, 1H), 3.96 (s, 2H), 3.48 (br s, 2H), 2.38 (m, 4H), 1.64 (m, 4H) ppm. ES-LC/MS m/z=604 [M+H]$^+$.

Example 62

N-[5-(3-{2-[(5-{[2-(Dimethylamino)ethyl]oxy}-2-methylphenyl)amino]-4-pyrimidinyl}pyrazolo[1,5-a]pyridin-2-yl)-2-fluorophenyl]-2-(2-thienyl)acetamide

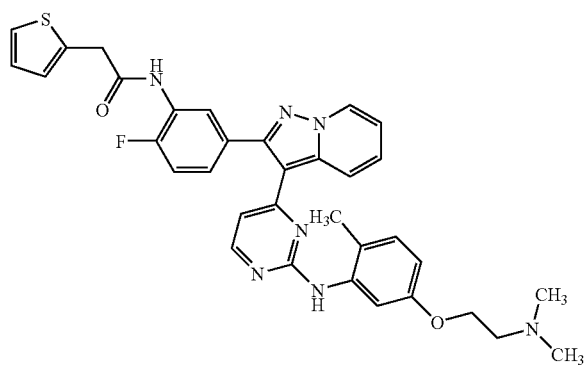

N-{5-[3-(2-Chloro-4-pyrimidinyl)pyrazolo[1,5-a]pyridin-2-yl]-2-fluorophenyl}-2-(2-thienyl)acetamide (100 mg, 0.22 mmol) and 5-{[2-(dimethylamino)ethyl]oxy}-2-methylaniline hydrochloride (102 mg, 0.44 mmol) were coupled according to the procedure of Example 56, Step H to give the title compound (38 mg, 28%). $^1$H NMR (400 MHz, $d_6$-DMSO) δ 10.13 (s, 1H), 8.76 (d, J=6.8 Hz, 1H), 8.67 (s, 1H), 8.26-8.19 (m, 2H), 8.12 (d, J=5.2 Hz, 1H), 7.39-7.28 (m, 4H), 7.16-7.11 (m, 2H), 7.07-7.04 (m, 1H), 7=6.96-6.94 (m, 2H), 6.68 (dd, J=8.4 and 2.8 Hz, 1H), 6.37 (d, J=5.2 Hz, 1H), 3.97 (m, 4H), 2.56 (m, 2H), 2.16 (s, 3H), 2.15 (s, 6H) ppm. ES-LC/MS m/z=622 [M+H]$^+$.

Example 63

N-[2-Fluoro-5-(3-{2-[(2-methyl-1,2,3,4-tetrahydro-7-isoquinolinyl)amino]-4-pyrimidinyl}pyrazolo[1,5-a]pyridin-2-yl)phenyl]-2-(2-thienyl)acetamide

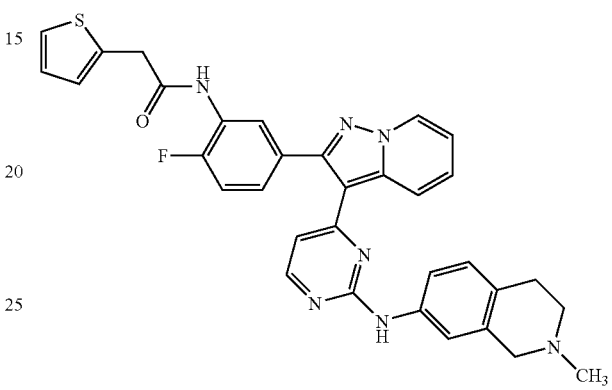

N-{5-[3-(2-Chloro-4-pyrimidinyl)pyrazolo[1,5-a]pyridin-2-yl]-2-fluorophenyl}-2-(2-thienyl)acetamide (100 mg, 0.22 mmol) and 2-methyl-1,2,3,4-tetrahydro-7-isoquinolinamine (72 mg, 0.44 mmol) were coupled according to the procedure of Example 56, Step H to give the title compound (42 mg, 32%). $^1$H NMR (400 MHz, $d_6$-DMSO) δ 10.12 (s, 1H), 9.39 (s, 1H), 8.80 (d, J=7.2 Hz, 1H), 8.39 (d, J=8.8 Hz, 1H), 8.26 (d, J=8.0 Hz, 1H), 8.22 (d, J=5.2 Hz, 1H), 7.45-7.41 (m, 2H), 7.37-7.32 (m, 4H), 7.09 (t, J=6.8 Hz, 1H), 6.95-6.92 (m, 3H), 6.48 (d, J=5.2 Hz, 1H), 3.95 (s, 2H), 3.34 (s, 2H), 2.72-2.70 (m, 2H), 2.54-2.51 (m, 2H), 2.27 (s, 3H) ppm. ES-LC/MS m/z=590 [M+H]$^+$.

Example 64

N-[5-(3-{2-[(3-{[2-(Dimethylamino)ethyl]oxy}-2-methylphenyl)amino]-4-pyrimidinyl}pyrazolo[1,5-a]pyridin-2-yl)-2-(methyloxy)phenyl]-2-(2-thienyl)acetamide

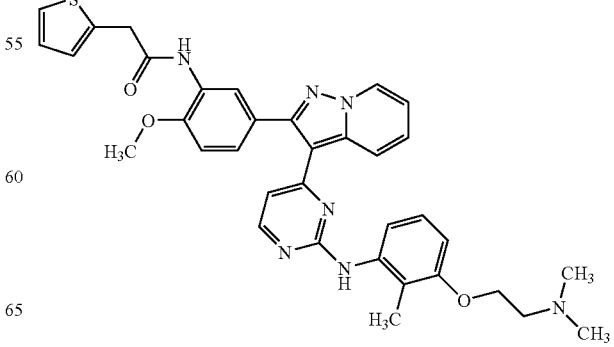

Step A: N-[5-Bromo-2-(methyloxy)phenyl]-2,2,2-trifluoroacetamide

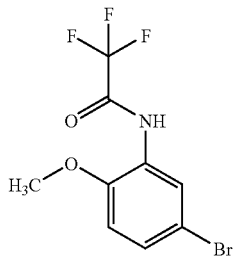

4-Bromo-2-nitroanisole (10 g, 43 mmol) was reduced and protected according to the procedure of Example 60, Step A to give the desired product (5.79 g, 45%). ES-LC/MS m/z=296 [M−H]⁻.

Step B: 2,2,2-Trifluoro-N-{2-(methyloxy)-5-[(trimethylsilyl)ethynyl]phenyl}-acetamide

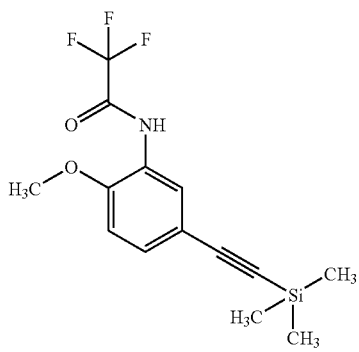

N-[5-Bromo-2-(methyloxy)phenyl]-2,2,2-trifluoroacetamide (5.79 g, 19.4 mmol) and (trimethylsilyl)acetylene (4.1 mL, 29.1 mmol) were coupled according to the procedure of Example 56, Step B to give the desired product (2.32 g, 38%). ES-LC/MS m/z=314 [M−H]⁻.

Step C: N-[5-Ethynyl-2-(methyloxy)phenyl]-2,2,2-trifluoroacetamide

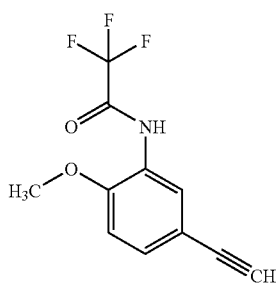

2,2,2-Trifluoro-N-{2-(methyloxy)-5-[(trimethylsilyl)ethynyl]phenyl}-acetamide was deprotected according to the procedure of Example 56, Step C to give the desired product (1.80 g, 99%). ES-LC/MS m/z=242 [M−H]⁻.

Step D: N-[5-[(2-Chloro-4-pyrimidinyl)ethynyl]-2-(methyloxy)phenyl]-2,2,2-trifluoroacetamide

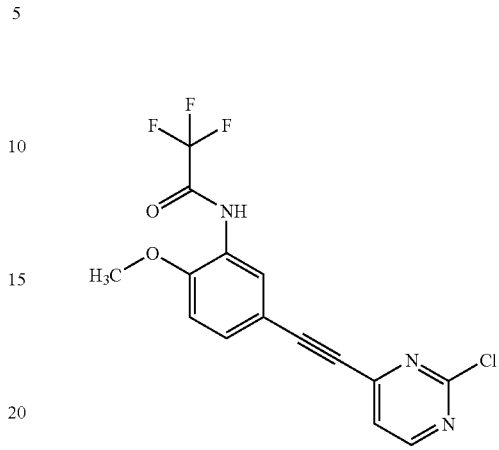

Batches of N-[5-ethynyl-2-(methyloxy)phenyl]-2,2,2-trifluoroacetamide (2.01 g, 8.3 mmol) and 2,4-dichloropyrimidine (3.1 g, 20.8 mmol) were coupled according to the procedure of Example 56, Step D to give the title compound (1.7 g, 58%). ES-LC/MS m/z=356 [M+H]⁺.

Step E: N-[5-[3-(2-Chloro-4-pyrimidinyl)pyrazolo[1,5-a]pyridin-2-yl]-2-(methyloxy)phenyl]-2,2,2-trifluoroacetamide

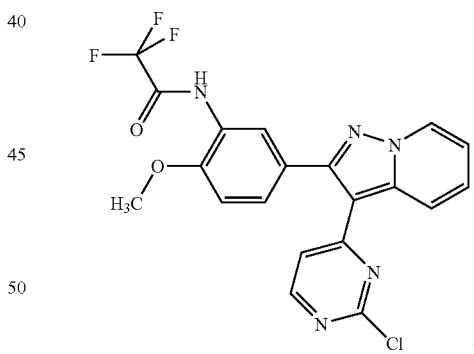

N-[5-[(2-Chloro-4-pyrimidinyl)ethynyl]-2-(methyloxy)phenyl]-2,2,2-trifluoroacetamide (1.7 g, 4.8 mmol) was subjected to cyclization with N-aminopyridinium iodide (2.1 g, 9.6 mmol) according to the procedure of Example 56, Step E to give the desired product (1.15 g, 53%). ¹H NMR (400 MHz, d₆-DMSO) δ 10.82 (s, 1H), 8.88 (d, J=6.8 Hz, 1H), 8.45 (d, J=5.6 Hz, 1H), 8.39 (d, J=8.4 Hz, 1H), 7.70 (d, J=2.0 Hz, 1H), 7.64-7.60 (m, 1H), 7.57 (dd, J=8.6 and 1.8 Hz, 1H), 7.28 (d, J=8.4 Hz, 1H), 7.21-7.18 (m, 1H), 7.11 (d, J=5.6 Hz, 1H), 3.90 (s, 3H) ppm.

Step F: 5-[3-(2-Chloro-4-pyrimidinyl)pyrazolo[1,5-a]pyridin-2-yl]-2-(methyloxy)aniline

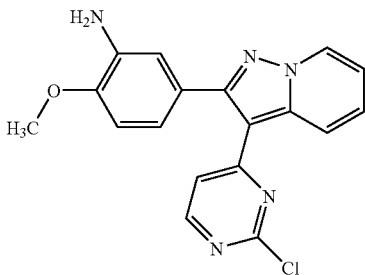

N-[5-[3-(2-Chloro-4-pyrimidinyl)pyrazolo[1,5-a]pyridin-2-yl]-2-(methyloxy)phenyl]-2,2,2-trifluoroacetamide (1.15 g, 2.6 mmol) was deprotected according to the procedure of Example 56, Step F to give the desired product (898 mg, 98%). $^1$H NMR (400 MHz, d$_6$-DMSO) δ 8.84 (s, J=7.2 Hz, 1H), 8.44-8.39 (m, 2H), 7.62-7.58 (m, 1H), 7.16 (dt, J=6.8 and 1.2 Hz, 1H), 7.07 (d, J=5.6 Hz, 1H), 6.90 (d, J=8.0 Hz, 1H), 6.84 (d, J=2.0 Hz, 1H), 6.72 (dd, J=8.2 and 2.2 Hz, 1H), 4.92 (s, 2H), 3.82 (s, 3H) ppm.

Step G: N-[5-[3-(2-Chloro-4-pyrimidinyl)pyrazolo[1,5-a]pyridin-2-yl]-2-(methyloxy)phenyl]-2-(2-thienyl)acetamide

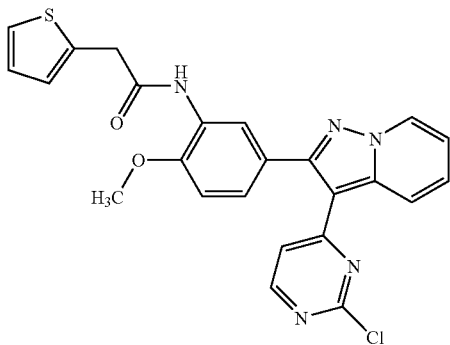

5-[3-(2-Chloro-4-pyrimidinyl)pyrazolo[1,5-a]pyridin-2-yl]-2-(methyloxy)aniline (400 mg, 1.14 mmol) and thiophene-2-acetyl chloride (148 mL, 1.50 mmol) were coupled according to the procedure of Example 56, Step G to give the desired product (454 mg, 84%). $^1$H NMR (400 MHz, d$_6$-DMSO) δ 9.51 (s, 1H), 8.87 (D, J=7.2 Hz, 1H), 8.42-8.38 (m, 2H), 8.27 (s, 1H), 7.61 (d, J=8.0 Hz, 1H), 7.37-7.36 (m, 1H), 7.30 (dd, J=8.4 and 2.0 Hz, 1H), 7.19-7.16 (m, 2H), 7.09 (d, J=5.6 Hz, 1H), 6.96-6.94 (m, 2H), 3.98 (s, 2H), 3.91 (s, 3H) ppm.

Step H: N-[5-(3-{2-[(3-{[2-(Dimethylamino)ethyl]oxy}-2-methylphenyl)amino]-4-pyrimidinyl}pyrazolo[1,5-a]pyridin-2-yl)-2-(methyloxy)phenyl]-2-(2-thienyl)acetamide (Title Compound)

N-[5-[3-(2-Chloro-4-pyrimidinyl)pyrazolo[1,5-a]pyridin-2-yl]-2-(methyloxy)phenyl]-2-(2-thienyl)acetamide (119 mg, 0.25 mmol) and 3-{[2-(dimethylamino)ethyl]oxy}-2-methylaniline hydrochloride (115 mg, 0.50 mmol) were coupled according to the procedure of Example 56, Step H to give the title compound (32 mg, 20%). $^1$H NMR (400 MHz, d$_6$-DMSO) δ 8.70 (s, 1H), 8.44 (d, J=6.8 Hz, 1H), 8.26 (d, J=8.8 Hz, 1H), 8.09 (d, J=5.6 Hz, 1H), 8.01 (s, 1H), 7.55 (d, J=8.4 Hz, 1H), 7.29-7.24 (m, 2H), 7.20-7.13 (m, 2H), 7.04-7.03 (m, 2H), 6.88-6.82 (m, 3H), 6.69 (d, J=8.4 Hz, 1H), 6.55 (d, J=5.6 Hz, 1H), 4.16-4.13 (m, 2H), 3.94 (s, 2H), 3.82 (s, 3H), 2.83 (m, 2H), 2.40 (s, 6H), 2.22 (s, 3H) ppm. ES-LC/MS m/z=634 [M+H]$^+$.

Example 65

N-[5-(3-{2-[(3-{[2-(Dimethylamino)ethyl]oxy}phenyl)amino]-4-pyrimidinyl}pyrazolo[1,5-a]pyridin-2-yl)-2-(methyloxy)phenyl]-2-(2-thienyl)acetamide

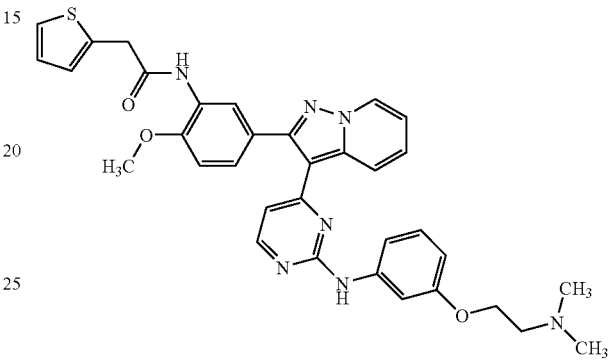

N-[5-[3-(2-Chloro-4-pyrimidinyl)pyrazolo[1,5-a]pyridin-2-yl]-2-(methyloxy)phenyl]-2-(2-thienyl)acetamide (119 mg, 0.25 mmol) and 3-{[2-(dimethylamino)ethyl]oxy}-aniline dihydrochloride (127 mg, 0.50 mmol) were coupled according to the procedure of Example 56, Step H to give the title compound (46 mg, 30%). $^1$H NMR (400 MHz, d$_6$-DMSO) δ 8.80 (s, 1H), 8.48 (d, J=7.2 Hz, 1H), 8.35 (d, J=9.2 Hz, 1H), 8.16 (d, J=5.2 Hz, 1H), 8.01 (s, 1H), 7.49 (s, 1H), 7.28-7.24 (m, 4H), 7.22-7.18 (m, 1H), 7.12 (d, J=8.4 Hz, 1H), 7.04-7.03 (m, 2H), 6.89-6.86 (m, 2H), 6.61-6.59 (m, 2H), 4.09 (m, 2H), 3.95 (s, 2H), 3.81 (s, 3H), 2.76 (m, 2H), 2.35 (s, 6H) ppm. ES-LC/MS m/z=620 [M+H]$^+$.

Example 66

N-[5-(3-{2-[(5-{[2-(Dimethylamino)ethyl]oxy}-2-methylphenyl)amino]-4-pyrimidinyl}pyrazolo[1,5-a]pyridin-2-yl)-2-(methyloxy)phenyl]-2-(2-thienyl)acetamide

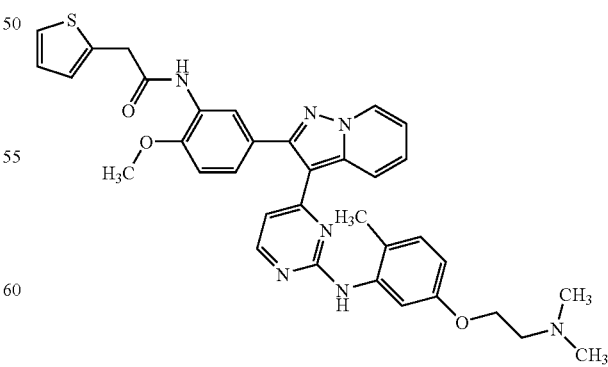

N-[5-[3-(2-Chloro-4-pyrimidinyl)pyrazolo[1,5-a]pyridin-2-yl]-2-(methyloxy)phenyl]-2-(2-thienyl)acetamide (119 mg, 0.25 mmol) and 5-{[2-(dimethylamino)ethyl]-oxy}-2- methylaniline hydrochloride (116 mg, 0.50 mmol) were coupled according to the procedure of Example 56, Step H to give the title compound (45 mg, 28%). $^1$H NMR (400 MHz, d$_6$-DMSO) δ 8.70 (d, J=1.6 Hz, 1H), 8.46 (d, J=7.2 Hz, 1H), 8.33 (d, J=8.8 Hz, 1H), 8.11 (d, J=5.6 Hz, 1H), 8.01 (s, 1H), 7.80 (d, J=2.4 Hz, 1H), 7.30-7.20 (m, 3H), 7.11 (d, J=8.4 Hz, 1H), 7.04-7.03 (m, 2H), 6.89-6.84 (m, 3H), 6.63 (dd, J=8.4 and 2.4 Hz, 1H), 6.56 (d, J=5.2 Hz, 1H), 4.06 (m, 2H), 3.94 (s, 2H), 3.82 (s, 3H), 2.74 (m, 2H), 2.33 (s, 6H), 2.28 (s, 3H) ppm. ES-LC/MS m/z=634 [M+H]$^+$.

Example 67

N-{3-[3-{2-[(3-{[2-(Dimethylamino)ethyl]oxy}phenyl)amino]-4-pyrimidinyl}-6-(methyloxy)pyrazolo[1,5-a]pyridin-2-yl]phenyl}-1-phenylcyclopropanecarboxamide

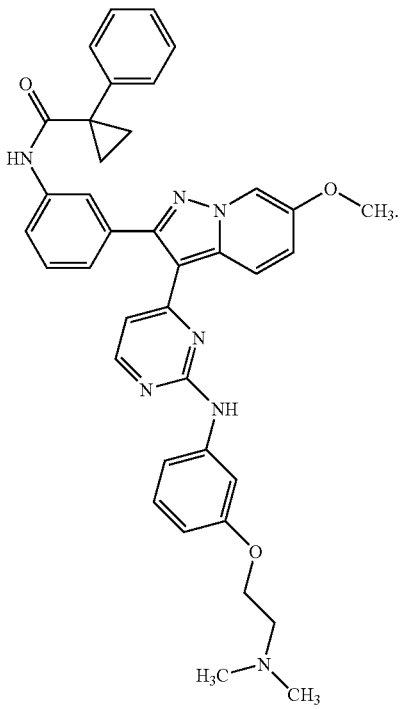

Step A: N-{3-[3-(2-Chloro-4-pyrimidinyl)-6-(methyloxy)pyrazolo[1,5-a]pyridin-2-yl]phenyl}-2,2,2-trifluoroacetamide

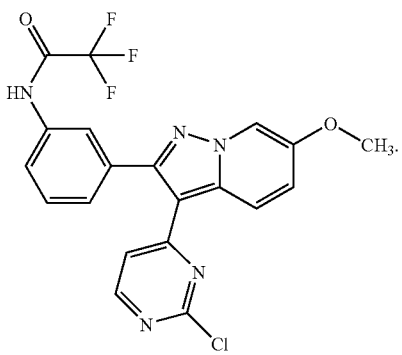

N-[3-(2-Chloro-pyrimidin-4-ylethenyl)-phenyl]-2,2,2-trifluoro-acetamide (See Example 1, step B) (2.0 g, 6.1 mmol), 1-amino-3-(methyloxy)pyridinium 2,4,6-trimethylbenzenesulfonate (2.3 g, 12.3 mmol), and K$_2$CO$_3$ (2.4 g, 18.4 mmol) were stirred in DMF (60 mL) at rt for 16 h. The reaction mixture was then poured into water (300 mL) and filtered to give the crude product, which was purified by silica gel chromatography to afford the title compound as a yellow solid (0.264 g, 9.5%). ES-LC/MS m/z=448 [M+H]$^+$. In addition, N-{3-[3-(2-chloro-4-pyrimidinyl)-4-(methyloxy)pyrazolo[1,5-a]pyridin-2-yl]phenyl}-2,2,2-trifluoroacetamide, the lower R$_f$ compound, was also isolated (1.10 g, 40%). ES-LC/MS m/z=448 [M+H]$^+$.

Step B: 4-[2-(3-Aminophenyl)-6-(methyloxy)pyrazolo[1,5-a]pyridin-3-yl]-N-(3-{[2-(dimethylamino)ethyl]oxy}phenyl)-2-pyrimidinamine

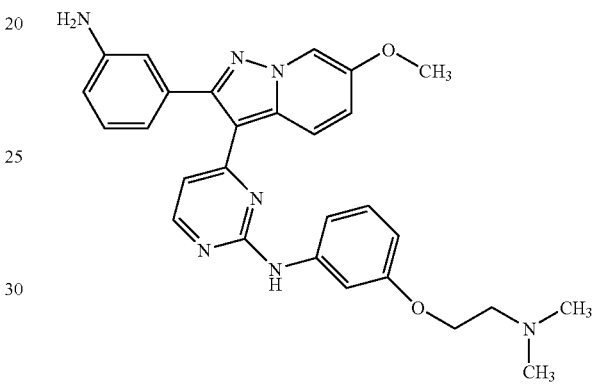

N-{3-[3-(2-chloro-4-pyrimidinyl)-6-(methyloxy)pyrazolo[1,5-a]pyridin-2-yl]phenyl}-2,2,2-trifluoroacetamide (0.26 g, 0.58 mmol) and {2-[(3-aminophenyl)oxy]ethyl}dimethylamine dihydrochloride (0.18 g, 0.70 mmol) were combined in i-PrOH (4 mL)) and microwaved for 15 min. at 160° C. The reaction mixture was concentrated to dryness to afford N-{3-[3-{2-[(3-{[2-(dimethylamino)ethyl]oxy}phenyl)amino]-4-pyrimidinyl}-6-(methyloxy)pyrazolo[1,5-a]pyridin-2-yl]phenyl}-2,2,2-trifluoroacetamide as a brown solid. The solid was dissolved in THF (5 mL) and water (0.5 mL) and treated with 1N NaOH (3 mL) and stirred for 16 h at rt after which time the reaction was incomplete by LC/MS. 1N NaOH (1 mL) was added and the mixture heated at 40° C. for 2 h and then cooled to rt and diluted with DCM and water. The organic layer was washed with brine, dried over MgSO$_4$ and concentrated to give the title compound as crude yellow solid (320 mg, >100%), which was used as such in Step C. ES-LC/MS m/z=496 [M+H]$^+$.

Step C: N-{3-[3-{2-[(3-{[2-(Dimethylamino)ethyl]oxy}phenyl)amino]-4-pyrimidinyl}-6-(methyloxy)pyrazolo[1,5-a]pyridin-2-yl]phenyl}-1-phenylcyclopropanecarboxamide (title compound)

4-[2-(3-Aminophenyl)-6-(methyloxy)pyrazolo[1,5-a]pyridin-3-yl]-N-(3-{[2-(dimethylamino)ethyl]oxy}phenyl)-2-pyrimidinamine (100 mg, 0.21 mmol), 1-phenylcyclopropanecarboxylic acid (41 mg, 0.25 mmol), and diisopropylethylamine (0.10 mL, 1.0 mmol) were combined in DMF (1 mL) followed by the addition of HATU [O-(7- azabenzotriazole-1 yloxy)tripyrrolidinophosphonium hexafluorophosphate] (78 mg, 0.21 mmol). The mixture was stirred for 2 h at rt after which time additional HATU (80 mg, 0.21 mmol), 1-phenylcyclopropanecarboxylic acid (40 mg, 0.25 mmol), and diisopropylethylamine (0.10 mL, 1.0 mmol) were added. The mixture was stirred for 16 h after which time the mixture was poured into water, extracted with DCM, and the organic phase concentrated and purified by silica get chromatography to afford the title compound as a yellow solid (55 mg, 41%). $^1$H NMR (400 MHz, DMSO-$d_6$) δ 9.53 (s, 1H), 9.24 (s, 1H), 8.53 (d, J=2.1 Hz, 1H), 8.43 (d, J=10.4 Hz, 1H), 8.20 (d, J=5.2 Hz, 1H), 7.85 (br s, 1H), 7.66 (d, J=8.3 Hz, 1H), 7.52 (br s, 1H), 7.39-7.31 (m, 5H), 7.28-7.20 (m, 4H), 7.13 (t, J=8.1 Hz, 1H), 6.51 (dd, J=7.9, 2.3 Hz, 1H), 6.43 (d, J=5.2 Hz, 1H), 3.97 (t, J=6.5 Hz, 2H), 3.86 (s, 3H), 2.65-2.60 (m, 2H), 2.20 (s, 6H), 1.42 (m, 2H), 1.09 (m, 2H). ES-LC/MS m/z=640 [M+H]$^+$.

Example 68

(2E)-N-{3-[3-{2-[(3-{[2-(Dimethylamino)ethyl] oxy}phenyl)amino]-4-pyrimidinyl}-6-(methyloxy) pyrazolo[1,5-a]pyridin-2-yl]phenyl}-3-phenyl-propenamide

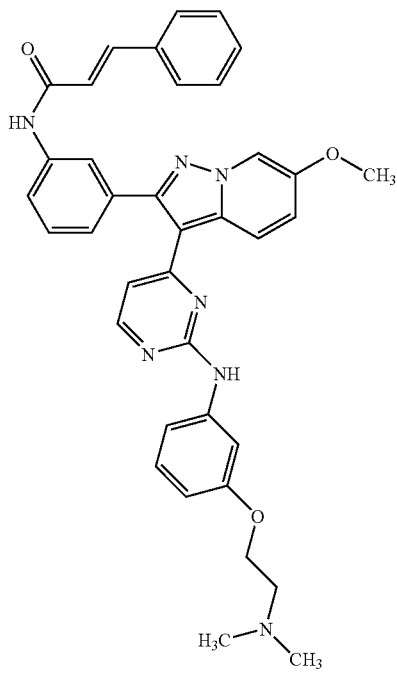

4-[2-(3-Aminophenyl)-6-(methyloxy)pyrazolo[1,5-a]pyridin-3-yl]-N-(3-{[2-(dimethylamino)ethyl]oxy}phenyl)-2-pyrimidinamine (97 mg, 0.20 mmol) and (2E)-3-phenyl-2-propenyl chloride (40 mg, 0.24 mmol) were combined in THF (2 mL) and stirred for 1 h. The mixture was diluted with DCM and TEA (2 drops), absorbed onto silica gel, and purified by silica gel chromatography to afford the title compound as a yellow solid (56 mg, 45%). $^1$H NMR (400 MHz, DMSO-$d_6$) δ 10.34 (s, 1H), 9.55 (s, 1H), 8.57 (d, J=2.0 Hz, 1H), 8.45 (d, J=9.3 Hz, 1H), 8.23 (d, J=5.6 Hz, 1H), 7.97 (br s, 1H), 7.82 (d, J=7.9 Hz, 1H), 7.62-7.59 (m, 3H), 7.55-7.53 (m, 1H), 7.47-7.39 (m, 4H), 7.30-7.26 (m, 3H), 7.14 (m, 1H), 6.81 (d, J=15.6 Hz, 1H), 6.52 (dd, J=8.2, 2.5 Hz, 1H), 6.48 (d, J=5.3 Hz, 1H), 3.99 (t, J=6.0 Hz, 3H), 3.87 (s, 3H), 2.68-2.64 (m, 2H), 2.23 (s, 6H). ES-LC/MS m/z=626 [M+H]$^+$.

Example 69

N-{3-[3-{2-[(3-{[2-(Dimethylamino)ethyl] oxy}phenyl)amino]-4-pyrimidinyl}-6-(methyloxy) pyrazolo[1,5-a]pyridin-2-yl]phenyl}-N-[(1R)-1-phenylethyl]urea

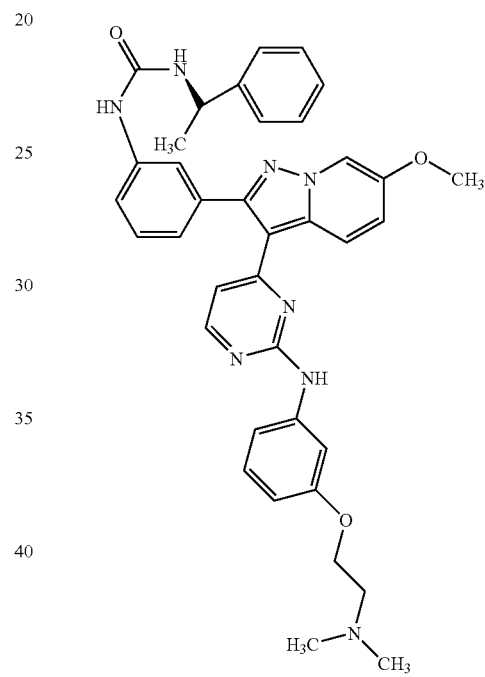

4-[2-(3-Aminophenyl)-6-(methyloxy)pyrazolo[1,5-a]pyridin-3-yl]-N-(3-{[2-(dimethylamino)ethyl]oxy}phenyl)-2-pyrimidinamine (61 mg, 0.12 mmol) and [(1R)-1-isocyanatoethyl]benzene (34 mg, 0.23 mmol) were combined in THF (2 mL) and stirred for 2 h, after which time additional [(1R)-1-isocyanatoethyl]benzene (10 mg, 0.068 mmol) was added in portions until the reaction was complete by LC/MS. The mixture was absorbed onto silica get and purified by silica gel chromatography to afford the title compound as a yellow solid (34 mg, 44%). $^1$H NMR (400 MHz, DMSO-$d_6$) δ 9.50 (s, 1H), 8.53 (d, J=5.9 Hz, 2H), 8.45 (d, J=9.9 Hz, 1H), 8.20 (d, J=5.5 Hz, 1H), 7.64 (s, 1H), 7.51 (s, 1H), 7.44 (d, J=7.4 Hz, 1H), 7.32-7.19 (m, 7H), 7.15-7.04 (m, 3H), 6.61 (d, J=8.5 Hz, 1H), 6.51 (d, J=8.1 Hz, 1H), 6.44 (d, J=5.2 Hz, 1H), 4.78 (t, J=7.4 Hz, 1H), 3.96 (t, J=5.5 Hz, 2H), 3.85 (s, 3H), 2.56 (t, J=5.7 Hz, 2H), 2.16 (s, 6H), 1.36 (d, J=7.1 Hz, 3H). ES-LC/MS m/z 643 [M+H]$^+$.

Example 70

N-{3-[3-{2-[(3-{[2-(Dimethylamino)ethyl]oxy}phenyl)amino]-4-pyrimidinyl}-6-(methyloxy)pyrazolo[1,5-a]pyridin-2-yl]phenyl}-N'-[(4-fluorophenyl)methyl]urea

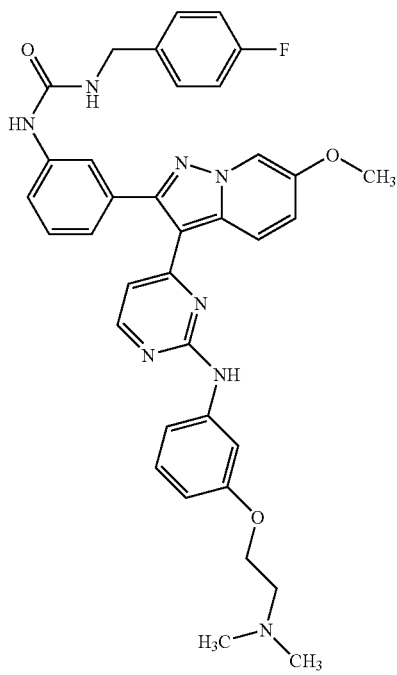

The title compound was prepared from 4-[2-(3-aminophenyl)-6-(methyloxy)pyrazolo[1,5-a]pyridin-3-yl]-N-(3-{[2-(dimethylamino)ethyl]oxy}phenyl)-2-pyrimidinamine (57 mg, 0.12 mmol) and 1-fluoro-4-(isocyanatomethyl)benzene (46 mg, 0.30 mmol) in a manner analogous to Example 69. $^1$H NMR (400 MHz, DMSO-$d_6$) δ 9.50 (s, 1H), 8.70 (s, 1H), 8.53 (s, 1H), 8.44 (d, J=10.0 Hz, 1H), 8.20 (d, J=5.1 Hz, 1H), 7.66 (s, 1H), 7.50-7.47 (m, 2H), 7.33-7.23 (m, 5H), 7.14-7.04 (m, 4H), 6.61 (t, J=6.1 Hz, 1H), 6.51-6.49 (m, 1H), 6.44 (d, J=6.2 Hz, 1H), 4.23 (d, J=6.5 Hz, 2H), 3.95 (t, J=5.8 Hz, 2H), 3.85 (s, 3H), 2.55 (t, J=5.9 Hz, 2H), 2.14 (s, 6H). ES-LC/MS m/z=647 [M+H]$^+$.

Example 71

N-{3-[6-Methyl-3-(2-{[3-(1-pyrrolidinylmethyl)phenyl]amino}-4-pyrimidinyl)pyrazolo[1,5-a]pyridin-2-yl]phenyl}-2-(2-thienyl)acetamide

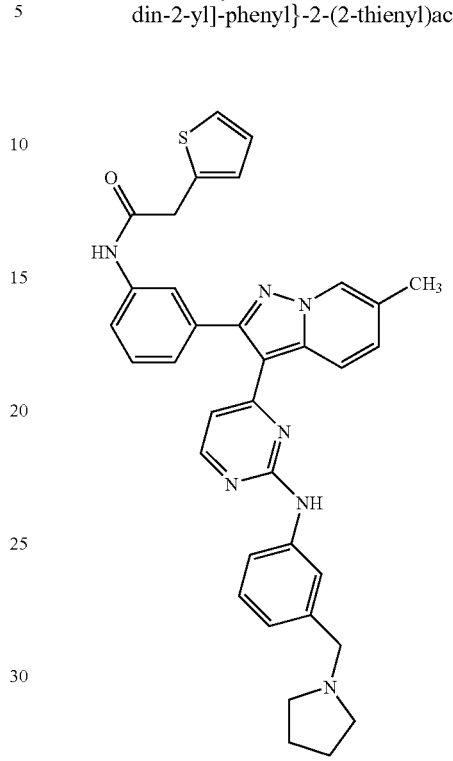

Step A: N-{3-[3-(2-Chloro-4-pyrimidinyl)-6-methylpyrazolo[1,5-a]pyridin-2-yl]phenyl}-2,2,2-trifluoroacetamide

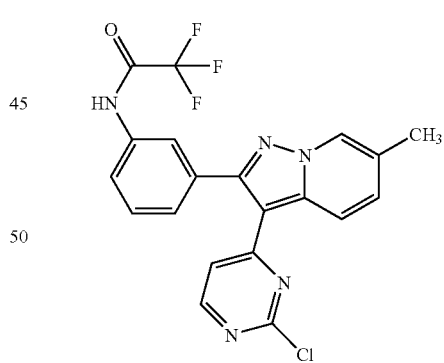

N-[3-(2-Chloro-pyrimidin-4-ylethenyl)-phenyl]-2,2,2-trifluoro-acetamide (5.00 g, 18.45 mmol) and 1-amino-3-methylpyridinium nitrate (6.19 g, 36.90 mmol) were combined in a procedure analogous to Example 67, Step A to afford 1.80 g of crude material, which was purified via HPLC separation to give N-{3-[3-(2-chloro-4-pyrimidinyl)-6-methylpyrazolo[1,5-a]pyridin-2-yl]phenyl}-2,2,2-trifluoroacetamide (1.70 g, 21%). $^1$H NMR (400 MHz, DMSO-$d_6$) δ 11.37 (s, 1H), 8.73 (s, 1H), 8.43 (d, J=5.6 Hz, 1H), 8.28 (d, J=9.2 Hz, 1H), 7.92 (s, 1H), 7.83 (d, J=8.4 Hz, 1H), 7.56-7.49 (m, 2H), 7.45-7.40 (m, 1H), 7.03 (d, J=5.6 Hz, 1H), 2.37 (s, 3H).

Step B: {3-[3-(2-Chloro-4-pyrimidinyl)-6-methylpyrazolo[1,5-a]pyridin-2-yl]phenyl}amine

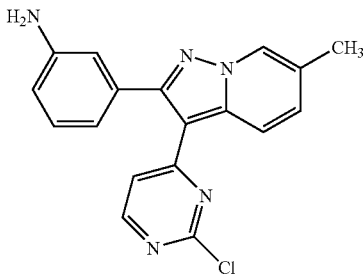

N-{3-[3-(2-Chloro-4-pyrimidinyl)-6-methylpyrazolo[1,5-a]pyridin-2-yl]phenyl}-2,2,2-trifluoroacetamide (1.70 g, 3.94 mmol) and LiOH (0.50 g, 11.8 mmol) were combined in THF (30 mL) and water (5 mL) and stirred at 40° C. for 3 h. The mixture was cooled, concentrated to remove the THF, and extracted with DCM. The organic phase was concentrated to afford {3-[3-(2-chloro-4-pyrimidinyl)-6-methylpyrazolo[1,5-a]pyridin-2-yl]phenyl}amine which was carried on crude to Step C. ES-LC/MS m/z=336 [M+H]$^+$.

Step C: N-{3-[3-(2-Chloro-4-pyrimidinyl)-6-methylpyrazolo[1,5-a]pyridin-2-yl]phenyl}-2-(2-thienyl)acetamide

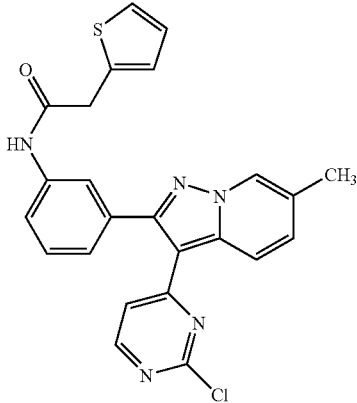

{3-[3-(2-Chloro-4-pyrimidinyl)-6-methylpyrazolo[1,5-a]pyridin-2-yl]phenyl}amine (0.57 g, 1.68 mmol) and 2-thienylacetyl chloride (0.25 mL, 2.00 mmol) were stirred in THF (30 mL) and stirred for 16 h. Additional 2-thienylacetyl chloride was added until reaction was complete by LC/MS. The mixture was concentrated to dryness and partitioned between aqueous NaHCO$_3$ (saturated) and DCM. The organic layers were concentrated and purified by column chromatography to afford N-{3-[3-(2-chloro-4-pyrimidinyl)-6-methylpyrazolo[1,5-a]pyridin-2-yl]phenyl}-2-(2-thienyl)acetamide as a yellow solid (0.69 g, 89%). ES-LC/MS m/z=460 [M+H]$^+$.

Step D: N-{3-[6-methyl-3-(2-{[3-(1-pyrrolidinylmethyl)phenyl]amino}-4-pyrimidinyl)pyrazolo[1,5-a]pyridin-2-yl]phenyl}-2-(2-thienyl)acetamide (title compound)

N-{3-[3-(2-chloro-4-pyrimidinyl)-6-methylpyrazolo[1,5-a]pyridin-2-yl]phenyl}-2-(2-thienyl)acetamide (100 mg, 0.22 mml), [3-(1-pyrrolidinylmethyl)phenyl]amine (46 mg, 0.26 mmol), and 4N HCl in dioxane (0.10 mL) were combined in i-PrOH (3 mL) in a procedure analogous to Example 67, Step B to afford the title compound as a yellow solid (70 mg, 53%). $^1$H NMR (300 MHz, DMSO-d$_6$) δ 10.40 (s, 1H), 9.55 (s, 1H), 8.71 (s, 1H), 8.47 (d, J=9.8 Hz, 1H), 8.26 (d, J=5.3 Hz, 1H), 7.91 (s, 1H), 7.78 (d, J=7.7 Hz, 1H), 7.72-7.67 (m, 2H), 7.48-7.36 (m, 3H), 7.31-7.19 (m, 2H), 7.00-7.01 (m, 2H), 6.92 (d, J=7.5 Hz, 1H), 6.50 (d, J=5.6 Hz, 1H), 3.91 (s, 2H), 3.57 (s, 2H), 2.52-2.45 (m, 4H), 2.41 (s, 3H), 1.74-1.69 (m, 4H). ES-LC/MS m/z=600 [M+H]$^+$.

Example 72

N-[3-(3-{2-[(3-{[2-(Dimethylamino)ethyl]oxy}phenyl)amino]-4-pyrimidinyl}-6-methylpyrazolo[1,5-a]pyridin-2-yl)phenyl]-2-(2-thienyl)acetamide

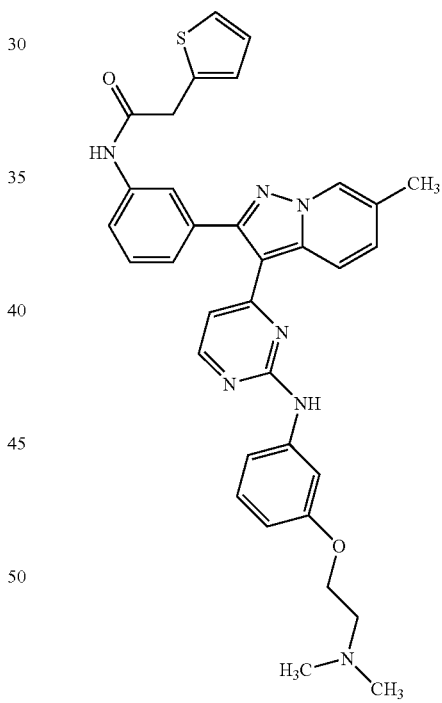

N-{3-[3-(2-Chloro-4-pyrimidinyl)-6-methylpyrazolo[1,5-a]pyridin-2-yl]phenyl}-2-(2-thienyl)acetamide (100 mg, 0.22 mml) and (2-[(3-aminophenyl)oxy]ethyl)dimethylamine dihydrochloride (66 mg, 0.26 mmol) were combined in i-PrOH (3 mL) in a procedure analogous to Example 67, Step B to afford the title compound as a yellow solid (84 mg, 63%). $^1$H NMR (300 MHz, DMSO-d$_6$) δ 10.39 (s, 1H), 9.57 (s, 1H), 8.71 (s, 1H), 8.47 (d, J=9.4 Hz, 1H), 8.27 (d, J=5.2 Hz, 1H), 7.90 (s, 1H), 7.78 (d, J=8.2 Hz, 1H), 7.57 (t, J=2.1 Hz, 1H), 7.48-7.37 (m, 3H), 7.32-7.27 (m, 2H), 7.20-7.15 (m, 1H), 7.02-6.99 (m, 3H), 6.50 (d, J=5.6 Hz, 1H), 4.02 (t, J=5.7

Hz, 2H), 3.91 (s, 2H), 2.63 (t, J=5.1 Hz, 2H), 2.41 (s, 3H), 2.22 (s, 6H). ES-LC/MS m/z=604 [M+H]+.

Example 73

N-{3-[3-(2-{[4-(4-Acetyl-1-piperazinyl)phenyl]amino}-4-pyrimidinyl)-6-methylpyrazolo[1,5-a]pyridin-2-yl]phenyl}-2-(2-thienyl)acetamide

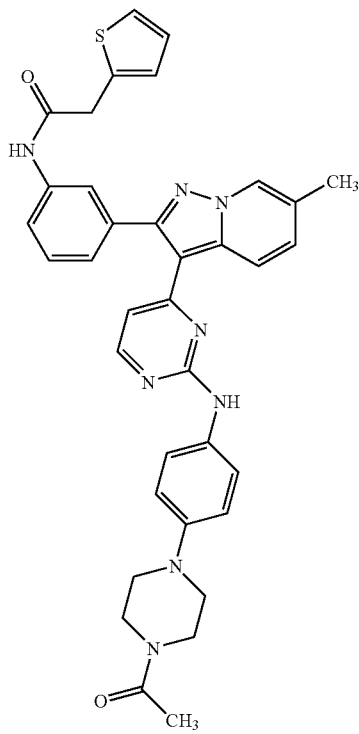

N-{3-[3-(2-Chloro-4-pyrimidinyl)-6-methylpyrazolo[1,5-a]pyridin-2-yl]phenyl}-2-(2-thienyl)acetamide (60 mg, 0.13 mmol), [4-(4-acetyl-1-piperazinyl)phenyl]amine (35 mg, 0.16 mmol), and 4N HCl in dioxane (0.04 mL) were combined in i-PrOH (3 mL) and microwaved for 10 min. at 180° C. to afford the title compound as a yellow solid (42 mg, 50%). $^1$H NMR (400 MHz, DMSO-d$_6$) δ 10.31 (s, 1H), 9.27 (s, 1H), 8.63 (s, 1H), 8.15 (d, J=5.1 Hz, 1H), 7.83 (s, 1H), 7.71 (d, J=7.6 Hz, 1H), 7.50 (d, J=9.0 Hz, 2H), 7.40-7.35 (m, 2H), 7.30 (d, J=9.8 Hz, 1H), 7.21 (d, J=7.7 Hz, 1H), 6.95-6.93 (m, 2H), 6.84 (d, J=8.7 Hz, 2H), 6.41 (d, J=5.0 Hz, 2H), 3.84 (s, 2H), 3.56-3.52 (m, 4H), 3.03 (t, J=4.6 Hz, 2H), 2.96 (t, J=4.7 Hz, 2H), 2.34 (s, 3H), 2.01 (s, 3H). ES-LC/MS m/z=643 [M+H]+.

BIOLOGICAL EXAMPLES

Compounds of the present invention were tested for ErbB family protein tyrosine kinase inhibitory activity in substrate phosphorylation assays and cell proliferation assays.

A. Enzyme Assays:

Compounds of the present invention were tested for EGFR, ErbB-2, and ErbB-4 protein tyrosine kinase inhibitory activity in substrate phosphorylation assays using enzymes purified from a baculovirus expression system. Reagent production was conducted essentially as described in Brignola, P. S., et al, (2002) J. Biol. Chem. 277(2): 1576-1585.

The method measures the ability of the isolated enzyme to catalyse the transfer of the gamma-phosphate from ATP onto the tyrosine residue of a biotinylated synthetic peptide referenced "Peptide C" in Brignola, P. S., et al, (2002) J. Biol. Chem. 277(2):1576-1585. The extent of tyrosine phosphorylation was measured using an anti-phosphotyrosine antibody, and quantified by homogenous time-resolved fluorescence (HTRF).

Reactions were performed in black 384-well polystyrene flat-bottom plates in a final volume of 20 µl. Assays were performed by adding 10 µl of each of the following solutions, substrate Mix and enzyme mix: The Substrate mix contained 100 mM 3-[N-morpholino]propanesulfonic acid (MOPS) (pH 7.5), 2 mM MnCl$_2$, 20 µM ATP, 0.01% Tween-20, 0.1 mg/mL (BSA), 0.8 uM peptide substrate, and 1 mM dithiothreitol. The enzyme mix contained 100 mM MOPS (pH7.5); 0.01% Tween-20; 0.1 mg/mL BSA, and either 0.8 nM EGFR, 10 nM ErbB2, or 1 nM ErbB4

During the course of these studies, two separate methods have been used to measure the potency of compounds. In Method A, the substrate mix was added to the compound plates first, then the reaction was started by adding the enzyme mix. In Method B, the enzyme mix was added to the compound plates and the plates were incubated at 20° C. for 1 hour. The reactions were then started by adding the substrate mix.

After initiating the reaction with either method describe above, the reactions were allowed to proceed for 90 minutes at 20° C. The reactions were then terminated by the addition of 20 µl 100 mM EDTA to each well. 40 µl/well of HTRF detection mix were added to the assay plates. The final concentrations of the detection reagents were: 100 mM HEPES (pH7.5), 0.1 mg/mL BSA, 15 nM streptavidin-labeled allophycocyanin (PerkinElmer), and 1 nM europium-labeled anti-phosphotyrosine antibody (PerkinElmer). Assay plates were left unsealed and were counted in a Wallac Multilabel Counter 1420 (PerkinElmer).

Compounds under analysis were dissolved in Me$_2$SO to 1.0 mM and serially diluted 1 to 3 with Me$_2$SO through twelve dilutions. 1 µl of each concentration was transferred to the corresponding well of an assay plate. This creates a final compound concentration range from 0.00027 to 47.6 µM.

The data for dose responses were plotted as % Inhibition calculated with the data reduction formula 100*(1−(U1−C2)/(C1−C2)) versus concentration of compound where U is the unknown value, C1 is the average control value obtained for 4.76% DMSO, and C2 is the average control value obtained for 0.035 M EDTA. Data were fitted with a curve described by:

$$y=((V\text{max}*x)/(K+x))+Y2$$

where Vmax is the upper asymptote, Y2 is the Y intercept, and K is the IC50. The results for each compound were recorded as pIC50s, calculated as follows:

$$pIC50=-\text{Log }10(K)$$

Many of the exemplified compounds Examples 1-73 were run in the recited assay and the results are reported in the following Table 1. In the following table:

"+" indicates no pIC50 measurement greater than 6 against either ErbB2 or EGFR;

"++" indicates at least one pIC50 measurement greater than 6 against either ErbB2 or EGFR but no measurement greater than pIC50 of 7; and "+++" indicates at least one pIC50 measurement of greater than 7 against either ErbB2 or EGFR.

TABLE 1

| Example | Activity (Method) |
|---|---|
| 1 | +++ (B) |
| 2 | +++ (B) |
| 3 | ++ (A) |
| 4 | ++ (A) |
| 5 | + (A) |
| 6 | ++ (A) |
| 7 | +++ (B) |
| 8 | +++ (B) |
| 9 | +++ (B) |
| 10 | +++ (B) |
| 11 | +++ (B) |
| 12 | +++ (B) |
| 13 | +++ (B) |
| 14 | +++ (B) |
| 15 | +++ (B) |
| 16 | +++ (B) |
| 17 | +++ (B) |
| 18 | ++ (B) |
| 19 | +++ (B) |
| 20 | +++ (B) |
| 21 | +++ (B) |
| 22 | +++ (B) |
| 23 | +++ (B) |
| 24 | +++ (B) |
| 25 | ++ (B) |
| 26 | ++ (B) |
| 27 | ++ (B) |
| 28 | +++ (B) |
| 29 | + (B) |
| 30 | ++ (B) |
| 31 | ++ (B) |
| 32 | + (B) |
| 33 | ++ (B) |
| 34 | +++ (B) |
| 35 | ++ (B) |
| 36 | ++ (B) |
| 37 | +++ (B) |
| 38 | ++ (B) |
| 39 | +++ (B) |
| 40 | +++ (B) |
| 41 | +++ (B) |
| 42 | +++ (B) |
| 43 | +++ (B) |
| 44 | +++ (B) |
| 45 | ++ (B) |
| 46 | +++ (B) |
| 47 | +++ (B) |
| 48 | + (B) |
| 49 | + (B) |
| 50 | +++ (B) |
| 51 | +++ (B) |
| 52 | +++ (B) |
| 53 | +++ (B) |
| 54 | +++ (B) |
| 55 | +++ (B) |
| 56 | ++ (B) |
| 57 | ++ (B) |
| 58 | ++ (B) |
| 59 | ++ (B) |
| 60 | ++ (B) |
| 61 | ++ (B) |
| 62 | + (B) |
| 63 | +++ (B) |
| 64 | + (B) |
| 65 | + (B) |
| 66 | + (B) |
| 67 | ++ (B) |
| 68 | +++ (B) |
| 69 | +++ (B) |
| 70 | +++ (B) |
| 71 | +++ (B) |
| 72 | +++ (B) |
| 73 | +++ (B) |

B. Cellular Assays

Method A: Methylene Blue Growth Inhibition Assay

Human breast (BT474) and head and neck (HN5) were cultured in low glucose DMEM (Life Technologies 12320-032) containing 10% fetal bovine serum (FBS). Human colon tumor cells (Colo205) were cultured in DMEM (Invitrogen, 10564) containing 10% FBS. The SV40 transformed human mammary epithelial cell line to HB4a was transfected with either human H-ras cDNA (HB4a r4.2) or the human c-ErbB2 cDNA (HB4a c5.2). The HB4a clones were cultured in RPMI containing 10% FBS, insulin (5 g/mL), hydrocortisone (5 g/mL), supplemented with the selection agent hygromycin B (50 g/mL). All lines were grown in a humidified incubator at 37° C. in 95% air, 5% $CO_2$. Cells were harvested using trypsin/EDTA, counted using a haemocytometer, and plated in 100 microliters of the appropriate media, at the following densities, in a 96-well tissue culture plate (Falcon 3075): BT474 10,000 cells/well, HN5 3,000 cells/well. The next day, compounds were diluted in DMEM containing 100 mg/mL gentamicin, at twice the final required concentration, from 10 mM stock solutions in DMSO. 100 microliters/well of these dilutions were added to the 100 microliters of media currently on the cell plates. Medium containing 0.6% DMSO was added to control wells. Compounds diluted in DMEM were added to all cell lines. The final concentration of DMSO in all wells was 0.3%. Cells were returned to the incubator (37° C., 10% $CO_2$) for 3 days. Medium was then removed by aspiration. Cell biomass was estimated by staining cells with 90 microliters per well methylene blue (Sigma M9140, 0.5% in 1:1 ethanol:water), and incubation at rt for at least 30 minutes. Stain was removed, and the plates rinsed by immersion in deionized water and air-dried. To release stain from the cells 100 microliters of solubilization solution was added (1% N-lauroyl sarcosine, Sodium salt, Sigma L5125, in PBS), and plates were shaken gently for about 30 minutes. Optical density at 620 nM was measured on a microplate reader. Percent inhibition of cell growth was calculated relative to vehicle treated control wells. Concentration of compound that inhibits 50% of control cell growth ($IC_{50}$) was interpolated using nonlinear regression (Levenberg-Marquardt) and the equation, $$y = V\max*(1-(x/(K+x))) + Y2, \text{ where "K" was equal to the } IC_{50}.$$

Method B: Celltiter Glo® Growth Inhibition Assays

Human breast tumor cells (BT474) were cultured in RPMI, (Invitrogen, 22400) containing 10% fetal bovine serum (FBS). Human head and neck tumor cells (HN5) were cultured in low glucose DMEM (Invitrogen, 12320) containing 10% FBS. Human colon tumor cells (Colo205) were cultured in DMEM (Invitrogen, 10564) containing 10% FBS. All cell lines were maintained at 37° C. in a humidified 5% $CO_2$, 95% air incubator. Cells were harvested using trypsin/EDTA, counted using a haemocytometer, and plated in 30 microliters of the appropriate media described above, at the following densities, in a half area, black-walled, 96-well tissue culture plate (Corning 3882): BT474 3,000 cells/well, HN5 500 cells/well and Colo205 cells, 3,000 cells/well. The next day, compounds were diluted in DMEM containing 100 mg/ml gentamicin, from 10 mM stock solutions in DMSO. 30 microliters/well of these dilutions were added to the 30 microliters/well of media currently on the cell plates. Medium containing 0.6% DMSO was added to control wells. The final concentration of DMSO in all wells was 0.3%. Cells were incubated at 37° C., 5% $CO_2$ for 3 days. Cell biomass was estimated using Celltiter Glo (Promega G7571). Briefly, plates were removed from the incubator and allowed to equilibrate to rt for 30 minutes. 60 microliters of Celltiter Glo reagent were added to each well of the treated cells and plates were shaken on an orbital plate shaker for 2 min. Plates were incubated without shaking for 30 more min and read in a luminometer with an integration time of 0.5 seconds per well. Percent inhibition of cell growth was calculated relative to vehicle treated control wells. Concentration of compound that inhibits 50% of vehicle control cell growth (IC50) was interpolated using nonlinear regression (Levenberg-Marquardt) and the equation, $y=V_{max}*(1-(x/(K+x)))+Y2$, where "K" was equal to the IC50.

The compounds of selected Examples were run in the recited assay and the results are reported in the following Table 2. In the following table:

"+" indicates that the compound showed activity of >1 µM in both BT474 and HN5 tumor cell lines;

"++" indicates that the compound showed activity of between 100 nM and 1 µM in at least one of BT474 and HN5 tumor cell lines; and "+++" indicates that the compound showed activity of less than 100 nM in at least one of BT474 and HN5 tumor cell lines.

TABLE 2

| Example | Activity (Method) |
|---|---|
| 1 | ++ (A) |
| 2 | +++ (A) |
| 3 | + (A) |
| 7 | ++ (B) |
| 9 | + (A) |
| 10 | ++ (A) |
| 11 | ++ (A) |
| 12 | ++ (A) |
| 13 | ++ (A) |
| 14 | ++ (A) |
| 15 | ++ (A) |
| 16 | ++ (A) |
| 17 | ++ (B) |
| 18 | ++ (B) |
| 19 | ++ (B) |
| 20 | ++ (B) |
| 21 | ++ (B) |
| 22 | + (B) |
| 23 | ++ (B) |
| 24 | ++ (A) |
| 25 | + (A) |
| 26 | + (A) |
| 27 | + (A) |
| 28 | + (A) |
| 29 | + (A) |
| 30 | + (B) |
| 31 | + (B) |
| 32 | + (B) |
| 33 | + (B) |
| 34 | ++ (B) |
| 35 | ++ (B) |
| 36 | ++ (B) |
| 37 | +++ (B) |
| 38 | ++ (B) |
| 39 | ++ (A) |
| 40 | ++ (B) |
| 41 | ++ (B) |
| 42 | ++ (B) |
| 43 | ++ (A) |
| 44 | + (A) |
| 45 | + (A) |
| 46 | + (B) |
| 47 | ++ (B) |
| 48 | ++ (B) |
| 49 | + (B) |
| 50 | ++ (B) |
| 51 | ++ (B) |
| 52 | ++ (B) |
| 53 | ++ (A) |
| 54 | +++ (A) |
| 55 | ++ (A) |
| 56 | + (B) |
| 57 | + (B) |
| 58 | ++ (B) |
| 59 | ++ (B) |
| 61 | ++ (B) |
| 62 | + (B) |

The compounds of selected Examples were run in the recited assay using Colo205 cell lines and the results are reported in the following Table 3. In the following table:

"+" indicates that the compound showed activity of >1 µM in Colo205 tumor cell lines;

"++" indicates that the compound showed activity of between 100 nM and 1 µM in Colo205 tumor cell lines; and "+++" indicates that the compound showed activity of less than 100 nM in Colo205 tumor cell lines.

TABLE 3

| Example | Activity (Method) |
|---|---|
| 1 | ++ (A) |
| 2 | ++ (A) |
| 3 | + (A) |
| 7 | ++ (B) |
| 9 | + (A) |
| 10 | ++ (A) |
| 11 | ++ (A) |
| 12 | ++ (A) |
| 13 | ++ (A) |
| 14 | ++ (A) |
| 15 | ++ (A) |
| 16 | ++ (A) |
| 17 | ++ (B) |
| 18 | + (B) |
| 19 | + (B) |
| 20 | ++ (B) |
| 21 | + (B) |
| 22 | + (B) |
| 23 | ++ (B) |
| 24 | ++ (A) |
| 25 | ++ (A) |
| 26 | + (A) |
| 27 | + (A) |
| 28 | + (A) |
| 29 | + (A) |
| 30 | + (B) |
| 31 | + (B) |
| 32 | + (B) |
| 33 | + (B) |
| 34 | ++ (B) |
| 35 | + (B) |
| 36 | ++ (B) |
| 37 | ++ (B) |
| 38 | ++ (B) |
| 39 | ++ (A) |
| 40 | ++ (B) |
| 41 | ++ (B) |
| 42 | + (B) |
| 43 | + (A) |
| 44 | + (A) |
| 45 | + (A) |
| 46 | + (B) |
| 47 | +++ (B) |
| 48 | ++ (B) |
| 49 | ++ (B) |
| 50 | ++ (B) |
| 51 | ++ (B) |
| 52 | ++ (B) |

TABLE 3-continued

| Example | Activity (Method) |
|---------|-------------------|
| 53 | ++ (A) |
| 54 | ++ (A) |
| 55 | ++ (A) |
| 56 | + (B) |
| 57 | + (B) |
| 58 | ++ (B) |
| 59 | + (B) |
| 61 | ++ (B) |
| 62 | ++ (B) |

That which is claimed is:

1. A compound of formula (I):

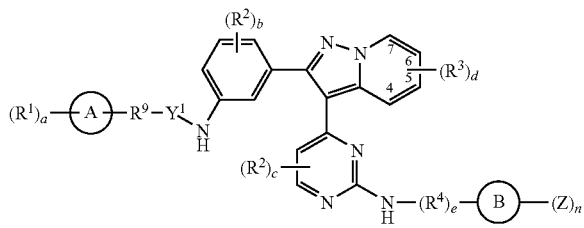

I wherein:
a is 0, 1, 2 or 3;
each $R^1$ is the same or different and is independently selected from halo, alkyl, alkenyl, alkynyl, cycloalkyl, cycloalkenyl, Ay, Het, —$OR^6$, —$R^4OR^6$, —$OC(O)R^6$, —$C(O)R^6$, —$R^4C(O)R^6$, —$C(O)NR^6R^7$, —$R^4C(O)NR^6R^7$, —$CO_2R^6$, —$C(S)R^6$, —$C(S)NR^6R^7$, —$S(O)_fR^6$, —$R^4S(O)_fR^6$, —$S(O)_2NR^6R^7$, —$NR^6R^7$, —$R^4NR^6R^7$, —$N(R^6)$—$R^4R^7$, —$N(R^6)$—$R^4$—$OR^7$, —$N(R^6)$—$R^4$—$S(O)_fR^7$, —$N(R^6)$—$R^4$—CN, —$C(NH)NR^6R^7$, —$N(R^6)C(O)R^6$, —$N(R^6)S(O)_2R^6$, —$N(R^6)$—$C(O)$—$NR^6R^7$, —$N(R^6)$—$S(O)_2$—$NR^6R^7$, —CN, and —$NO_2$;
f is 0, 1 or 2;
Ay is aryl optionally substituted 1, 2 or 3 times with a substituent selected from halo, $C_{1-3}$alkyl, $C_{1-3}$alkoxy, $NH_2$, $N(H)C_{1-3}$alkyl, $N(C_{1-3}$alkyl$)_2$, CN and $NO_2$;
Het is a 5-6 membered heterocycle or heteroaryl having 1 or 2 heteroatoms selected from N, O and S and optionally substituted 1, 2 or 3 times with a substituent selected from halo, $C_{1-3}$alkyl, $C_{1-3}$alkoxy, hydroxyl, oxo, C(O)($C_{1-3}$alkyl), $SO_3(H)$, $SO_2(C_{1-3}$alkyl), $C_{1-3}$alkyl-$SO_3(H)$, $C_{1-3}$alkyl-$SO_2(C_{1-3}$alkyl), $NH_2$, $N(H)C_{1-3}$alkyl, $N(C_{1-3}$alkyl$)_2$, CN and $NO_2$;
Ring A is selected from aryl, heterocycle and heteroaryl;
$R^9$ is $C_{1-4}$alkylene, $C_{2-4}$alkenylene or $C_{3-4}$cycloalkylene;
$Y^1$ is —C(O)—, —N(H)C(O)—, —C(S)— or —N(H)C(S)—;
b and c are each the same or different and are each independently 0, 1 or 2;
each $R^2$ is the same or different and is independently selected from halo, alkyl, —$OR^6$, —$S(O)_fR^6$, —$NR^6R^7$, —CN and —$NO_2$;
d is 0, 1 or 2;
each $R^3$ is the same or different and is independently selected from halo, alkyl, alkenyl, alkynyl, cycloalkyl, cycloalkenyl, Ay, Het, —$OR^6$, —$R^4OR^6$, —OAy, —$R^4OAy$, —$OC(O)R^6$, —$COR^6$, —$R^4C(O)R^6$, —C(O)Ay, —C(O)$NR^6R^7$, —$R^4C(O)NR^6R^7$, —C(O)N(H)Ay, —C(O)N(H)Het, —$CO_2R^6$, —$CO_2Ay$, —$C(S)R^6$, —C(S)$NR^6R^7$, —$S(O)_fR^6$, —$R^4S(O)_fR^6$, —$S(O)_fAy$, —$S(O)_2NR^6R^7$, —$NR^6R^7$, —$R^4NR^6R^7$, —$N(R^8)Ay$, —$R^4N(H)Ay$, —N(H)Het, —N(H)$R^4$Het, —$N(R^6)$—$R^4R^7$, —$N(R^6)$—$R^4$—$OR^7$, —$N(R^6)$—$R^4$—$S(O)_fR^7$, —$N(R^6)$—$R^4$—CN, —C(NH)$NR^6R^7$, —N(H)C(O)$R^6$, —N(H)C(O)Ay, —N(H)$SO_2R^6$, —$N(R^6)$—C(O)—$NR^6R^7$, —$N(R^6)$—$S(O)_2$—$NR^6R^7$, —CN and —$NO_2$;
each $R^4$ is the same or different and is independently $C_{1-4}$alkylene or $C_{3-4}$alkenylene;
e is 0 or 1;
Ring B is selected from aryl and heteroaryl;
g is 0, 1, 2, 3 or 4;
each Z is the same or different and is independently a moiety of formula ii:

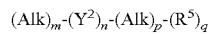

wherein:
m, n and p are the same or different and are each independently 0 or 1;
each Alk is the same or different and is independently selected from $C_{1-4}$alkylene and $C_{3-4}$alkenylene;
$Y^2$ is —O—, —C(O)—, —$S(O)_f$—, —N(H)— or —N(Alk)-;
q is 1 or 2;
each $R^5$ is the same or different and is independently selected from H, halo, alkyl, alkenyl, cycloalkyl, cycloalkenyl, Ay, Het, oxo, —$OR^6$, —OAy, —$C(O)R^6$, —$OC(O)R^6$, —C(O)Ay, —OC(O)Ay, —C(O)$NR^6R^7$, —$CO_2R^6$, —$CO_2Ay$, —$S(O)_fR^6$, —$S(O)_fAy$, —$S(O)_2NR^6R^7$, —$C(S)R^6$, —C(S)$NR^6R^7$, —C(S)N(H)Ay, —$NR^6R^7$, —$N(R^8)Ay$, —$N(R^8)Het$, —$N(R^6)$—$R^4R^7$, —$N(R^6)$—$R^4$—$OR^7$, —$N(R^6)$—$R^4$—$S(O)_fR^7$, —$N(R^6)$—$R^4$—CN, —NHC(O)$R^6$, —N(H)$SO_2R^6$, —C(NH)$NR^6R^7$, —$N(R^6)$—C(O)—$NR^6R^7$, —$N(R^6)$—$S(O)_2$—$NR^6R^7$, —$N(R^6)$—C(O)—$R^4NR^6R^7$, —$N(R^6)$—$S(O)_2$—$R^4NR^6R^7$, —CN and —$NO_2$;
each $R^6$ and $R^7$ are the same or different and are each independently selected from H, alkyl, alkenyl, alkynyl, $C_{3-6}$cycloalkyl and $C_{3-6}$cycloalkenyl; and
each $R^8$ is the same or different and is H or alkyl,
or a pharmaceutically acceptable salt thereof.

2. The compound according to claim 1, wherein a is 1 or 2.

3. The compound according to claim 1, wherein each $R^1$ is the same or different and is independently selected from halo, alkyl, alkenyl, alkynyl, cycloalkyl, cycloalkenyl, Ay, Het, —$OR^6$, —$R^4OR^6$, —$OC(O)R^6$, —$C(O)R^6$, —$R^4C(O)R^6$, —C(O)$NR^6R^7$, —$CO_2R^6$, $C(S)R^6$, $C(S)NR^6R^7$, —$S(O)_fR^6$, —$R^4S(O)_fR^6$, —$S(O)_2NR^6R^7$, —$NR^6R^7$, —$R^4NR^6R^7$, —$N(R^6)C(O)R^6$, —$N(R^6)S(O)_2R^6$, —$N(R^6)$—C(O)—$NR^6R^7$, —$N(R^6)$—$S(O)_2$—$NR^6R^7$, —CN and —$NO_2$.

4. The compound according to claim 1, wherein Ring A is aryl or heteroaryl.

5. The compound according to claim 1, wherein $Y^1$ is —C(O)— or —N(H)C(O)—.

6. The compound according to claim 1, wherein each $R^2$ is the same or different and is independently selected from halo, alkyl, —$OR^6$, —$NR^6R^7$ and —CN.

7. The compound according to claim 1, wherein b is 0.

8. The compound according to claim 1, wherein c is 0.

9. The compound according to claim 1, wherein d is 0 or 1.

10. The compound according to claim 1, wherein each $R^3$ is the same or different and is independently selected from halo, alkyl, alkenyl, alkynyl, cycloalkyl, Ay, Het, —$OR^6$, —$R^4OR^6$, —$OC(O)R^6$, —$COR^6$, —$R^4C(O)R^6$, —C(O)$NR^6R^7$, —$S(O)_fR^6$, —$R^4S(O)_fR^6$, —$S(O)_2NR^6R^7$, —$NR^6R^7$, —$R^4NR^6R^7$, —$N(R^8)Ay$, —$R^4N(H)Ay$, —N(H)

Het, —N(R⁶)—R⁴—OR⁷, —N(R⁶)—R⁴—S(O)ⱼR⁷, —N(R⁶)—R⁴—CN, —N(H)C(O)R⁶, —N(H)SO₂R⁶, —N(R⁶)—C(O)—NR⁶R⁷, —N(R⁶)—S(O)₂—NR⁶R⁷, —CN and —NO₂.

11. The compound according to claim 1, wherein (R⁴)ₑ is C₁₋₄alkylene.

12. The compound according to claim 1, wherein e is 0.

13. The compound according to claim 1, wherein Ring B is aryl.

14. The compound according to claim 1, wherein g is 0, 1, 2 or 3.

15. The compound according to claim 1, wherein each Alk is the same or different and is independently C₁₋₃alkylene.

16. The compound according to claim 1, wherein n is 1.

17. The compound according to claim 1, wherein n is 0.

18. The compound according to claim 1, wherein Y² is —O—, —C(O)— or —N(H)—.

19. The compound according to claim 1, wherein q is 1.

20. The compound according to claim 1, wherein each R⁵ is the same or different and is independently selected from H, halo, alkyl, alkenyl, cycloalkyl, Ay, Het, oxo, —OR⁶, —OAy, —C(O)R⁶, —OC(O)R⁶, —C(O)Ay, —C(O)NR⁶R⁷, —CO₂R⁶, —S(O)ⱼR⁶, —S(O)₂NR⁶R⁷, —C(S)NR⁶R⁷, —NR⁶R⁷, —N(R⁸)Ay, —N(R⁸)Het, —N(R⁶)—R⁴R⁷, —N(R⁶)—R⁴—OR⁷, —N(R⁶)—R⁴—S(O)ⱼR⁷, —N(R⁶)—R⁴—CN, —NHC(O)R⁶, —N(H)S(O)₂R⁶, —C(NH)NR⁶R⁷, —N(R⁶)—C(O)—NR⁶R⁷, —N(R⁶)—S(O)₂—NR⁶R⁷, —N(R⁶)—C(O)—R⁴NR⁶R⁷, —CN and —NO₂.

21. A compound selected from:
N-[3-(3-{2-[(2-Methyl-1,2,3,4-tetrahydro-7-isoquinolinyl)amino]-4-pyrimidinyl}pyrazolo[1,5-a]pyridin-2-yl)phenyl]-2-(2-thienyl)acetamide;
N-[3-(3-{2-[(3-{[2-(1-Pyrrolidinyl)ethyl]oxy}phenyl)amino]-4-pyrimidinyl}pyrazolo[1,5-a]pyridin-2-yl)phenyl]-2-(2-thienyl)acetamide;
N-{5-[3-(2-{[2-(Dimethylamino)-2,3-dihydro-1H-inden-5-yl]amino}pyrimidin-4-yl)pyrazolo[1,5-a]pyridin-2-yl]-2-methoxyphenyl}-2-(2-thienyl)acetamide;
N-[2-Methoxy-5-(3-{2-[(2-methyl-1,2,3,4-tetrahydroisoquinolin-7-yl)amino]pyrimidin-4-yl}pyrazolo[1,5-a]pyridin-2-yl)phenyl]-2-(2-thienyl)acetamide;
N-{3-[3-(2-{[3-(4-methyl-1,3-oxazol-5-yl)phenyl]amino}pyrimidin-4-yl)pyrazolo[1,5-a]pyridin-2-yl]phenyl}-2-(2-thienyl)acetamide;
N-{3-[3-(2-{[2-(Dimethylamino)-2,3-dihydro-1H-inden-5-yl]amino}pyrimidin-4-yl)pyrazolo[1,5-a]pyridin-2-yl]phenyl}-2-(2-thienyl)acetamide;
N-{2-Methyl-5-[3-(2-{[3-(1-pyrrolidinylmethyl)phenyl]amino}-4-pyrimidinyl)pyrazolo[1,5-a]pyridin-2-yl]phenyl}-2-(2-thienyl)acetamide;
N-[5-(3-{2-[(5-{[2-(Dimethylamino)ethyl]oxy}-2-methylphenyl)amino]-4-pyrimidinyl}pyrazolo[1,5-a]pyridin-2-yl)-2-methylphenyl]-2-(2-thienyl)acetamide;
N-[5-(3-{2-[(3-{[2-(Dimethylamino)ethyl]oxy}phenyl)amino]-4-pyrimidinyl}pyrazolo[1,5-a]pyridin-2-yl)-2-methylphenyl]-2-(2-thienyl)acetamide;
N-[2-Methyl-5-(3-{2-[(2-methyl-1,2,3,4-tetrahydro-7-isoquinolinyl)amino]-4-pyrimidinyl}pyrazolo[1,5-a]pyridin-2-yl)phenyl]-2-(2-thienyl)acetamide;
N-[5-(3-{2-[(3-{[2-(Dimethylamino)ethyl]oxy}-2-methylphenyl)amino]-4-pyrimidinyl}pyrazolo[1,5-a]pyridin-2-yl)-2-fluorophenyl]-2-(2-thienyl)acetamide;
N-{2-Fluoro-5-[3-(2-{[3-(1-pyrrolidinylmethyl)phenyl]amino}-4-pyrimidinyl)pyrazolo[1,5-a]pyridin-2-yl]phenyl}-2-(2-thienyl)acetamide;
N-[5-(3-{2-[(3-{[2-(Dimethylamino)ethyl]oxy}-2-methylphenyl)amino]-4-pyrimidinyl}pyrazolo[1,5-a]pyridin-2-yl)-2-fluorophenyl]-2-(2-thienyl)acetamide;
N-[2-Fluoro-5-(3-{2-[(2-methyl-1,2,3,4-tetrahydro-7-isoquinolinyl)amino]-4-pyrimidinyl}pyrazolo[1,5-a]pyridin-2-yl)phenyl]-2-(2-thienyl)acetamide;
N-[5-(3-{2-[(3-{[2-(Dimethylamino)ethyl]oxy}-2-methylphenyl)amino]-4-pyrimidinyl}pyrazolo[1,5-a]pyridin-2-yl)-2-(methyloxy)phenyl]-2-(2-thienyl)acetamide;
N-[5-(3-{2-[(3-{[2-(Dimethylamino)ethyl]oxy}phenyl)amino]-4-pyrimidinyl}pyrazolo[1,5-a]pyridin-2-yl)-2-(methyloxy)phenyl]-2-(2-thienyl)acetamide;
N-[5-(3-{2-[(5-{[2-(Dimethylamino)ethyl]oxy}-2-methylphenyl)amino]-4-pyrimidinyl}pyrazolo[1,5-a]pyridin-2-yl)-2-(methyloxy)phenyl]-2-(2-thienyl)acetamide;
N-{3-[6-Methyl-3-(2-{[3-(1-pyrrolidinylmethyl)phenyl]amino}-4-pyrimidinyl)pyrazolo[1,5-a]pyridin-2-yl]phenyl}-2-(2-thienyl)acetamide;
N-[3-(3-{2-[(3-{[2-(Dimethylamino)ethyl]oxy}phenyl)amino]-4-pyrimidinyl}-6-methylpyrazolo[1,5-a]pyridin-2-yl)phenyl]-2-(2-thienyl)acetamide; and
N-{3-[3-(2-{[4-(4-Acetyl-1-piperazinyl)phenyl]amino}-4-pyrimidinyl)-6-methylpyrazolo[1,5-a]pyridin-2-yl]phenyl}-2-(2-thienyl)acetamide,
and pharmaceutically acceptable salts thereof.

22. A pharmaceutical composition comprising a compound according to claim 1 and a pharmaceutically acceptable carrier, diluent or excipient.

23. The pharmaceutical composition according to claim 22 further comprising a chemotherapeutic agent.

24. A method for treating breast cancer in a human in need thereof, said method comprising administering to the human a therapeutically effective amount of a compound according to claim 1.

25. A process for preparing a compound according to claim 1, said process comprising the steps of:
a) reacting a compound of formula (VII):

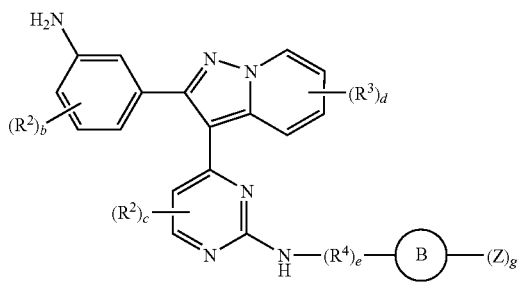

with a compound of formula (VIII) or a compound of formula (IX):

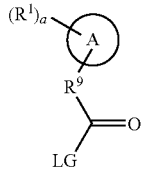

-continued

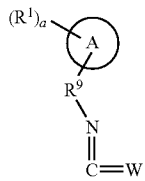

IX wherein LG is a leaving group and W is O or S;
to prepare a compound of formula (I);

b) optionally converting the compound of formula (I) to a pharmaceutically acceptable salt thereof; and c) optionally converting the compound of formula (I) or a pharmaceutically acceptable salt thereof to a different compound of formula (I) or a pharmaceutically acceptable salt thereof.

* * * * *